United States Patent
Eastman et al.

(10) Patent No.: US 10,351,546 B2
(45) Date of Patent: *Jul. 16, 2019

(54) PYRIDIN-3-YL ACETIC ACID DERIVATIVES AS INHIBITORS OF HUMAN IMMUNODEFICIENCY VIRUS REPLICATION

(71) Applicant: ViiV Healthcare UK (No. 5) Limited, Brentford, Middlesex (GB)

(72) Inventors: Kyle J. Eastman, Wallingford, CT (US); John F. Kadow, Wallingford, CT (US); B. Narasimhulu Naidu, Wallingford, CT (US); Kyle E. Parcella, Wallingford, CT (US); Manoj Patel, Wallingford, CT (US); Prasanna Sivaprakasam, Wallingford, CT (US); Yong Tu, Wallingford, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/749,584

(22) PCT Filed: Aug. 10, 2016

(86) PCT No.: PCT/IB2016/054830
§ 371 (c)(1),
(2) Date: Feb. 1, 2018

(87) PCT Pub. No.: WO2017/025915
PCT Pub. Date: Feb. 16, 2017

(65) Prior Publication Data
US 2018/0230124 A1 Aug. 16, 2018

Related U.S. Application Data

(60) Provisional application No. 62/204,239, filed on Aug. 12, 2015.

(51) Int. Cl.
| | |
|---|---|
| A61K 31/444 | (2006.01) |
| C07D 401/14 | (2006.01) |
| C07D 405/14 | (2006.01) |
| C07D 401/04 | (2006.01) |
| C07D 487/04 | (2006.01) |
| A61P 31/18 | (2006.01) |
| A61K 31/5365 | (2006.01) |

(52) U.S. Cl.
CPC ............ *C07D 401/04* (2013.01); *A61P 31/18* (2018.01); *C07D 401/14* (2013.01); *C07D 405/14* (2013.01); *C07D 487/04* (2013.01); *A61K 31/5365* (2013.01); *A61K 2300/00* (2013.01)

(58) Field of Classification Search
CPC .. A61K 31/444; C07D 401/14; C07D 405/14; C07D 401/04; C07D 487/04
See application file for complete search history.

(56) References Cited

U.S. PATENT DOCUMENTS

| | | | |
|---|---|---|---|
| 9,193,720 B2* | 11/2015 | Naidu ................ | C07D 417/14 |
| 2018/0147196 A1* | 5/2018 | Eastman ............. | C07D 401/14 |
| 2018/0170904 A1* | 6/2018 | Kadow ............... | C07D 401/14 |
| 2018/0222890 A1* | 8/2018 | Kadow ............... | C07D 473/18 |
| 2018/0230129 A1* | 8/2018 | Eastman ............. | A61K 31/444 |
| 2018/0230134 A1* | 8/2018 | Kadow ............... | C07D 401/14 |

FOREIGN PATENT DOCUMENTS

| | | |
|---|---|---|
| WO | WO 2009/062285 A1 | 5/2009 |
| WO | WO 2010/130034 A1 | 11/2010 |
| WO | WO 2011/076765 A1 | 6/2011 |
| WO | WO 2015/126726 A1 | 8/2015 |

* cited by examiner

*Primary Examiner* — Brenda L Coleman
(74) *Attorney, Agent, or Firm* — Robert H. Brink; Kathryn A. Lutomski; Edward R. Gimmi

(57) ABSTRACT

Disclosed are compounds of Formula I, including pharmaceutically acceptable salts, pharmaceutical compositions comprising the compounds, methods for making the compounds and their use in inhibiting HIV integrase and treating those infected with HIV.

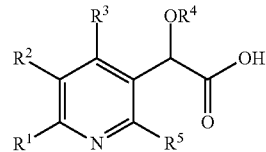

19 Claims, No Drawings

PYRIDIN-3-YL ACETIC ACID DERIVATIVES AS INHIBITORS OF HUMAN IMMUNODEFICIENCY VIRUS REPLICATION

CROSS REFERENCE TO RELATED INVENTION

This application is a § 371 of International Application No. PCT/IB2016/054830, filed 10 Aug. 2016, which claims the benefit of U.S. Provisional Application No. 62/204,239, filed 12 Aug. 2015.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See, for example, the following patent applications: WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, WO2014159959, and WO2015126726.

What is now needed in the art are additional compounds which are novel and useful in the treatment of HIV. Additionally, these compounds may desireably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

By virtue of the present invention, it is now possible to provide compounds that are novel and are useful in the treatment of HIV. Additionally, the compounds may provide advantages for pharmaceutical uses, for example, with regard to one or more of their mechanism of action, binding, inhibition efficacy, target selectivity, solubility, safety profiles, or bioavailability.

The invention also provides pharmaceutical compositions comprising the compounds of the invention, including pharmaceutically acceptable salts thereof, and a pharmaceutically acceptable carrier, excipient, and/or diluent.

In addition, the invention provides methods of treating HIV infection comprising administering a therapeutically effective amount of the compounds of the invention to a patient.

In addition, the invention provides methods for inhibiting HIV integrase.

Also provided in accordance with the invention are methods for making the compounds of the invention.

The present invention is directed to these, as well as other important ends, hereinafter described.

DESCRIPTION OF THE INVENTION

Unless specified otherwise, these terms have the following meanings.

"Alkyl" means a straight or branched saturated hydrocarbon comprised of 1 to 10 carbons, and preferably 1 to 6 carbons.

"Alkenyl" means a straight or branched alkyl group comprised of 2 to 10 carbons with at least one double bond and optionally substituted with 0-3 halo or alkoxy group.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic groups include, but are not limited to, indanyl, indenyl, naphthyl, phenyl, tetrahydronaphthyl and cyclopropylphenyl. The aryl group can be attached to the parent structure through any substitutable carbon atom in the group.

"Arylalkyl" is a $C_1$-$C_5$ alkyl group attached to 1 to 2 aryl groups and linked to the parent structure through the alkyl moiety. Examples include, but are not limited to, —$(CH_2)_n$Ph with n=1-5, —$CH(CH_3)$Ph, —$CH(Ph)_2$.

"Aryloxy" is an aryl group attached to the parent structure by oxygen.

"Cycloalkyl" means a monocyclic ring system composed of 3 to 7 carbons.

"Halo" includes fluoro, chloro, bromo, and iodo.

"Haloalkyl" and "haloalkoxy" include all halogenated isomers from monohalo to perhalo.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —$(CH_2)_n$—$R^z$ or —$CH(CH_3)$—$(R^z)$ where n=1-5 and that $R^z$ is chosen from benzimidazole, imidazole, indazole, isooxazole, phenyl-pyrazole, pyridine, quinoline, thiazole, triazole, triazolone, oxadiazole.

Terms with a hydrocarbon moiety (e.g. alkoxy) include straight and branched isomers for the hydrocarbon portion with the indicated number of carbon atoms.

Bonding and positional bonding relationships are those that are stable as understood by practitioners of organic chemistry.

Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

"Combination," "coadministration," "concurrent" and similar terms referring to the administration of a compound of Formula I with at least one anti-HIV agent mean that the components are part of a combination antiretroviral therapy or highly active antiretroviral therapy ("HAART") as understood by practitioners in the field of AIDS and HIV infection.

"Therapeutically effective" means the amount of agent required to provide a benefit to a patient as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus.

"Treatment," "therapy," "regimen," "HIV infection," "ARC," "AIDS" and related terms are used as understood by practitioners in the field of AIDS and HIV infection.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I:

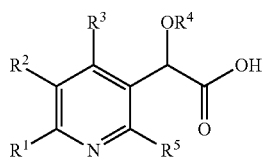

I wherein:
$R^1$ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy) alkyl, (halocycloalkoxy)alkyl, (halophenoxy)alkyl, $(Ar^1)$ alkyl, $(Ar^2)$alkyl, $((R^{10})(R^{11})N)$alkyl, (trialkylammonium)alkyl, $(R^6)$alkyl, alkenyl, (alkoxy) alkenyl, hydroxy, alkoxy, $(Ar^1)$alkoxy, $(R^{10})(R^{11})N$, $CO_2R^{10}$, $CON(R^{10})(R^{11})$, $((Ar^1)$alkyl)imidazolyl, or halobenzimidazolyl;
provided that when $R^1$ is hydrogen $R^5$ is not alkyl;
$R^2$ is selected from halo, phenyl or tetrahydroisoquinolinyl and is substituted with 1 $R^7$ substituent and with 0-3 substituents selected from halo, alkyl, haloalkyl, alkoxy, and haloalkoxy;
provided that when $R^2$ is halo, $R^1$ and $R^5$ are not simultaneously alkyl;
$R^3$ is selected from azetidinyl, pyrrolidinyl, piperidinyl, piperazinyl, or homopiperidinyl substituted with 0-3 halo or alkyl substituents;
$R^4$ is selected from alkyl or haloalkyl;
$R^5$ is selected from hydrogen, alkyl, haloalkyl, hydroxy, hydroxyalkyl, alkoxy, alkoxyalkyl, (alkoxy)alkoxyalkyl, (((alkoxy)alkoxy)alkoxy)alkyl, ((benzyloxy)alkoxy) alkyl, $((R^{10})(R^{11})N)$alkyl, or $(R^6)$alkyl;
provided that $R^1$ and $R^5$ are not simultaneously alkyl;

$R^6$ is selected from (oxetanyl)alkyl, ((oxetanyl)alkoxy)alkyl, (tetrahydropyranyloxy)alkyl, (tetrahydropyranyl)alkoxy) alkyl, ((pyrrolidinonyl)alkoxy)alkyl, $(Ar^1O)$alkyl, $((Ar^1)$ alkoxy)alkyl, $((Ar^2)$alkoxy)alkyl, (oxetanyl)oxy, $((R^8)$ $(R^9)N)$alkoxy, alkylthio, alkylsulfonyl, or $(R^8)(R^9)N$;
$R^7$ is selected from $(Ar^1)$alkyl, $(Ar^1)$alkoxy, N-alkoxycarbonyl, or $((Ar^1)$alkyl)HNCO;
or $R^7$ is selected from pyrimidinyl, benzofuropyrimidinyl, or pyrazolopyrimidinyl substituted with 0-1 alkyl substituents;
$R^8$ is selected from hydrogen, alkyl, (cycloalkyl)alkyl, alkoxyalkyl, (tetrahydropyanyl)alkyl, tetrahydropyanyl, or alkoxyphenyl;
$R^9$ is selected from hydrogen or alkyl;
or $(R^8)(R^9)N$ taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents;
$R^{10}$ is selected from hydrogen, alkyl, or alkoxyalkyl;
$R^{11}$ is selected from hydrogen, alkyl, (cycloalkyl)alkyl, hydroxyalkyl, alkoxyalkyl, (oxetanyl)alkyl, (tetrahydropyanyl)alkyl, $(Ar^1)$alkyl, $(Ar^2)$alkyl, $(((Ar^1)$alkyl)carbonyl)alkyl, oxetanyl, $Ar^1$, formyl, alkylcarbonyl, $(Ar^2)$ carbonyl, (dialkylamino)oxoacetyl, or alkylsulfonyl;
or $(R^{10})(R^{11})N$ taken together is selected from azetidinyl, bicyclo[0.1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 $(C_{3-7})$spiroalkylenyl substituents;
$Ar^1$ is phenyl substituted with 0-3 substituents selected from halo, alkyl, haloalkyl, alkoxy, and haloalkoxy; and
$Ar^2$ is selected from pyrazolyl, oxazolyl, thiazolyl, triazolyl, oxadiazolyl, or pyridinyl and is substituted with 0-3 halo or alkyl substituents;
or a pharmaceutically acceptable salt thereof.

In an aspect of the invention, $R^1$ is hydrogen and $R^5$ is hydrogen, haloalkyl, hydroxyalkyl, alkoxyalkyl, (alkoxy) alkoxyalkyl, (((alkoxy)alkoxy)alkoxy)alkyl, ((benzyloxy) alkoxy)alkyl, $((R^{10})(R^{11})N)$alkyl, or $(R^6)$alkyl.

In an aspect of the invention, $R^1$ is alkyl and $R^5$ is hydrogen, haloalkyl, hydroxyalkyl, alkoxyalkyl, (alkoxy) alkoxyalkyl, (((alkoxy)alkoxy)alkoxy)alkyl, ((benzyloxy) alkoxy)alkyl, $((R^{10})(R^{11})N)$alkyl, or $(R^6)$alkyl.

In an aspect of the invention, $R^2$ is phenyl substituted with 1 $R^7$ substituent and with 0-3 substituents selected from halo, alkyl, haloalkyl, alkoxy, and haloalkoxy.

In an aspect of the invention, $R^2$ is tetrahydroisoquinolinyl and is substituted with 1 $R^7$ substituent.

In an aspect of the invention, $R^3$ is piperidinyl substituted with 0-3 halo or alkyl substituents.

In an aspect of the invention, one of $R^1$ or $R^5$ are alkyl

In an aspect of the invention, $R^2$ is halo. In an aspect of the invention wherein $R^2$ is halo, one of $R^1$ or $R^5$ are alkyl.

In an aspect of the invention, $R^4$ is selected from alkyl or haloalkyl. In an aspect of the invention wherein $R^4$ is selected from alkyl or haloalkyl, one of $R^1$ or $R^5$ are alkyl.

In an aspect of the invention, $R^7$ is selected from $(Ar^1)$ alkyl, $(Ar^1)$alkoxy, N-alkoxycarbonyl, or $((Ar^1)$alkyl) HNCO.

In an aspect of the invention, $R^7$ is selected from pyrimidinyl, benzofuropyrimidinyl, or pyrazolopyrimidinyl substituted with 0-1 alkyl substituents.

In an aspect of the invention, $R^9$ is selected from hydrogen or alkyl. In an aspect of the invention, $(R^8)(R^9)N$ taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents.

In an aspect of the invention, $R^{11}$ is selected from hydrogen, alkyl, (cycloalkyl)alkyl, hydroxyalkyl, alkoxyalkyl, (oxetanyl)alkyl, (tetrahydropyanyl)alkyl, $(Ar^1)$alkyl, $(Ar^2)$alkyl, $(((Ar^1)$alkyl)carbonyl)alkyl, oxetanyl, $Ar^1$, formyl, alkylcarbonyl, $(Ar^2)$carbonyl, (dialkylamino)oxoacetyl, or alkylsulfonyl.

In an aspect of the invention, $(R^{10})(R^{11})N$ taken together is selected from azetidinyl, bicyclo[1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 $(C_{3-7})$ spiroalkylenyl substituents.

In an aspect of the invention, there is provided a compound of Formula I:

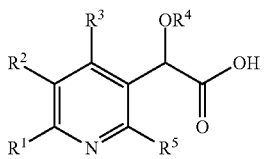

wherein:
$R^1$ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy)alkyl, (halocycloalkoxy)alkyl, (halophenoxy)alkyl, $(Ar^1)$alkyl, $(Ar^2)$alkyl, $((R^{10})(R^{11})N)$alkyl, (trialkylammonium)alkyl, $(R^6)$alkyl, alkenyl, (alkoxy)alkenyl, hydroxy, alkoxy, $(Ar^1)$alkoxy, $(R^{10})(R^{11})N$, $CO_2R^{10}$, $CON(R^{10})(R^{11})$, $((Ar^1)$alkyl)imidazolyl, or halobenzimidazolyl;
provided that when $R^1$ is hydrogen $R^5$ is not alkyl;
$R^2$ is selected from halo, phenyl or tetrahydroisoquinolinyl and is substituted with 1 $R^7$ substituent and with 0-3 substituents selected from halo, alkyl, haloalkyl, alkoxy, and haloalkoxy;
provided that when $R^2$ is halo, $R^1$ and $R^5$ are not simultaneously alkyl;
$R^3$ is selected from azetidinyl, pyrrolidinyl, piperidinyl, piperazinyl, or homopiperidinyl substituted with 0-3 halo or alkyl substituents;
$R^4$ is selected from alkyl or haloalkyl;
$R^5$ is selected from hydrogen, alkyl, haloalkyl, hydroxy, hydroxyalkyl, alkoxy, alkoxyalkyl, (alkoxy)alkoxyalkyl, (((alkoxy)alkoxy)alkoxy)alkyl, ((benzyloxy)alkoxy)alkyl, $((R^{10})(R^{11})N)$alkyl, or $(R^6)$alkyl;
provided that $R^1$ and $R^5$ are not simultaneously alkyl;
$R^6$ is selected from (oxetanyl)alkyl, ((oxetanyl)alkoxy)alkyl, (tetrahydropyranyloxy)alkyl, (tetrahydropyranyl)alkoxy)alkyl, ((pyrrolidinonyl)alkoxy)alkyl, $(Ar^1O)$alkyl, $((Ar^1)$alkoxy)alkyl, $((Ar^2)$alkoxy)alkyl, (oxetanyl)oxy, $((R^8)(R^9)N)$alkyl, alkylthio, alkylsulfonyl, or $(R^8)(R^9)N$;
$R^7$ is selected from $(Ar^1)$alkyl, $(Ar^1)$alkoxy, N-alkoxycarbonyl, or $((Ar^1)$alkyl)HNCO;

$R^8$ is selected from hydrogen, alkyl, (cycloalkyl)alkyl, alkoxyalkyl, (tetrahydropyanyl)alkyl, tetrahydropyanyl, or alkoxyphenyl;
$R^9$ is selected from hydrogen or alkyl;
or $(R^8)(R^9)N$ taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents;
$R^{10}$ is selected from hydrogen, alkyl, or alkoxyalkyl;
$R^{11}$ is selected from hydrogen, alkyl, (cycloalkyl)alkyl, hydroxyalkyl, alkoxyalkyl, (oxetanyl)alkyl, (tetrahydropyanyl)alkyl, $(Ar^1)$alkyl, $(Ar^2)$alkyl, $(((Ar^1)$alkyl)carbonyl)alkyl, oxetanyl, $Ar^1$, formyl, alkylcarbonyl, $(Ar^2)$carbonyl, (dialkylamino)oxoacetyl, or alkylsulfonyl;
or $(R^{10})(R^{11})N$ taken together is selected from azetidinyl, bicyclo[0.1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 $(C_{3-7})$spiroalkylenyl substituents;
$Ar^1$ is phenyl substituted with 0-3 substituents selected from halo, alkyl, haloalkyl, alkoxy, and haloalkoxy; and
$Ar^2$ is selected from pyrazolyl, oxazolyl, thiazolyl, triazolyl, oxadiazolyl, or pyridinyl and is substituted with 0-3 halo or alkyl substituents;
or a pharmaceutically acceptable salt thereof.

In an aspect of the invention, there is provided a compound of Formula I:

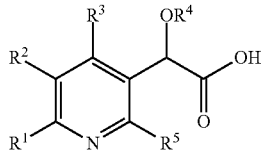

wherein:
$R^1$ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy)alkyl, (halocycloalkoxy)alkyl, (halophenoxy)alkyl, $(Ar^1)$alkyl, $(Ar^2)$alkyl, $((R^{10})(R^{11})N)$alkyl, (trialkylammonium)alkyl, $(R^6)$alkyl, alkenyl, (alkoxy)alkenyl, hydroxy, alkoxy, $(Ar^1)$alkoxy, $(R^{10})(R^{11})N$, $CO_2R^{10}$, $CON(R^{10})(R^{11})$, $((Ar^1)$alkyl)imidazolyl, or halobenzimidazolyl;
provided that when $R^1$ is hydrogen $R^5$ is not alkyl;
$R^2$ is selected from halo, phenyl or tetrahydroisoquinolinyl and is substituted with 1 $R^7$ substituent and with 0-3 substituents selected from halo, alkyl, haloalkyl, alkoxy, and haloalkoxy;
provided that when $R^2$ is halo, $R^1$ and $R^5$ are not simultaneously alkyl;
$R^3$ is selected from azetidinyl, pyrrolidinyl, piperidinyl, piperazinyl, or homopiperidinyl substituted with 0-3 halo or alkyl substituents;
$R^4$ is selected from alkyl or haloalkyl;
$R^5$ is selected from hydrogen, alkyl, haloalkyl, hydroxy, hydroxyalkyl, alkoxy, alkoxyalkyl, (alkoxy)alkoxyalkyl, (((alkoxy)alkoxy)alkoxy)alkyl, ((benzyloxy)alkoxy)alkyl, $((R^{10})(R^{11})N)$alkyl, or $(R^6)$alkyl;

provided that R¹ and R⁵ are not simultaneously alkyl;
R⁶ is selected from (oxetanyl)alkyl, ((oxetanyl)alkoxy)alkyl, (tetrahydropyranyloxy)alkyl, (tetrahydropyranyl)alkoxy) alkyl, ((pyrrolidinonyl)alkoxy)alkyl, (Ar¹O)alkyl, ((Ar¹)alkoxy)alkyl, ((Ar²)alkoxy)alkyl, (oxetanyl)oxy, ((R⁸)(R⁹)N)alkoxy, alkylthio, alkylsulfonyl, or (R⁸)(R⁹)N;
R⁷ is selected from pyrimidinyl, benzofuropyrimidinyl, or pyrazolopyrimidinyl substituted with 0-1 alkyl substituents;
R⁸ is selected from hydrogen, alkyl, (cycloalkyl)alkyl, alkoxyalkyl, (tetrahydropyanyl)alkyl, tetrahydropyanyl, or alkoxyphenyl;
R⁹ is selected from hydrogen or alkyl;
or (R⁸)(R⁹)N taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents;
R¹⁰ is selected from hydrogen, alkyl, or alkoxyalkyl;
R¹¹ is selected from hydrogen, alkyl, (cycloalkyl)alkyl, hydroxyalkyl, alkoxyalkyl, (oxetanyl)alkyl, (tetrahydropyanyl)alkyl, (Ar¹)alkyl, (Ar²)alkyl, (((Ar¹)alkyl)carbonyl)alkyl, oxetanyl, Ar¹, formyl, alkylcarbonyl, (Ar²)carbonyl, (dialkylamino)oxoacetyl, or alkylsulfonyl;
or (R¹⁰)(R¹¹)N taken together is selected from azetidinyl, bicyclo[0.1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 (C₃₋₇)spiroalkylenyl substituents;
Ar¹ is phenyl substituted with 0-3 substituents selected from halo, alkyl, haloalkyl, alkoxy, and haloalkoxy; and
Ar² is selected from pyrazolyl, oxazolyl, thiazolyl, triazolyl, oxadiazolyl, or pyridinyl and is substituted with 0-3 halo or alkyl substituents;
or a pharmaceutically acceptable salt thereof.

In an aspect of the invention, there is provided a compound of Formula I:

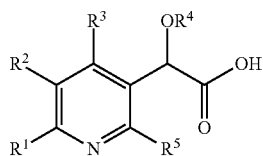

I wherein:
R¹ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy)alkyl, (halocycloalkoxy)alkyl, (halophenoxy)alkyl, (Ar¹)alkyl, (Ar²)alkyl, ((R¹⁰)(R¹¹)N)alkyl, (trialkylammonium)alkyl, (R⁶)alkyl, alkenyl, (alkoxy)alkenyl, hydroxy, alkoxy, (Ar¹)alkoxy, (R¹⁰)(R¹¹)N, CO₂R¹⁰, CON(R¹⁰)(R¹¹), ((Ar¹)alkyl)imidazolyl, or halobenzimidazolyl;
provided that when R¹ is hydrogen R⁵ is not alkyl;
R² is selected from halo, phenyl or tetrahydroisoquinolinyl and is substituted with 1 R⁷ substituent and with 0-3 substituents selected from halo, alkyl, haloalkyl, alkoxy, and haloalkoxy;

provided that when R² is halo, R¹ and R⁵ are not simultaneously alkyl;
R³ is selected from azetidinyl, pyrrolidinyl, piperidinyl, piperazinyl, or homopiperidinyl substituted with 0-3 halo or alkyl substituents;
R⁴ is selected from alkyl or haloalkyl;
R⁵ is selected from hydrogen, alkyl, haloalkyl, hydroxy, hydroxyalkyl, alkoxy, alkoxyalkyl, (alkoxy)alkoxyalkyl, (((alkoxy)alkoxy)alkoxy)alkyl, ((benzyloxy)alkoxy) alkyl, ((R¹⁰)(R¹¹)N)alkyl, or (R⁶)alkyl;
provided that R¹ and R⁵ are not simultaneously alkyl;
R⁶ is selected from (oxetanyl)alkyl, ((oxetanyl)alkoxy)alkyl, (tetrahydropyranyloxy)alkyl, (tetrahydropyranyl)alkoxy) alkyl, ((pyrrolidinonyl)alkoxy)alkyl, (Ar¹O)alkyl, ((Ar¹)alkoxy)alkyl, ((Ar²)alkoxy)alkyl, (oxetanyl)oxy, ((R⁸)(R⁹)N)alkoxy, alkylthio, alkylsulfonyl, or (R⁸)(R⁹)N;
R⁷ is selected from (Ar¹)alkyl, (Ar¹)alkoxy, N-alkoxycarbonyl, or ((Ar¹)alkyl)HNCO;
or R⁷ is selected from pyrimidinyl, benzofuropyrimidinyl, or pyrazolopyrimidinyl substituted with 0-1 alkyl substituents;
R⁸ is selected from hydrogen, alkyl, (cycloalkyl)alkyl, alkoxyalkyl, (tetrahydropyanyl)alkyl, tetrahydropyanyl, or alkoxyphenyl;
R⁹ is selected from hydrogen or alkyl;
R¹⁰ is selected from hydrogen, alkyl, or alkoxyalkyl;
R¹¹ is selected from hydrogen, alkyl, (cycloalkyl)alkyl, hydroxyalkyl, alkoxyalkyl, (oxetanyl)alkyl, (tetrahydropyanyl)alkyl, (Ar¹)alkyl, (Ar²)alkyl, (((Ar¹)alkyl)carbonyl)alkyl, oxetanyl, Ar¹, formyl, alkylcarbonyl, (Ar²)carbonyl, (dialkylamino)oxoacetyl, or alkylsulfonyl;
or (R¹⁰)(R¹¹)N taken together is selected from azetidinyl, bicyclo[0.1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 (C₃₋₇)spiroalkylenyl substituents;
Ar¹ is phenyl substituted with 0-3 substituents selected from halo, alkyl, haloalkyl, alkoxy, and haloalkoxy; and
Ar² is selected from pyrazolyl, oxazolyl, thiazolyl, triazolyl, oxadiazolyl, or pyridinyl and is substituted with 0-3 halo or alkyl substituents;
or a pharmaceutically acceptable salt thereof.

In an aspect of the invention, there is provided a compound of Formula I:

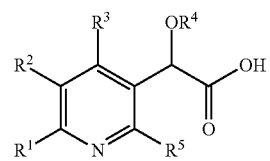

I wherein:
R¹ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy) alkyl, (halocycloalkoxy)alkyl, (halophenoxy)alkyl, (Ar¹)alkyl, (Ar²)alkyl, ((R¹⁰)(R¹¹)N)alkyl, (trialkylammonium)alkyl, (R⁶)alkyl, alkenyl, (alkoxy)

alkenyl, hydroxy, alkoxy, (Ar¹)alkoxy, (R¹⁰)(R¹¹)N, CO₂R¹⁰, CON(R¹⁰)(R¹¹), ((Ar¹)alkyl)imidazolyl, or halobenzimidazolyl;

provided that when R¹ is hydrogen R⁵ is not alkyl;

R² is selected from halo, phenyl or tetrahydroisoquinolinyl and is substituted with 1 R⁷ substituent and with 0-3 substituents selected from halo, alkyl, haloalkyl, alkoxy, and haloalkoxy;

provided that when R² is halo, R¹ and R⁵ are not simultaneously alkyl;

R³ is selected from azetidinyl, pyrrolidinyl, piperidinyl, piperazinyl, or homopiperidinyl substituted with 0-3 halo or alkyl substituents;

R⁴ is selected from alkyl or haloalkyl;

R⁵ is selected from hydrogen, alkyl, haloalkyl, hydroxy, hydroxyalkyl, alkoxy, alkoxyalkyl, (alkoxy)alkoxyalkyl, (((alkoxy)alkoxy)alkoxy)alkyl, ((benzyloxy)alkoxy) alkyl, ((R¹⁰)(R¹¹)N)alkyl, or (R⁶)alkyl;

provided that R¹ and R⁵ are not simultaneously alkyl;

R⁶ is selected from (oxetanyl)alkyl, ((oxetanyl)alkoxy)alkyl, (tetrahydropyranyloxy)alkyl, (tetrahydropyranyl)alkoxy) alkyl, ((pyrrolidinonyl)alkoxy)alkyl, (Ar¹O)alkyl, ((Ar¹) alkoxy)alkyl, ((Ar²)alkoxy)alkyl, (oxetanyl)oxy, ((R⁸) (R⁹)N)alkoxy, alkylthio, alkylsulfonyl, or (R⁸)(R⁹)N;

R⁷ is selected from (Ar¹)alkyl, (Ar¹)alkoxy, N-alkoxycarbonyl, or ((Ar¹)alkyl)HNCO;

or R⁷ is selected from pyrimidinyl, benzofuropyrimidinyl, or pyrazolopyrimidinyl substituted with 0-1 alkyl substituents;

(R⁸)(R⁹)N taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents;

R¹⁰ is selected from hydrogen, alkyl, or alkoxyalkyl;

R¹¹ is selected from hydrogen, alkyl, (cycloalkyl)alkyl, hydroxyalkyl, alkoxyalkyl, (oxetanyl)alkyl, (tetrahydropyanyl)alkyl, (Ar¹)alkyl, (Ar²)alkyl, (((Ar¹)alkyl)carbonyl)alkyl, oxetanyl, Ar¹, formyl, alkylcarbonyl, (Ar²) carbonyl, (dialkylamino)oxoacetyl, or alkylsulfonyl;

or (R¹⁰)(R¹¹)N taken together is selected from azetidinyl, bicyclo[0.1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 (C₃₋₇)spiroalkylenyl substituents;

Ar¹ is phenyl substituted with 0-3 substituents selected from halo, alkyl, haloalkyl, alkoxy, and haloalkoxy; and Ar² is selected from pyrazolyl, oxazolyl, thiazolyl, triazolyl, oxadiazolyl, or pyridinyl and is substituted with 0-3 halo or alkyl substituents;

or a pharmaceutically acceptable salt thereof.

In an aspect of the invention, there is provided a compound of Formula I:

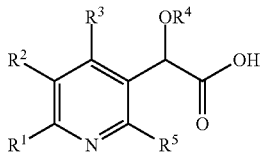

wherein:

R¹ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy) alkyl, (halocycloalkoxy)alkyl, (halophenoxy)alkyl, (Ar¹) alkyl, (Ar²)alkyl, ((R¹⁰)(R¹¹)N)alkyl, (trialkylammonium)alkyl, (R⁶)alkyl, alkenyl, (alkoxy) alkenyl, hydroxy, alkoxy, (Ar¹)alkoxy, (R¹⁰)(R¹¹)N, CO₂R¹⁰, CON(R¹⁰)(R¹¹), ((Ar¹)alkyl)imidazolyl, or halobenzimidazolyl;

provided that when R¹ is hydrogen R⁵ is not alkyl;

R² is selected from halo, phenyl or tetrahydroisoquinolinyl and is substituted with 1 R⁷ substituent and with 0-3 substituents selected from halo, alkyl, haloalkyl, alkoxy, and haloalkoxy;

provided that when R² is halo, R¹ and R⁵ are not simultaneously alkyl;

R³ is selected from azetidinyl, pyrrolidinyl, piperidinyl, piperazinyl, or homopiperidinyl substituted with 0-3 halo or alkyl substituents;

R⁴ is selected from alkyl or haloalkyl;

R⁵ is selected from hydrogen, alkyl, haloalkyl, hydroxy, hydroxyalkyl, alkoxy, alkoxyalkyl, (alkoxy)alkoxyalkyl, (((alkoxy)alkoxy)alkoxy)alkyl, ((benzyloxy)alkoxy) alkyl, ((R¹⁰)(R¹¹)N)alkyl, or (R⁶)alkyl;

provided that R¹ and R⁵ are not simultaneously alkyl;

R⁶ is selected from (oxetanyl)alkyl, ((oxetanyl)alkoxy)alkyl, (tetrahydropyranyloxy)alkyl, (tetrahydropyranyl)alkoxy) alkyl, ((pyrrolidinonyl)alkoxy)alkyl, (Ar¹O)alkyl, ((Ar¹) alkoxy)alkyl, ((Ar²)alkoxy)alkyl, (oxetanyl)oxy, ((R⁸) (R⁹)N)alkoxy, alkylthio, alkylsulfonyl, or (R⁸)(R⁹)N;

R⁷ is selected from (Ar¹)alkyl, (Ar¹)alkoxy, N-alkoxycarbonyl, or ((Ar¹)alkyl)HNCO;

or R⁷ is selected from pyrimidinyl, benzofuropyrimidinyl, or pyrazolopyrimidinyl substituted with 0-1 alkyl substituents;

R⁸ is selected from hydrogen, alkyl, (cycloalkyl)alkyl, alkoxyalkyl, (tetrahydropyanyl)alkyl, tetrahydropyanyl, or alkoxyphenyl;

R⁹ is selected from hydrogen or alkyl;

or (R⁸)(R⁹)N taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents;

R¹⁰ is selected from hydrogen, alkyl, or alkoxyalkyl;

R¹¹ is selected from hydrogen, alkyl, (cycloalkyl)alkyl, hydroxyalkyl, alkoxyalkyl, (oxetanyl)alkyl, (tetrahydropyanyl)alkyl, (Ar¹)alkyl, (Ar²)alkyl, (((Ar¹)alkyl)carbonyl)alkyl, oxetanyl, Ar¹, formyl, alkylcarbonyl, (Ar²) carbonyl, (dialkylamino)oxoacetyl, or alkylsulfonyl;

Ar¹ is phenyl substituted with 0-3 substituents selected from halo, alkyl, haloalkyl, alkoxy, and haloalkoxy; and Ar² is selected from pyrazolyl, oxazolyl, thiazolyl, triazolyl, oxadiazolyl, or pyridinyl and is substituted with 0-3 halo or alkyl substituents;

or a pharmaceutically acceptable salt thereof.

In an aspect of the invention, there is provided a compound of Formula I:

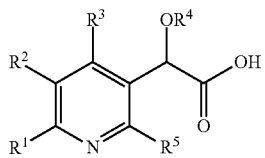

wherein:

R$^1$ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy) alkyl, (halocycloalkoxy)alkyl, (halophenoxy)alkyl, (Ar$^1$) alkyl, (Ar$^2$)alkyl, ((R$^{10}$)(R$^{11}$)N)alkyl, (trialkylammonium)alkyl, (R$^6$)alkyl, alkenyl, (alkoxy) alkenyl, hydroxy, alkoxy, (Ar$^1$)alkoxy, (R$^{10}$)(R$^{11}$)N, CO$_2$R$^{10}$, CON(R$^{10}$)(R$^{11}$), ((Ar$^1$)alkyl)imidazolyl, or halobenzimidazolyl;

provided that when R$^1$ is hydrogen R$^5$ is not alkyl;

R$^2$ is selected from halo, phenyl or tetrahydroisoquinolinyl and is substituted with 1 R$^7$ substituent and with 0-3 substituents selected from halo, alkyl, haloalkyl, alkoxy, and haloalkoxy;

provided that when R$^2$ is halo, R$^1$ and R$^5$ are not simultaneously alkyl;

R$^3$ is selected from azetidinyl, pyrrolidinyl, piperidinyl, piperazinyl, or homopiperidinyl substituted with 0-3 halo or alkyl substituents;

R$^4$ is selected from alkyl or haloalkyl;

R$^5$ is selected from hydrogen, alkyl, haloalkyl, hydroxy, hydroxyalkyl, alkoxy, alkoxyalkyl, (alkoxy)alkoxyalkyl, (((alkoxy)alkoxy)alkoxy)alkyl, ((benzyloxy)alkoxy) alkyl, ((R$^{10}$)(R$^{11}$)N)alkyl, or (R$^6$)alkyl;

provided that R$^1$ and R$^5$ are not simultaneously alkyl;

R$^6$ is selected from (oxetanyl)alkyl, ((oxetanyl)alkoxy)alkyl, (tetrahydropyranyloxy)alkyl, (tetrahydropyranyl)alkoxy) alkyl, ((pyrrolidinonyl)alkoxy)alkyl, (Ar$^1$O)alkyl, ((Ar$^1$) alkoxy)alkyl, ((Ar$^2$)alkoxy)alkyl, (oxetanyl)oxy, ((R$^8$) (R$^9$)N)alkoxy, alkylthio, alkylsulfonyl, or (R$^8$)(R$^9$)N;

R$^7$ is selected from (Ar$^1$)alkyl, (Ar$^1$)alkoxy, N-alkoxycarbonyl, or ((Ar$^1$)alkyl)HNCO;

or R$^7$ is selected from pyrimidinyl, benzofuropyrimidinyl, or pyrazolopyrimidinyl substituted with 0-1 alkyl substituents;

R$^8$ is selected from hydrogen, alkyl, (cycloalkyl)alkyl, alkoxyalkyl, (tetrahydropyanyl)alkyl, tetrahydropyanyl, or alkoxyphenyl;

R$^9$ is selected from hydrogen or alkyl;

or (R$^8$)(R$^9$)N taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents; (R$^{10}$)(R$^{11}$)N taken together is selected from azetidinyl, bicyclo[1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 (C$_{3-7}$)spiroalkylenyl substituents;

Ar$^1$ is phenyl substituted with 0-3 substituents selected from halo, alkyl, haloalkyl, alkoxy, and haloalkoxy; and Ar$^2$ is selected from pyrazolyl, oxazolyl, thiazolyl, triazolyl, oxadiazolyl, or pyridinyl and is substituted with 0-3 halo or alkyl substituents;

or a pharmaceutically acceptable salt thereof.

For a particular compound of Formula I, the scope of any instance of a variable substituent, including R$^1$, R$^2$, R$^3$, R$^4$, R$^5$, R$^6$, R$^7$, R$^8$, R$^9$, R$^{10}$, R$^{11}$, Ar$^1$ and Ar$^2$ can be used independently with the scope of any other instance of a variable substituent. As such, the invention includes combinations of the different aspects.

In an aspect of the invention, there is provided a composition useful for treating HIV infection comprising a therapeutic amount of a compound of Formula I and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir. In an aspect of the invention, the other agent is administered to the patient prior to, simultaneously with, or subsequently to the compound of Formula I.

Preferred compounds in accordance with the present invention include the following:

(S)-2-(tert-Butoxy)-2-(4-(4,4-dimethylpiperidin-1-yl)-5-(4-(4-fluorophenethoxy)phenyl)-2-(hydroxymethyl)-6-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(hydroxymethyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(methoxymethyl)-2-methylpyridin-3-yl)acetic acid;

(S)-2-(tert-Butoxy)-2-(6-(difluoromethyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-6-(fluoromethyl)-5-(4-(4-fluorophenethoxy)phenyl)-2-methylpyridin-3-yl)acetic acid;

(S)-2-(tert-Butoxy)-2-(6-((4-chlorophenoxy)methyl)-4-(4,4-dimethylpiperidin-1-yl)-5-(4-(4-fluorophenethoxy)phenyl)-2-methylpyridin-3-yl)acetic acid (S)-2-(tert-Butoxy)-2-(4-(4,4-dimethylpiperidin-1-yl)-5-(4-(4-fluorophenethoxy)phenyl)-2-methyl-6-((oxetan-3-ylmethoxy)methyl)pyridin-3-yl)acetic acid;

(S)-2-(tert-Butoxy)-2-(4-(4,4-dimethylpiperidin-1-yl)-6-(ethoxymethyl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(isopropoxymethyl)-2-methylpyridin-3-yl)acetic acid;

(S)-2-(tert-Butoxy)-2-(4-(4,4-dimethylpiperidin-1-yl)-6-((2-ethoxyethoxy)methyl)-5-(4-(4-fluorophenethoxy) phenyl)-2-methylpyridin-3-yl)acetic acid;

(S)-2-(tert-Butoxy)-2-(6-((cyclopentyloxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((tetrahydro-2H-pyran-4-yl)oxy)methyl)pyridin-3-yl)acetic acid;

(S)-2-(tert-Butoxy)-2-(6-((cyclopentylmethoxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((oxazol-2-ylmethoxy)methyl)pyridin-3-yl)acetic acid;

(S)-2-(tert-Butoxy)-2-(6-(((3-chlorophenoxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-(((3-chlorobenzyl)oxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((methylthio)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((methyl sulfonyl)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((tetrahydro-2H-pyran-4-yl)methoxy)methyl)pyridin-3-yl)acetic acid;

(S)-2-(tert-Butoxy)-2-(4-(4,4-dimethylpiperidin-1-yl)-6-(((4,5-dimethylthiazol-2-yl)methoxy)methyl)-5-(4-(4-fluorophenethoxy)phenyl)-2-methylpyridin-3-yl)acetic acid;

(S)-2-(tert-Butoxy)-2-(6-(((1-(tert-butoxycarbonyl)azetidin-3-yl)methoxy)methyl)-4-(4,4-dimethylpiperidin-1-yl)-5-(4-(4-fluorophenethoxy)phenyl)-2-methylpyridin-3-yl)acetic acid;

(S)-2-(6-((Azetidin-3-ylmethoxy)methyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(tert-Butoxy)-2-(6-((2-(diethyl amino)ethoxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((2-morpholinoethoxy)methyl)pyridin-3-yl)acetic acid;

(S)-2-(tert-Butoxy)-2-(6-(((3,5-dimethyl-1H-pyrazol-1-yl)methoxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((2-oxopyrrolidin-1-yl)methoxy)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((2-(piperidin-1-yl)ethoxy)methyl)pyridin-3-yl)acetic acid;

(S)-2-(tert-Butoxy)-2-(4-(4,4-dimethylpiperidin-1-yl)-6-((2-(1,1-dioxidothiomorpholino)ethoxy)methyl)-5-(4-(4-fluorophenethoxy)phenyl)-2-methylpyridin-3-yl)acetic acid;

(S)-2-(tert-Butoxy)-2-(6-((cyclobutylmethoxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-(((3,3-difluorocyclobutyl)methoxy)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((3-methyl-1H-1,2,4-triazol-1-yl)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((5-methyl-1H-1,2,4-triazol-1-yl)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((3-methyl-4H-1,2,4-triazol-4-yl)methyl)pyridin-3-yl)acetic acid;

(S)-2-(tert-Butoxy)-2-(4-(4,4-dimethylpiperidin-1-yl)-6-((2-ethoxyethoxy)methyl)-2-methyl-5-phenylpyridin-3-yl)acetic acid;

(S)-2-(tert-Butoxy)-2-(4-(4,4-dimethylpiperidin-1-yl)-6-((2-ethoxyethoxy)methyl)-2-methylpyridin-3-yl)acetic acid (S)-2-(tert-Butoxy)-2-(4-(4,4-dimethylpiperidin-1-yl)-6-((2-ethoxyethoxy)methyl)-2,5-dimethylpyridin-3-yl)acetic acid;

(S)-2-(5-Bromo-4-(4,4-dimethylpiperidin-1-yl)-6-((2-ethoxyethoxy)methyl)-2-methylpyridin-3-yl)-2-(tert-butoxy)acetic acid;

(S)-5-(tert-Butoxy(carboxy)methyl)-4-(4,4-dimethylpiperidin-1-yl)-3-(4-(4-fluorophenethoxy)phenyl)-6-methylpicolinic acid;

(S)-2-(tert-Butoxy)-2-(4-(4,4-dimethylpiperidin-1-yl)-5-(4-(4-fluorophenethoxy)phenyl)-6-((2-methoxyethyl)carbamoyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(methylcarbamoyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(methyl((tetrahydro-2H-pyran-4-yl)methyl)carbamoyl)pyridin-3-yl) acetic acid;

(S)-2-(tert-Butoxy)-2-(6-((cyclohexylmethyl)(methyl)carbamoyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-(butyl(methyl)carbamoyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-(6-chloro-1H-benzo[d]imidazol-2-yl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-6-(5-(4-fluorobenzyl)oxazol-2-yl)-5-(4-(4-fluorophenethoxy)phenyl)-2-methylpyridin-3-yl)acetic acid;

(S)-2-(6-Amino-4-(4,4-dimethylpiperidin-1-yl)-5-(4-(4-fluorophenethoxy)phenyl)-2-methylpyridin-3-yl)-2-(tert-butoxy)acetic acid;

(S)-2-(6-Acetamido-4-(4,4-dimethylpiperidin-1-yl)-5-(4-(4-fluorophenethoxy)phenyl)-2-methylpyridin-3-yl)-2-(tert-butoxy)acetic acid;

(S)-2-(tert-Butoxy)-2-(4-(4,4-dimethylpiperidin-1-yl)-5-(4-(4-fluorophenethoxy)phenyl)-2-methyl-6-(methyl sulfonamido)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(methylamino)pyridin-3-yl)acetic acid;

(S)-2-(tert-Butoxy)-2-(4-(4,4-dimethylpiperidin-1-yl)-5-(4-(4-fluorophenethoxy)phenyl)-6-hydroxy-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-methoxy-2-methylpyridin-3-yl)acetic acid;

(S)-2-(tert-Butoxy)-2-(6-chloro-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(piperidin-1-yl)pyridin-3-yl)acetic acid;

(S,E)-2-(tert-Butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetic acid;

(S,Z)-2-(tert-Butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(3-isopropoxypropyl)-2-methylpyridin-3-yl)acetic acid;

(S,E)-2-(tert-Butoxy)-2-(4-(4,4-dimethylpiperidin-1-yl)-5-(4-(4-fluorophenethoxy)phenyl)-6-(2-methoxyvinyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(2-methoxyethyl)-2-methylpyridin-3-yl)acetic acid;

(S)-2-(tert-Butoxy)-2-(6-(3-(dimethylamino)propyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(4-methoxybenzyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-vinylpyridin-3-yl)acetic acid;

(S)-2-(5-Bromo-4-(4,4-dimethylpiperidin-1-yl)-2-methylpyridin-3-yl)-2-(tert-butoxy)acetic acid;

(S)-2-(tert-Butoxy)-2-(4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((methylamino)methyl)pyridin-3-yl)acetic acid;

(S)-2-(tert-Butoxy)-2-(6-((dimethylamino)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-((isopropylamino)methyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((((tetrahydro-2H-pyran-4-yl)methyl)amino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-6-(((2-methoxyethyl)amino)methyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(((2-hydroxyethyl)amino)methyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(morpholinomethyl)pyridin-3-yl)acetic acid;

(S)-2-(tert-Butoxy)-2-(4-(4,4-dimethylpiperidin-1-yl)-6-((ethylamino)methyl)-5-(4-(4-fluorophenethoxy)phenyl)-2-methylpyridin-3-yl)acetic acid;

(S)-2-(6-((Benzylamino)methyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(tert-Butoxy)-2-(4-(4,4-dimethylpiperidin-1-yl)-5-(4-(4-fluorophenethoxy)phenyl)-2-methyl-6-((phenylamino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((pyridin-4-yl)methyl)amino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(pyrrolidin-1-ylmethyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((oxetan-3-yl)methyl)amino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((oxetan-3-ylamino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((oxazol-4-ylmethyl)amino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(thiomorpholinomethyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(piperidin-1-ylmethyl)pyridin-3-yl)acetic acid;

(S)-2-(6-(Azetidin-1-ylmethyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(6-(7-Azaspiro[3.5]nonan-7-ylmethyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(tert-Butoxy)-2-(4-(4,4-dimethylpiperidin-1-yl)-6-((1,1-dioxidothiomorpholino)methyl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((methyl((tetrahydro-2H-pyran-4-yl)methyl)amino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-6-((4-methoxypiperidin-1-yl)methyl)-2-methylpyridin-3-yl)acetic acid;

(S)-2-(tert-Butoxy)-2-(6-((4,4-difluoropiperidin-1-yl)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-((4-hydroxypiperidin-1-yl)methyl)-2-methylpyridin-3-yl)acetic acid;

(S)-2-(tert-Butoxy)-2-(4-(4,4-dimethylpiperidin-1-yl)-6-((4,4-dimethylpiperidin-1-yl)methyl)-5-(4-(4-fluorophenethoxy)phenyl)-2-methylpyridin-3-yl)acetic acid;

(S)-2-(tert-Butoxy)-2-(6-((3,4-dihydroquinolin-1(2H)-yl)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-((4-fluoropiperidin-1-yl)methyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(((2-methoxyphenyl)amino)methyl)-2-methylpyridin-3-yl)acetic acid;

(2S)-2-(tert-Butoxy)-2-(6-((2,6-dimethylmorpholino)methyl)-4-(4,4-dimethylpiperidin-1-yl)-5-(4-(4-fluorophenethoxy)phenyl)-2-methylpyridin-3-yl)acetic acid;

(S)-2-(6-((Bis(2-methoxyethyl)amino)methyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(tert-Butoxy)-2-(4-(4,4-dimethylpiperidin-1-yl)-5-(4-(4-fluorophenethoxy)phenyl)-2-methyl-6-((4-methylpiperazin-1-yl)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((pyridin-2-yl)methyl)amino)methyl)pyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(((1R,5S)-3-methyl-3,8-diazabicyclo[3.2.1]octan-8-yl)methyl)pyridin-3-yl)acetic acid;

(S)-2-(6-((Benzyl(methyl)amino)methyl)-4-(4,4-dimethylpiperidin-1-yl)-5-(4-(4-fluorophenethoxy)phenyl)-2-methylpyridin-3-yl)-2-(tert-butoxy)acetic acid;

(2S)-2-(6-((3-Benzyl-3,6-diazabicyclo[3.1.1]heptan-6-yl)methyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(tert-Butoxy)-2-(6-(((cyclohexylmethyl)amino)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-(((cyclohexylmethyl)(methyl)amino)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((N-methylacetamido)methyl)pyridin-3-yl)acetic acid;

(S)-2-(tert-Butoxy)-2-(6-((2-(dimethylamino)-N-methyl-2-oxoacetamido)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-((N, 5-dimethyl-1,3,4-oxadiazole-2-carboxamido)methyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-((5-methyl-1,3,4-oxadiazole-2-carboxamido)methyl)pyridin-3-yl)acetic acid;

(S)-2-(tert-Butoxy)-2-(6-((2-(dimethylamino)-2-oxoacetamido)methyl)-4-(4,4-dimethylpiperidin-1-yl)-5-(4-(4-fluorophenethoxy)phenyl)-2-methylpyridin-3-yl)acetic acid;

(S)-2-(6-(Acetamidomethyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(tert-Butoxy)-2-(4-(4,4-dimethylpiperidin-1-yl)-5-(4-(4-fluorophenethoxy)phenyl)-6-(formamidomethyl)-2-methylpyridin-3-yl)acetic acid;

(S)-2-(tert-Butoxy)-2-(4-(4,4-dimethylpiperidin-1-yl)-2-((2-ethoxyethoxy)methyl)-5-(4-(4-fluorophenethoxy)phenyl)-6-methylpyridin-3-yl)acetic acid;

(S)-2-(tert-Butoxy)-2-(4-(4,4-dimethylpiperidin-1-yl)-5-(4-(4-fluorophenethoxy)phenyl)-6-methyl-2-((oxetan-3-ylmethoxy)methyl)pyridin-3-yl)acetic acid;

(S)-2-(tert-Butoxy)-2-(4-(4,4-dimethylpiperidin-1-yl)-2-((2-(2-ethoxyethoxy)ethoxy)methyl)-5-(4-(4-fluorophenethoxy)phenyl)-6-methylpyridin-3-yl)acetic acid;

(S)-2-(2-((3-(Benzyloxy)propoxy)methyl)-4-(4,4-dimethylpiperidin-1-yl)-5-(4-(4-fluorophenethoxy)phenyl)-6-methylpyridin-3-yl)-2-(tert-butoxy)acetic acid;

(S)-2-(tert-Butoxy)-2-(2-((dimethylamino)methyl)-4-(4,4-dimethylpiperidin-1-yl)-5-(4-(4-fluorophenethoxy)phenyl)-6-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(hydroxymethyl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((methylamino)methyl)pyridin-3-yl)acetic acid;

(S)-2-(tert-Butoxy)-2-(6-((dimethylamino)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(((2-methoxyethyl)amino)methyl)-2-methylpyridin-3-yl)acetic acid;

(S)-2-(6-(Azetidin-1-ylmethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(pyrrolidin-1-ylmethyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(piperidin-1-ylmethyl)pyridin-3-yl)acetic acid;

(S)-2-(tert-Butoxy)-2-(4-(4,4-dimethylpiperidin-1-yl)-6-((4,4-dimethylpiperidin-1-yl)methyl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(morpholinomethyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(thiomorpholinomethyl)pyridin-3-yl)acetic acid;

(S)-2-(tert-Butoxy)-2-(4-(4,4-dimethylpiperidin-1-yl)-6-((1,1-dioxidothiomorpholino)methyl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((pyridin-4-ylmethyl)amino)methyl)pyridin-3-yl)acetic acid;

(S)—N-((5-(tert-Butoxy(carboxy)methyl)-4-(4,4-dimethylpiperidin-1-yl)-3-(2-(4-fluoro-2-methylbenzyl)-1,2,3,4-tetrahydroisoquinolin-6-yl)-6-methylpyridin-2-yl)methyl)-N,N-diethylethanaminium;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((pyridin-3-ylmethyl)amino)methyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((((tetrahydro-2H-pyran-4-yl)methyl)amino)methyl)pyridin-3-yl)acetic acid;

(S)-2-(tert-Butoxy)-2-(6-((4,4-difluoropiperidin-1-yl)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(6-((3,3-difluoropiperidin-1-yl)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-((4-fluoropiperidin-1-yl)methyl)-2-methylpyridin-3-yl)acetic acid;

(2S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-((3-fluoropiperidin-1-yl)methyl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(((S)-3-fluoropyrrolidin-1-yl)methyl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(((R)-3-fluoropyrrolidin-1-yl)methyl)-2-methylpyridin-3-yl)acetic acid;

(S)-2-(6-(7-Azaspiro[3.5]nonan-7-ylmethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-((4-hydroxypiperidin-1-yl)methyl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((4-methylpiperazin-1-yl)methyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((methyl((tetrahydro-2H-pyran-4-yl)methyl)amino)methyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((1R,5 S)-3-methyl-3,8-diazabicyclo[3.2.1]octan-8-yl)methyl)pyridin-3-yl)acetic acid;

(S)-2-(6-(Aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid;

(S)-2-(6-(Acetamidomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((5-methyl-1,3,4-oxadiazole-2-carboxamido)methyl)pyridin-3-yl)acetic acid;

(S)-2-(tert-Butoxy)-2-(6-((2-(dimethylamino)-2-oxoacetamido)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((N-methylacetamido)methyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((3-methyl-1H-1,2,4-triazol-1-yl)methyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((5-methyl-1H-1,2,4-triazol-1-yl)methyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((3-methyl-4H-1,2,4-triazol-4-yl)methyl)pyridin-3-yl)acetic acid;

(S)-2-(6-Amino-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid;

(S)-2-(6-Amino-4-(4,4-dimethylpiperidin-1-yl)-2-methyl-5-(2-(6-methylpyrimidin-4-yl)-1,2,3,4-tetrahydroisoquinolin-6-yl)pyridin-3-yl)-2-(tert-butoxy)acetic acid;

(S)-2-(6-Amino-4-(4,4-dimethylpiperidin-1-yl)-2-methyl-5-(2-(1-methyl-1H-pyrazolo[3,4-d]pyrimidin-4-yl)-1,2,3,4-tetrahydroisoquinolin-6-yl)pyridin-3-yl)-2-(tert-butoxy)acetic acid;

(2S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(1-(methyl((tetrahydro-2H-pyran-4-yl)methyl)amino)ethyl)pyridin-3-yl)acetic acid;

(2S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(1-hydroxyethyl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((oxetan-3-ylmethoxy)methyl)pyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((tetrahydro-2H-pyran-4-yl)oxy)methyl)pyridin-3-yl)acetic acid;

(S)-2-(tert-Butoxy)-2-(4-(4,4-dimethylpiperidin-1-yl)-6-(ethoxymethyl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(methoxymethyl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(isopropoxymethyl)-2-methylpyridin-3-yl)acetic acid;

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((tetrahydro-2H-pyran-4-yl)methoxy)methyl)pyridin-3-yl)acetic acid;

(S)-2-(tert-Butoxy)-2-(4-(4,4-dimethylpiperidin-1-yl)-6-((2-ethoxyethoxy)methyl)-5-(2-(4-fluoro-2-methylbenzyl)-1,2,3,4-tetrahydroisoquinolin-6-yl)-2-methylpyridin-3-yl)acetic acid;

(S)-2-(tert-Butoxy)-2-(4-(4,4-dimethylpiperidin-1-yl)-6-ethynyl-5-(4-(4-fluorophenethoxy)phenyl)-2-methylpyridin-3-yl)acetic acid;

(S)-2-(tert-Butoxy)-2-(6-cyano-4-(4,4-dimethylpiperidin-1-yl)-5-(4-(4-fluorophenethoxy)phenyl)-2-methylpyridin-3-yl)acetic acid;

(S)-2-(tert-Butoxy)-2-(4-(4,4-dimethylpiperidin-1-yl)-5-(4-(4-fluorophenethoxy)phenyl)-2-methyl-6-(prop-1-yn-1-yl)pyridin-3-yl)acetic acid;

(S)-2-(6-Amino-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid;

(S)-2-(tert-Butoxy)-2-(5-(2-(2-chloro-6-methylbenzyl)-1,2,3,4-tetrahydroisoquinolin-6-yl)-4-(4,4-dimethylpiperidin-1-yl)-6-(hydroxymethyl)-2-methylpyridin-3-yl)acetic acid;

(S)-2-(tert-Butoxy)-2-(5-(2-(2-chloro-6-methylbenzyl)-1,2,3,4-tetrahydroisoquinolin-6-yl)-6-cyano-4-(4,4-dimethylpiperidin-1-yl)-2-methylpyridin-3-yl)acetic acid;

(S)-2-(6-Amino-5-(2-(benzofuro[3,2-d]pyrimidin-4-yl)-1,2,3,4-tetrahydroisoquinolin-6-yl)-4-(4,4-dimethylpiperidin-1-yl)-2-methylpyridin-3-yl)-2-(tert-butoxy)acetic acid;

(S)-2-(tert-Butoxy)-2-(4-(4,4-dimethylpiperidin-1-yl)-5-(4-(4-fluorophenethoxy)phenyl)-2-methyl-6-(1-methyl-1H-1,2,3-triazol-4-yl)pyridin-3-yl)acetic acid;

(S)-2-(5-(2-(Benzofuro[3,2-d]pyrimidin-4-yl)-1,2,3,4-tetrahydroisoquinolin-6-yl)-4-(4,4-dimethylpiperidin-1-yl)-6-(hydroxymethyl)-2-methylpyridin-3-yl)-2-(tert-butoxy)acetic acid;

(S)-2-(tert-Butoxy)-2-(4-(4,4-dimethylpiperidin-1-yl)-6-(4-fluorobenzyl)-5-(4-(4-fluorophenethoxy)phenyl)-2-methylpyridin-3-yl)acetic acid;

(S)-2-(tert-Butoxy)-2-(6-(cyclohex-1-en-1-ylmethyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-(cyclohexylmethyl)-4-(4,4-dimethylpiperidin-1-yl)-5-(4-(4-fluorophenethoxy)phenyl)-2-methylpyridin-3-yl)acetic acid;

(S)-2-(tert-Butoxy)-2-(6-((4,4-dimethylcyclohexyl)methyl)-4-(4,4-dimethylpiperidin-1-yl)-5-(4-(4-fluorophenethoxy)phenyl)-2-methylpyridin-3-yl)acetic acid;

(S)-2-(6-((Bicyclo[1.1.1]pentan-1-ylamino)methyl)-4-(4,4-dimethylpiperidin-1-yl)-5-(4-(4-fluorophenethoxy)phenyl)-2-methylpyridin-3-yl)-2-(tert-butoxy)acetic acid;

(S)-2-(6-(Azetidin-1-ylmethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid;

(S)-2-(tert-Butoxy)-2-(5-(2-(2-chloro-6-methylbenzyl)-1,2, 3,4-tetrahydroisoquinolin-6-yl)-4-(4,4-dimethylpiperidin-1-yl)-2-methyl-6-(pyrrolidin-1-ylmethyl)pyridin-3-yl)acetic acid;

(S)-2-(tert-Butoxy)-2-(5-(2-(2-chloro-6-methylbenzyl)-1,2, 3,4-tetrahydroisoquinolin-6-yl)-4-(4,4-dimethylpiperidin-1-yl)-2-methyl-6-(piperidin-1-ylmethyl)pyridin-3-yl)acetic acid;

(S)-2-(6-((6-Azaspiro[2.5]octan-6-yl)methyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid;

(S)-2-(tert-Butoxy)-2-(5-(2-(2-chloro-6-methylbenzyl)-1,2, 3,4-tetrahydroisoquinolin-6-yl)-4-(4,4-dimethylpiperidin-1-yl)-6-((4,4-dimethylpiperidin-1-yl)methyl)-2-methylpyridin-3-yl)acetic acid;

(S)-2-(6-((7-Azaspiro[3.5]nonan-7-yl)methyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid;

(S)-2-(tert-Butoxy)-2-(4-(4,4-dimethylpiperidin-1-yl)-5-(4-(4-fluorophenethoxy)phenyl)-6-(hydroxymethyl)pyridin-3-yl)acetic acid;

(S)-2-(tert-Butoxy)-2-(4-(4,4-dimethylpiperidin-1-yl)-5-(4-(4-fluorophenethoxy)phenyl)-6-methylpyridin-3-yl)acetic acid;

(S)-2-(tert-Butoxy)-2-(4-(4,4-dimethylpiperidin-1-yl)-5-(4-(4-fluorophenethoxy)phenyl)-6-(methoxymethyl)pyridin-3-yl)acetic acid; and (S)-2-(tert-Butoxy)-2-(6-(chloromethyl)-4-(4,4-dimethylpiperidin-1-yl)-5-(4-(4-fluorophenethoxy)phenyl)pyridin-3-yl)acetic acid;

and pharmaceutically acceptable salts thereof.

The compounds of the invention herein described may typically be administered as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 milligram ("mg") of the active ingredient per dose are typical. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 milligram per milliliter ("mg/mL"). Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 milligram per kilogram ("mg/kg") body weight daily. Generally, more compound is required orally and less parenterally. The specific dosing regimen, however, will be determined by a physician using sound medical judgment.

The compounds of this invention desireably have activity against HIV. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, HIV capsid inhibitors, anti-infectives, and immunomodulators, such as, for example, PD-1 inhibitors, PD-L1 inhibitors, antibodies, and the like. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Examples of nucleoside HIV reverse transcriptase inhibitors include abacavir, didanosine, emtricitabine, lamivudine, stavudine, tenofovir, zalcitabine, and zidovudine.

Examples of non-nucleoside HIV reverse transcriptase inhibitors include delavirdine, efavirenz, etrivirine, nevirapine, and rilpivirine.

Examples of HIV protease inhibitors include amprenavir, atazanavir, darunavir, fosamprenavir, indinavir, lopinavir, nelfinavir, ritonavir, saquinavir and, tipranavir.

An example of an HIV fusion inhibitor is enfuvirtide or T-1249.

An example of an HIV entry inhibitor is maraviroc.

Examples of HIV integrase inhibitors include dolutegravir, elvitegravir, or raltegravir.

An example of an HIV attachment inhibitor is fostemsavir.

An example of an HIV maturation inhibitor is BMS-955176, having the following structure:

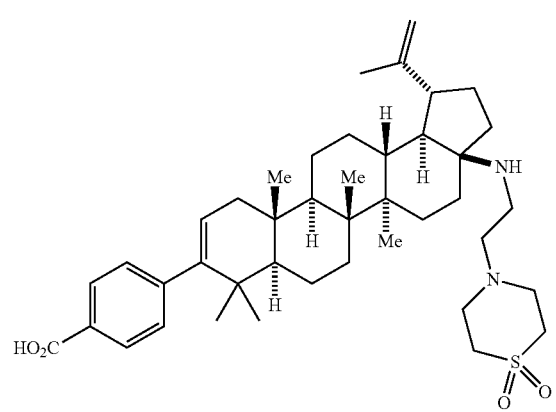

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

Antivirals

| Drug Name | Manufacturer | Indication |
|---|---|---|
| ANTIVIRALS | | |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences Ethigen | HIV infection ARC, PGL |
| AL-721 | (Los Angeles, CA) | HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoromethyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |

-continued

| Drug Name | Manufacturer | Indication |
|---|---|---|
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |

-continued

| Drug Name | Manufacturer | Indication |
|---|---|---|
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor TIVICAY ® dolutegravir | GSK | HIV infection AIDS |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |

| Drug Name | Manufacturer | Indication |
|---|---|---|
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Methods of Synthesis

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized form an appropriately substituted heterocycle I-1 according to Scheme I, Compounds I-1 and I-6 are commercially available or synthesized by reactions well known in the art. Treatment of compound I-1 with bromine provided the dibromo intermediates I-2 which was converted to the chloropyridine I-3 by reacting with POCl₃. Intermediate I-3 conveniently transformed to ketoester I-5 using conditions well-known to those skilled in the art, including reacting I-3 with Grignard reagent in the presence of catalytic copper(I) bromide dimethylsulfide complex followed by alkyl 2-chloro-2-oxoacetate. Coupling of amines 1-5 with intermediate 1-6 in the presence of an organic base such as Hunig's base provided intermediate 1-7. Chiral Lewis acid such as I-8 mediated reduction of ketoester I-7 with catecholborane furnished chiral alcohol 1-9. Tertiary butylation of alcohol I-9 by well-known conditions, including but not limited to tertiary-butyl acetate and perchloric acid, gave intermediate 1-10. Intermediates 1-10 are conveniently transformed to intermediates I-11 using conditions well-known in the art, including but not limited to the Suzuki coupling between intermediates I-10 and R⁶B(OR)₂. The boronate or boronic acid coupling reagents, well-known in the art, are commercially available or are prepared by reactions well-known to those skilled in the art. Hydrolysis of intermediate I-11 by using conditions well-known to those skilled in the art furnished carboxylic acid I-12.

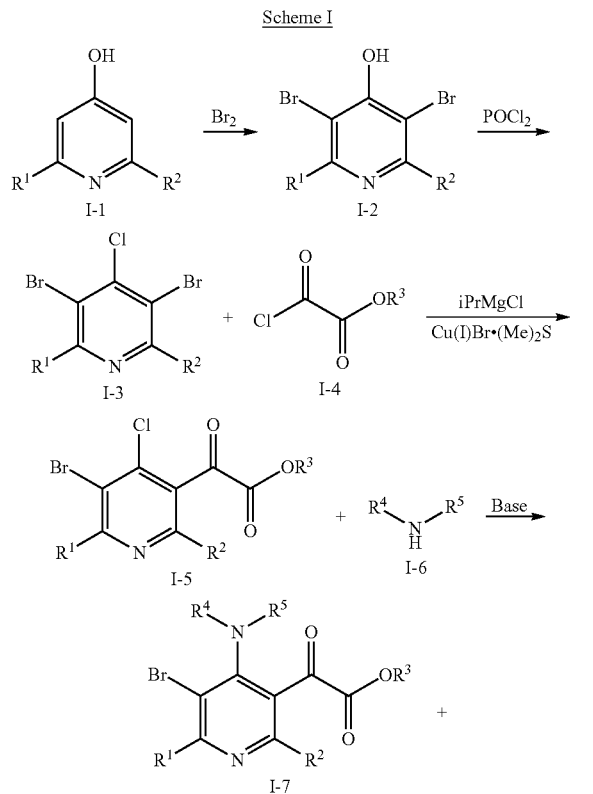

Scheme I

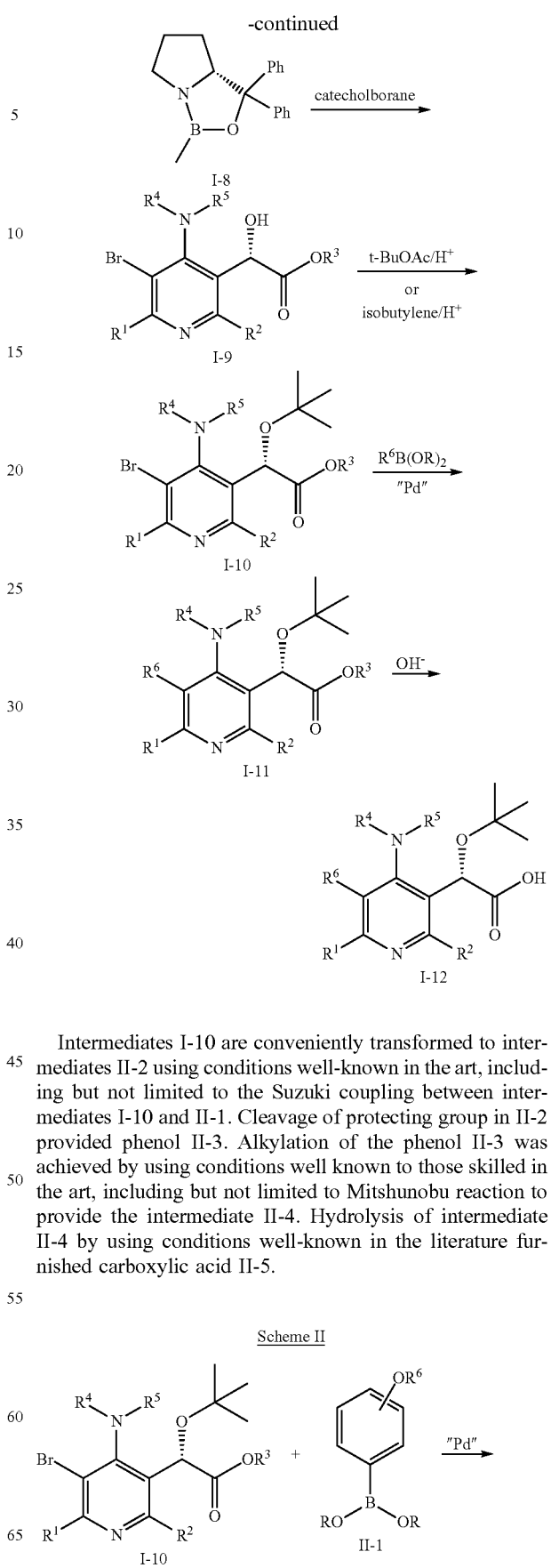

Intermediates I-10 are conveniently transformed to intermediates II-2 using conditions well-known in the art, including but not limited to the Suzuki coupling between intermediates I-10 and II-1. Cleavage of protecting group in II-2 provided phenol II-3. Alkylation of the phenol II-3 was achieved by using conditions well known to those skilled in the art, including but not limited to Mitshunobu reaction to provide the intermediate II-4. Hydrolysis of intermediate II-4 by using conditions well-known in the literature furnished carboxylic acid II-5.

Scheme II

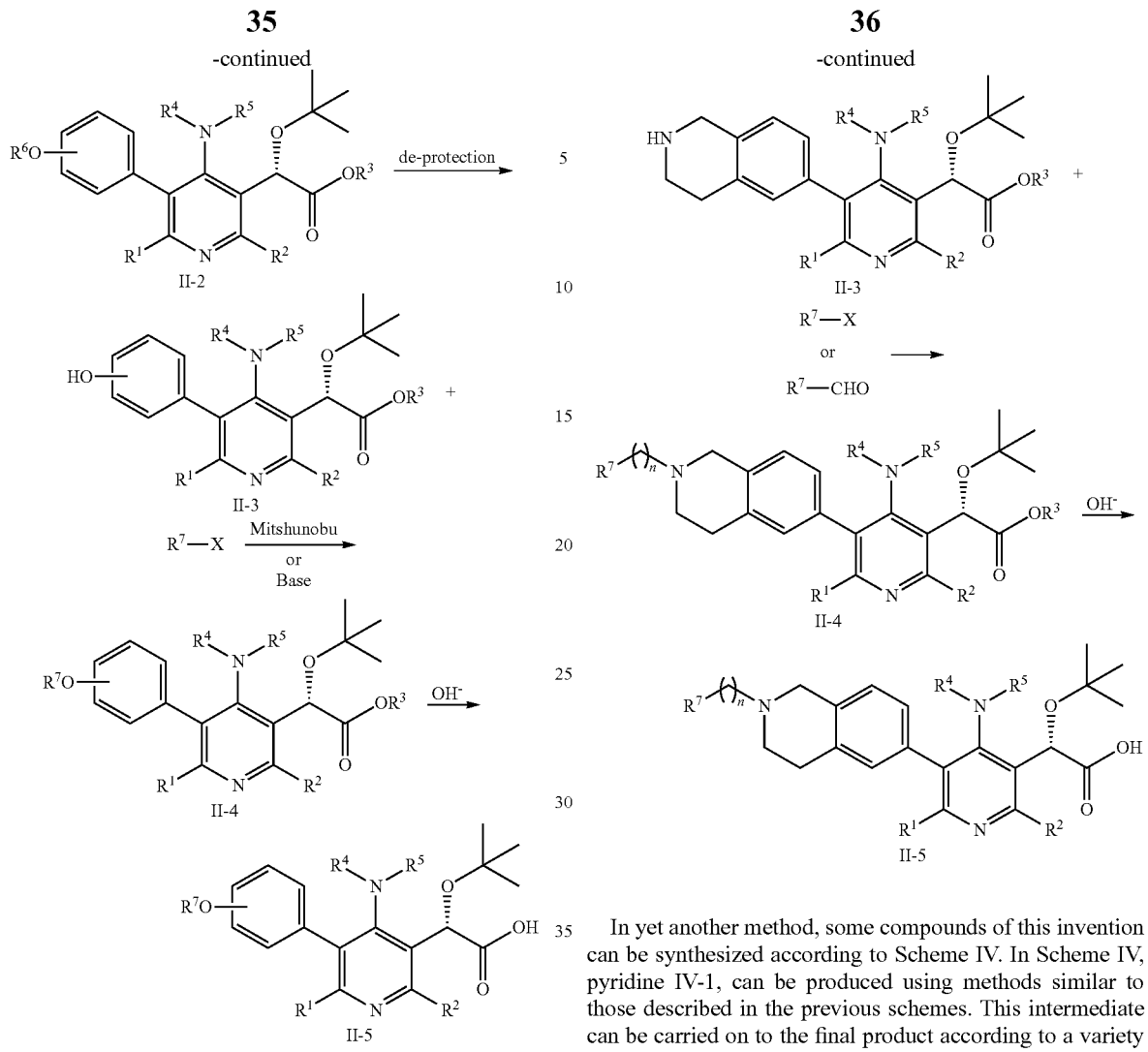

In yet another method, some compounds of this invention can be synthesized according to Scheme III.

In yet another method, some compounds of this invention can be synthesized according to Scheme IV. In Scheme IV, pyridine IV-1, can be produced using methods similar to those described in the previous schemes. This intermediate can be carried on to the final product according to a variety of paths. In one, the C2 and C6 alkyl groups can be oxidized to furnish intermediates IV-3 and/or IV-4 which can be further transformed to final compounds IV-9 or IV-10 by several paths.

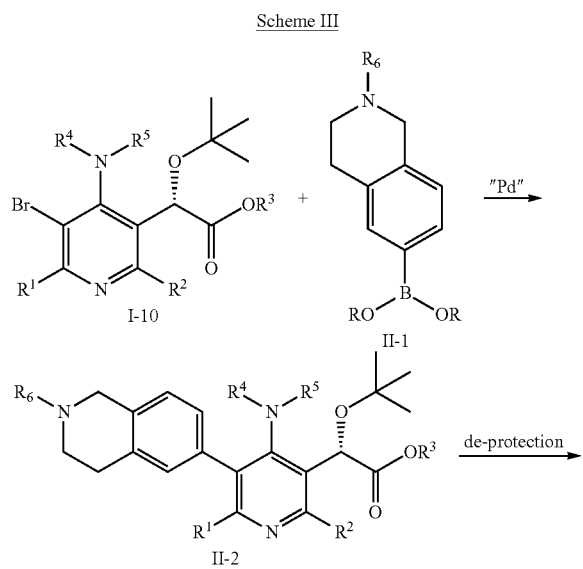

Scheme III

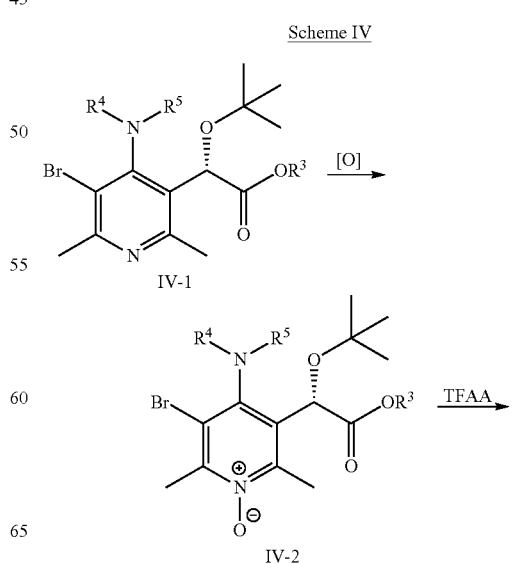

Scheme IV

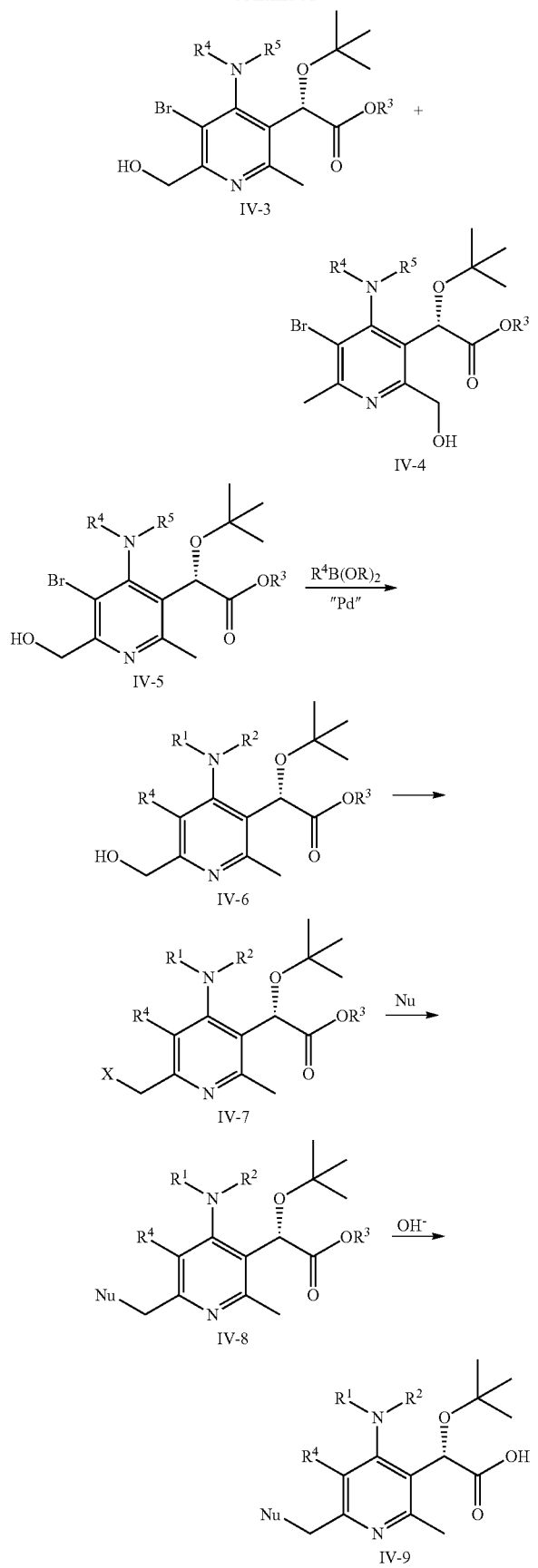

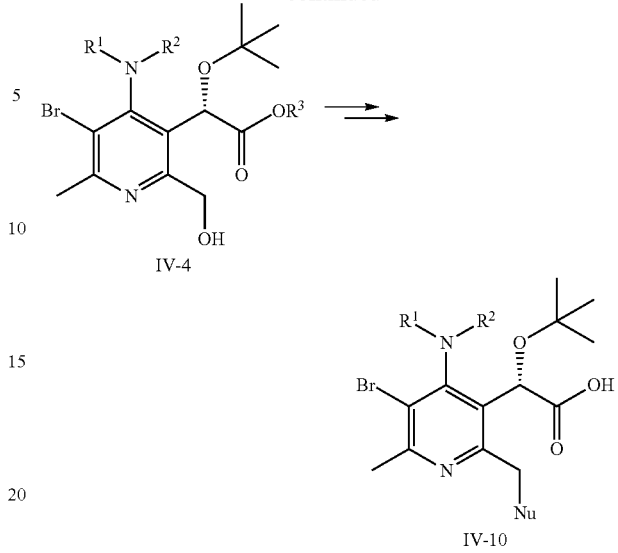

X = halide, OMs, TsO, NsO

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 μm; 19 or 30×100 mm) or Waters Xbridge C18 column (5 μM; 19×200 or 30×100 mm) or Water Atlantis (5 μm; 19 or 30×100 mm) using the following mobile phases. Mobile phase A: 9:1 $H_2O$/acetonitrile with 10 mM $NH_4OAc$ and mobile phase B:A: 9:1 acetonitrile/$H_2O$ with 10 mM $NH_4OAc$; or mobile phase A: 9:1 $H_2O$/acetonitrile with 0.1% TFA and mobile phase B:A: 9:1 acetonitrile/$H_2O$ with 0.1% TFA; or mobile phase A: water/MeOH (9:1) with 20 mM $NH_4OAc$ and mobile phase B: 95:5 MeOH/$H_2O$ with 20 mM $NH_4OAc$ or mobile phase A: water/MeOH (9:1) with 0.1% TFA and mobile phase B: 95:5 MeOH/$H_2O$ with 0.1% TFA or mobile Phase A: 5:95 acetonitrile: water with 10-mM ammonium acetate; Mobile Phase B: 95:5 acetonitrile: water with 10-mM ammonium acetate.

All Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

Compounds purified by preparative HPLC were diluted in methanol (1.2 mL) or DMF and purified using a Shimadzu LC-8A or LC-10A automated preparative HPLC system.

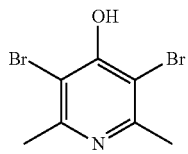

3,5-Dibromo-2,6-dimethylpyridin-4-ol: A 3-neck R.B-flask equipped with mechanical stirrer, addition funnel and condenser is charged with 2,6-dimethylpyridin-4-ol (100 g, 812 mmol), $CH_2Cl_2$ (1000 mL) and MeOH (120 mL). To the resulting light brown or tan solution was added tert-$BuNH_2$ (176 ml, 1665 mmol), cooled in water bath maintained between 5-10° C. (ice-water) and added drop wise Br2 (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-d$_6$) δ 12.08 (br. s., 1H), 2.41 (s, 6H). LCMS (M+H)=281.9.

Alternative Procedure: Bromine (72.8 mL, 1.4 mol) was added via addition funnel over 60 min to a mechanically stirred cold (ice-water bath) solution of 2,6-dimethylpyridin-4-ol (87 g, 706 mmol) and 4-methylmorpholine (156 mL, 1.4 mol) in dichloromethane (1 L) and methanol (100 mL) and then stirred for 2 h at rt. Additional bromine (~15 mL) was added based on monitoring by LCMS. The product was filtered, washed with ether, and dried under vacuum to give 3,5-dibromo-2,6-dimethylpyridin-4-ol 176.8 g (88%).

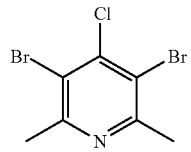

3,5-Dibromo-4-chloro-2,6-dimethyl-pyridine: Triethylamine (28.8 mL, 206 mmol) was added to a nitrogen purged solution of 3,5-dibromo-2,6-dimethylpyridin-4-ol (58 g, 206 mmol) and phosphorous oxychloride (57.7 mL, 619 mmol) in chloroform (450 mL) and stirred for 1 h at rt, then 3 h at 80° C. The reaction was removed form heating and immediately concentrated under house vacuum; then under high vacuum. The appearance was a cream colored solid, which was azeotroped with toluene (2×100 mL); treated with ice (200 g) for 10 min and carefully neutralized with NaHCO$_3$ (powder), and 1N NaOH solution, and extracted with DCM (2×400 mL). The combined organic layers were dried (MgSO$_4$), concentrated, and a beige solid was obtained that was washed with hexanes and dried under high vacuum to give 3,5-dibromo-4-chloro-2,6-dimethyl-pyridine 52.74 g (85.1%). Concentration of the hexanes gave 3.5 g of less pure product. $^1$H NMR (500 MHz, CDCl$_3$) δ 2.59 (s, 6H). LCMS (M+H)=300.0.

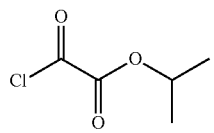

Isopropyl 2-chloro-2-oxoacetate: The propan-2-ol (38.2 mL, 499 mmol) was added drop wise over 15 min to a cold (0° C.), nitrogen purged solution of oxalyl dichloride (101 g, 799 mmol) and the reaction was stirred at room temperature for 2.5 h. Then a reflux condenser was fitted and a slight vacuum was applied for about 1 h until HCl gas was removed (the HCl was trapped in by a sat'd solution of NaHCO$_3$). The reflux condenser was removed and the flask was fitted with a short path distillation head. Excess reagent was removed by distillation under house vacuum (oil bath heated to 65° C.), and then the temperature was raised to between 85-95° C. and the product was distilled (NOTE: The 1$^{st}$ fraction of ~5 mL was discarded) to provide isopropyl 2-chloro-2-oxoacetate 52.62 g (70%).

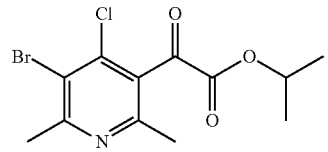 [SMILES: Cc1nc(C)c(C(=O)C(=O)OC(C)C)c(Cl)c1Br]

Isopropyl 2-(5-bromo-4-chloro-2,6-dimethylpyridin-3-yl)-2-oxoacetate: A solution of 2M isopropyl magnesium chloride (84 mL, 168 mmol) was added drop wise over 20 min to a cold (−70° C.), nitrogen purged solution of 3,5-dibromo-4-chloro-2,6-dimethylpyridine (48 g, 160 mmol) and copper(I)bromide-dimethyl sulfide complex (1.65 g, 8.02 mmol) in THF (240 mL), which was then allowed to warm to −10° C. over 60 min. The reaction mixture was transferred via cannula into a 1 L RB-flask containing isopropyl 2-chloro-2-oxoacetate (26.6 g, 176 mmol) in THF (160 mL) maintained at −60° C., and the reaction stirred an additional 2.5 h while being allowed to warm to −10° C. The reaction was quenched upon diluted with a mixture of 10% NH$_4$Cl solution (80 mL) in ether (320 mL). The organic layer was washed with 160 mL of sat'd NaHCO$_3$/10% NH$_4$Cl solution (1:1), brine, and dried (Na$_2$SO$_4$). The crude product was charged (DCM solution) to a 330 g ISCO silica gel cartridge and gradient eluted (5-20% EtOAc/hexanes) using an Isolera chromatography station gave isopropyl 2-(5-bromo-4-chloro-2,6-dimethylpyridin-3-yl)-2-oxoacetate 40.38 g (76%). $^1$H NMR (500 MHz, CDCl$_3$) δ 5.28-5.21 (m, 1H), 2.77 (s, 3H), 2.47 (s, 3H), 1.40 (d, J=6.3 Hz, 6H). LCMS (M+H)=336.04.

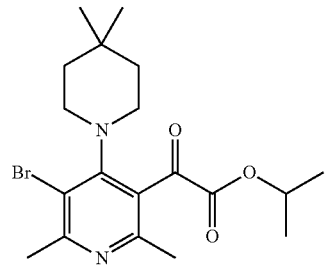 [SMILES: Cc1nc(C)c(C(=O)C(=O)OC(C)C)c(N2CCC(C)(C)CC2)c1Br]

Isopropyl 2-(5-bromo-4-(4,4-dimethylpiperidin-1-yl)-2,6-dimethylpyridin-3-yl)-2-oxoacetate: To a stirred solution of isopropyl 2-(5-bromo-4-chloro-2,6-dimethylpyridin-3-yl)-2-oxoacetate (7.2 g, 21.52 mmol) and DIEA (4.13 mL, 23.67 mmol) in anhydrous acetonitrile (15 mL) was added 4,4-dimethylpiperidine (2.68 g, 23.67 mmol) in acetonitrile (15 mL). The resulting solution was placed in a pre-heated oil bath at 75° C. After heating (75-78° C.) for 24 h and the temperature was raised to 85° C. for 24 h. Another portion of DIEA (3.5 mL, 20.04 mmol) and 4,4-dimethylpiperidine (0.27 g, 2.4 mmol) in acetonitrile (3 mL) was added and hearted at 85° C. for a day. The reaction mixture was diluted with ether (100 mL), washed with water (100 mL), brine (50 mL), dried (MgSO$_4$), filtered, concentrated and purified by ISCO 120 g cartridge (EtOAc/hex: 0 to 20%) to afford isopropyl 2-(5-bromo-4-(4,4-dimethylpiperidin-1-yl)-2,6-dimethylpyridin-3-yl)-2-oxoacetate (6.8 g, 16.53 mmol, 77% yield). $^1$H NMR (500 MHz, CDCl$_3$) δ 5.25-5.11 (m, 1H), 3.17 (br. s., 4H), 2.71 (s, 3H), 2.41 (s, 3H), 1.42-1.37 (m, 10H), 1.00 (s, 6H).). LCMS (M+H)=413.3.

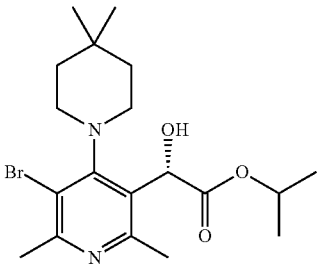 [SMILES: Cc1nc(C)c([C@H](O)C(=O)OC(C)C)c(N2CCC(C)(C)CC2)c1Br]

(S)-Isopropyl 2-(5-bromo-4-(4,4-dimethylpiperidin-1-yl)-2,6-dimethylpyridin-3-yl)-2-hydroxyacetate: To a yellow solution of isopropyl 2-(5-bromo-4-(4,4-dimethylpiperidin-1-yl)-2,6-dimethylpyridin-3-yl)-2-oxoacetate (7.7 g, 18.72 mmol) and (R)-1-methyl-3,3-diphenylhexahydropyrrolo[1,2-c][1,3,2]oxazaborole (7.5 mL, 7.50 mmol) in anhydrous toluene (100 mL) was added drop wise 50% catecholborane/toluene (6 mL, 28.0 mmol) over 5 min at −50° C. Then, the reaction mixture was slowly warmed to −30° C. over 1 h and left in refrigerator (−20° C.) for 3 days. Then, the reaction mixture was diluted with EtOAc (100 mL) and 20 mL of 1M $Na_2CO_3$, and vigorously stirred for 30 min. Aqueous layer separated and organic layer washed with sat'd $Na_2CO_3$ (2×25 mL) by vigorously stirring for 15 each time, then dried ($MgSO_4$), filtered and concentrated to give crude product as light purple paste which was purified by flash chromatography using 0 to 40% EtOAc/hex to afford (S)-isopropyl 2-(5-bromo-4-(4,4-dimethylpiperidin-1-yl)-2,6-dimethylpyridin-3-yl)-2-hydroxyacetate (6.7 g, 15.72 mmol, 84% yield) as colorless thick paste. $^1$H NMR (500 MHz, $CDCl_3$) δ 5.85 (d, J=5.7 Hz, 1H), 5.59 (d, J=7.4 Hz, 1H), 5.08 (dt, J=12.5, 6.3 Hz, 1H), 3.98-3.88 (m, 1H), 3.88-3.78 (m, 1H), 2.76-2.68 (m, 1H), 2.67 (s, 3H), 2.64-2.58 (m, 1H), 2.57 (s, 3H), 1.73 (td, J=12.8, 4.8 Hz, 1H), 1.65-1.59 (m, 1H), 1.47-1.35 (m, 2H), 1.27 (d, J=6.3 Hz, 3H), 1.17 (d, J=6.1 Hz, 3H), 1.09 (s, 3H), 1.04 (s, 3H). LCMS (M+H)=414.6.

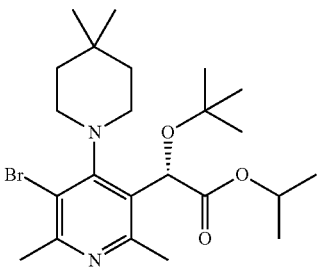 [SMILES: Cc1nc(C)c([C@H](OC(C)(C)C)C(=O)OC(C)C)c(N2CCC(C)(C)CC2)c1Br]

(S)-Isopropyl 2-(5-bromo-4-(4,4-dimethylpiperidin-1-yl)-2,6-dimethylpyridin-3-yl)-2-(tert-butoxy)acetate: A stirred ice-cold yellow mixture of (S)-isopropyl 2-(5-bromo-4-(4,4-dimethylpiperidin-1-yl)-2,6-dimethylpyridin-3-yl)-2-hydroxyacetate (6.7 g, 16.21 mmol) and 70% $HClO_4$ (2.2 mL, 25.6 mmol) in dichloromethane (400 mL) was saturated with isobutylene gas by bubbling through the reaction mixture (10 min). The reaction mixture was cloudy sealed in a seal tube, stirred for 24 h at rt. The reaction mixture was recooled in a −10° C. bath, bubbled additional isobutylene (~15 min). The reaction mixture became a clear solution at this point. The tube was sealed and stirred at rt for 16 h. LCMs at this point showed incomplete reaction. So, the reaction mixture was cooled down to −30° C. and bubbled isobutene (~15 min). After 24 h, reaction mixture was neutralized with sat. $Na_2CO_3$ (20 mL), organic layer separated and aqueous layer was extracted with $CH_2Cl_2$ (25 mL). The combined organic layers were dried ($MgSO_4$), filtered, concentrated and purified on a ISCO 120 g column (EtOAc/hex: 0 to 40%) to afford (S)-isopropyl 2-(5-bromo-4-(4,4-dimethylpiperidin-1-yl)-2,6-dimethylpyridin-3-yl)-2-(tert-butoxy)acetate (5.43 g, 9.83 mmol, 60.7% yield) as a viscous oil. $^1$H NMR (500 MHz, $CDCl_3$) δ 6.26 (br. s., 1H), 5.09-4.97 (m, 1H), 4.06 (br. s., 1H), 3.51 (br. s., 1H), 2.90 (br. s., 1H), 2.65 (s, 3H), 2.56 (s, 3H), 1.72-1.54 (m, 3H), 1.47 (br. s., 1H), 1.37 (br. s., 1H), 1.23-1.20 (m, 12H), 1.15 (d, J=6.1 Hz, 3H), 1.09 (br. s., 3H), 1.04 (br. s., 3H). LCMS (M+H)=471.3.

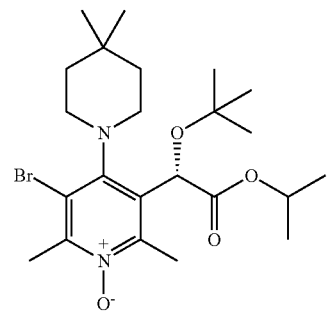

To a stirred solution of (S)-isopropyl 2-(5-bromo-4-(4,4-dimethylpiperidin-1-yl)-2,6-dimethylpyridin-3-yl)-2-(tert-butoxy)acetate (1.81 g, 3.86 mmol) in DCM (25 mL) was added mCPBA (1.296 g, 5.78 mmol) at rt. After 2 h, the reaction mixture was washed with sat. Na2CO3 (3×10 mL), dried (MgSO4), filtered and concentrated to give (S)-3-bromo-5-(1-(tert-butoxy)-2-isopropoxy-2-oxoethyl)-4-(4,4-dimethylpiperidin-1-yl)-2,6-dimethylpyridine 1-oxide (1.854 g, 3.82 mmol, 99% yield) as pale yellow foam which was used in the next step without purification. LCMS (M+H)=487.1.

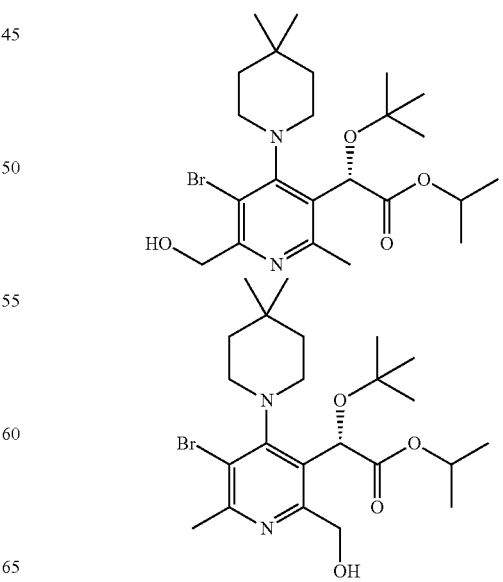

To a stirred solution of (S)-3-bromo-5-(1-(tert-butoxy)-2-isopropoxy-2-oxoethyl)-4-(4,4-dimethylpiperidin-1-yl)-2,6-dimethylpyridine 1-oxide (1.874 g, 3.86 mmol) in anhydrous DCM (20 mL) was added trifluoroacetic anhydride (1.090 ml, 7.72 mmol) at rt and then refluxed for 2.5 h. Then, MeOH (1 mL) and Et₃N (0.7 mL, 5 mmol) were added and stirred for 30 min. Then, cooled, washed with sat Na₂CO₃ (10 mL), dried (MgSO₄), filtered, concentrated and purified by flash chromatography using 5 and 10% EtOAc/hex to afford two compounds.

(S)-Isopropyl 2-(5-bromo-4-(4,4-dimethylpiperidin-1-yl)-6-(hydroxymethyl)-2-methylpyridin-3-yl)-2-(tert-butoxy)acetate: Viscous colorless oil which turns into white solid over the time, 1.3311 g (71%). ¹H NMR (500 MHz, CDCl₃) δ 6.25 (br. s., 1H), 5.06 (spt, J=6.3 Hz, 1H), 4.75-4.79 (m, 1H), 4.74-4.62 (m, 2H), 4.02-4.12 (br. s., 1H), 3.54-3.46 (m, 1H), 2.93 (d, J=11.5 Hz, 1H), 2.70-2.63 (m, 1H), 2.61 (s, 3H), 1.65-1.56 (m, 2H), 1.50-1.43 (m, 1H), 1.35-1.40 (m, 1H), 1.23 (d, J=6.2 Hz, 3H), (1.22 (s, 9H), 1.16 (d, J=6.3 Hz, 3H), 1.09 (s, 3H), 1.05 (s, 3H). LCMS (M+H)=485.35 and 487.2.

(S)-Isopropyl 2-(5-bromo-4-(4,4-dimethylpiperidin-1-yl)-2-(hydroxymethyl)-6-methylpyridin-3-yl)-2-(tert-butoxy)acetate: Pale yellow paste, 0.2762 g (15%). ¹H NMR (500 MHz, CDCl₃) δ 6.21 (br. s., 1H), 5.03 (spt, J=6.3 Hz, 1H), 4.95 (d, J=15.1 Hz, 1H), 4.64 (dd, J=15.3, 5.0 Hz, 1H), 4.50 (br. s., 1H), 4.05-3.97 (m, 1H), 3.57 (td, J=12.1, 2.5 Hz, 1H), 2.84 (d, J=11.8 Hz, 1H), 2.69 (s, 3H), 2.62 (d, J=11.8 Hz, 1H), 1.66-1.55 (m, 2H), 1.47 (dd, J=13.2, 2.0 Hz, 1H), 1.40-1.34 (m, 1H), 1.23 (d, J=6.3 Hz, 3H), 1.22 (s, 9H), 1.16 (d, J=6.1 Hz, 3H), 1.09 (s, 3H), 1.05 (s, 3H). LCMS (M+H)=485.2 and 487.05.

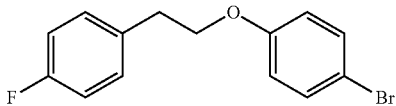 [SMILES: Fc1ccc(CCOc2ccc(Br)cc2)cc1]

1-Bromo-4-(4-fluorophenethoxy)benzene: To a stirred solution of 4-bromophenol (81.7 g, 472 mmol), 2-(4-fluorophenyl)ethanol (79 g, 567 mmol) and Ph₃P (149 g, 567 mmol) in THF (100 mL) cooled in an ice-water bath was added drop wise DEAD (93 ml, 590 mmol) over 20 min. Note: The reaction is exothermic and efficient cooling is highly recommended before initiating large scale reaction. After 1 h, cold bath was removed and stirred overnight (17 h) at rt. Then, the reaction mixture was concentrated, the resulting residue triturated with hexanes, filtered and the filter cake washed with 10% ether/hexanes (2-lit). The filtrate was concentrated and purified by flash chromatography (silica gel column 3"×11") using 4-lit hexanes and 2-lit 2% EtOAc/Hex to afford 1-bromo-4-(4-fluorophenethoxy)benzene (142 g, 469 mmol, 99% yield) as colorless liquid (contaminated with ~2.5% Ph₃P by ¹HNMR). ¹H NMR (500 MHz, CDCl₃) δ 7.41-7.36 (m, 2H), 7.28-7.22 (m, 2H), 7.05-6.99 (m, 2H), 6.82-6.76 (m, 2H), 4.14 (t, J=6.9 Hz, 2H), 3.08 (t, J=6.9 Hz, 2H).

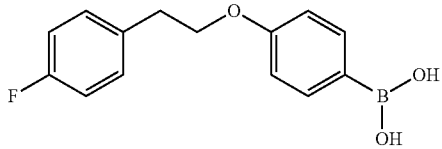 [SMILES: OB(O)c1ccc(OCCc2ccc(F)cc2)cc1]

(4-(4-Fluorophenethoxy)phenyl)boronic acid: To a stirred solution of 1-bromo-4-(4-fluorophenethoxy)benzene (142 g, 469 mmol) in THF (1000 mL) was added 2M n-BuLi/cyclohexane (293 ml, 586 mmol) over 15 min at −78° C. After 1.5 h, triisopropyl borate (131 ml, 563 mmol) was added to the light pink reaction mixture over 5 min and stirred for 2 h at −78° C. Then, the reaction was quenched by careful addition of 3M HCl (375 mL), cold bath was replaced with water bath, stirred for 1 h, diluted with ether (500 mL), aq. layer separated and organic layer washed with water (2×200 mL). The combined aq. layers extracted with ether (200 mL) and combined ether layers washed with brine (100 mL), dried (MgSO₄), filtered and concentrated to 200 mL. To this was added 250 mL hexanes and concentrated to about 300 mL and allowed to stand at rt. The precipitated solid was triturated with hexanes and filtered to give white solid which was used in next step without purification. ¹H NMR (500 MHz, CDCl₃) δ 8.18-8.15 (m, 2H), 7.32-7.28 (m, 2H), 7.07-7.00 (m, 4H), 4.26 (t, J=6.9 Hz, 2H), 3.14 (t, J=6.9 Hz, 2H).

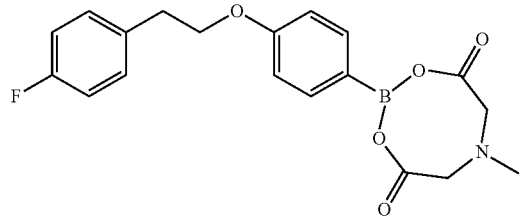 [SMILES: CN1CC(=O)OB(c2ccc(OCCc3ccc(F)cc3)cc2)OC(=O)C1]

2-(4-(4-Fluorophenethoxy)phenyl)-6-methyl-1,3,6,2-dioxazaborocane-4,8-dione: A slurry of (4-(4-fluorophenethoxy)phenyl)boronic acid (122 g, 469 mmol) and 2,2'-(methylazanediyl)diacetic acid (76 g, 516 mmol) in anhydrous toluene (500 mL) and DMSO (200 mL) was refluxed for 4 h. Then, cooled, diluted with EtOAc (500 mL), washed with water (5×200 mL), brine (2×100 mL), dried (MgSO₄), filtered and concentrated to give light orange foam which was purified by flash chromatography using 5-40% acetone/CH₂Cl₂ (5% increment per 2-lit) to afford 2-(4-(4-fluorophenethoxy)phenyl)-6-methyl-1,3,6,2-dioxazaborocane-4,8-dione (131.38 g, 354 mmol, 75% yield) as white solid. ¹H NMR (500 MHz, CDCl₃) δ 7.43 (d, J=8.4 Hz, 2H), 7.28-7.24 (m, 2H), 7.04-6.99 (m, 2H), 6.92 (d, J=8.5 Hz, 2H), 4.17 (t, J=6.9 Hz, 2H), 4.00 (d, J=16.6 Hz, 2H), 3.76 (d, J=16.6 Hz, 2H), 3.08 (t, J=6.8 Hz, 2H), 2.54 (s, 3H). LCMS (M+H)=372.3.

EXAMPLE 1

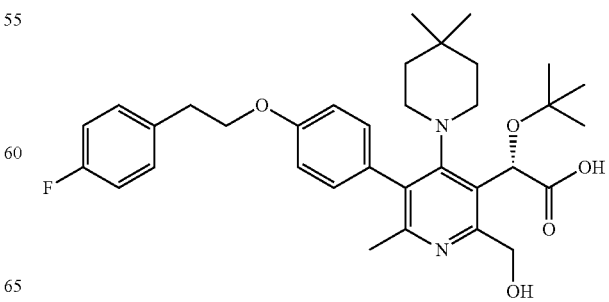

(S)-2-(tert-Butoxy)-2-(4-(4,4-dimethylpiperidin-1-yl)-5-(4-(4-fluorophenethoxy)phenyl)-2-(hydroxymethyl)-6-methylpyridin-3-yl)acetic acid: A mixture of (S)-isopropyl 2-(5-bromo-4-(4,4-dimethylpiperidin-1-yl)-2-(hydroxymethyl)-6-methylpyridin-3-yl)-2-(tert-butoxy)acetate (0.274 g, 0.564 mmol), (4-(4-fluorophenethoxy)phenyl)boronic acid (0.220 g, 0.847 mmol) and 2M Na₂CO₃ (0.706 ml, 1.411 mmol) in DMF (5 mL) was degassed for 10 min by bubbling N₂ through the reaction mixture. Then, Pd(Ph₃P)₄ (0.033 g, 0.028 mmol) was added, degassed for 5 min and placed in a pre-heated oil bath at 100° C. After 3 h at 120° C., cooled and purified by prep-HPLC to afford (S)-2-(tert-butoxy)-2-(4-(4,4-dimethylpiperidin-1-yl)-5-(4-(4-fluorophenethoxy)phenyl)-2-(hydroxymethyl)-6-methylpyridin-3-yl)acetic acid (0.0791 g, 0.137 mmol, 24.22% yield), pale purple solid. $^1$H NMR (500 MHz, CDCl₃) δ 7.32-7.27 (m, 2H), 7.16 (dd, J=8.6, 2.1 Hz, 1H), 7.10-7.02 (m, 3H), 7.02-6.97 (m, 2H), 5.91 (br. s., 1H), 4.98 (d, $J_{AB}$=14.8 Hz, 1H), 4.67 (d, $J_{AB}$=14.8 Hz, 1H), 4.28-4.20 (m, 2H), 3.13 (t, J=6.9 Hz, 2H), 2.79-2.50 (m, 1H), 2.25 (s, 3H), 1.38-1.26 (m, 3H), 1.24 (s, 9H), 1.22-1.19 (m, 1H), 0.78 (br. s., 6H). 3 piperidine and CO2H protons were not resolved. LCMS (M+H)=579.5. One additional byproduct shown below was also isolated.

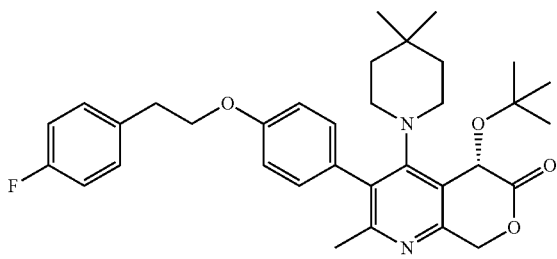 [SMILES: Cc1nc2c(c(N3CCC(C)(C)CC3)c1-c1ccc(OCCc3ccc(F)cc3)cc1)[C@H](OC(C)(C)C)C(=O)OC2]

(S)-5-(tert-butoxy)-4-(4,4-dimethylpiperidin-1-yl)-3-(4-(4-fluorophenethoxy)phenyl)-2-methyl-5H-pyrano[3,4-b]pyridin-6(8H)-one: White solid (0.0445 g, 0.079 mmol, 14.06% yield). $^1$H NMR (500 MHz, CDCl₃) δ 7.32-7.27 (m, 2H), 7.13-7.09 (m, 1H), 7.08-7.02 (m, 3H), 6.98 (d, J=9.0 Hz, 2H), 5.88 (d, $J_{AB}$=13.7 Hz, 1H), 5.34 (s, 1H), 5.16 (d, $J_{AB}$=13.7 Hz, 1H), 4.23 (t, J=6.9 Hz, 2H), 3.13 (t, J=6.9 Hz, 2H), 2.71 (br. s., 2H), 2.64-2.57 (m, 2H), 2.23 (s, 3H), 1.37 (s, 9H), 1.32-1.24 (m, 4H), 0.82 (br. s., 6H). LCMS (M+H)=561.15.

Alternative procedure: A mixture of (S)-isopropyl 2-(5-bromo-4-(4,4-dimethylpiperidin-1-yl)-2-(hydroxymethyl)-6-methylpyridin-3-yl)-2-(tert-butoxy)acetate (690 mg, 1.421 mmol), 2-(4-(4-fluorophenethoxy)phenyl)-6-methyl-1,3,6,2-dioxazaborocane-4,8-dione (580 mg, 1.563 mmol), 2-dicyclohexylphosphino-2',6'-dimethoxybiphenyl (117 mg, 0.284 mmol) and 2M K₃PO₄ (5.33 mL, 10.66 mmol) in 1,4-Dioxane (12 mL) and Water (2.400 mL) was degassed for 10 min. Then, Pd(OAc)₂ (31.9 mg, 0.142 mmol) was added, degassed for 5 min and mixture was heated at 80° C. for 3 h. At this point LCMS indicated major product as acid instead of desired ester and also cyclyzed product. After cooling to room temp, water was added and the mixture was extracted with ethyl acetate, washed with brine, dried (Na2SO4), filtered and concentrated. the residue was then purified by Biotage (0-50% CH2Cl2/MeOH) to afford (S)-2-(tert-butoxy)-2-(4-(4,4-dimethylpiperidin-1-yl)-5-(4-(4-fluorophenethoxy)phenyl)-2-(hydroxymethyl)-6-methylpyridin-3-yl)acetic acid (300 mg, 0.518 mmol, 36.5% yield) as off-white solid.

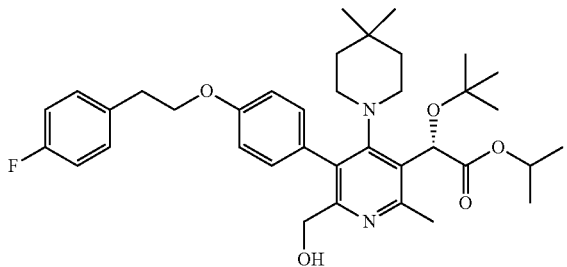 [SMILES: Cc1nc(CO)c(-c2ccc(OCCc3ccc(F)cc3)cc2)c(N2CCC(C)(C)CC2)c1[C@H](OC(C)(C)C)C(=O)OC(C)C]

(S)-Isopropyl 2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetate: A mixture of (S)-isopropyl 2-(5-bromo-4-(4,4-dimethylpiperidin-1-yl)-6-(hydroxymethyl)-2-methylpyridin-3-yl)-2-(tert-butoxy) acetate (1.3 g, 2.68 mmol), (4-(4-fluorophenethoxy)phenyl) boronic acid (1.045 g, 4.02 mmol) and 2M Na₂CO₃ (3.35 ml, 6.69 mmol) in DMF (10 mL) was degassed for 10 min by bubbling N2 through the reaction mixture. Then, Pd(Ph₃P)₄ (0.155 g, 0.134 mmol) was added, degassed for 5 min and placed in a pre-heated oil bath at 100° C. After h at 110° C., the reaction mixture was cooled, diluted with ether (100 mL), washed with water (4×10 ml), brine (10 mL), dried (MgSO4), filtered, concentrated and purified by flash chromatography using EtOAc/Hex to afford (S)-isopropyl 2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetate (1.026 g, 1.653 mmol, 61.7% yield) as off-white solid. $^1$H NMR (500 MHz, CDCl₃) δ 7.33-7.26 (m, 2H), 7.13 (d, J=7.9 Hz, 1H), 7.09-7.02 (m, 3H), 7.01-6.93 (m, 2H), 6.05 (br. s., 1H), 5.08-5.13 (m, 1H), 4.41 (d, $J_{AB}$=15.4 Hz, 1H), 4.29-4.19 (m, 2H), 4.07 (d, $J_{AB}$=15.4 Hz, 1H), 3.24 (d, J=8.8 Hz, 1H), 3.14 (t, J=6.8 Hz, 2H), 2.89 (t, J=11.7 Hz, 1H), 2.64 (s, 3H), 2.30 (br. s., 1H), 2.13 (t, J=11.0 Hz, 1H), 1.57 (br. s., 1H), 1.37 (d, J=10.4 Hz, 1H), 1.24 (dd, J=10.9, 6.3 Hz, 7H), 1.20 (s, 9H), 1.10 (d, J=11.5 Hz, 1H), 0.92 (br. s., 3H), 0.68 (br. s., 3H). LCMS (M+H)=621.55.

EXAMPLE 2

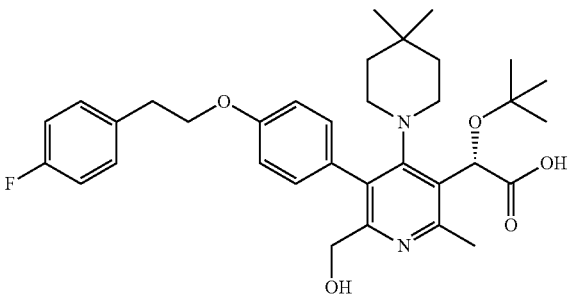 [SMILES: Cc1nc(CO)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-6-(hydroxymethyl)-2-methylpyridin-3-yl)acetic acid: A mixture of (S)-isopropyl 2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetate (0.045 g, 0.072 mmol) and KOH (0.092 g, 1.450 mmol) in 90% EtOH (2 mL) was refluxed for 2.5 h. Then, cooled and purified by prep-HPLC to afford (S)-2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetic acid (0.0323 g, 0.056 mmol, 77% yield) as off-white solid. $^1$H NMR (500 MHz, CDCl$_3$) δ 7.31-7.26 (m, 2H), 7.16-7.12 (m, 1H), 7.08-7.01 (m, 3H), 6.99-6.94 (m, 2H), 5.90 (br. s., 1H), 4.45 (d, J$_{AB}$=15.3 Hz, 1H), 4.27-4.18 (m, 2H), 4.13 (d, J$_{AB}$=15.3 Hz, 1H), 3.13 (t, J=6.9 Hz, 2H), 2.67 (s, 3H), 2.63-2.31 (m, 1H), 1.41-1.26 (m, 4H), 1.22 (s, 9H), 0.79 (br. s., 6H). Three piperidine, OH and CO2H protons were not resolved. LCMS (M+H)=579.35.

EXAMPLE 3

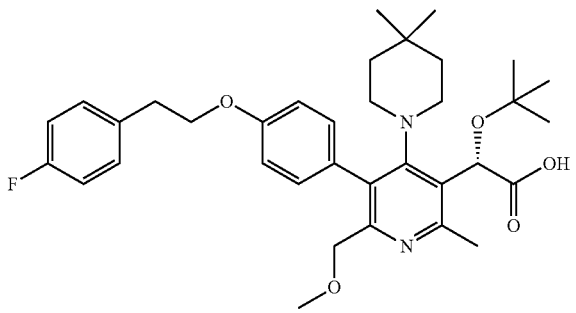 [SMILES: COCc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-5-(4-(4-fluorophenethoxy)phenyl)-6-(methoxymethyl)-2-methylpyridin-3-yl)acetic acid: To a stirred solution of (S)-isopropyl 2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetate (0.102 g, 0.164 mmol) in dry CH$_2$Cl$_2$ (3 mL) at −78 C was added Deoxofluor (0.033 ml, 0.181 mmol) at once. After 4 h, the reaction was quenched with MeOH (0.5 mL), stirred 15 min at rt, diluted with ether (25 mL), washed with sat. Na$_2$CO$_3$ (5 mL), dried (MgSO$_4$), filtered and concentrated to give residue which was used in the next step without purification. LCMS (M+H)=641.3. A mixture of above residue and KOH (0.092 g, 1.643 mmol) in 9:1 MeOH/H$_2$O was refluxed for 24 h. Then, cooled and purified by prep-HPLC to afford (S)-2-(tert-butoxy)-2-(4-(4,4-dimethylpiperidin-1-yl)-5-(4-(4-fluorophenethoxy)phenyl)-6-(methoxymethyl)-2-methylpyridin-3-yl)acetic acid (0.0331 g, 0.056 mmol, 34.0% yield) as off-white solid. $^1$H NMR (500 MHz, CDCl$_3$) δ 7.32-7.25 (m, 3H), 7.14-7.09 (m, 1H), 7.07-7.01 (m, 2H), 6.99-6.95 (m, 2H), 6.06 (br. s., 1H), 4.29-4.19 (m, 2H), 4.17-4.07 (m, 2H), 3.54 (br. s., 1H), 3.26 (s, 3H), 3.13 (t, J=6.9 Hz, 2H), 2.94 (br. s., 1H), 2.63 (s, 3H), 2.25 (br. s., 1H), 2.07 (br. s., 1H), 1.60-1.48 (m, 1H), 1.41-1.27 (m, 2H), 1.22 (s, 9H), 1.14-1.04 (m, 1H), 0.90 (br. s., 3H), 0.67 (br. s., 3H). LCMS (M+H)=593.8

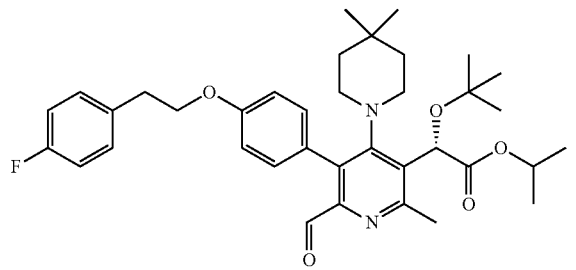 [SMILES: Cc1nc(C=O)c(-c2ccc(OCCc3ccc(F)cc3)cc2)c(N2CCC(C)(C)CC2)c1[C@H](OC(C)(C)C)C(=O)OC(C)C]

(S)-Isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate: To a stirred solution of (S)-isopropyl 2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetate (1 g, 1.611 mmol) in CH$_2$Cl$_2$ (5 mL) was added Dess-MartinPeriodinane (0.820 g, 1.933 mmol) at once at rt. After 2 h, the reaction mixture was diluted with ethyl acetate (50 mL), washed with sat. NaHCO$_3$ (10 ml), brine (10 mL), dried (Na$_2$SO$_4$), filtered and concentrated to give yellow paste which was purified by Biotage (5-30% EtOAc/hexane) to afford(S)-isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate (900 mg, 1.454 mmol, 90% yield) as white foam. $^1$H NMR (500 MHz, CDCl$_3$) δ 9.84 (s, 1H), 7.31 (br. s., 2H), 7.22 (t, J=9.1 Hz, 2H), 7.10-6.90 (m, 4H), 6.09 (br. s., 1H), 5.13 (dt, J=12.5, 6.2 Hz, 1H), 4.32-4.18 (m, 2H), 3.24 (br. s., 1H), 3.14 (t, J=6.9 Hz, 2H), 2.98 (br. s., 1H), 2.72 (s, 3H), 2.31 (br. s., 1H), 2.13 (br. s., 1H), 1.59 (s, 2H), 1.38 (br. s., 1H), 1.25 (dd, J=10.8, 6.2 Hz, 6H), 1.19 (s, 9H), 1.12 (d, J=11.0 Hz, 1H), 0.93 (br. s., 3H), 0.71 (br. s., 3H). LCMS (M+H)=619.25.

EXAMPLE 4

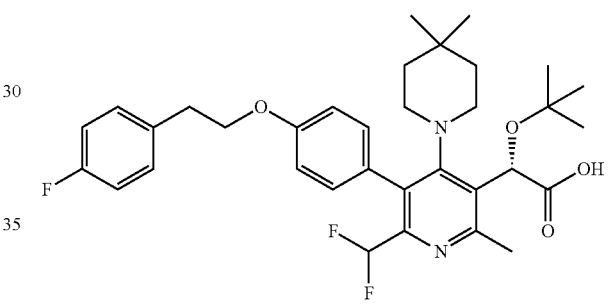

(S)-2-(tert-Butoxy)-2-(6-(difluoromethyl)-4-(4,4-dimethylpiperidin-1-yl)-5-(4-(4-fluorophenethoxy)phenyl)-2-methylpyridin-3-yl)acetic acid: To a stirred solution of (S)-isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate (0.124 g, 0.2 mmol) in dry CH$_2$Cl$_2$ (3 mL) was added Deoxofluor (0.063 ml, 0.340 mmol) at rt. EtOH (2.336 µl, 0.040 mmol) was added and the yellow mixture was stirred at rt for 24 h. Then, diluted with ether (25 mL), washed with sat. Na$_2$CO$_3$ (5 mL), dried (MgSO$_4$), filtered and concentrated to give (S)-isopropyl 2-(tert-butoxy)-2-(6-(difluoromethyl)-4-(4,4-dimethylpiperidin-1-yl)-5-(4-(4-fluorophenethoxy)phenyl)-2-methylpyridin-3-yl)acetate as burgandy paste. LCMS (M+H)=641.3.

A mixture of (S)-isopropyl 2-(tert-butoxy)-2-(6-(difluoromethyl)-4-(4,4-dimethylpiperidin-1-yl)-5-(4-(4-fluorophenethoxy)phenyl)-2-methylpyridin-3-yl)acetate and solid KOH (0.112 g, 2.000 mmol) in 90% EtOH (3 mL) was refluxed for 4 h. Then, cooled and purified by prep-HPLC to afford (S)-2-(tert-butoxy)-2-(6-(difluoromethyl)-4-(4,4-dimethylpiperidin-1-yl)-5-(4-(4-fluorophenethoxy)phenyl)-2-methylpyridin-3-yl)acetic acid (0.0897 g, 0.150 mmol, 74.9% yield) as light brown solid. $^1$H NMR (500 MHz, CDCl$_3$) δ 7.31-7.27 (m, 2H), 7.25-7.21 (m, 1H), 7.18-7.14 (m, 1H), 7.08-7.02 (m, 2H), 7.01-6.96 (m, 2H), 6.41-6.17 (m, 1H), 6.10 (br. s., 1H), 4.29-4.19 (m, 2H), 3.55 (br. s., 1H), 3.14 (t, J=6.9 Hz, 2H), 2.96 (t, J=12.3 Hz, 1H), 2.66 (s, 3H), 2.26 (d, J=11.0 Hz, 1H), 2.10-2.02 (m, 1H), 1.58-1.50 (m, 1H), 1.39-1.28 (m, 2H), 1.24 (s, 9H), 1.14-1.08 (m, 1H), 0.91 (s, 3H), 0.68 (s, 3H). LCMS (M+H)=599.7.

EXAMPLE 5 and 6

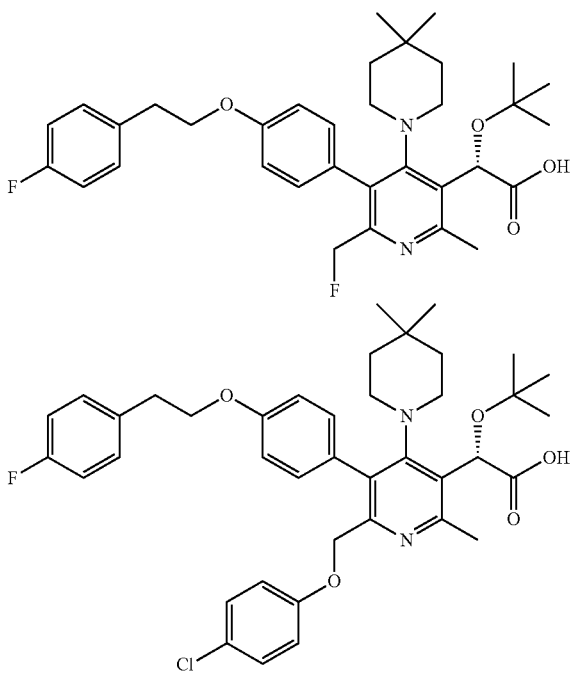

(S)-2-(tert-Butoxy)-2-(4-(4,4-dimethylpiperidin-1-yl)-6-(fluoromethyl)-5-(4-(4-fluorophenethoxy)phenyl)-2-methylpyridin-3-yl)acetic acid and (S)-2-(tert-butoxy)-2-(6-((4-chlorophenoxy)methyl)-4-(4,4-dimethylpiperidin-1-yl)-5-(4-(4-fluorophenethoxy)phenyl)-2-methylpyridin-3-yl)acetic acid: To a stirred solution of (S)-isopropyl 2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetate (75 mg, 0.121 mmol) in dry CH$_2$Cl$_2$ (3 mL) at −78° C. was added Deoxofluor (0.025 mL, 0.133 mmol) at once. After 4 h, 4-chlorophenol (31.1 mg, 0.242 mmol) was added and the mixture was stirred for 16 h. At this point LCMS indicated major product as fluor compound and minor as 4-chlorophenyl derivative. Mixture was then concentrated and treated with 10N NaOH (0.121 mL, 1.208 mmol) in EtOH (2 mL) at 80° C. for 4 h. Mixture was then cooled and purified by prep-HPLC to afford (S)-2-(tert-butoxy)-2-(4-(4,4-dimethylpiperidin-1-yl)-6-(fluoromethyl)-5-(4-(4-fluorophenethoxy)phenyl)-2-methylpyridin-3-yl)acetic acid (11.7 mg, 0.020 mmol, 16.68% yield): $^1$H NMR (500 MHz, DMSO-d$_6$) δ 7.41-7.34 (m, 2H), 7.24 (d, J=8.1 Hz, 1H), 7.18-7.08 (m, 3H), 7.04 (t, J=8.3 Hz, 2H), 5.84 (br. s., 1H), 5.10 (d, J=9.5 Hz, 0.5H), 4.99 (t, J=11.0 Hz, 1H), 4.89 (d, J=9.9 Hz, 0.5H), 4.34-4.15 (m, 2H), 3.70-3.62 (m, 1H), 3.06 (t, J=6.6 Hz, 2H), 2.84 (t, J=11.9 Hz, 1H), 2.48 (s, 3H), 2.19 (br. s., 1H), 1.51 (br. s., 1H), 1.29 (br. s., 1H), 1.20 (d, J=13.6 Hz, 1H), 1.13 (s, 9H), 1.04 (d, J=13.6 Hz, 1H), 0.86 (br. s., 3H), 0.62 (br. s., 3H). LCMS (M+H)=581.2; and (S)-2-(tert-butoxy)-2-(6-((4-chlorophenoxy)methyl)-4-(4,4-dimethylpiperidin-1-yl)-5-(4-(4-fluorophenethoxy)phenyl)-2-methylpyridin-3-yl)acetic acid (4.9 mg, 7.11 μmol, 5.88% yield): $^1$H NMR (500 MHz, DMSO-d$_6$) δ 7.36-7.29 (m, 2H), 7.29-7.19 (m, 3H), 7.15-7.07 (m, 3H), 6.99 (d, J=8.4 Hz, 2H), 6.88 (d, J=8.4 Hz, 1H), 6.85 (d, J=8.8 Hz, 2H), 5.81 (br. s., 1H), 4.72 (d, J=9.9 Hz, 1H), 4.55 (d, J=9.9 Hz, 1H), 4.25-4.04 (m, 2H), 3.41 (br. s., 2H), 2.99 (t, J=6.6 Hz, 2H), 2.85-2.77 (m, 1H), 2.48 (s, 3H), 2.20 (d, J=11.4 Hz, 1H), 1.51 (br. s., 1H), 1.30 (br. s., 1H), 1.26-1.18 (m, 1H), 1.14 (s, 9H), 1.03 (d, J=13.6 Hz, 1H), 0.85 (br. s., 3H), 0.61 (br. s., 3H). LCMS (M+H)=689.1.

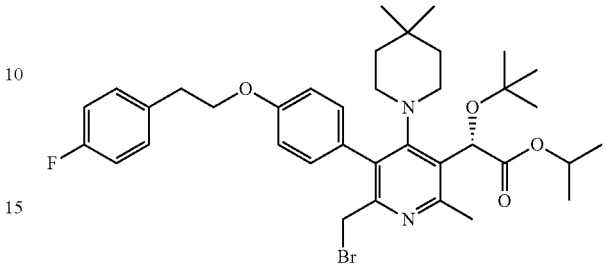

(S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate: To a solution of (S)-isopropyl 2-(tert-butoxy)-2-(4-(4,4-dimethylpiperidin-1-yl)-5-(4-(4-fluorophenethoxy)phenyl)-6-(hydroxymethyl)-2-methylpyridin-3-yl)acetate (930 mg, 1.498 mmol) in CH$_2$Cl$_2$ (20 mL) was added CBr$_4$ (546 mg, 1.648 mmol) followed by Ph$_3$P (432 mg, 1.648 mmol) and the resulting mixture was stirred at room temp for 16 h. Water (10 mL) was then added and the mixture was extracted with dichloromethane (10 mL), dried (Na$_2$SO$_4$), filtered and concentrated. The residue was then purified by Biotage (5-30% EtOAc/hexane) to afford(S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (850 mg, 1.243 mmol, 83% yield) as white solid. $^1$H NMR (500 MHz, CDCl$_3$) δ 7.38 (d, J=8.2 Hz, 1H), 7.31 (br. s., 1H), 7.13 (d, J=7.7 Hz, 2H), 7.05 (t, J=8.4 Hz, 2H), 6.99 (t, J=7.2 Hz, 2H), 6.07 (br. s., 1H), 5.11 (dt, J=12.5, 6.3 Hz, 1H), 4.34 (d, J=9.3 Hz, 1H), 4.25 (br. s., 2H), 4.18 (d, J=9.3 Hz, 1H), 3.20 (d, J=11.7 Hz, 1H), 3.14 (t, J=6.9 Hz, 2H), 2.87 (t, J=12.7 Hz, 1H), 2.63 (s, 3H), 2.30 (d, J=9.6 Hz, 1H), 2.11-1.96 (m, 1H), 1.51 (br. s., 1H), 1.37 (br. s., 1H), 1.24 (d, J=6.3 Hz, 3H), 1.26 (d, J=6.5 Hz, 3H), 1.20 (s, 9H), 1.09 (d, J=14.5 Hz, 1H), 0.91 (br. s., 3H), 0.66 (br. s., 3H). LCMS (M+2H)=685.4.

EXAMPLE 7

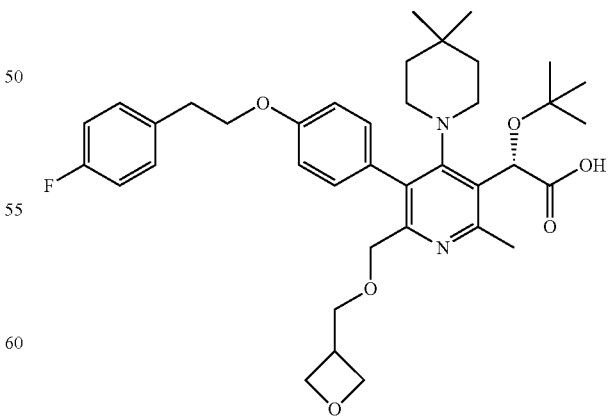

(S)-2-(tert-Butoxy)-2-(4-(4,4-dimethylpiperidin-1-yl)-5-(4-(4-fluorophenethoxy)phenyl)-2-methyl-6-((oxetan-3-yl-methoxy)methyl)pyridin-3-yl)acetic acid: To a solution of oxetan-3-ylmethanol (10.31 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((oxetan-3-ylmethoxy)methyl)pyridin-3-yl)acetic acid (20.4 mg, 0.031 mmol, 53.7% yield). $^1$H NMR (500 MHz, DMSO-d$_6$) δ 7.41-7.33 (m, 2H), 7.23 (d, J=8.1 Hz, 1H), 7.14 (t, J=8.8 Hz, 2H), 7.09-6.95 (m, 3H), 5.83 (br. s., 1H), 4.53 (t, J=7.0 Hz, 2H), 4.29-4.20 (m, 2H), 4.20-4.12 (m, 3H), 4.01 (d, J=9.9 Hz, 1H), 3.40 (d, J=6.6 Hz, 2H), 3.31 (d, J=12.1 Hz, 1H), 3.05 (t, J=6.4 Hz, 2H), 3.02-2.94 (m, 1H), 2.82 (t, J=11.4 Hz, 1H), 2.47 (s, 3H), 2.16 (br. s., 1H), 1.98-1.88 (m, 1H), 1.49 (br. s., 1H), 1.29 (br. s., 1H), 1.18 (d, J=13.2 Hz, 1H), 1.12 (s, 9H), 1.02 (d, J=12.5 Hz, 1H), 0.85 (br. s., 3H), 0.61 (br. s., 3H). LCMS (M+H)=649.2.

EXAMPLE 8

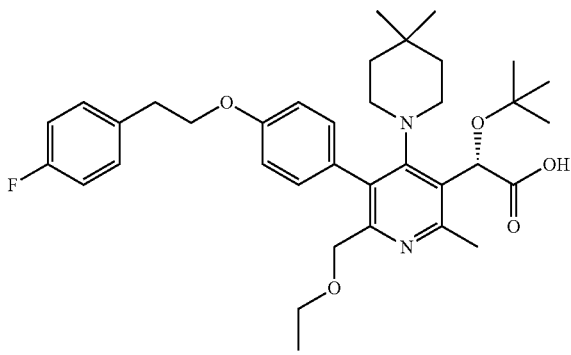 [SMILES: CCOCc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-6-(ethoxymethyl)-5-(4-(4-fluorophenethoxy)phenyl)-2-methylpyridin-3-yl)acetic acid: To a solution of anhydrous ethanol (27.0 mg, 0.585 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-6-(ethoxymethyl)-5-(4-(4-fluorophenethoxy)phenyl)-2-methylpyridin-3-yl)acetic acid (23.7 mg, 0.039 mmol, 66.8% yield). $^1$H NMR (500 MHz, DMSO-d$_6$) δ 7.41-7.34 (m, 2H), 7.26 (d, J=8.4 Hz, 1H), 7.14 (t, J=8.8 Hz, 2H), 7.09-6.96 (m, 3H), 5.81 (br. s., 1H), 4.30-4.16 (m, 2H), 4.10 (d, J=9.5 Hz, 1H), 3.95 (d, J=9.5 Hz, 1H), 3.35 (br. s., 1H), 3.20 (d, J=7.0 Hz, 2H), 3.05 (t, J=6.6 Hz, 2H), 2.86-2.78 (m, 1H), 2.47 (s, 3H), 2.16 (br. s., 1H), 1.93 (br. s., 1H), 1.50 (br. s., 1H), 1.29 (br. s., 1H), 1.18 (d, J=11.7 Hz, 1H), 1.12 (s, 9H), 1.02 (d, J=12.8 Hz, 1H), 0.98 (t, J=7.0 Hz, 3H), 0.85 (br. s., 3H), 0.61 (br. s., 3H). LCMS (M+H)=607.2.

EXAMPLE 9

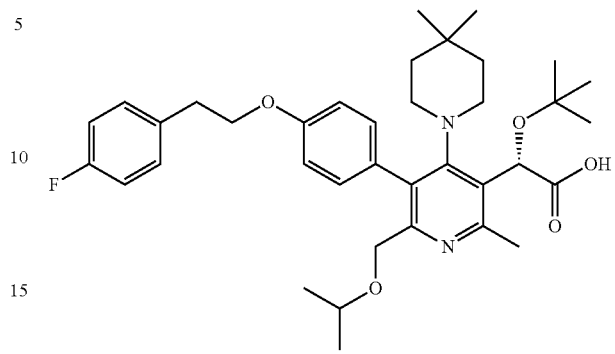

(S)-2-(tert-Butoxy)-2-(4-(4,4-dimethylpiperidin-1-yl)-5-(4-(4-fluorophenethoxy)phenyl)-6-(isopropoxymethyl)-2-methylpyridin-3-yl)acetic acid: To a solution of anhydrous propan-2-ol (35.2 mg, 0.585 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in Ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-6-(isopropoxymethyl)-2-methylpyridin-3-yl)acetic acid (21 mg, 0.034 mmol, 57.8% yield). $^1$H NMR (500 MHz, DMSO-d$_6$) δ 7.41-7.34 (m, 2H), 7.27 (d, J=8.4 Hz, 1H), 7.14 (t, J=9.0 Hz, 2H), 7.09-6.96 (m, 3H), 5.81 (br. s., 1H), 4.31-4.16 (m, 2H), 4.12 (d, J=9.2 Hz, 1H), 3.92 (d, J=9.2 Hz, 1H), 3.35 (br. s., 1H), 3.24 (dt, J=12.0, 5.9 Hz, 2H), 3.04 (d, J=6.6 Hz, 1H), 2.85-2.76 (m, 1H), 2.47 (s, 3H), 2.18 (d, J=12.1 Hz, 1H), 1.99-1.92 (m, 1H), 1.49 (d, J=9.9 Hz, 1H), 1.37-1.24 (m, 1H), 1.18 (d, J=12.5 Hz, 1H), 1.13 (s, 9H), 1.02 (d, J=12.8 Hz, 1H), 0.95 (d, J=6.2 Hz, 3H), 0.89 (d, J=6.2 Hz, 3H), 0.85 (s, 3H), 0.61 (s, 3H). LCMS (M+H)=621.2.

EXAMPLE 10

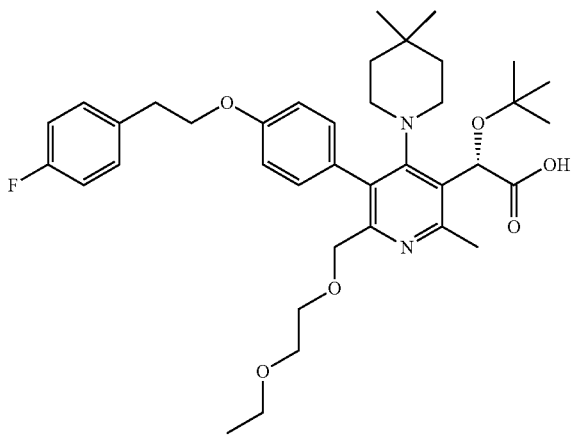 [SMILES: CCOCCOCc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-6-((2-ethoxyethoxy)methyl)-5-(4-(4-fluorophenethoxy)phenyl)-2-methylpyridin-3-yl)acetic acid: To a solution of anhydrous 2-ethoxyethanol (10.55 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-6-((2-ethoxyethoxy)methyl)-5-(4-(4-fluorophenethoxy)phenyl)-2-methylpyridin-3-yl)acetic acid (20.5 mg, 0.031 mmol, 53.8% yield). $^1$H NMR (500 MHz, DMSO-$d_6$) δ 7.38 (t, J=6.6 Hz, 2H), 7.29 (d, J=8.4 Hz, 1H), 7.14 (t, J=8.6 Hz, 2H), 7.09-7.00 (m, 2H), 6.98 (d, J=8.4 Hz, 1H), 5.82 (br. s., 1H), 4.30-4.18 (m, 2H), 4.13 (d, J=9.5 Hz, 1H), 3.99 (d, J=9.9 Hz, 1H), 3.34-3.26 (m, 3H), 3.06 (t, J=6.6 Hz, 2H), 2.82 (t, J=11.7 Hz, 1H), 2.47 (s, 3H), 2.17 (d, J=10.6 Hz, 1H), 1.99-1.87 (m, 1H), 1.51 (br. s., 1H), 1.35-1.24 (m, 1H), 1.19 (d, J=12.8 Hz, 1H), 1.13 (s, 9H), 1.07-1.02 (m, 4H), 0.85 (br. s., 3H), 0.62 (br. s., 3H). 4 piperidine hydrogens are not resolved. LCMS (M+H)=651.2.

EXAMPLE 11

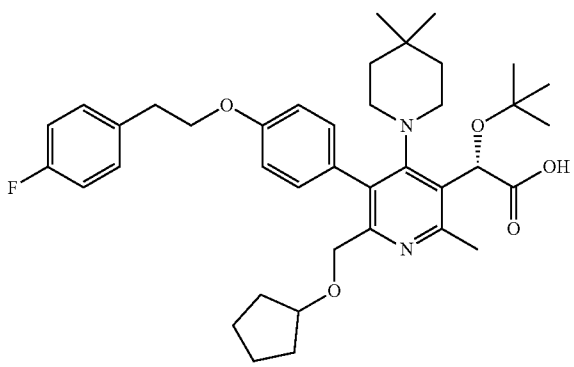 [SMILES: Cc1nc(COC2CCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((cyclopentyloxy)methyl)-4-(4,4-dimethylpiperidin-1-yl)-5-(4-(4-fluorophenethoxy)phenyl)-2-methylpyridin-3-yl)acetic acid: To a solution of anhydrous cyclopentanol (10.08 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in ethanol (1 mL) at 80° C. for 4 h. Mixture was then cooled and purified by prep HPLC to afford (S)-2-(tert-butoxy)-2-(6-((cyclopentyloxy)methyl)-4-(4,4-dimethylpiperidin-1-yl)-5-(4-(4-fluorophenethoxy)phenyl)-2-methyl-pyridin-3-yl)acetic acid (12.5 mg, 0.019 mmol, 33.0% yield). $^1$H NMR (500 MHz, DMSO-$d_6$) δ 7.40-7.34 (m, 2H), 7.25 (d, J=8.4 Hz, 1H), 7.14 (t, J=8.6 Hz, 2H), 7.08-6.97 (m, 3H), 5.84 (br. s., 1H), 4.31-4.16 (m, 2H), 4.08 (d, J=9.2 Hz, 1H), 3.90 (d, J=8.8 Hz, 1H), 3.61 (br. s., 1H), 3.30 (br. s., 1H), 3.05 (t, J=6.6 Hz, 2H), 2.85-2.76 (m, 1H), 2.47 (s, 3H), 2.17 (br. s., 1H), 1.99-1.91 (m, 1H), 1.54-1.41 (m, 5H), 1.35 (br. s., 3H), 1.25 (br. s., 2H), 1.18 (d, J=12.1 Hz, 1H), 1.13 (s, 9H), 1.02 (d, J=11.0 Hz, 1H), 0.85 (s, 3H), 0.61 (s, 3H). LCMS (M+H)=647.2.

EXAMPLE 12

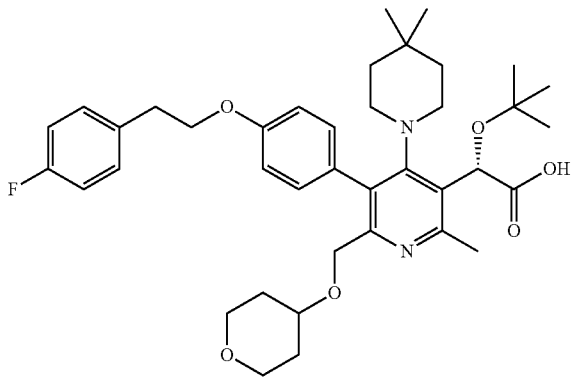 [SMILES: Cc1nc(COC2CCOCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(((tetrahydro-2H-pyran-4-yl)oxy)methyl)pyridin-3-yl)acetic acid: To a solution of anhydrous tetrahydro-2H-pyran-4-ol (11.95 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methyl-pyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in Ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((tetra-hydro-2H-pyran-4-yl)oxy)methyl)pyridin-3-yl)acetic acid (24.9 mg, 0.038 mmol, 64.2% yield). $^1$H NMR (500 MHz, DMSO-$d_6$) δ 7.40-7.35 (m, 2H), 7.28 (d, J=8.1 Hz, 1H), 7.14 (t, J=8.8 Hz, 2H), 7.10-7.05 (m, 1H), 7.05-6.98 (m, 2H), 5.82 (br. s., 1H), 4.28-4.18 (m, 3H), 4.00 (d, J=9.2 Hz, 1H), 3.74-3.58 (m, 2H), 3.33 (br. s., 1H), 3.25-3.13 (m, 3H), 3.05 (t, J=6.6 Hz, 2H), 2.87-2.77 (m, 1H), 2.47 (s, 3H), 2.17 (br. s., 1H), 1.97 (br. s., 1H), 1.72-1.56 (m, 2H), 1.50 (br. s., 1H), 1.38-1.22 (m, 2H), 1.18 (dt, J=8.8, 4.4 Hz, 2H), 1.13 (s, 9H), 1.03 (d, J=12.1 Hz, 1H), 0.85 (s, 3H), 0.61 (s, 3H). LCMS (M+H)=663.2.

EXAMPLE 13

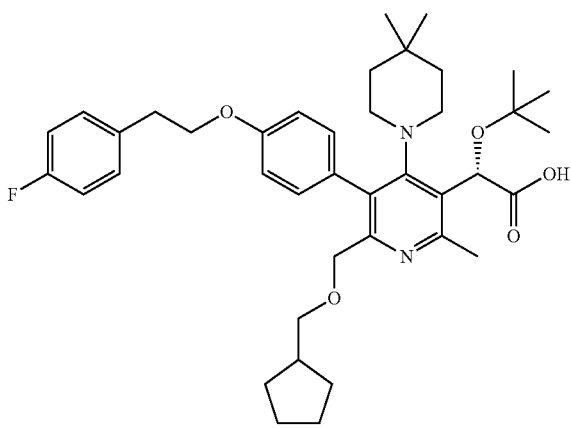 [SMILES: Cc1nc(COCC2CCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((cyclopentylmethoxy)methyl)-4-(4,4-dimethylpiperidin-1-yl)-5-(4-(4-fluorophenethoxy)phenyl)-2-methylpyridin-3-yl)acetic acid: To a solution of anhydrous cyclopentylmethanol (11.72 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in EtOH (1 mL) at 80° C. for 4 h. Mixture was then cooled and purified by prep HPLC to afford (S)-2-(tert-butoxy)-2-(6-((cyclopentylmethoxy)methyl)-4-(4,4-dimethylpiperidin-1-yl)-5-(4-(4-fluorophenethoxy)phenyl)-2-methylpyridin-3-yl)acetic acid (17.1 mg, 0.026 mmol, 44.2% yield). $^1$H NMR (500 MHz, DMSO-d$_6$) δ 7.41-7.34 (m, 2H), 7.27 (d, J=8.1 Hz, 1H), 7.14 (t, J=8.8 Hz, 2H), 7.09-7.00 (m, 2H), 6.98 (d, J=8.4 Hz, 1H), 5.84 (br. s., 1H), 4.30-4.16 (m, 2H), 4.11 (d, J=9.9 Hz, 1H), 3.96 (d, J=9.9 Hz, 1H), 3.31 (br. s., 1H), 3.09-2.99 (m, 4H), 2.87-2.77 (m, 1H), 2.47 (s, 3H), 2.18 (d, J=11.4 Hz, 1H), 2.02-1.88 (m, 2H), 1.61-1.49 (m, 3H), 1.49-1.36 (m, 4H), 1.30 (br. s., 1H), 1.19 (d, J=12.1 Hz, 1H), 1.13 (s, 9H), 1.10-0.98 (m, 3H), 0.85 (br. s., 3H), 0.61 (br. s., 3H). LCMS (M+H)=661.2.

EXAMPLE 14

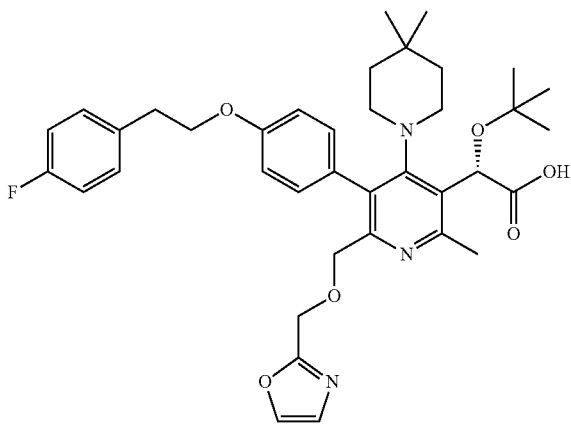 [SMILES: Cc1nc(COCc2ncco2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-((oxazol-2-ylmethoxy)methyl)pyridin-3-yl)acetic acid: To a solution of anhydrous oxazol-2-ylmethanol (11.59 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in Ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((oxazol-2-ylmethoxy)methyl)pyridin-3-yl)acetic acid (29.3 mg, 0.044 mmol, 76% yield). $^1$H NMR (500 MHz, DMSO-d$_6$) δ 8.00 (s, 1H), 7.42-7.35 (m, 2H), 7.21 (d, J=8.1 Hz, 1H), 7.18-7.10 (m, 3H), 7.07-6.97 (m, 2H), 6.94 (d, J=8.8 Hz, 1H), 5.81 (br. s., 1H), 4.48-4.29 (m, 2H), 4.29-4.14 (m, 3H), 4.07 (d, J=9.5 Hz, 1H), 3.33 (br. s., 2H), 3.06 (t, J=6.4 Hz, 2H), 2.85-2.76 (m, 1H), 2.47 (s, 3H), 2.17 (d, J=12.1 Hz, 1H), 1.50 (br. s., 1H), 1.29 (br. s., 1H), 1.18 (d, J=12.1 Hz, 1H), 1.12 (s, 9H), 1.02 (d, J=12.5 Hz, 1H), 0.85 (br. s., 3H), 0.61 (br. s., 3H). LCMS (M+H)=660.1.

EXAMPLE 15

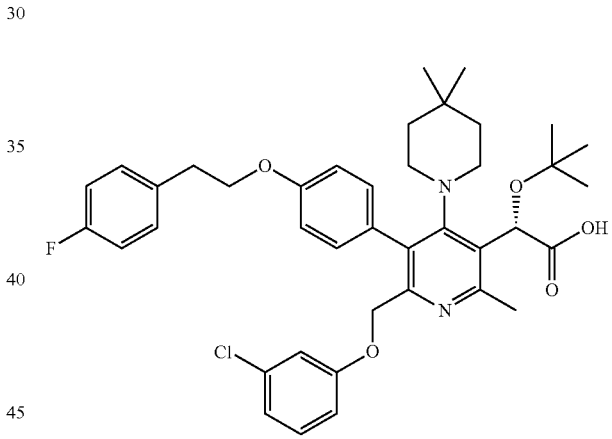

(S)-2-(tert-Butoxy)-2-(6-((3-chlorophenoxy)methyl)-4-(4,4-dimethylpiperidin-1-yl)-5-(4-(4-fluorophenethoxy)phenyl)-2-methylpyridin-3-yl)acetic acid: To a solution of anhydrous (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in Ethanol (1 mL) at 80° C. for 4 h. Mixture was then cooled and purified by prep HPLC to afford (S)-2-(tert-butoxy)-2-(6-((3-chlorophenoxy)methyl)-4-(4,4-dimethylpiperidin-1-yl)-5-(4-(4-fluorophenethoxy)phenyl)-2-methylpyridin-3-yl)acetic acid (27.3 mg, 0.040 mmol, 67.7% yield). $^1$H NMR (500 MHz, DMSO-d$_6$) δ 7.36-7.30 (m, 2H), 7.27 (d, J=7.7 Hz, 1H), 7.22 (t, J=8.1 Hz, 1H), 7.12 (t, J=8.3 Hz, 3H), 7.00 (d, J=8.1 Hz, 1H), 6.94-6.88 (m, 3H), 6.80 (d, J=8.1 Hz, 1H), 5.84 (br. s., 1H), 4.76 (d, J=9.9 Hz, 1H), 4.59 (d, J=9.9 Hz, 1H), 4.23-4.06 (m, 2H), 3.34 (br. s., 2H), 3.00 (t, J=6.4 Hz, 2H), 2.87-2.77 (m, 1H), 2.50 (br. s., 3H), 2.21 (d, J=11.4 Hz, 1H), 1.51 (br. s., 1H), 1.31 (br. s., 1H), 1.20 (d, J=12.5 Hz, 1H), 1.14 (s, 9H), 1.03 (d, J=12.1 Hz, 1H), 0.86 (br. s., 3H), 0.61 (br. s., 3H). LCMS (M+H)=689.1.

EXAMPLE 16

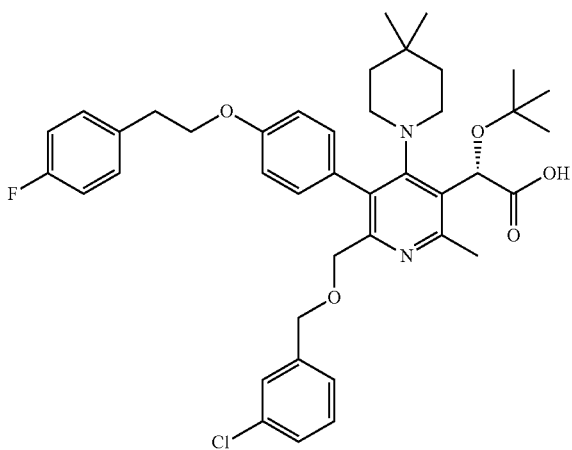 [SMILES: Cc1nc(COCc2cccc(Cl)c2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-(((3-chlorobenzyl)oxy)methyl)-4-(4,4-dimethylpiperidin-1-yl)-5-(4-(4-fluorophenethoxy)phenyl)-2-methylpyridin-3-yl)acetic acid: To a solution of anhydrous (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in Ethanol (1 mL) at 80° C. for 4 h. Mixture was then cooled and purified by prep HPLC to afford (S)-2-(tert-butoxy)-2-(6-(((3-chlorobenzyl)oxy) methyl)-4-(4,4-dimethylpiperidin-1-yl)-5-(4-(4-fluorophenethoxy)phenyl)-2-methylpyridin-3-yl)acetic acid (27.5 mg, 0.039 mmol, 66.8% yield). $^1$H NMR (500 MHz, DMSO-d$_6$) δ 7.42-7.34 (m, 2H), 7.30-7.21 (m, 4H), 7.17-7.06 (m, 4H), 7.04-6.99 (m, 1H), 6.97 (d, J=7.7 Hz, 1H), 5.82 (br. s., 1H), 4.31 (s, 2H), 4.28-4.19 (m, 3H), 4.06 (d, J=9.5 Hz, 1H), 3.34 (br. s., 1H), 3.06 (t, J=6.4 Hz, 2H), 2.82 (t, J=13.0 Hz, 1H), 2.49 (s, 3H), 2.18 (d, J=11.7 Hz, 1H), 1.93 (br. s., 1H), 1.50 (br. s., 1H), 1.29 (br. s., 1H), 1.19 (d, J=13.2 Hz, 1H), 1.12 (s, 9H), 1.02 (d, J=12.1 Hz, 1H), 0.85 (br. s., 3H), 0.61 (s, 3H). LCMS (M+H)=703.1.

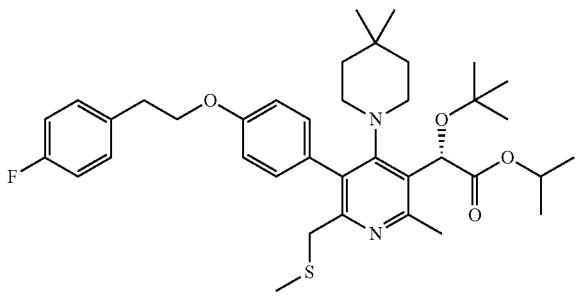 [SMILES: CSCc1nc(C)c([C@H](OC(C)(C)C)C(=O)OC(C)C)c(N2CCC(C)(C)CC2)c1-c1ccc(OCCc2ccc(F)cc2)cc1]

(S)-Isopropyl 2-(tert-butoxy)-2-(4-(4,4-dimethylpiperidin-1-yl)-5-(4-(4-fluorophenethoxy)phenyl)-2-methyl-6-((methylthio)methyl)pyridin-3-yl)acetate: To a solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (100 mg, 0.146 mmol) in DMF (1.5 mL) was added sodium thiomethoxide (12.30 mg, 0.176 mmol) and the resulting mixture was stirred at room temp for 2 h. Mixture was then diluted with ethyl acetate and washed with sat. NaHCO$_3$ and brine, dried (Na$_2$SO$_4$), filtered and concentrated. to afford (S)-isopropyl 2-(tert-butoxy)-2-(4-(4,4-dimethylpiperidin-1-yl)-5-(4-(4-fluorophenethoxy)phenyl)-2-methyl-6-((methylthio)methyl) pyridin-3-yl)acetate (92 mg, 0.141 mmol, 97% yield) as off-white solid, which was used in the next step without further purification. $^1$H NMR (500 MHz, CDCl$_3$) δ 7.35-7.31 (m, 3H), 7.11 (d, J=7.9 Hz, 1H), 7.05 (t, J=8.4 Hz, 2H), 6.97 (d, J=8.0 Hz, 2H), 6.07 (br. s., 1H), 5.10 (dt, J=12.4, 6.2 Hz, 1H), 4.30-4.19 (m, 2H), 3.55 (d, J=12.6 Hz, 1H), 3.44 (d, J=12.5 Hz, 1H), 3.25-3.17 (m, 1H), 3.13 (t, J=6.8 Hz, 2H), 2.87 (t, J=12.1 Hz, 1H), 2.61 (s, 3H), 2.29 (d, J=11.3 Hz, 1H), 2.10 (s, 3H), 2.04 (t, J=11.7 Hz, 1H), 1.55 (br. s., 1H), 1.37 (t, J=11.8 Hz, 1H), 1.24 (dd, J=13.0, 6.2 Hz, 7H), 1.20 (s, 9H), 1.08 (d, J=11.7 Hz, 1H), 0.91 (br. s., 3H), 0.66 (br. s., 3H). LCMS (M+H)=651.5.

EXAMPLE 17

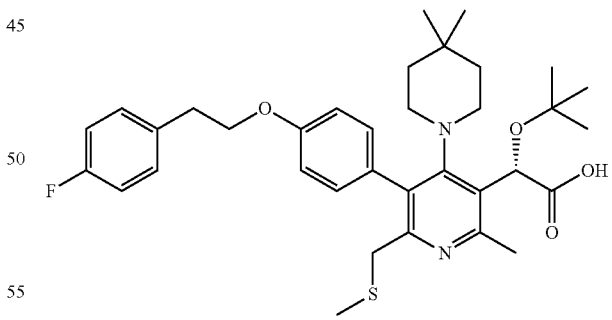

(S)-2-(tert-Butoxy)-2-(4-(4,4-dimethylpiperidin-1-yl)-5-(4-(4-fluorophenethoxy)phenyl)-2-methyl-6-((methylthio) methyl)pyridin-3-yl)acetic acid: To a solution of (S)-isopropyl 2-(tert-butoxy)-2-(4-(4,4-dimethylpiperidin-1-yl)-5-(4-(4-fluorophenethoxy)phenyl)-2-methyl-6-((methylthio) methyl)pyridin-3-yl)acetate (25 mg, 0.038 mmol) in ethanol (1 mL) was added 10N NaOH (0.038 mL, 0.384 mmol) and the resulting mixture was heated at 80° C. for 3 h. Mixture was then cooled and purified by prep HPLC to afford (S)-2-(tert-butoxy)-2-(4-(4,4-dimethylpiperidin-1-yl)-5-(4-

(4-fluorophenethoxy)phenyl)-2-methyl-6-((methylthio)methyl)pyridin-3-yl)acetic acid (15.3 mg, 0.025 mmol, 65.4% yield). $^1$H NMR (500 MHz, DMSO-d$_6$) δ 7.42-7.33 (m, 2H), 7.28 (d, J=8.4 Hz, 1H), 7.14 (t, J=8.6 Hz, 2H), 7.10-6.97 (m, 3H), 5.84 (br. s., 1H), 4.30-4.15 (m, 2H), 3.43 (d, J=12.5 Hz, 2H), 3.32-3.24 (m, 2H), 3.05 (t, J=6.6 Hz, 2H), 2.84-2.75 (m, 1H), 2.46 (s, 3H), 2.19 (d, J=12.1 Hz, 1H), 1.94-1.88 (m, 2H), 1.49 (br. s., 1H), 1.29 (br. s., 1H), 1.18 (d, J=12.1 Hz, 1H), 1.13 (s, 9H), 1.02 (d, J=13.2 Hz, 1H), 0.85 (s, 3H), 0.60 (s, 3H). LCMS (M+H)=609.1.

EXAMPLE 18

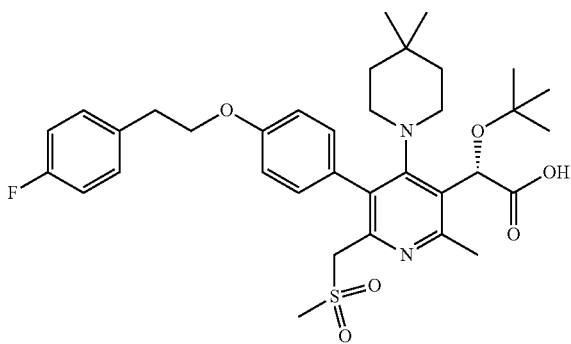 [SMILES: Cc1nc(CS(C)(=O)=O)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-((methylsulfonyl)methyl)pyridin-3-yl)acetic acid: To a solution of (S)-isopropyl 2-(tert-butoxy)-2-(4-(4,4-dimethylpiperidin-1-yl)-5-(4-(4-fluorophenethoxy)phenyl)-2-methyl-6-((methylthio)methyl)pyridin-3-yl)acetate (70 mg, 0.108 mmol) in MeOH (2 mL) and water (2 mL) was added oxone (198 mg, 0.323 mmol) and stirred for 1 h at rt. Then, diluted with water (10 mL), extracted with EtOAc (2×20 mL), dried (Na$_2$SO$_4$), filtered, concentrated. The residue was then treated with 10N NaOH (0.108 mL, 1.075 mmol) in ethanol (1.5 mL) at 80° C. for 4 h. Mixture was then cooled and purified by prep HPLC to give (S)-2-(tert-butoxy)-2-(4-(4,4-dimethylpiperidin-1-yl)-5-(4-(4-fluorophenethoxy)phenyl)-2-methyl-6-((methylsulfonyl)methyl)pyridin-3-yl)acetic acid (39.6 mg, 0.062 mmol, 57.5% yield). $^1$H NMR (500 MHz, DMSO-d$_6$) δ 7.41-7.34 (m, 2H), 7.27 (d, J=9.5 Hz, 1H), 7.14 (t, J=8.6 Hz, 2H), 7.07 (br. s., 3H), 5.85 (br. s., 1H), 4.26 (q, J=7.1 Hz, 2H), 4.19 (d, J=14.3 Hz, 1H), 4.11 (d, J=14.3 Hz, 1H), 3.39 (br. s., 3H), 3.30 (d, J=8.8 Hz, 1H), 3.14 (s, 3H), 3.06 (t, J=6.8 Hz, 2H), 2.85-2.76 (m, 1H), 2.16 (br. s., 1H), 1.91-1.82 (m, 1H), 1.50 (br. s., 1H), 1.29 (br. s., 1H), 1.19 (d, J=12.5 Hz, 1H), 1.13 (s, 9H), 1.03 (d, J=11.4 Hz, 1H), 0.85 (br. s., 3H), 0.61 (br. s., 3H). LCMS (M+H)=641.2.

EXAMPLE 19

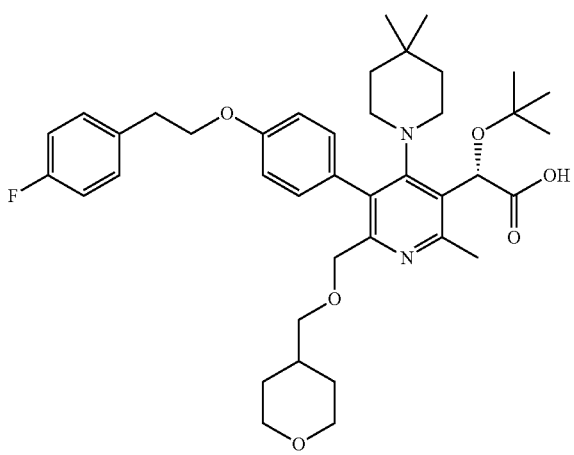

(S)-2-(tert-Butoxy)-2-(4-(4,4-dimethylpiperidin-1-yl)-5-(4-(4-fluorophenethoxy)phenyl)-2-methyl-6-(((tetrahydro-2H-pyran-4-yl)methoxy)methyl)pyridin-3-yl)acetic acid: To a solution of (tetrahydro-2H-pyran-4-yl)methanol (16.99 mg, 0.146 mmol) in THF (1) at 0° C. was added NaH (5.85 mg, 0.146 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methyl-pyridin-3-yl)-2-(tert-butoxy)acetate (50 mg, 0.073 mmol) in THF (0.5 mL) was then added and the mixture was stirred for 4 h. At this point LCMS indicated completion of reaction. Mixture was then concentrated and treated with 10N NaOH (0.073 mL, 0.731 mmol) in Ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((tetrahydro-2H-pyran-4-yl)methoxy)methyl)pyridin-3-yl)acetic acid (41 mg, 0.061 mmol, 83% yield). $^1$H NMR (500 MHz, DMSO-d$_6$) δ 7.44-7.31 (m, 2H), 7.25 (d, J=7.7 Hz, 1H), 7.14 (t, J=8.6 Hz, 2H), 7.10-6.93 (m, 3H), 5.70 (br. s., 1H), 4.34-4.16 (m, 2H), 4.12 (d, J=9.5 Hz, 1H), 3.97-3.84 (m, 1H), 3.76 (d, J=10.3 Hz, 2H), 3.22-3.15 (m, 2H), 3.10-2.97 (m, 4H), 2.46 (s, 3H), 2.16 (d, J=8.8 Hz, 1H), 1.90 (s, 3H), 1.61 (br. s., 1H), 1.50 (br. s., 1H), 1.42 (d, J=12.8 Hz, 2H), 1.29 (br. s., 1H), 1.17 (d, J=12.1 Hz, 1H), 1.11 (s, 9H), 1.08-0.96 (m, 3H), 0.85 (br. s., 3H), 0.62 (br. s., 3H). LCMS (M+H)=677.3.

EXAMPLE 20

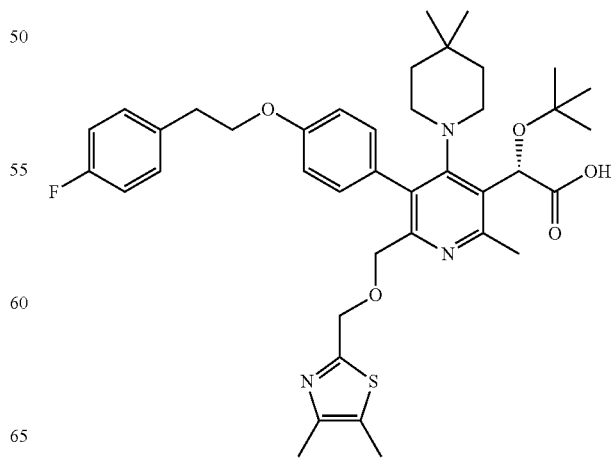

(S)-2-(tert-Butoxy)-2-(4-(4,4-dimethylpiperidin-1-yl)-6-(((4,5-dimethylthiazol-2-yl)methoxy)methyl)-5-(4-(4-fluorophenethoxy)phenyl)-2-methylpyridin-3-yl)acetic acid: To a solution of (4,5-dimethylthiazol-2-yl)methanol (20.95 mg, 0.146 mmol) in THF (1) at 0° C. was added NaH (5.85 mg, 0.146 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (50 mg, 0.073 mmol) in THF (0.5 mL) was then added and the mixture was stirred for 4 h. At this point LCMS indicated completion of reaction. Mixture was then concentrated and treated with 10N NaOH (0.073 mL, 0.731 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-6-(((4,5-dimethylthiazol-2-yl)methoxy)methyl)-5-(4-(4-fluorophenethoxy)phenyl)-2-methylpyridin-3-yl)acetic acid (18.3 mg, 0.026 mmol, 35.5% yield). $^1$H NMR (500 MHz, DMSO-d$_6$) δ 7.43-7.32 (m, 2H), 7.23 (d, J=8.4 Hz, 1H), 7.14 (t, J=8.8 Hz, 2H), 7.09-6.98 (m, 2H), 6.94 (d, J=8.1 Hz, 1H), 5.82 (br. s., 1H), 4.54-4.35 (m, 2H), 4.30-4.15 (m, 3H), 4.12 (d, J=9.9 Hz, 1H), 3.05 (t, J=6.6 Hz, 2H), 2.85-2.77 (m, 1H), 2.48 (s, 3H), 2.26 (s, 3H), 2.17 (s, 3H), 1.97-1.87 (m, 1H), 1.50 (br. s., 1H), 1.38-1.23 (m, 1H), 1.19 (d, J=12.1 Hz, 1H), 1.12 (s, 9H), 1.02 (d, J=11.7 Hz, 1H), 0.85 (br. s., 3H), 0.61 (br. s., 3H). LCMS (M+H)=704.2.

EXAMPLE 21

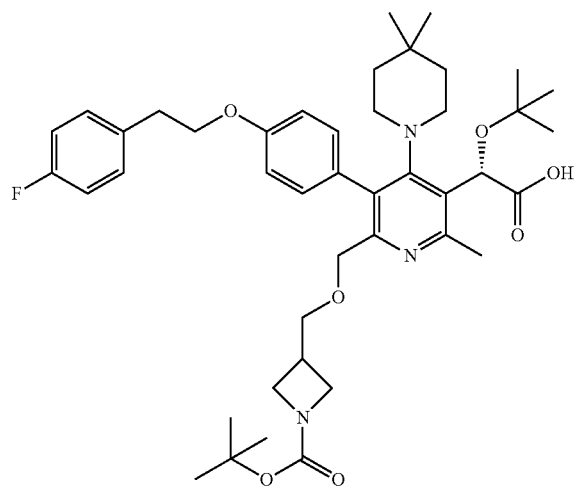 [SMILES: Cc1nc(COCC2CN(C(=O)OC(C)(C)C)C2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-(((1-(tert-butoxycarbonyl)azetidin-3-yl)methoxy)methyl)-4-(4,4-dimethylpiperidin-1-yl)-5-(4-(4-fluorophenethoxy)phenyl)-2-methylpyridin-3-yl) acetic acid: To a solution of tert-butyl 3-(hydroxymethyl) azetidine-1-carboxylate (21.91 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in ethanol (1 mL) at 80° C. for 4 h. Mixture was then cooled and purified by prep HPLC to afford (S)-2-(tert-butoxy)-2-(6-(((1-(tert-butoxycarbonyl)azetidin-3-yl) methoxy)methyl)-4-(4,4-dimethylpiperidin-1-yl)-5-(4-(4-fluorophenethoxy)phenyl)-2-methylpyridin-3-yl)acetic acid (30 mg, 0.040 mmol, 68.6% yield). $^1$H NMR (500 MHz, DMSO-d$_6$) δ 7.41-7.34 (m, 2H), 7.25 (d, J=8.1 Hz, 1H), 7.14 (t, J=8.4 Hz, 3H), 7.03 (s, 1H), 6.97 (d, J=9.2 Hz, 1H), 5.58 (s, 1H), 4.28-4.18 (m, 5H), 4.13 (d, J=10.3 Hz, 2H), 4.00 (d, J=9.9 Hz, 2H), 3.77 (br. s., 5H), 3.44 (br. s., 2H), 3.30 (d, J=5.5 Hz, 2H), 2.58 (br. s., 1H), 2.46 (s, 3H), 1.34 (s, 9H), 1.15 (d, J=10.3 Hz, 1H), 1.09 (s, 9H), 0.84 (s, 3H), 0.62 (s, 3H). LCMS (M+H)=748.2.

EXAMPLE 22

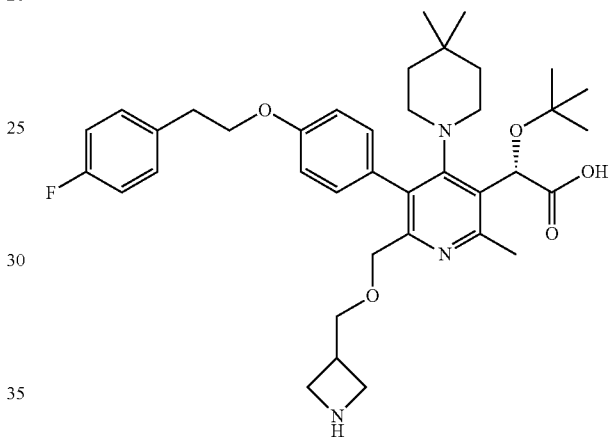

(S)-2-(6-((Azetidin-3-ylmethoxy)methyl)-4-(4,4-dimethylpiperidin-1-yl)-5-(4-(4-fluorophenethoxy)phenyl)-2-methylpyridin-3-yl)-2-(tert-butoxy)acetic acid: The (S)-2-(tert-butoxy)-2-(6-(((1-(tert-butoxycarbonyl)azetidin-3-yl) methoxy)methyl)-4-(4,4-dimethylpiperidin-1-yl)-5-(4-(4-fluorophenethoxy)phenyl)-2-methylpyridin-3-yl)acetic acid was then treated with TFA (0.090 mL, 1.170 mmol) in CH$_2$Cl$_2$ (1 mL) for 1 h. The mixture was then concentrated and purified by prep HPLC to afford (S)-2-(6-((azetidin-3-ylmethoxy)methyl)-4-(4,4-dimethylpiperidin-1-yl)-5-(4-(4-fluorophenethoxy)phenyl)-2-methylpyridin-3-yl)-2-(tert-butoxy)acetic acid (16 mg, 0.025 mmol, 42.2% yield). $^1$H NMR (500 MHz, DMSO-d$_6$) δ 7.41-7.34 (m, 2H), 7.24 (d, J=8.4 Hz, 1H), 7.14 (t, J=8.8 Hz, 2H), 7.09-7.04 (m, 1H), 7.04-6.96 (m, 2H), 5.68 (br. s., 1H), 4.29-4.17 (m, 3H), 4.09 (d, J=10.3 Hz, 1H), 3.87-3.72 (m, 2H), 3.67-3.53 (m, 3H), 3.36-3.32 (m, 3H), 3.25-3.19 (m, 1H), 3.05 (t, J=6.8 Hz, 2H), 2.84 (br. s., 1H), 2.82-2.69 (m, 1H), 2.45 (s., 3H), 2.16 (br. s., 1H), 1.94-1.85 (m, 1H), 1.50 (br. s., 1H), 1.29 (br. s., 1H), 1.16 (d, J=12.5 Hz, 1H), 1.10 (s, 9H), 1.01 (d, J=12.1 Hz, 1H), 0.84 (br. s., 3H), 0.61 (s, 3H). LCMS (M+H)=648.2.

EXAMPLE 23

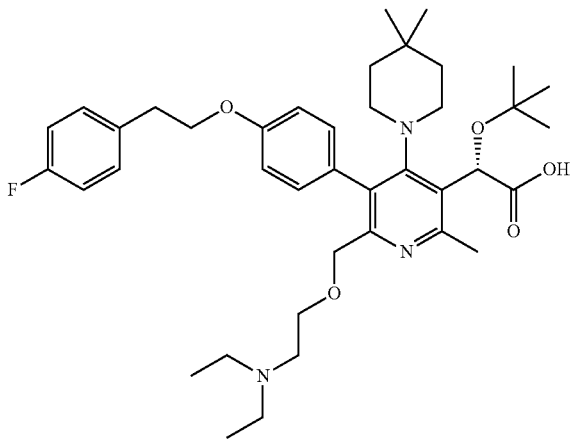 [SMILES: CCN(CC)CCOCc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(6-((2-(diethylamino)ethoxy)methyl)-4-(4,4-dimethylpiperidin-1-yl)-5-(4-(4-fluorophenethoxy)phenyl)-2-methylpyridin-3-yl)acetic acid: To a solution of 2-(diethylamino)ethanol (8.57 mg, 0.073 mmol) in THF (1) at 0° C. was added NaH (2.93 mg, 0.073 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (25 mg, 0.037 mmol) in THF (0.5 mL) was then added and the mixture was stirred for 4 h. At this point LCMS indicated completion of reaction. Mixture was then concentrated and treated with 10N NaOH (0.037 mL, 0.366 mmol) in Ethanol (1 mL) at 80° C. for 4 h. Mixture was then cooled and purified by prep HPLC to afford (S)-2-(tert-butoxy)-2-(6-((2-(diethylamino)ethoxy)methyl)-4-(4,4-dimethylpiperidin-1-yl)-5-(4-(4-fluorophenethoxy)phenyl)-2-methylpyridin-3-yl)acetic acid (18.5 mg, 0.027 mmol, 74.6% yield). $^1$H NMR (500 MHz, DMSO-$d_6$) δ 7.41-7.33 (m, 2H), 7.28 (d, J=8.1 Hz, 1H), 7.14 (t, J=8.4 Hz, 2H), 7.03 (br. s., 2H), 6.98 (d, J=8.1 Hz, 1H), 5.71 (br. s., 1H), 4.22 (dd, J=14.3, 6.6 Hz, 2H), 4.12 (d, J=10.3 Hz, 1H), 3.98 (d, J=9.2 Hz, 1H), 3.51 (br. s., 2H), 3.25-3.18 (m, 3H), 2.79 (br. s., 1H), 2.46 (s, 3H), 2.39 (d, J=7.0 Hz, 4H), 2.42-2.33 (m, 2H), 2.16 (d, J=9.5 Hz, 1H), 1.51 (br. s., 1H), 1.29 (br. s., 1H), 1.17 (d, J=11.0 Hz, 1H), 1.10 (s, 9H), 1.02 (d, J=11.4 Hz, 1H), 0.90-0.79 (m, 9H), 0.62 (br. s., 3H). LCMS (M+H)=678.2.

EXAMPLE 24

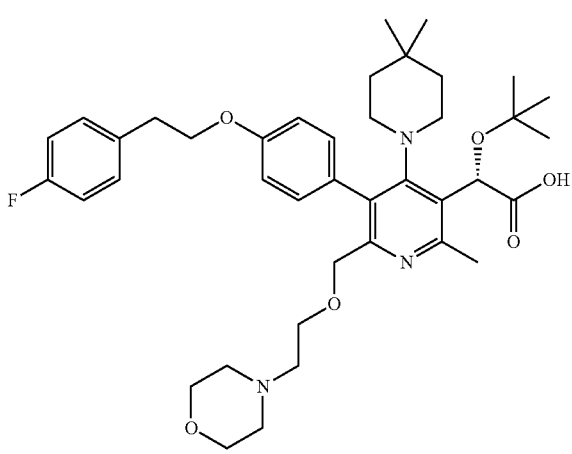 [SMILES: Cc1nc(COCCN2CCOCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-((2-morpholinoethoxy)methyl)pyridin-3-yl)acetic acid: To a solution of 2-morpholinoethanol (9.59 mg, 0.073 mmol) in THF (1) at 0° C. was added NaH (2.93 mg, 0.073 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (25 mg, 0.037 mmol) in THF (0.5 mL) was then added and the mixture was stirred for 4 h. At this point LCMS indicated completion of reaction. Mixture was then concentrated and treated with 10N NaOH (0.037 mL, 0.366 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((2-morpholinoethoxy)methyl)pyridin-3-yl)acetic acid (16.9 mg, 0.024 mmol, 66.8% yield). $^1$H NMR (500 MHz, DMSO-$d_6$) δ 7.41-7.34 (m, 2H), 7.28 (d, J=8.4 Hz, 1H), 7.14 (t, J=8.6 Hz, 2H), 7.09-7.00 (m, 2H), 6.98 (d, J=9.9 Hz, 1H), 5.78 (br. s., 1H), 4.30-4.16 (m, 2H), 4.13 (d, J=9.9 Hz, 1H), 3.99 (d, J=9.9 Hz, 1H), 3.49 (d, J=4.0 Hz, 1H), 3.39 (br. s., 2H), 3.29 (t, J=5.5 Hz, 3H), 3.06 (t, J=6.6 Hz, 2H), 2.81 (t, J=12.1 Hz, 1H), 2.47 (s, 3H), 2.33-2.23 (m, 6H), 2.16 (d, J=9.9 Hz, 1H), 1.96-1.90 (m, 2H), 1.50 (br. s., 1H), 1.30 (br. s., 1H), 1.18 (d, J=12.1 Hz, 1H), 1.12 (s, 9H), 1.02 (d, J=12.8 Hz, 1H), 0.85 (br. s., 3H), 0.62 (br. s., 3H). LCMS (M+H)=692.4.

EXAMPLE 25

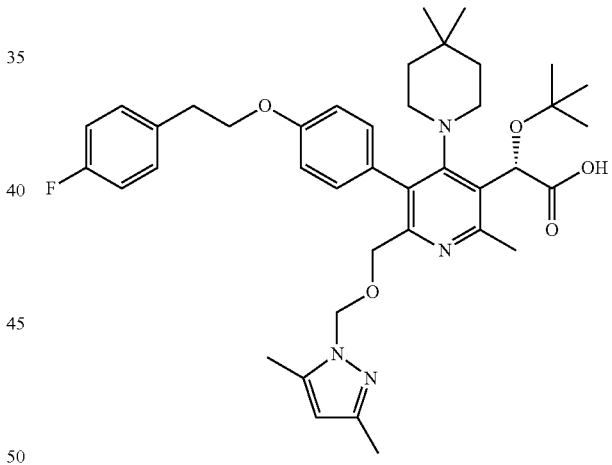

(S)-2-(tert-Butoxy)-2-(6-(((3,5-dimethyl-1H-pyrazol-1-yl)methoxy)methyl)-4-(4,4-dimethylpiperidin-1-yl)-5-(4-(4-fluorophenethoxy)phenyl)-2-methylpyridin-3-yl)acetic acid: To a solution of (3,5-dimethyl-1H-pyrazol-1-yl)methanol (14.76 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 4 h. At this point LCMS indicated completion of reaction. Mixture was then concentrated and treated with 10N NaOH (0.059 mL, 0.585 mmol) in ethanol (1 mL) at 80° C. for 4 h. Mixture was then cooled and purified by prep HPLC to afford (S)-2-(tert-butoxy)-2-(6-(((3,5-dimethyl-1H-pyrazol-1-yl)methoxy)methyl)-4-(4,4- dimethylpiperidin-1-yl)-5-(4-(4-fluorophenethoxy)phenyl)-2-methylpyridin-3-yl)acetic acid (27.1 mg, 0.039 mmol, 67.4% yield). $^1$H NMR (500 MHz, DMSO-d$_6$) δ 7.42-7.34 (m, 2H), 7.24-7.07 (m, 3H), 6.98 (s, 2H), 6.87 (d, J=8.8 Hz, 1H), 5.73 (s, 1H), 5.68 (br. s., 1H), 5.19-5.08 (m, 2H), 4.23 (dd, J=13.4, 6.1 Hz, 2H), 4.10 (d, J=10.3 Hz, 1H), 4.01 (d, J=9.9 Hz, 1H), 3.51 (br. s., 3H), 3.06 (t, J=6.4 Hz, 2H), 2.75 (d, J=13.9 Hz, 1H), 2.46 (s, 3H), 2.13 (s, 4H), 1.98 (s, 3H), 1.49 (br. s., 1H), 1.27 (d, J=9.5 Hz, 1H), 1.16 (d, J=13.6 Hz, 1H), 1.10 (s, 9H), 1.00 (d, J=12.8 Hz, 1H), 0.84 (br. s., 3H), 0.61 (br. s., 3H). LCMS (M+H)=687.2.

EXAMPLE 26

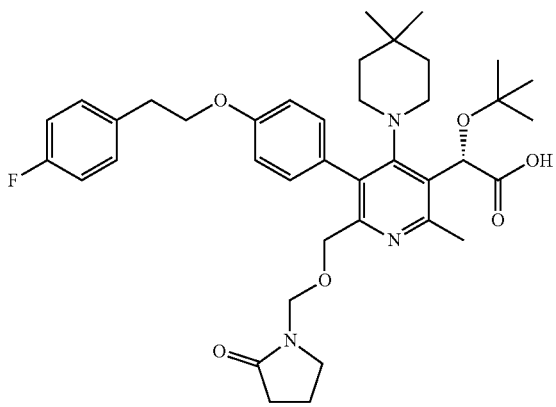 [SMILES: Cc1nc(COCN2CCCC2=O)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(((2-oxopyrrolidin-1-yl)methoxy)methyl)pyridin-3-yl)acetic acid: To a solution of 1-(hydroxymethyl)pyrrolidin-2-one (13.47 mg, 0.117 mmol) in THF (1) at 0° C. was added NaH (4.68 mg, 0.117 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (40 mg, 0.059 mmol) in THF (0.5 mL) was then added and the mixture was stirred for 16 h. At this point LCMS indicated completion of reaction. Mixture was then concentrated and treated with 10N NaOH (0.059 mL, 0.585 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((2-oxopyrrolidin-1-yl)methoxy)methyl)pyridin-3-yl)acetic acid (13 mg, 0.019 mmol, 32.9% yield). $^1$H NMR (500 MHz, DMSO-d$_6$) δ 7.41-7.34 (m, 2H), 7.23 (d, J=7.3 Hz, 1H), 7.15 (t, J=8.8 Hz, 2H), 7.10-7.05 (m, 1H), 7.05-6.98 (m, 2H), 5.84 (br. s., 1H), 4.52 (d, J=10.3 Hz, 1H), 4.42 (d, J=10.3 Hz, 1H), 4.30-4.17 (m, 2H), 4.09 (d, J=9.5 Hz, 1H), 3.96-3.87 (m, 1H), 3.32 (d, J=16.1 Hz, 1H), 3.24-3.12 (m, 1H), 3.10-2.99 (m, 3H), 2.86-2.75 (m, 1H), 2.47 (s, 3H), 2.16 (br. s., 1H), 2.13-2.04 (m, 2H), 1.96-1.89 (m, 1H), 1.80-1.65 (m, 2H), 1.50 (br. s., 1H), 1.28 (d, J=11.0 Hz, 1H), 1.19 (d, J=11.0 Hz, 1H), 1.13 (s, 9H), 1.03 (d, J=12.5 Hz, 1H), 0.85 (s, 3H), 0.61 (s, 3H). LCMS (M+H)=676.2.

EXAMPLE 27

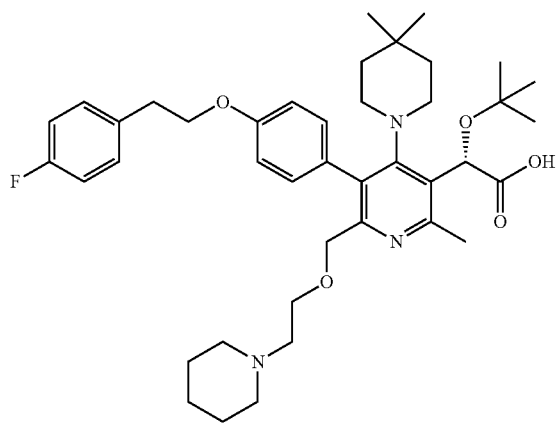 [SMILES: Cc1nc(COCCN2CCCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-((2-(piperidin-1-yl)ethoxy)methyl)pyridin-3-yl)acetic acid: To a solution of 2-(piperidin-1-yl)ethanol (9.45 mg, 0.073 mmol) in THF (1) at 0° C. was added NaH (2.93 mg, 0.073 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (25 mg, 0.037 mmol) in THF (0.5 mL) was then added and the mixture was stirred for 4 h. At this point LCMS indicated completion of reaction. Mixture was then concentrated and treated with 10N NaOH (0.037 mL, 0.366 mmol) in ethanol (1 mL) at 80° C. for 16 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((2-(piperidin-1-yl)ethoxy)methyl)pyridin-3-yl)acetic acid (14.5 mg, 0.021 mmol, 57.5% yield). $^1$H NMR (500 MHz, DMSO-d$_6$) δ 7.41-7.34 (m, 2H), 7.29 (d, J=8.8 Hz, 1H), 7.14 (t, J=8.8 Hz, 2H), 7.06-6.94 (m, 3H), 5.76 (s, 1H), 4.32-4.16 (m, 2H), 4.12 (d, J=9.9 Hz, 1H), 3.98 (d, J=9.9 Hz, 1H), 3.42 (br. s., 2H), 3.05 (t, J=6.4 Hz, 2H), 2.84-2.76 (m, 1H), 2.47 (s, 3H), 2.33-2.21 (m, 6H), 2.16 (d, J=8.8 Hz, 1H), 1.95 (br. s., 1H), 1.50 (br. s., 1H), 1.45-1.38 (m, 4H), 1.32 (br. s., 3H), 1.18 (d, J=14.3 Hz, 1H), 1.12 (s, 9H), 1.02 (d, J=11.4 Hz, 1H), 0.85 (br. s., 3H), 0.62 (br. s., 3H). LCMS (M+H)=690.3.

EXAMPLE 28

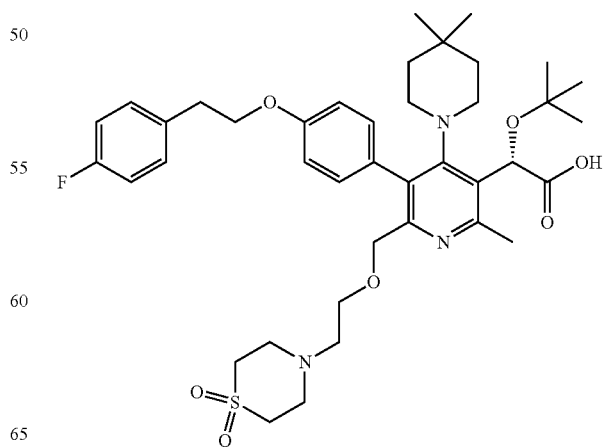

(S)-2-(tert-Butoxy)-2-(4-(4,4-dimethylpiperidin-1-yl)-6-((2-(1,1-dioxidothiomorpholino)ethoxy)methyl)-5-(4-(4-fluorophenethoxy)phenyl)-2-methylpyridin-3-yl)acetic acid: To a solution of 4-(2-hydroxyethyl)thiomorpholine 1,1-dioxide (13.11 mg, 0.073 mmol) in THF (1) at 0° C. was added NaH (2.93 mg, 0.073 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (25 mg, 0.037 mmol) in THF (0.5 mL) was then added and the mixture was stirred for 4 h. At this point LCMS indicated completion of reaction. Mixture was then concentrated and treated with 10N NaOH (0.037 mL, 0.366 mmol) in ethanol (1 mL) at 80° C. for 16 h. Mixture was then cooled and purified by prep HPLC to afford (S)-2-(tert-butoxy)-2-(4-(4,4-dimethylpiperidin-1-yl)-6-((2-(1,1-dioxidothiomorpholino)ethoxy)methyl)-5-(4-(4-fluorophenethoxy)phenyl)-2-methylpyridin-3-yl)acetic acid (19.3 mg, 0.026 mmol, 71.3% yield). $^1$H NMR (500 MHz, DMSO-$d_6$) δ 7.41-7.33 (m, 2H), 7.26 (d, J=8.1 Hz, 1H), 7.14 (t, J=8.6 Hz, 2H), 7.08-6.96 (m, 3H), 5.79 (br. s., 1H), 4.30-4.18 (m, 2H), 4.15 (d, J=10.3 Hz, 1H), 4.01 (d, J=9.9 Hz, 1H), 3.30 (dd, J=13.0, 5.3 Hz, 2H), 3.06 (t, J=6.8 Hz, 2H), 3.04-2.97 (m, 4H), 2.85 (br. s., 4H), 2.83-2.78 (m, 1H), 2.56-2.53 (m, 3H), 2.47 (s, 3H), 2.17 (d, J=12.5 Hz, 1H), 1.91 (s, 1H), 1.50 (br. s., 1H), 1.30 (br. s., 1H), 1.18 (d, J=13.6 Hz, 1H), 1.12 (s, 9H), 1.02 (d, J=13.2 Hz, 1H), 0.85 (br. s., 3H), 0.61 (br. s., 3H). LCMS (M+H)=740.2.

EXAMPLE 29

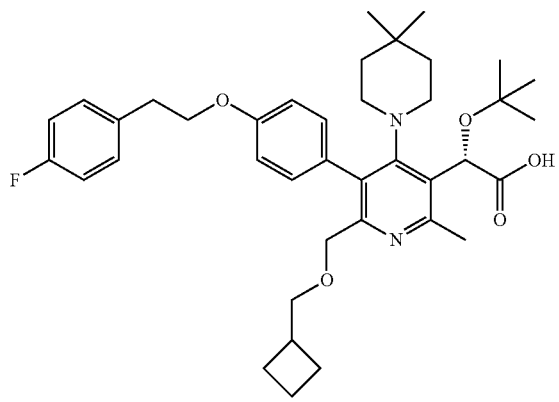 [SMILES: Cc1nc(COCC2CCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((cyclobutylmethoxy)methyl)-4-(4,4-dimethylpiperidin-1-yl)-5-(4-(4-fluorophenethoxy)phenyl)-2-methylpyridin-3-yl)acetic acid: To a solution of cyclobutylmethanol (6.30 mg, 0.073 mmol) in THF (1) at 0° C. was added NaH (2.93 mg, 0.073 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (25 mg, 0.037 mmol) in THF (0.5 mL) was then added and the mixture was stirred for 16 h. At this point LCMS indicated completion of reaction. Mixture was then concentrated and treated with 10N NaOH (0.037 mL, 0.366 mmol) in ethanol (1 mL) at 80° C. for 4 h. Mixture was then cooled and purified by prep HPLC to afford (S)-2-(tert-butoxy)-2-(6-((cyclobutylmethoxy)methyl)-4-(4,4-dimethylpiperidin-1-yl)-5-(4-(4-fluorophenethoxy)phenyl)-2-methylpyridin-3-yl)acetic acid (19.9 mg, 0.031 mmol, 84% yield). $^1$H NMR (500 MHz, DMSO-$d_6$) δ 7.38 (dd, J=8.3, 5.7 Hz, 2H), 7.26 (d, J=8.4 Hz, 1H), 7.14 (t, J=8.8 Hz, 2H), 7.08-6.97 (m, 3H), 5.80 (br. s., 1H), 4.30-4.17 (m, 2H), 4.10 (d, J=9.5 Hz, 1H), 3.95 (d, J=9.5 Hz, 1H), 3.36 (br. s., 2H), 3.14 (d, J=6.6 Hz, 2H), 3.05 (t, J=6.6 Hz, 2H), 2.85-2.78 (m, 1H), 2.47 (s, 3H), 2.35 (dt, J=14.8, 7.5 Hz, 1H), 2.17 (d, J=11.4 Hz, 1H), 1.97-1.84 (m, 3H), 1.83-1.67 (m, 2H), 1.63-1.46 (m, 3H), 1.34-1.23 (m, 1H), 1.19 (d, J=9.9 Hz, 1H), 1.12 (s, 9H), 1.02 (d, J=11.4 Hz, 1H), 0.85 (s, 3H), 0.61 (s, 3H). LCMS (M+H)=647.2.

EXAMPLE 30

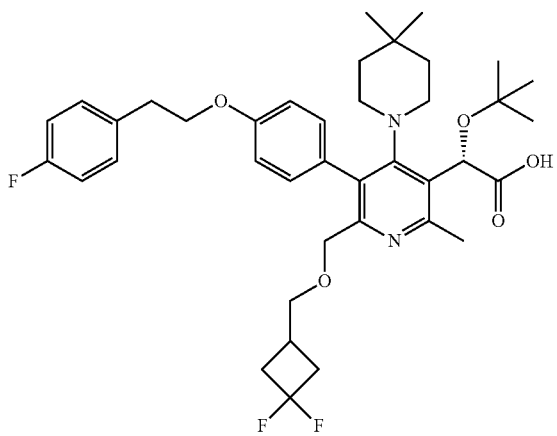 [SMILES: Cc1nc(COCC2CC(F)(F)C2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-(((3,3-difluorocyclobutyl)methoxy)methyl)-4-(4,4-dimethylpiperidin-1-yl)-5-(4-(4-fluorophenethoxy)phenyl)-2-methylpyridin-3-yl)acetic acid: To a solution of (3,3-difluorocyclobutyl)methanol (8.93 mg, 0.073 mmol) in THF (1) at 0° C. was added NaH (2.93 mg, 0.073 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (25 mg, 0.037 mmol) in THF (0.5 mL) was then added and the mixture was stirred for 16 h. At this point LCMS indicated completion of reaction. Mixture was then concentrated and treated with 10N NaOH (0.037 mL, 0.366 mmol) in ethanol (1 mL) at 80° C. for 4 h. Mixture was then cooled and purified by prep HPLC to afford (S)-2-(tert-butoxy)-2-(6-(((3,3-difluorocyclobutyl)methoxy)methyl)-4-(4,4-dimethylpiperidin-1-yl)-5-(4-(4-fluorophenethoxy)phenyl)-2-methylpyridin-3-yl)acetic acid (21.7 mg, 0.032 mmol, 87% yield). $^1$H NMR (500 MHz, DMSO-$d_6$) δ 7.41-7.34 (m, 2H), 7.24 (d, J=8.1 Hz, 1H), 7.14 (t, J=8.6 Hz, 2H), 7.03 (s, 2H), 6.99 (d, J=8.4 Hz, 1H), 5.65 (br. s., 1H), 4.28-4.18 (m, 2H), 4.15 (d, J=9.9 Hz, 1H), 4.00 (d, J=9.9 Hz, 1H), 3.60 (br. s., 1H), 3.60 (br. s., 2H), 3.23 (d, J=5.1 Hz, 2H), 3.05 (t, J=6.6 Hz, 2H), 2.82-2.75 (m, 1H), 2.46 (s, 3H), 2.28-2.07 (m, 4H), 1.90 (s, 1H), 1.51 (br. s., 1H), 1.29 (br. s., 1H), 1.16 (d, J=11.7 Hz, 1H), 1.10 (s, 9H), 1.01 (d, J=11.0 Hz, 1H), 0.85 (s, 3H), 0.62 (s, 3H). LCMS (M+H)=683.3.

EXAMPLE 31, 32 and 33

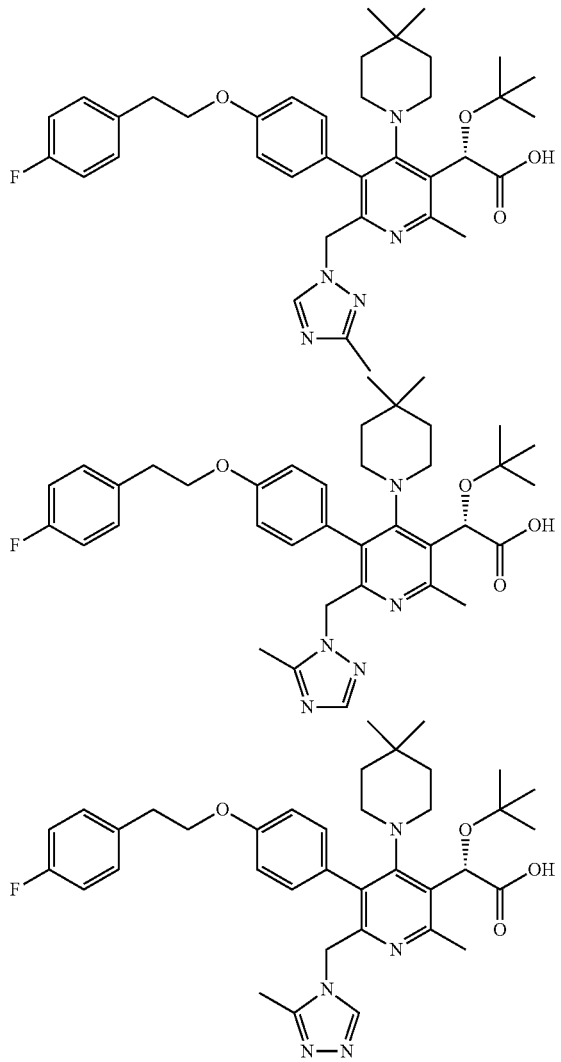

(S)-2-(tert-Butoxy)-2-(4-(4,4-dimethylpiperidin-1-yl)-5-(4-(4-fluorophenethoxy)phenyl)-2-methyl-6-((3-methyl-1H-1,2,4-triazol-1-yl)methyl)pyridin-3-yl)acetic acid, (S)-2-(tert-butoxy)-2-(4-(4,4-dimethylpiperidin-1-yl)-5-(4-(4-fluorophenethoxy)phenyl)-2-methyl-6-((5-methyl-1H-1,2,4-triazol-1-yl)methyl)pyridin-3-yl)acetic acid & (S)-2-(tert-butoxy)-2-(4-(4,4-dimethylpiperidin-1-yl)-5-(4-(4-fluorophenethoxy)phenyl)-2-methyl-6-((3-methyl-4H-1,2,4-triazol-4-yl)methyl)pyridin-3-yl)acetic acid: To a solution of 3-methyl-1H-1,2,4-triazole (45.6 mg, 0.548 mmol) in THF (2 mL) at 0° C. was added NaH (21.94 mg, 0.548 mmol) and the resulting mixture was stirred for 10 min. (S)-Isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (75 mg, 0.110 mmol) in THF (0.5 mL) was then added and the mixture was stirred for 16 h. At this point LCMS indicated completion of reaction. Mixture was then concentrated and treated with 10N NaOH (0.110 mL, 1.097 mmol) in Ethanol (1 mL) at 80° C. for 4 h. Mixture was then cooled and purified by prep HPLC to afford three compounds: (S)-2-(tert-butoxy)-2-(4-(4,4-dimethylpiperidin-1-yl)-5-(4-(4-fluorophenethoxy)phenyl)-2-methyl-6-((3-methyl-1H-1,2,4-triazol-1-yl)methyl)pyridin-3-yl)acetic acid (8 mg, 0.012 mmol, 10.76% yield). $^1$H NMR (500 MHz, DMSO-$d_6$) δ 8.02 (s, 1H), 7.39 (dd, J=8.1, 5.9 Hz, 2H), 7.32 (d, J=8.1 Hz, 1H), 7.15 (t, J=8.8 Hz, 2H), 7.12-7.03 (m, 3H), 5.62 (br. s., 1H), 4.91 (d, J=16.1 Hz, 1H), 4.74 (d, J=15.8 Hz, 1H), 4.35-4.14 (m, 2H), 3.62 (br. s., 1H), 3.07 (t, J=6.6 Hz, 2H), 2.76 (br. s., 1H), 2.38 (s, 3H), 2.19 (br. s., 1H), 2.10 (s, 3H), 1.90 (br.s, 1H), 1.51 (br. s., 1H), 1.29 (br. s., 1H), 1.16 (d, J=10.6 Hz, 1H), 1.09 (s, 9H), 1.02 (d, J=12.5 Hz, 1H), 0.85 (br. s., 3H), 0.62 (s, 3H). LCMS (M+H)=644.2.

(S)-2-(tert-butoxy)-2-(4-(4,4-dimethylpiperidin-1-yl)-5-(4-(4-fluorophenethoxy)-phenyl)-2-methyl-6-((5-methyl-1H-1,2,4-triazol-1-yl)methyl)pyridin-3-yl)acetic acid (3.2 mg, 4.72 μmol, 4.30% yield): $^1$H NMR (500 MHz, METHANOL-$d_4$) δ 7.84 (s, 1H), 7.36 (dd, J=8.4, 5.5 Hz, 2H), 7.27 (d, J=8.2 Hz, 1H), 7.09-7.01 (m, 3H), 7.01-6.91 (m, 2H), 6.02 (s, 1H), 5.21 (d, J=14.7 Hz, 1H), 5.06 (d, J=14.7 Hz, 1H), 4.27 (td, J=6.6, 2.9 Hz, 2H), 3.12 (t, J=6.6 Hz, 2H), 2.58 (s, 3H), 2.26 (s, 3H), 1.33 (d, J=7.4 Hz, 3H), 1.22 (s, 9H), 0.79 (br. s., 6H). 4 piperidine hydrogens are not resolved. LCMS (M+H)=644.2.

(S)-2-(tert-butoxy)-2-(4-(4,4-dimethylpiperidin-1-yl)-5-(4-(4-fluorophenethoxy)-phenyl)-2-methyl-6-((3-methyl-4H-1,2,4-triazol-4-yl)methyl)pyridin-3-yl)acetic acid (2.1 mg, 3.10 μmol, 2.82% yield): $^1$H NMR (500 MHz, METHANOL-$d_4$) δ 7.74 (s, 1H), 7.36 (dd, J=8.4, 5.7 Hz, 2H), 7.20-7.14 (m, 1H), 7.10-6.99 (m, 5H), 6.01 (s, 1H), 5.09 (s, 2H), 4.27 (td, J=6.6, 3.2 Hz, 2H), 3.15-3.07 (m, 2H), 2.54 (s, 3H), 2.18 (s, 3H), 1.32 (t, J=7.2 Hz, 3H), 1.21 (s, 9H), 0.78 (br. s., 6H). 4 piperidine hydrogens are not resolved. LCMS (M+H)=644.2.

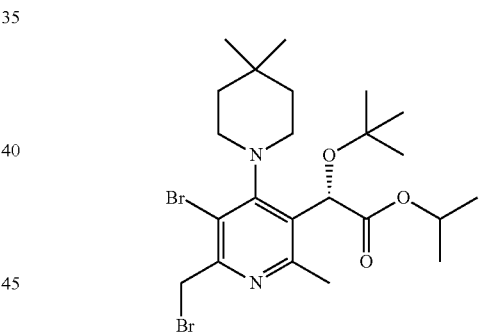

(S)-Isopropyl 2-(5-bromo-6-(bromomethyl)-4-(4,4-dimethylpiperidin-1-yl)-2-methylpyridin-3-yl)-2-(tert-butoxy)acetate: To a solution of (S)-isopropyl 2-(5-bromo-4-(4,4-dimethylpiperidin-1-yl)-6-(hydroxymethyl)-2-methylpyridin-3-yl)-2-(tert-butoxy)acetate (500 mg, 1.030 mmol) in $CH_2Cl_2$ (10 mL) was added $CBr_4$ (376 mg, 1.133 mmol) followed by $Ph_3P$ (297 mg, 1.133 mmol) and the resulting mixture was stirred at roomtep for 16 h. Water (2 mL) was then added and the mixture was extracted with dichloromethane (10 mL), dried ($Na_2SO_4$), filtered and concentrated. The residue was then purified by Biotage (5-30% EtOAc/hexane) to afford (S)-isopropyl 2-(5-bromo-6-(bromomethyl)-4-(4,4-dimethylpiperidin-1-yl)-2-methylpyridin-3-yl)-2-(tert-butoxy)acetate (350 mg, 0.638 mmol, 62.0% yield) as white solid. $^1$H NMR (500 MHz, $CDCl_3$) δ 6.25 (br. s., 1H), 5.14-4.94 (m, 1H), 4.76 (d, J=9.6 Hz, 1H), 4.69 (d, J=9.6 Hz, 1H), 4.04 (br. s., 1H), 3.51 (t, J=11.9 Hz, 1H), 2.91 (d, J=11.5 Hz, 1H), 2.66 (d, J=12.1 Hz, 1H), 2.58 (s, 3H), 1.68-1.55 (m, 2H), 1.47 (d, J=12.5 Hz, 1H), 1.37 (d, J=12.8 Hz, 1H), 1.26-1.23 (m, 3H), 1.22 (s, 9H), 1.16 (d, J=6.1 Hz, 3H), 1.09 (s, 3H), 1.04 (s, 3H). LCMS (M+2H) =549.2.

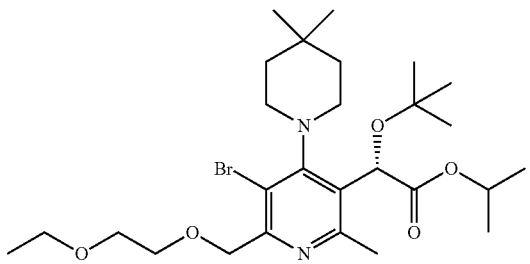 [SMILES: CCOCCOCc1nc(C)c([C@H](OC(C)(C)C)C(=O)OC(C)C)c(N2CCC(C)(C)CC2)c1Br]

(S)-Isopropyl 2-(5-bromo-4-(4,4-dimethylpiperidin-1-yl)-6-((2-ethoxyethoxy)methyl)-2-methylpyridin-3-yl)-2-(tert-butoxy)acetate: To a solution of anhydrous 2-ethoxyethanol (99 mg, 1.094 mmol) in THF (5 mL) at 0° C. was added NaH (43.8 mg, 1.094 mmol) and the resulting mixture was stirred for 10 min. (S)-Isopropyl 2-(5-bromo-6-(bromomethyl)-4-(4,4-dimethylpiperidin-1-yl)-2-methylpyridin-3-yl)-2-(tert-butoxy)acetate (300 mg, 0.547 mmol) in THF (5 mL) was then added and the mixture was stirred for 16 h. At this point LCMS indicated completion of reaction. Water was then added and the mixture was extracted with ether, dried (Na₂SO₄), filtered and concentrated. The residue was then purified by Biotage (5-30% EtOAc/hexane) to afford (S)-isopropyl 2-(5-bromo-4-(4,4-dimethylpiperidin-1-yl)-6-((2-ethoxyethoxy)methyl)-2-methylpyridin-3-yl)-2-(tert-butoxy)acetate (200 mg, 0.359 mmol, 65.6% yield) as viscous oil. ¹H NMR (500 MHz, CDCl₃) δ 5.05 (dt, J=12.5, 6.2 Hz, 1H), 4.87-4.68 (m, 2H), 4.07 (br. s., 1H), 3.86-3.76 (m, 2H), 3.73-3.65 (m, 2H), 3.62-3.55 (m, 2H), 3.55-3.43 (m, 1H), 2.95-2.86 (m, 1H), 2.65 (d, J=11.5 Hz, 1H), 2.59 (s, 3H), 1.64-1.52 (m, 2H), 1.50-1.41 (m, 1H), 1.36 (d, J=12.5 Hz, 1H), 1.26-1.21 (m, 5H), 1.21 (s, 9H), 1.15 (d, J=6.1 Hz, 3H), 1.09 (s, 3H), 1.04 (s, 3H). LCMS (M+2H)=559.3.

EXAMPLE 34 and 35

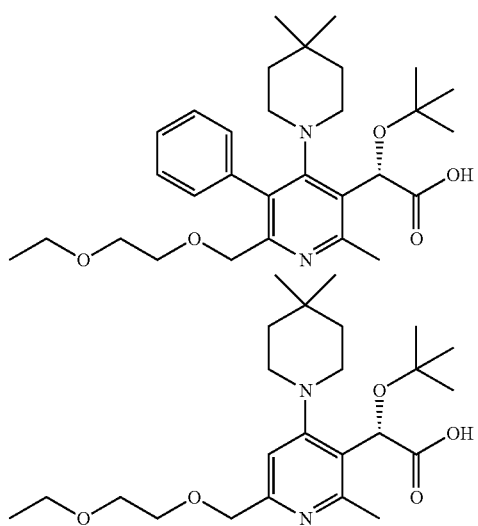

(S)-2-(tert-Butoxy)-2-(4-(4,4-dimethylpiperidin-1-yl)-6-((2-ethoxyethoxy)methyl)-2-methyl-5-phenylpyridin-3-yl)

acetic acid & (S)-2-(tert-butoxy)-2-(4-(4,4-dimethylpiperidin-1-yl)-6-((2-ethoxyethoxy)methyl)-2-methylpyridin-3-yl)acetic acid: A mixture of (S)-isopropyl 2-(5-bromo-4-(4,4-dimethylpiperidin-1-yl)-6-((2-ethoxyethoxy)methyl)-2-methylpyridin-3-yl)-2-(tert-butoxy)acetate (30 mg, 0.054 mmol), phenylboronic acid (19.68 mg, 0.161 mmol) and 2M Na₂CO₃ (0.081 mL, 0.161 mmol) in DMF (3 mL) was degassed by bubbling N₂ through the reaction mixture for 10 min. Then, Pd(Ph₃P)₄ (6.22 mg, 5.38 µmol) was added, degassed for 5 min and placed in pre-heated oil-bath at 100° C. After 3 h at 130° C., the reaction mixture was cooled, diluted with water, extracted with ether, dried (Na₂SO₄), filtered and concentrated. The residue was then treated with 10N NaOH (0.054 mL, 0.538 mmol) in EtOH (1 mL) at 80° C. for 3 h. Mixture was then cooled and purified by prep HPLC to give two compounds. (S)-2-(tert-butoxy)-2-(4-(4,4-dimethylpiperidin-1-yl)-6-((2-ethoxyethoxy)methyl)-2-methyl-5-phenylpyridin-3-yl)acetic acid (7.7 mg, 0.015 mmol, 27.9% yield): ¹H NMR (500 MHz, DMSO-d₆) δ 7.52-7.36 (m, 4H), 7.17 (d, J=7.0 Hz, 1H), 5.86 (br. s., 1H), 4.15 (d, J=9.9 Hz, 1H), 3.99 (d, J=9.9 Hz, 1H), 3.37-3.33 (m, 6H), 3.28 (d, J=4.0 Hz, 2H), 2.85-2.76 (m, 1H), 2.49 (s, 3H), 2.17 (br. s., 1H), 1.85 (t, J=11.2 Hz, 1H), 1.49 (br. s., 1H), 1.34-1.24 (m, 1H), 1.19 (d, J=12.1 Hz, 1H), 1.14 (s, 9H), 1.09-1.03 (m, 3H), 0.99 (d, J=12.8 Hz, 1H), 0.85 (br. s., 3H), 0.58 (s, 3H). LCMS (M+H)=513.1. And (S)-2-(tert-butoxy)-2-(4-(4,4-dimethylpiperidin-1-yl)-6-((2-ethoxyethoxy)methyl)-2-methylpyridin-3-yl)acetic acid (1.6 mg, 3.66 µmol, 6.81% yield): ¹H NMR (500 MHz, DMSO-d₆) δ 7.06 (s, 1H), 5.58 (s, 1H), 4.46 (s, 2H), 3.62 (d, J=4.4 Hz, 2H), 3.58-3.51 (m, 2H), 3.46 (q, J=7.3 Hz, 2H), 3.36 (br. s., 1H), 3.23 (br. s., 2H), 2.66 (br. s., 2H), 2.37 (s, 3H), 1.55 (d, J=7.3 Hz, 2H), 1.45 (br. s., 2H), 1.16-1.11 (m, 2H), 1.10 (s, 9H), 1.00 (s, 6H). LCMS (M+H)=437.1.

EXAMPLE 36 and 37

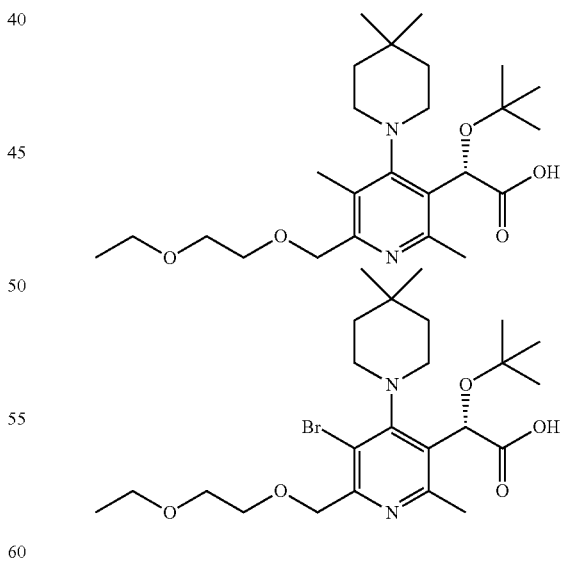

(S)-2-(tert-Butoxy)-2-(4-(4,4-dimethylpiperidin-1-yl)-6-((2-ethoxyethoxy)methyl)-2,5-dimethylpyridin-3-yl)acetic acid & (S)-2-(5-bromo-4-(4,4-dimethylpiperidin-1-yl)-6-((2-ethoxyethoxy)methyl)-2-methylpyridin-3-yl)-2-(tert-butoxy)acetic acid: A mixture of (S)-isopropyl 2-(5-bromo-4-(4,4-dimethylpiperidin-1-yl)-6-((2-ethoxyethoxy)methyl)-2-methylpyridin-3-yl)-2-(tert-butoxy)acetate (60 mg, 0.108 mmol), methylboronic acid (32.2 mg, 0.538 mmol) and 2M Na₂CO₃ (0.269 mL, 0.538 mmol) in DMF (3 mL) was degassed by bubbling N₂ through the reaction mixture for 10 min. Then, Pd(Ph₃P)₄ (12.44 mg, 10.76 μmol) was added, degassed for 5 min and placed in pre-heated oil-bath at 100° C. After 3 h at 100° C., the reaction mixture was cooled, diluted with ethyl acetate and washed water, brine, dried (Na₂SO₄), filtered and concentrated. The residue was then treated with 10N NaOH (0.108 mL, 1.076 mmol) in ethanol (2 mL) at 80° C. for 3 h. Mixture was then cooled and purified by prep HPLC to afford two compounds. (S)-2-(tert-butoxy)-2-(4-(4,4-dimethylpiperidin-1-yl)-6-((2-ethoxyethoxy)methyl)-2,5-dimethylpyridin-3-yl)acetic acid (1.8 mg, 3.99 μmol, 3.71% yield): ¹H NMR (500 MHz, DMSO-d₆) δ 5.93 (br. s., 1H), 4.57-4.41 (m, 2H), 3.63-3.52 (m, 2H), 3.49 (t, J=4.6 Hz, 3H), 3.45-3.28 (m, 3H), 3.16 (t, J=11.2 Hz, 1H), 3.04 (br. s., 1H), 2.64 (br. s., 1H), 2.41 (s, 3H), 2.30 (s, 3H), 1.68-1.50 (m, 2H), 1.39 (d, J=12.1 Hz, 1H), 1.30 (d, J=11.4 Hz, 1H), 1.13 (s, 9H), 1.09 (t, J=7.0 Hz, 3H), 1.02 (br. s., 3H), 0.98 (br. s., 3H). LCMS (M+H)=451.1. And (S)-2-(5-bromo-4-(4,4-dimethylpiperidin-1-yl)-6-((2-ethoxyethoxy)methyl)-2-methylpyridin-3-yl)-2-(tert-butoxy)acetic acid (1.6 mg, 3.10 μmol, 2.88% yield): ¹H NMR (500 MHz, DMSO-d₆) δ 5.89 (br. s., 1H), 4.67-4.48 (m, 2H), 3.95 (t, J=11.2 Hz, 1H), 3.67-3.59 (m, 2H), 3.51 (t, J=4.8 Hz, 2H), 3.45-3.38 (m, 2H), 3.38-3.26 (m, 1H), 3.01 (d, J=9.5 Hz, 1H), 2.58-2.55 (m, 1H), 2.45 (s, 3H), 1.63-1.46 (m, 2H), 1.41 (d, J=12.1 Hz, 1H), 1.30 (d, J=12.5 Hz, 1H), 1.14 (s, 9H), 1.11-1.07 (m, 3H), 1.03 (s, 3H), 0.98 (s, 3H). LCMS (M+H)=515.0.

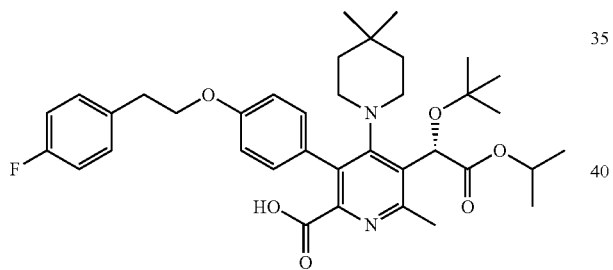

(S)-5-(1-(tert-Butoxy)-2-isopropoxy-2-oxoethyl)-4-(4,4-dimethylpiperidin-1-yl)-3-(4-(4-fluorophenethoxy)phenyl)-6-methylpicolinic acid: To a solution of (S)-isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate (900 mg, 1.454 mmol) in DMSO (25 mL) was added KH₂PO₄ (1386 mg, 10.18 mmol) in water (10 mL) followed by sodium chlorite (1052 mg, 11.64 mmol) in water (10 mL) and the mixture was stirred for 48 h. The mixture was then saturated with brine and extracted with ethyl acetate, dried (Na₂SO₄), filtered and concentrated. The residue was then purified by Biotage (5-100% EtOAc/hexane) to afford (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (500 mg, 0.788 mmol, 54.2% yield) as off-white solid. ¹H NMR (500 MHz, CDCl₃) δ 7.30-7.23 (m, 3H), 7.09-7.02 (m, 3H), 6.96 (d, J=8.4 Hz, 2H), 6.05 (br. s., 1H), 5.13 (dt, J=12.4, 6.2 Hz, 1H), 4.30-4.18 (m, 2H), 3.16-3.07 (m, 3H), 2.67 (s, 3H), 2.64 (s, 4H), 1.30-1.23 (m, 9H), 1.20 (s, 9H), 0.81 (br. s., 6H). LCMS (M+H)=635.3.

EXAMPLE 38

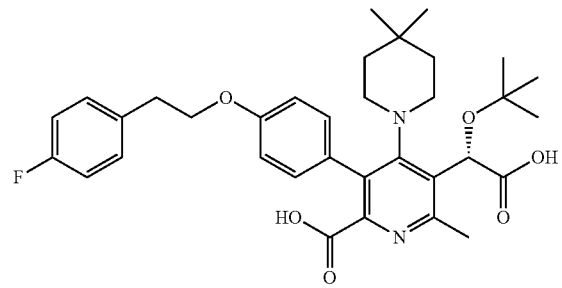 [SMILES: Cc1nc(C(=O)O)c(-c2ccc(OCCc3ccc(F)cc3)cc2)c(N2CCC(C)(C)CC2)c1[C@H](OC(C)(C)C)C(=O)O]

(S)-5-(tert-Butoxy(carboxy)methyl)-4-(4,4-dimethylpiperidin-1-yl)-3-(4-(4-fluorophenethoxy)phenyl)-6-methylpicolinic acid: A mixture of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (20 mg, 0.032 mmol) and 10N NaOH (0.032 mL, 0.315 mmol) in Ethanol (1 mL) was heated at 80° C. for 3 h. Mixture was then cooled and purified by prep HPLC to afford (S)-5-(tert-butoxy(carboxy)methyl)-4-(4,4-dimethylpiperidin-1-yl)-3-(4-(4-fluorophenethoxy)phenyl)-6-methylpicolinic acid (12.7 mg, 0.021 mmol, 68.0% yield). ¹H NMR (500 MHz, DMSO-d₆) δ 7.37 (dd, J=8.4, 5.5 Hz, 2H), 7.19 (d, J=8.4 Hz, 1H), 7.16-7.06 (m, 3H), 6.94 (d, J=8.4 Hz, 1H), 6.97 (d, J=8.1 Hz, 1H), 5.79 (s, 1H), 4.28-4.14 (m, 2H), 3.48 (br. s., 1H), 3.04 (t, J=6.6 Hz, 2H), 2.46 (s, 3H), 1.25 (br. s., 3H), 1.12 (s, 9H), 0.74 (br. s., 6H). 4 piperidin hydrogens are not resolved. LCMS (M+H)=593.2.

EXAMPLE 39

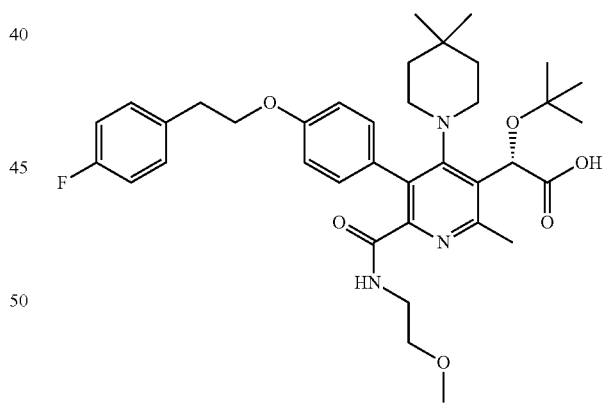

(S)-2-(tert-Butoxy)-2-(4-(4,4-dimethylpiperidin-1-yl)-5-(4-(4-fluorophenethoxy)phenyl)-6-((2-methoxyethyl)carbamoyl)-2-methylpyridin-3-yl)acetic acid: To a solution of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (40 mg, 0.063 mmol) and 2-methoxyethanamine (9.47 mg, 0.126 mmol) in DMF (1 mL) was added DIEA (0.055 mL, 0.315 mmol) followed by HATU (47.9 mg, 0.126 mmol) and the resulting mixture was stirred at room temp for 2 h. Water was then added and the mixture was extracted with ethyl acetate, dried (Na₂SO₄), filtered and concentrated. The residue was then treated with 10N NaOH (0.063 mL, 0.630 mmol) in ethanol (1 mL) at 80° C. for 3 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-6-((2-methoxyethyl)carbamoyl)-2-methylpyridin-3-yl)acetic acid (23.2 mg, 0.036 mmol, 56.7% yield). $^1$H NMR (500 MHz, DMSO-d$_6$) δ 8.15 (br. s., 1H), 7.43-7.29 (m, 2H), 7.21-7.05 (m, 4H), 6.97 (d, J=7.7 Hz, 1H), 6.91 (d, J=8.4 Hz, 1H), 5.75 (br. s., 1H), 4.26-4.12 (m, 2H), 3.48 (br. s., 2H), 3.09-2.96 (m, 7H), 2.85 (br. s., 1H), 2.48 (s, 3H), 2.13 (br. s., 1H), 1.96 (br. s., 1H), 1.52 (br. s., 1H), 1.29 (br. s., 1H), 1.27-1.17 (m, 1H), 1.13 (s, 9H), 1.03 (d, J=11.7 Hz, 1H), 0.86 (br. s., 3H), 0.64 (br. s., 3H). LCMS (M+H)=650.1.

EXAMPLE 40

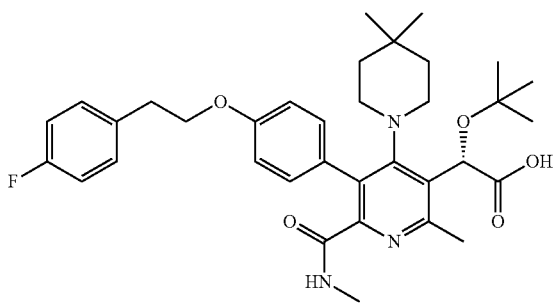 [SMILES: CNC(=O)c1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-5-(4-(4-fluorophenethoxy)phenyl)-2-methyl-6-(methylcarbamoyl)pyridin-3-yl)acetic acid: To a solution of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (20 mg, 0.032 mmol) and methanamine (0.032 mL, 0.063 mmol) in DMF (1 mL) was added DIEA (0.028 mL, 0.158 mmol) followed by HATU (23.96 mg, 0.063 mmol) and the resulting mixture was stirred at room temp for 16 h. Water was then added and the mixture was extracted with ethyl acetate, dried (Na$_2$SO$_4$), filtered and concentrated. The residue was then treated with 10N NaOH (0.032 mL, 0.315 mmol) in ethanol (1 mL) at 80° C. for 3 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(methylcarbamoyl)pyridin-3-yl)acetic acid (7.2 mg, 0.012 mmol, 37.7% yield). $^1$H NMR (500 MHz, DMSO-d$_6$) δ 8.04 (d, J=4.8 Hz, 1H), 7.37 (dd, J=8.6, 5.7 Hz, 2H), 7.14 (q, J=9.2 Hz, 3H), 7.07 (d, J=8.4 Hz, 1H), 6.96 (d, J=8.1 Hz, 1H), 6.92-6.86 (m, 1H), 5.74 (s, 1H), 4.28-4.12 (m, 2H), 3.04 (t, J=6.8 Hz, 2H), 2.84 (br. s., 1H), 2.48 (s, 3H), 2.45 (d, J=4.8 Hz, 3H), 2.13 (br. s., 1H), 1.52 (br. s., 1H), 1.29 (br. s., 1H), 1.27-1.15 (m, 3H), 1.13 (s, 9H), 1.06-0.96 (m, 1H), 0.86 (br. s., 3H), 0.63 (br. s., 3H). LCMS (M+H)=606.2.

EXAMPLE 41

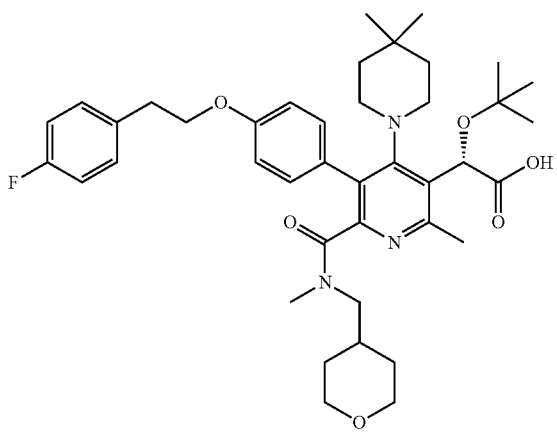 [SMILES: Cc1nc(C(=O)N(C)CC2CCOCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(methyl((tetrahydro-2H-pyran-4-yl)methyl)carbamoyl)pyridin-3-yl)acetic acid: To a solution of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (40 mg, 0.063 mmol) and N-methyl-1-(tetrahydro-2H-pyran-4-yl)methanamine (16.28 mg, 0.126 mmol) in DMF (1 mL) was added DIEA (0.055 mL, 0.315 mmol) followed by HATU (47.9 mg, 0.126 mmol) and the resulting mixture was stirred at room temp for 16 h. Water was then added and the mixture was extracted with ethyl acetate, dried (Na$_2$SO$_4$), filtered and concentrated. The residue was then treated with 10N NaOH (0.063 mL, 0.630 mmol) in ethanol (1 mL) at 80° C. for 3 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(methyl((tetrahydro-2H-pyran-4-yl)methyl)carbamoyl)pyridin-3-yl)acetic acid (13.2 mg, 0.019 mmol, 29.8% yield). $^1$H NMR (500 MHz, DMSO-d$_6$) δ 7.36 (dd, J=8.4, 5.5 Hz, 2H), 7.17 (d, J=8.1 Hz, 1H), 7.12 (t, J=8.8 Hz, 2H), 6.94 (d, J=8.4 Hz, 1H), 6.97 (d, J=8.4 Hz, 2H), 5.77 (s, 1H), 4.24-4.07 (m, 3H), 3.58 (d, J=10.3 Hz, 1H), 3.06-2.94 (m, 5H), 2.90 (s, 1H), 2.55 (s, 3H), 2.47 (s, 3H), 2.16 (br. s., 1H), 1.47 (br. s., 2H), 1.25 (br. s., 3H), 1.12 (s, 9H), 1.11 (s, 2H), 1.03 (br. s., 2H), 0.85 (br. s., 3H), 0.63 (br. s., 3H). 4 piperidine hydrogens are not resolved. LCMS (M+H)=704.2.

EXAMPLE 42

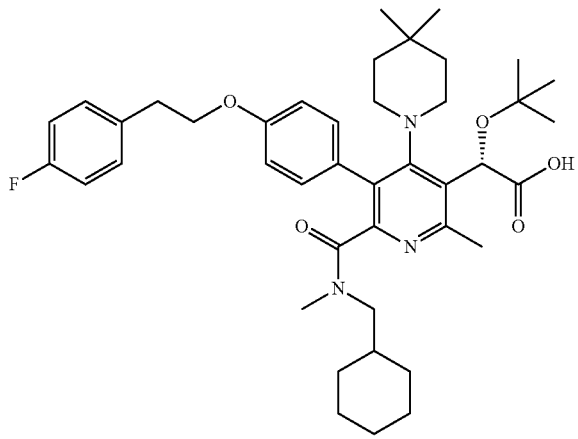 [SMILES: Cc1nc(C(=O)N(C)CC2CCCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((cyclohexylmethyl)(methyl)carbamoyl)-4-(4,4-dimethylpiperidin-1-yl)-5-(4-(4-fluorophenethoxy)phenyl)-2-methylpyridin-3-yl)acetic acid: To a solution of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (20 mg, 0.032 mmol) and 1-cyclohexyl-N-methylmethanamine (8.02 mg, 0.063 mmol) in DMF (1 mL) was added DIEA (0.028 mL, 0.158 mmol) followed by HATU (23.96 mg, 0.063 mmol) and the resulting mixture was stirred at room temp for 16 h. Water was then added and the mixture was extracted with ethyl acetate, dried ($Na_2SO_4$), filtered and concentrated. The residue was then treated with 10N NaOH (0.032 mL, 0.315 mmol) in ethanol (1 mL) at 80° C. for 3 h. Mixture was then cooled and purified by prep HPLC to afford (S)-2-(tert-butoxy)-2-(6-((cyclohexylmethyl)(methyl)carbamoyl)-4-(4,4-dimethylpiperidin-1-yl)-5-(4-(4-fluorophenethoxy)phenyl)-2-methylpyridin-3-yl)acetic acid (7.4 mg, 10.54 μmol, 33.5% yield). $^1$H NMR (500 MHz, DMSO-$d_6$) δ 7.35 (dd, J=8.4, 5.5 Hz, 2H), 7.18-7.06 (m, 4H), 6.98 (dd, J=8.4, 2.6 Hz, 1H), 6.92 (dd, J=8.4, 2.6 Hz, 1H), 5.76-5.60 (m, 1H), 4.26-4.05 (m, 2H), 3.03 (t, J=6.4 Hz, 2H), 2.85 (br. s., 1H), 2.53 (br. s., 1H), 2.47 (s, 2H), 2.15 (br. s., 1H), 1.54 (br. s., 2H), 1.42 (br. s., 3H), 1.23 (d, J=11.4 Hz, 3H), 1.12 (s, 9H), 1.06-1.00 (m, 2H), 0.96-0.78 (m, 7H), 0.64 (br. s., 4H), 0.61-0.46 (m, 2H). six piperidine hydrogens are not resolved. LCMS (M+H)=702.3.

EXAMPLE 43

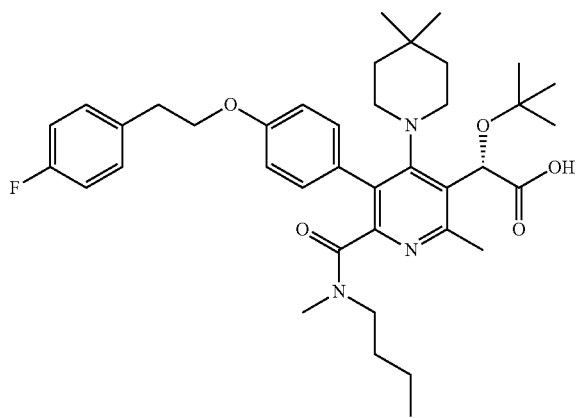 [SMILES: CCCCN(C)C(=O)c1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(6-(butyl(methyl)carbamoyl)-4-(4,4-dimethylpiperidin-1-yl)-5-(4-(4-fluorophenethoxy)phenyl)-2-methylpyridin-3-yl)acetic acid: To a solution of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (20 mg, 0.032 mmol) and N-methylbutan-1-amine (5.49 mg, 0.063 mmol) in DMF (1 mL) was added DIEA (0.028 mL, 0.158 mmol) followed by HATU (23.96 mg, 0.063 mmol) and the resulting mixture was stirred at room temp for 16 h. Water was then added and the mixture was extracted with ethyl acetate, dried ($Na_2SO_4$), filtered and concentrated. The residue was then treated with 10N NaOH (0.032 mL, 0.315 mmol) in ethanol (1 mL) at 80° C. for 3 h. Mixture was then cooled and purified by prep HPLC to afford (S)-2-(tert-butoxy)-2-(6-(butyl(methyl)carbamoyl)-4-(4,4-dimethylpiperidin-1-yl)-5-(4-(4-fluorophenethoxy)phenyl)-2-methylpyridin-3-yl)acetic acid (11.9 mg, 0.018 mmol, 57.1% yield). $^1$H NMR (500 MHz, DMSO-$d_6$) δ 7.41-7.30 (m, 2H), 7.17-7.03 (m, 4H), 7.01-6.96 (m, 1H), 6.93 (dd, J=8.3, 2.8 Hz, 1H), 5.69-5.63 (m, 1H), 4.29-4.08 (m, 2H), 3.09-2.98 (m, 2H), 2.86 (br. s., 1H), 2.48-2.43 (m, 3H), 2.15 (br. s., 1H), 1.53 (br. s., 1H), 1.24 (br. s., 2H), 1.11 (s, 6H), 1.09 (s, 3H), 1.06-0.95 (m, 3H), 0.91-0.77 (m, 4H), 0.73-0.62 (m, 6H). Eight piperidine hydrogens are not resolved. LCMS (M+H)=662.2.

EXAMPLE 44

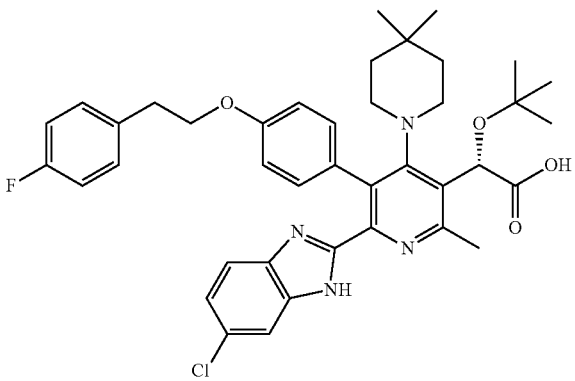 [SMILES: Cc1nc(-c2nc3ccc(Cl)cc3[nH]2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-(6-chloro-1H-benzo[d]imidazol-2-yl)-4-(4,4-dimethylpiperidin-1-yl)-5-(4-(4-fluorophenethoxy)phenyl)-2-methylpyridin-3-yl)acetic acid: To a solution of ((S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (80 mg, 0.126 mmol) and 4-chlorobenzene-1,2-diamine (25.2 mg, 0.176 mmol) in DMF (2 mL) was added DIEA (0.088 mL, 0.504 mmol) followed by HATU (67.1 mg, 0.176 mmol) and the resulting mixture was stirred at room temp for 2 h. Water was then added and the mixture was extracted with ethyl acetate, dried ($Na_2SO_4$), filtered and concentrated. The crude amide was then dissolved in acetic acid (3 mL) and heated at 80° C. for 1 h. Mixture was then concentrated, diluted with ethyl acetate and washed with sat. $NaHCO_3$ solution and brine. The layers were separated and the organic layer was dried ($Na_2SO_4$), filtered and concentrated. The residue was then treated with 10N NaOH (0.126 mL, 1.260 mmol) in EtOH (2 mL) at 80° C. for 3 h. Mixture was then cooled and purified by prep HPLC to afford (S)-2-(tert-butoxy)-2-(6-(6-chloro-1H-benzo[d]imidazol-2-yl)-4-(4,4-dimethylpiperidin-1-yl)-5-(4-(4-fluorophenethoxy)phenyl)-2-methylpyridin-3-yl)acetic acid (42.1 mg, 0.060 mmol, 47.8% yield). $^1$H NMR (500 MHz, DMSO-$d_6$) δ 7.43 (s, 1H), 7.40 (d, J=8.4 Hz, 1H), 7.35-7.26 (m, 2H), 7.18-7.06 (m, 5H), 6.95 (d, J=7.3 Hz, 1H), 6.78 (d, J=7.7 Hz, 1H), 5.85 (br. s., 1H), 4.24-4.03 (m, 2H), 3.47 (br. s., 1H), 3.37 (br. s., 1H), 2.99 (t, J=6.6 Hz, 2H), 2.90 (s, 2H), 2.59 (s, 3H), 2.20 (br. s., 1H), 1.99-1.81 (m, 1H), 1.54 (br. s., 1H), 1.32 (br. s., 1H), 1.22 (d, J=11.4 Hz, 1H), 1.16 (s, 9H), 1.04 (d, J=11.4 Hz, 1H), 0.87 (br. s., 3H), 0.64 (br. s., 3H). LCMS (M+H)=699.1.

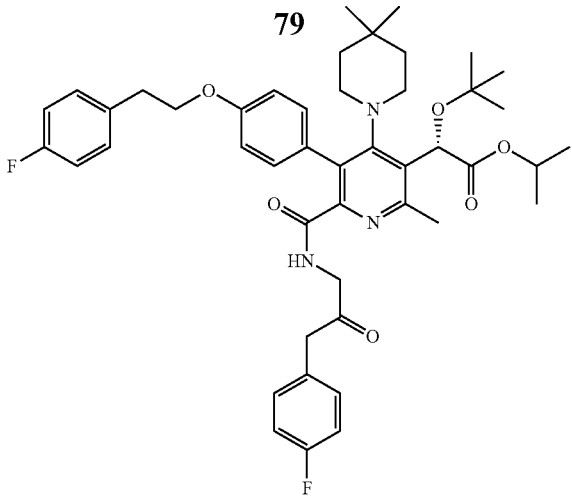 [SMILES: Cc1nc(C(=O)NCC(=O)Cc2ccc(F)cc2)c(-c2ccc(OCCc3ccc(F)cc3)cc2)c(N2CCC(C)(C)CC2)c1[C@H](OC(C)(C)C)C(=O)OC(C)C]

(S)-Isopropyl 2-(tert-butoxy)-2-(4-(4,4-dimethylpiperidin-1-yl)-5-(4-(4-fluorophenethoxy)phenyl)-6-((3-(4-fluorophenyl)-2-oxopropyl)carbamoyl)-2-methylpyridin-3-yl)acetate: To a solution of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (100 mg, 0.158 mmol) in $CH_2Cl_2$ (2 mL) was added 2M oxalyl chloride (0.095 mL, 0.189 mmol) followed by 1 drop of DMF and the resulting mixture was stirred at room temp for 15 min. At this point LCMS (in methanol) indicated completion of reaction (methyl ester mass, LCMS (M+H) =649.4). This solution was then added to a pre-stirred solution of 1-amino-3-(4-fluorophenyl)propan-2-one, 2 HCl (64.3 mg, 0.268 mmol) and TEA (0.110 mL, 0.788 mmol) in $CH_2Cl_2$ (2 mL) and the mixture was stirred for 1 h. Water was then added and the mixture was extracted with DCM, dried ($Na_2SO_4$), filtered and concentrated. The residue was then purified by Biotage (5-40% EtOAc/hexane) to afford (S)-isopropyl 2-(tert-butoxy)-2-(4-(4,4-dimethylpiperidin-1-yl)-5-(4-(4-fluorophenethoxy)phenyl)-6-((3-(4-fluorophenyl)-2-oxopropyl)carbamoyl)-2-methylpyridin-3-yl)acetate (110 mg, 0.140 mmol, 89% yield) as off-white solid. $^1$H NMR (500 MHz, $CDCl_3$) δ 8.31 (br. s., 1H), 7.26 (br. s., 1H), 7.22 (d, J=7.4 Hz, 1H), 7.15 (t, J=6.0 Hz, 2H), 7.08 (d, J=7.6 Hz, 1H), 7.02 (q, J=8.6 Hz, 4H), 6.91 (t, J=9.1 Hz, 2H), 6.10 (br. s., 1H), 5.16-5.04 (m, 1H), 4.29-4.09 (m, 3H), 3.68 (s, 2H), 3.18-3.06 (m, 3H), 3.00-2.84 (m, 1H), 2.64 (s, 3H), 2.28 (br. s., 1H), 2.07 (s, 1H), 2.05-1.93 (m, 1H), 1.41-1.32 (m, 2H), 1.29 (t, J=7.2 Hz, 2H), 1.24 (dd, J=11.2, 6.5 Hz, 6H), 1.20 (s, 9H), 1.09 (d, J=12.8 Hz, 1H), 0.91 (br. s., 3H), 0.67 (br. s., 3H). LCMS (M+H)=784.5.

EXAMPLE 45

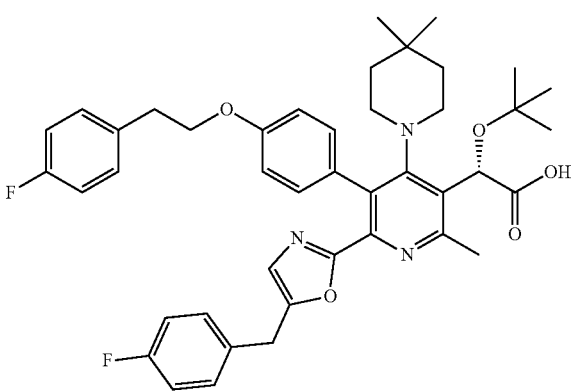 [SMILES: Cc1nc(-c2ncc(Cc3ccc(F)cc3)o2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-6-(5-(4-fluorobenzyl)oxazol-2-yl)-5-(4-(4-fluorophenethoxy)phenyl)-2-methylpyridin-3-yl)acetic acid: A 25 mL microwave vial was charged with (S)-isopropyl 2-(tert-butoxy)-2-(4-(4,4-dimethylpiperidin-1-yl)-5-(4-(4-fluorophenethoxy)phenyl)-6-((3-(4-fluorophenyl)-2-oxopropyl)carbamoyl)-2-methylpyridin-3-yl)acetate (25 mg, 0.032 mmol), Burgess reagent (15.20 mg, 0.064 mmol) and anhydrous THF (1 mL), sealed and placed in a pre-heated oil bath at 115° C. After 2.5 h, cooled, diluted with ether (20 mL), washed with water (5 mL), brine (5 mL), dried ($Na_2SO_4$), filtered, concentrated and the resulting residue was treated with 10N NaOH (0.032 mL, 0.319 mmol) in EtOH (1 mL) at 80° C. for 3 h. Mixture was then cooled and purified by prep HPLC to afford (S)-2-(tert-butoxy)-2-(4-(4,4-dimethylpiperidin-1-yl)-6-(5-(4-fluorobenzyl)oxazol-2-yl)-5-(4-(4-fluorophenethoxy)phenyl)-2-methylpyridin-3-yl)acetic acid (3.9 mg, 5.39 μmol, 16.90% yield). $^1$H NMR (500 MHz, DMSO-$d_6$) δ 7.42-7.30 (m, 2H), 7.13 (t, J=8.6 Hz, 2H), 7.08 (d, J=7.0 Hz, 5H), 6.93 (t, J=9.4 Hz, 2H), 6.79 (s, 1H), 6.74 (d, J=7.3 Hz, 1H), 5.67 (br. s., 1H), 4.22-4.05 (m, 2H), 3.88 (s, 2H), 3.64 (br. s., 1H), 3.35 (br. s., 2H), 3.03 (t, J=6.6 Hz, 2H), 2.83 (br. s., 1H), 2.14 (br. s., 1H), 1.52 (br. s., 1H), 1.30 (br. s., 1H), 1.24 (br. s., 1H), 1.18 (br. s., 1H), 1.12 (s, 9H), 1.02 (br. s., 1H), 0.85 (br. s., 3H), 0.63 (br. s., 3H). 4 missing piperidine hydrogens. LCMS (M+H)=724.1.

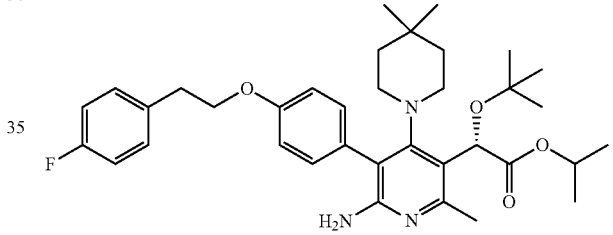

(S)-Isopropyl 2-(6-amino-4-(4,4-dimethylpiperidin-1-yl)-5-(4-(4-fluorophenethoxy)phenyl)-2-methylpyridin-3-yl)-2-(tert-butoxy)acetate: To a solution of (S)-5-(1-(tert-butoxy)-2-isopropoxy-2-oxoethyl)-4-(4,4-dimethylpiperidin-1-yl)-3-(4-(4-fluorophenethoxy)phenyl)-6-methylpicolinic acid (400 mg, 0.630 mmol) and TEA (0.176 mL, 1.260 mmol) in toluene (10 mL) was added water (0.057 mL, 3.15 mmol) followed by diphenylphosphoryl azide (0.272 mL, 1.260 mmol) and the resulting mixture was heated at 90° C. for 30 min, and then further portion of DPPA (0.07 mL) was added and the heating was continue for another 1 h. Mixture was then cooled to room temp, diluted with EtOAc (100 mL) and washed with sat. $NaHCO_3$ solution, water and brine. The organic layer was then dried ($Na_2SO_4$), filtered and concentrated. The residue was then purified by Biotage (5-80% EtOAc/hexane) to afford (S)-isopropyl 2-(6-amino-4-(4,4-dimethylpiperidin-1-yl)-5-(4-(4-fluorophenethoxy)phenyl)-2-methylpyridin-3-yl)-2-(tert-butoxy)acetate (300 mg, 0.495 mmol, 79% yield) as white solid. $^1$H NMR (500 MHz, $CDCl_3$) δ 7.29-7.23 (m, 3H), 7.14 (d, J=8.5 Hz, 1H), 7.08-6.95 (m, 4H), 5.92 (br. s., 1H), 5.08 (dt, J=12.4, 6.3 Hz, 1H), 4.27-4.19 (m, 2H), 4.16 (br. s., 2H), 3.27 (d, J=12.5 Hz, 1H), 3.13 (t, J=6.9 Hz, 2H), 2.84 (t, J=12.2 Hz, 1H), 2.48 (s, 3H), 2.30 (d, J=10.7 Hz, 1H), 2.07 (t, J=11.7 Hz, 1H), 1.71 (br. s., 1H), 1.56 (t, J=10.7 Hz, 1H), 1.43-1.34 (m, 1H), 1.24 (dd, J=8.5, 6.6 Hz, 6H), 1.20 (s, 9H), 1.08 (d, J=12.1 Hz, 1H), 0.90 (s, 3H), 0.67 (s, 3H). LCMS (M+H)=606.4.

EXAMPLE 46

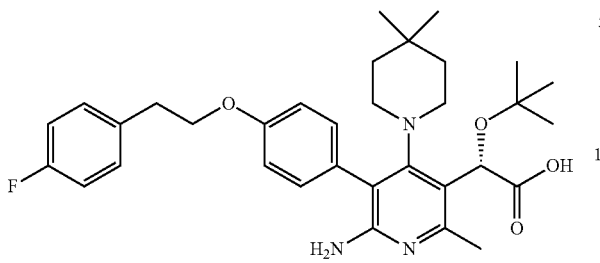

(S)-2-(6-Amino-4-(4,4-dimethylpiperidin-1-yl)-5-(4-(4-fluorophenethoxy)phenyl)-2-methylpyridin-3-yl)-2-(tert-butoxy)acetic acid: To a solution of (S)-isopropyl 2-(6-amino-4-(4,4-dimethylpiperidin-1-yl)-5-(4-(4-fluorophenethoxy)phenyl)-2-methylpyridin-3-yl)-2-(tert-butoxy)acetate (13 mg, 0.021 mmol) in ethanol (1 mL) was added 10N NaOH (0.021 mL, 0.215 mmol) and the resulting mixture was heated at 80° C. for 4 h. Mixture was then cooled and purified by prep HPLC to afford (S)-2-(6-amino-4-(4,4-dimethylpiperidin-1-yl)-5-(4-(4-fluorophenethoxy)phenyl)-2-methylpyridin-3-yl)-2-(tert-butoxy)acetic acid (7.6 mg, 0.013 mmol, 62.8% yield). $^1$H NMR (500 MHz, DMSO-$d_6$) δ 7.41-7.35 (m, 2H), 7.22-7.10 (m, 3H), 7.08-6.99 (m, 3H), 5.71 (br. s., 1H), 4.86 (br. s., 1H), 4.31-4.13 (m, 2H), 3.35 (br. s., 2H), 3.25 (br. s., 1H), 3.05 (t, J=6.4 Hz, 2H), 2.77 (t, J=11.4 Hz, 1H), 2.28 (s, 3H), 2.17 (d, J=13.6 Hz, 1H), 2.00-1.87 (m, 1H), 1.47 (br. s., 1H), 1.34-1.23 (m, 1H), 1.18 (br. s., 1H), 1.13 (s, 9H), 1.01 (d, J=10.6 Hz, 1H), 0.84 (s, 3H), 0.60 (s, 3H). LCMS (M+H)=564.2.

EXAMPLE 47

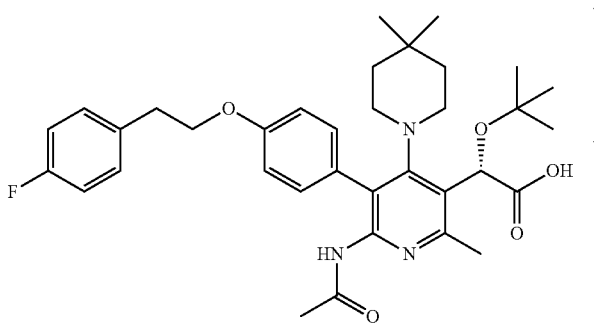

(S)-2-(6-Acetamido-4-(4,4-dimethylpiperidin-1-yl)-5-(4-(4-fluorophenethoxy)phenyl)-2-methylpyridin-3-yl)-2-(tert-butoxy)acetic acid: To a solution of (S)-2-(6-amino-4-(4,4-dimethylpiperidin-1-yl)-5-(4-(4-fluorophenethoxy)phenyl)-2-methylpyridin-3-yl)-2-(tert-butoxy)acetic acid (20 mg, 0.035 mmol) and DIEA (0.019 mL, 0.106 mmol) in DCM (0.5 mL) at 0° C. was added acetyl chloride (2.77 µl, 0.039 mmol). The mixture was stirred at rt for 16 h. Mixture was then concentrated and purified by prep HPLC to afford (S)-2-(6-acetamido-4-(4,4-dimethylpiperidin-1-yl)-5-(4-(4-fluorophenethoxy)phenyl)-2-methylpyridin-3-yl)-2-(tert-butoxy)acetic acid (3.4 mg, 5.61 µmol, 15.82% yield). $^1$H NMR (500 MHz, DMSO-$d_6$) δ 9.08 (br. s., 1H), 7.37 (dd, J=8.6, 5.7 Hz, 2H), 7.22-7.09 (m, 3H), 7.03-6.91 (m, 3H), 5.81 (s, 1H), 4.29-4.13 (m, 2H), 3.04 (t, J=6.8 Hz, 2H), 2.85 (br. s., 1H), 2.45 (s, 3H), 2.12 (br. s., 1H), 1.73 (s, 3H), 1.52 (br. s., 1H), 1.30 (br. s., 1H), 1.21 (d, J=12.5 Hz, 1H), 1.14 (s, 9H), 1.03 (d, J=13.2 Hz, 1H), 0.86 (br. s., 3H), 0.63 (br. s., 3H). 2 piperidine hydrogens are not resolved. LCMS (M+H)=606.2.

EXAMPLE 48

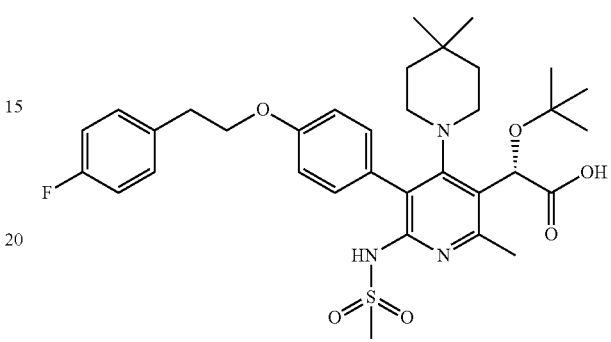

(S)-2-(tert-Butoxy)-2-(4-(4,4-dimethylpiperidin-1-yl)-5-(4-(4-fluorophenethoxy)phenyl)-2-methyl-6-(methylsulfonamido)pyridin-3-yl)acetic acid: To a solution of (S)-isopropyl 2-(6-amino-4-(4,4-dimethylpiperidin-1-yl)-5-(4-(4-fluorophenethoxy)phenyl)-2-methylpyridin-3-yl)-2-(tert-butoxy)acetate (15 mg, 0.025 mmol) and TEA (6.90 µl, 0.050 mmol) in $CH_2Cl_2$ (0.5 mL) at 0° C. was added methanesulfonyl chloride (3.83 µl, 0.050 mmol) and the resulting mixture was stirred at room temp for 16 h. Mixture was then concentrated and treated with 10N NaOH (0.025 mL, 0.248 mmol) in EtOH (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(methylsulfonamido)pyridin-3-yl)acetic acid (13.8 mg, 0.022 mmol, 87% yield). $^1$H NMR (500 MHz, DMSO-$d_6$) δ 7.38 (dd, J=8.3, 5.7 Hz, 2H), 7.23 (d, J=7.7 Hz, 1H), 7.14 (t, J=8.8 Hz, 2H), 7.09-6.96 (m, 3H), 5.57 (br. s., 1H), 4.31-4.18 (m, 2H) 3.41 (br. s., 5H), 3.06 (t, J=6.8 Hz, 3H), 2.76 (br. s., 1H), 2.43 (s, 3H), 2.12 (br. s., 1H), 1.51 (br. s., 1H), 1.24 (br. s., 1H), 1.20 (br. s., 1H), 1.12 (s, 9H), 1.01 (d, J=12.5 Hz, 1H), 0.85 (br. s., 3H), 0.63 (br. s., 3H). LCMS (M+H)=642.0.

EXAMPLE 49

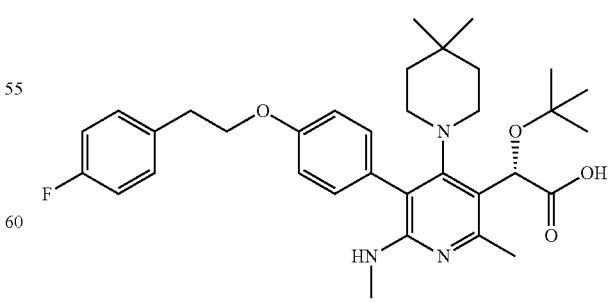

(S)-2-(tert-Butoxy)-2-(4-(4,4-dimethylpiperidin-1-yl)-5-(4-(4-fluorophenethoxy)phenyl)-2-methyl-6-(methylamino)pyridin-3-yl)acetic acid: To a solution of (S)-2-(6-amino-4-

(4,4-dimethylpiperidin-1-yl)-5-(4-(4-fluorophenethoxy) phenyl)-2-methylpyridin-3-yl)-2-(tert-butoxy)acetic acid (23 mg, 0.041 mmol) in THF (2 mL) at 0° C. was added NaH (6.53 mg, 0.163 mmol) and the resulting mixture was stirred at room temp for 30 min. Iodomethane (0.013 mL, 0.204 mmol) was then added and the mixture was heated at 60° C. for 6 h. Mixture was then concentrated and treated with 1N NaOH (0.408 mL, 0.408 mmol) in MeOH (1 mL) at 70° C. for 2 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(methylamino)pyridin-3-yl)acetic acid; $^1$H NMR (500 MHz, DMSO-$d_6$) δ 7.37 (dd, J=8.4, 5.5 Hz, 2H), 7.19-7.10 (m, 3H), 7.09-6.95 (m, 3H), 5.71 (s, 1H), 4.30-4.12 (m, 2H), 3.25 (d, J=11.4 Hz, 1H), 3.05 (t, J=6.6 Hz, 2H), 2.77-2.70 (m, 1H), 2.68 (d, J=4.8 Hz, 3H), 2.55 (s, 2H), 2.36-2.27 (m, 3H), 2.16 (d, J=11.7 Hz, 1H), 1.94-1.84 (m, 1H), 1.52-1.40 (m, 1H), 1.37-1.24 (m, 1H), 1.17-1.09 (m, 9H), 0.99 (d, J=11.4 Hz, 1H), 0.83 (s, 3H), 0.58 (s, 3H). LCMS (M+H)=578.2. And the compound shown below was isolated as byproduct.

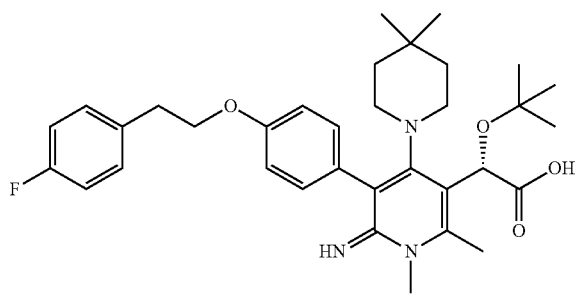 [SMILES: Cc1c([C@H](OC(C)(C)C)C(=O)O)c(N2CCC(C)(C)CC2)c(-c2ccc(OCCc3ccc(F)cc3)cc2)c(=N)n1C]

(S)-2-(tert-butoxy)-2-(4-(4,4-dimethylpiperidin-1-yl)-5-(4-(4-fluorophenethoxy)phenyl)-6-imino-1,2-dimethyl-1,6-dihydropyridin-3-yl)acetic acid: (2.2 mg, 3.81 μmol, 9.33% yield). $^1$H NMR (500 MHz, DMSO-$d_6$) δ 7.35 (dd, J=8.6, 5.7 Hz, 2H), 7.26 (dd, J=8.4, 2.2 Hz, 1H), 7.15-7.07 (m, 5H), 7.04 (dd, J=8.3, 2.4 Hz, 1H), 5.13 (s, 1H), 4.31-4.17 (m, 2H), 3.75-3.66 (m, 2H), 3.04 (t, J=6.4 Hz, 2H), 1.21 (br. s., 3H), 1.11-1.02 (m, 11H), 0.73 (br. s., 6H). 8 piperidine hydrogens are not resolved. LCMS (M+H)=578.2.

EXAMPLE 50, 51 and 52

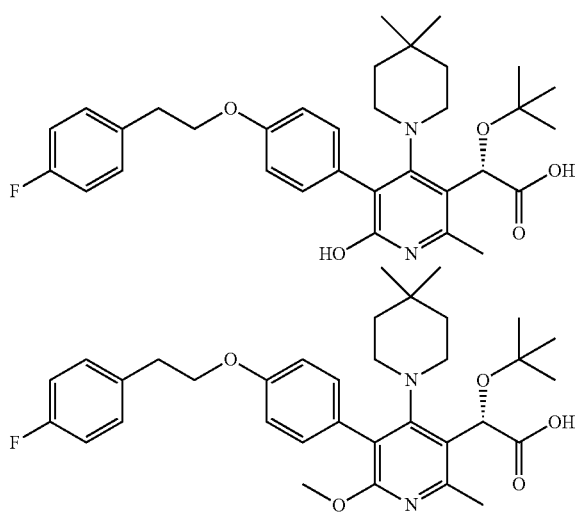

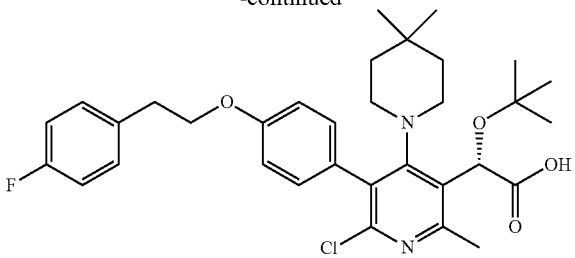

(S)-2-(tert-Butoxy)-2-(4-(4,4-dimethylpiperidin-1-yl)-5-(4-(4-fluorophenethoxy)phenyl)-6-hydroxy-2-methylpyridin-3-yl)acetic acid, (S)-2-(tert-butoxy)-2-(4-(4,4-dimethylpiperidin-1-yl)-5-(4-(4-fluorophenethoxy)phenyl)-6-methoxy-2-methylpyridin-3-yl)acetic acid & (S)-2-(tert-butoxy)-2-(6-chloro-4-(4,4-dimethylpiperidin-1-yl)-5-(4-(4-fluorophenethoxy)phenyl)-2-methylpyridin-3-yl)acetic acid: (S)-Isopropyl 2-(6-amino-4-(4,4-dimethylpiperidin-1-yl)-5-(4-(4-fluorophenethoxy)phenyl)-2-methylpyridin-3-yl)-2-(tert-butoxy)acetate (25 mg, 0.041 mmol) and CuCl$_2$ (16.65 mg, 0.124 mmol) were combined in 37% HCl (0.5 mL) and MeOH (0.5 mL). Mixture was then cooled to 0° C. and a solution of sodium nitrite (8.54 mg, 0.124 mmol) 0.2 mL H$_2$O was added. Flask was then sealed and the mixture was then warmed to room temperature and stirred for 16 h. Mixture was diluted with ethyl acetate and washed with water, brine, dried (Na$_2$SO$_4$), filtered and concentrated. The residue was then treated with 10N NaOH (0.041 mL, 0.413 mmol) in ethanol (1 mL) at 80° C. for 4 h. Mixture was then cooled and purified by prep HPLC to afford three compounds. First eluting: (S)-2-(tert-butoxy)-2-(4-(4,4-dimethylpiperidin-1-yl)-5-(4-(4-fluorophenethoxy)phenyl)-6-hydroxy-2-methylpyridin-3-yl)acetic acid (4.3 mg, 7.61 μmol, 18.45% yield): $^1$H NMR (500 MHz, DMSO-$d_6$) δ 7.38 (dd, J=8.6, 5.7 Hz, 2H), 7.14 (t, J=9.0 Hz, 3H), 6.94 (d, J=8.8 Hz, 3H), 5.28 (br. s., 1H), 4.28-4.12 (m, 2H), 3.05 (t, J=6.8 Hz, 2H), 2.71 (br. s., 1H), 2.21 (s, 3H), 2.07 (br. s., 1H), 1.52 (br. s., 1H), 1.24 (br. s., 1H), 1.20 (br. s., 1H), 1.12 (s, 9H), 1.00 (d, J=10.3 Hz, 1H), 0.84 (br. s., 3H), 0.67 (br. s., 3H). 2 piperidine hydrogens, acid and phenol protons are not resolved. LCMS (M+H)=565.2. Second eluting: (S)-2-(tert-butoxy)-2-(4-(4,4-dimethylpiperidin-1-yl)-5-(4-(4-fluorophenethoxy)phenyl)-6-methoxy-2-methylpyridin-3-yl)acetic acid (2.1 mg, 3.63 μmol, 8.79% yield): $^1$H NMR (500 MHz, DMSO-$d_6$) δ 7.38 (dd, J=8.6, 5.7 Hz, 2H), 7.22-7.09 (m, 3H), 6.98 (t, J=8.3 Hz, 3H), 5.66 (s, 1H), 4.30-4.13 (m, 2H), 3.05 (t, J=6.6 Hz, 2H), 2.82 (t, J=12.3 Hz, 1H), 2.41 (s, 3H), 2.14 (br. s., 1H), 1.51 (br. s., 1H), 1.30 (br. s., 1H), 1.19 (d, J=14.3 Hz, 1H), 1.12 (s, 9H), 1.03 (d, J=13.9 Hz, 1H), 0.85 (s, 3H), 0.64 (s, 3H). 5 piperidine hydrogens are not resolved. LCMS (M+H)=579.2. Third eluting: (S)-2-(tert-butoxy)-2-(6-chloro-4-(4,4-dimethylpiperidin-1-yl)-5-(4-(4-fluorophenethoxy)phenyl)-2-methylpyridin-3-yl)acetic acid (1.8 mg, 3.09 μmol, 7.48% yield): $^1$H NMR (500 MHz, DMSO-$d_6$) δ 7.38 (dd, J=8.6, 5.7 Hz, 2H), 7.29-7.22 (m, 1H), 7.18-7.11 (m, 2H), 7.08-6.99 (m, 3H), 5.69 (s, 1H), 4.29-4.16 (m, 2H), 3.06 (t, J=6.8 Hz, 2H), 2.80 (br. s., 1H), 2.46 (s, 3H), 2.21 (br. s., 1H), 1.50 (br. s., 1H), 1.29 (br. s., 1H), 1.23 (d, J=15.8 Hz, 1H), 1.12 (s, 9H), 1.07-0.99 (m, 1H), 0.86 (br. s., 3H), 0.62 (br. s., 3H). 2 piperidine hydrogens are not resolved. LCMS (M+H)=584.2.

EXAMPLE 53

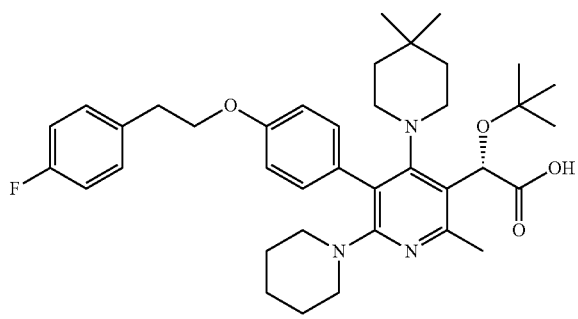 [SMILES: Cc1nc(N2CCCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(piperidin-1-yl)pyridin-3-yl)acetic acid: A mixture of (S)-isopropyl 2-(tert-butoxy)-2-(6-chloro-4-(4,4-dimethylpiperidin-1-yl)-5-(4-(4-fluorophenethoxy)phenyl)-2-methylpyridin-3-yl)acetate (10 mg, 0.016 mmol) and piperidine (0.158 mL, 1.599 mmol) in NMP (0.25 mL) was heated in microwave at 150° C. for 32 h. Mixture was then diluted with ethyl acetate and washed with water, dried (Na$_2$SO$_4$), filtered and concentrated. The residue was then treated with 10N NaOH (0.016 mL, 0.160 mmol) in EtOH (0.5 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(piperidin-1-yl)pyridin-3-yl)acetic acid (1.8 mg, 2.85 µmol, 17.81% yield). $^1$H NMR (500 MHz, DMSO-d$_6$) δ 7.36 (dd, J=8.4, 5.9 Hz, 2H), 7.25-7.13 (m, 4H), 7.01 (d, J=7.3 Hz, 2H), 5.73 (br. s., 1H), 4.27-4.17 (m, 2H), 3.94-3.77 (m, 1H), 3.04 (t, J=6.6 Hz, 2H), 2.94 (q, J=6.6 Hz, 1H), 2.88-2.79 (m, 3H), 2.75-2.65 (m, 2H), 2.40 (s, 3H), 2.07 (d, J=11.4 Hz, 1H), 1.52 (br. s., 2H), 1.32 (d, J=11.4 Hz, 2H), 1.24 (s, 4H), 1.13 (s, 9H), 0.97 (d, J=11.0 Hz, 1H), 0.89-0.79 (m, 4H), 0.64 (s, 3H). LCMS (M+H)=632.3.

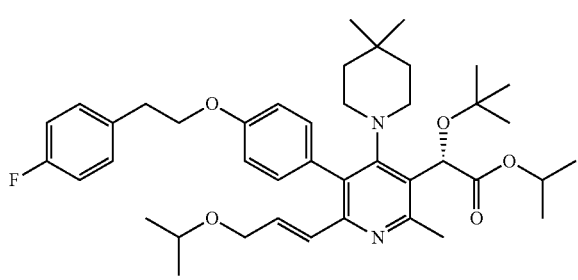

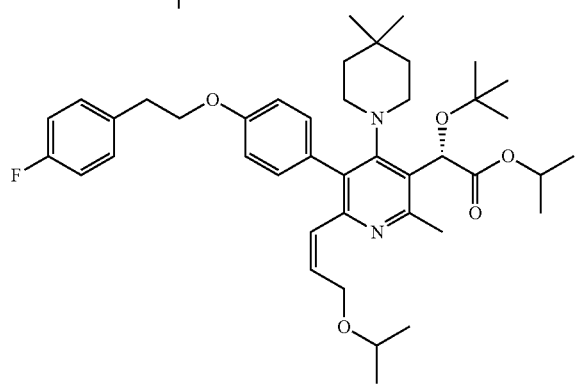

(S,E)-Isopropyl 2-(tert-butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetate & (S,Z)-isopropyl 2-(tert-butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetate: To a suspension of (2-isopropoxyethyl)triphenylphosphonium, bromide salt (69.4 mg, 0.162 mmol) in THF (1 ml) at 0° C. was added NaH (6.63 mg, 0.166 mmol) and the resulting mixture was stirred at rt for 45 min. (S)-Isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate (50 mg, 0.081 mmol) dissolved in THF (0.5 mL) THF (1 ml) was added dropwise and the mixture was stirred at 0° C. for 1 h then warmed to rt and stirred 2 h. The reaction was quenched with water and the product was extracted with EtOAc. The organic phase was washed with brine, dried (Na$_2$SO$_4$), filtered and concentrated. The residue was purified by flash chromatography (Biotage; 0%-30% EtOAc/hexane) to afford two products. (S,E)-Isopropyl 2-(tert-butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetate (33 mg, 0.048 mmol, 59.3% yield). $^1$H NMR (500 MHz, CDCl$_3$) δ 7.31 (br. s., 2H), 7.15 (d, J=7.6 Hz, 1H), 7.11-7.01 (m, 3H), 6.99-6.90 (m, 2H), 6.10 (br. s., 1H), 6.06 (d, J=12.1 Hz, 1H), 5.81-5.74 (m, 1H), 5.10 (dt, J=12.4, 6.1 Hz, 1H), 4.78-4.70 (m, 2H), 4.28-4.18 (m, 2H), 3.69 (dt, J=12.0, 6.0 Hz, 1H), 3.21 (d, J=10.7 Hz, 1H), 3.13 (t, J=6.8 Hz, 2H), 2.89 (t, J=12.0 Hz, 1H), 2.62 (s, 3H), 2.27 (d, J=11.0 Hz, 1H), 2.11-2.00 (m, 1H), 1.43-1.31 (m, 1H), 1.26-1.16 (m, 22H), 1.13-1.05 (m, 2H), 0.91 (br. s., 3H), 0.66 (br. s., 3H). LCMS (M+H)=689.5. And (S,Z)-isopropyl 2-(tert-butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetate (10 mg, 0.015 mmol, 17.96% yield). $^1$H NMR (500 MHz, CDCl$_3$) δ 7.31 (br. s., 2H), 7.16 (d, J=7.1 Hz, 1H), 7.10 (d, J=9.0 Hz, 1H), 7.05 (t, J=8.4 Hz, 2H), 7.00-6.93 (m, 2H), 6.90 (dt, J=15.2, 5.5 Hz, 1H), 6.33 (d, J=15.3 Hz, 1H), 6.08 (br. s., 1H), 5.10 (dt, J=12.4, 6.3 Hz, 1H), 4.29-4.19 (m, 2H), 4.05 (d, J=5.0 Hz, 2H), 3.57 (dt, J=12.1, 6.0 Hz, 1H), 3.21 (d, J=11.3 Hz, 1H), 3.13 (t, J=6.7 Hz, 2H), 2.88 (t, J=12.5 Hz, 1H), 2.28 (d, J=13.6 Hz, 1H), 2.11-1.98 (m, 1H), 1.42-1.27 (m, 3H), 1.26-1.16 (m, 19H), 1.08 (dd, J=9.1, 6.1 Hz, 6H), 0.91 (br. s., 3H), 0.66 (br. s., 3H). LCMS (M+H)=689.5.

EXAMPLE 54

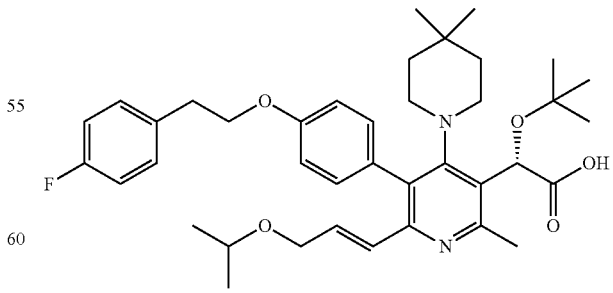

(S,E)-2-(tert-Butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetic acid: To a solution of (S,E)-isopropyl 2-(tert-butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetate (33 mg, 0.048 mmol) in ethanol (1 mL) was added 10N NaOH (0.048 mL, 0.479 mmol) and the resulting mixture was heated at 80° C. for 3 h. Mixture was then cooled and purified by prep HPLC to afford (S,E)-2-(tert-butoxy)-2-(4-(4,4-dimethylpiperidin-1-yl)-5-(4-(4-fluorophenethoxy) phenyl)-6-(3-isopropoxyprop-1-en-1-yl)-2-methylpyridin-3-yl)acetic acid (5.5 mg, 8.50 µmol, 17.75% yield). $^1$H NMR (500 MHz, DMSO-$d_6$) δ 7.42-7.32 (m, 2H), 7.14 (t, J=8.6 Hz, 3H), 7.09-6.96 (m, 3H), 5.92 (d, J=12.1 Hz, 1H), 5.86 (br. s., 1H), 5.69-5.59 (m, 1H), 4.58 (d, J=2.9 Hz, 2H), 4.29-4.17 (m, 2H), 3.59 (dt, J=11.8, 6.0 Hz, 1H), 3.26 (br. s., 1H), 3.06 (t, J=6.6 Hz, 2H), 2.81 (t, J=12.7 Hz, 1H), 2.50 (br. s., 3H), 2.19 (d, J=12.5 Hz, 1H), 1.99-1.85 (m, 1H), 1.49 (br. s., 1H), 1.35-1.24 (m, 1H), 1.18 (d, J=12.8 Hz, 1H), 1.13 (s, 9H), 1.08 (d, J=3.7 Hz, 3H), 1.09 (d, J=3.7 Hz, 3H), 1.02 (d, J=12.5 Hz, 1H), 0.85 (s, 3H), 0.60 (s, 3H). LCMS (M+H)=647.2.

EXAMPLE 55

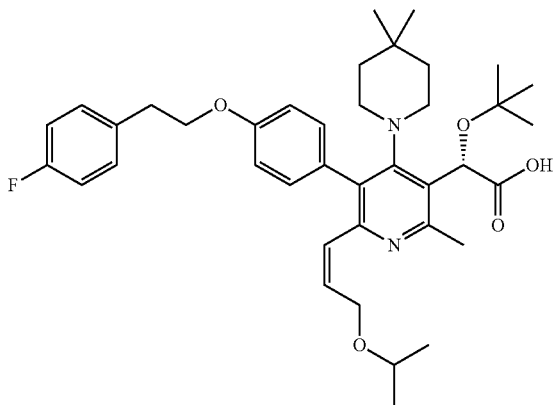 [SMILES: Cc1nc(/C=C\COC(C)C)c(-c2ccc(OCCc3ccc(F)cc3)cc2)c(N2CCC(C)(C)CC2)c1[C@H](OC(C)(C)C)C(=O)O]

(S,Z)-2-(tert-Butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetic acid: To a solution of (S,Z)-isopropyl 2-(tert-butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetate (10 mg, 0.015 mmol) in ethanol (0.5 mL) was added 10NNaOH (0.015 mL, 0.145 mmol) and the resulting mixture was heated at 80° C. for 3 h. Mixture was then cooled and purified by prep HPLC to afford (S,Z)-2-(tert-butoxy)-2-(4-(4,4-dimethylpiperidin-1-yl)-5-(4-(4-fluorophenethoxy) phenyl)-6-(3-isopropoxyprop-1-en-1-yl)-2-methylpyridin-3-yl)acetic acid (1.7 mg, 2.63 µmol, 18.11% yield). $^1$H NMR (500 MHz, DMSO-$d_6$) δ 7.37 (br. s., 2H), 7.14 (br. s., 3H), 7.09-6.95 (m, 3H), 6.70 (d, J=15.0 Hz, 1H), 6.19 (d, J=15.0 Hz, 1H), 5.86 (br. s., 1H), 4.23 (d, J=6.2 Hz, 2H), 3.94 (br. s., 2H), 3.24 (br. s., 1H), 3.05 (br. s., 2H), 2.82 (br. s., 1H), 2.48 (s, 3H), 2.18 (br. s., 1H), 1.93 (br. s., 1H), 1.49 (br. s., 1H), 1.27 (d, J=18.3 Hz, 1H), 1.19 (br. s., 1H), 1.13 (br. s., 9H), 1.08 (br. s., 1H), 1.02 (d, J=13.2 Hz, 1H), 0.96 (t, J=7.0 Hz, 6H), 0.85 (br. s., 3H), 0.60 (br. s., 3H). LCMS (M+H)=647.2.

EXAMPLE 56

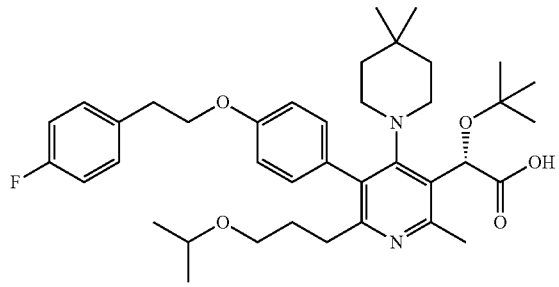 [SMILES: Cc1nc(CCCOC(C)C)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-6-(3-isopropoxypropyl)-2-methylpyridin-3-yl)acetic acid: To a solution of (S,E)-2-(tert-butoxy)-2-(4-(4,4-dimethylpiperidin-1-yl)-5-(4-(4-fluorophenethoxy)phenyl)-6-(3-isopropoxyprop-1-en-1-yl)-2-methylpyridin-3-yl)acetic acid (25 mg, 0.039 mmol) in ethanol (1 mL) was added 10% Pd-C (8.23 mg, 7.73 µmol) and the resulting mixture was stirred under balloon hydrogen atmosphere for 2 h. Mixture was then filtered and purified by prep HPLC to afford (S)-2-(tert-butoxy)-2-(4-(4,4-dimethylpiperidin-1-yl)-5-(4-(4-fluorophenethoxy)phenyl)-6-(3-isopropoxypropyl)-2-methylpyridin-3-yl)acetic acid (14.3 mg, 0.022 mmol, 57.0% yield). $^1$H NMR (500 MHz, DMSO-$d_6$) δ 7.37 (dd, J=8.3, 5.7 Hz, 2H), 7.20 (d, J=8.1 Hz, 1H), 7.14 (t, J=8.8 Hz, 2H), 7.08-6.94 (m, 3H), 5.89 (s, 1H), 4.31-4.14 (m, 2H), 3.36-3.31 (m, 1H), 3.24-3.14 (m, 4H), 3.05 (t, J=6.6 Hz, 2H), 2.79 (t, J=12.5 Hz, 1H), 2.45 (s, 3H), 2.35 (br. s., 2H), 2.19 (d, J=10.3 Hz, 1H), 1.72-1.57 (m, 2H), 1.48 (br. s., 1H), 1.29 (br. s., 1H), 1.17 (d, J=12.1 Hz, 1H), 1.13 (s, 9H), 1.02 (d, J=12.8 Hz, 1H), 0.95 (t, J=5.5 Hz, 6H), 0.84 (s, 3H), 0.59 (s, 3H). LCMS (M+H)=649.2.

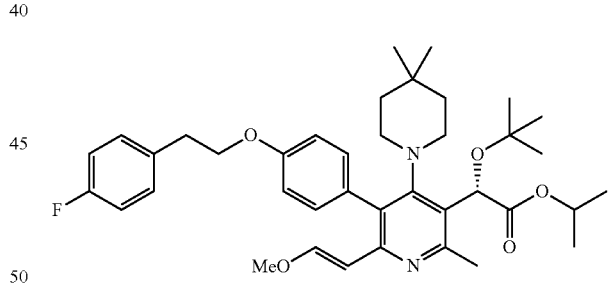

(S,E)-Isopropyl 2-(tert-butoxy)-2-(4-(4,4-dimethylpiperidin-1-yl)-5-(4-(4-fluorophenethoxy)phenyl)-6-(2-methoxyvinyl)-2-methylpyridin-3-yl)acetate: To a suspension of (methoxymethyl)triphenylphosphonium, chloride salt (78 mg, 0.226 mmol) in THF (2 ml) at 0° C. was added NaH (9.28 mg, 0.232 mmol) and the resulting mixture was stirred at rt for 45 min. (S)-Isopropyl 2-(tert-butoxy)-2-(4-(4,4-dimethylpiperidin-1-yl)-5-(4-(4-fluorophenethoxy) phenyl)-6-formyl-2-methylpyridin-3-yl)acetate (70 mg, 0.113 mmol) dissolved in THF (0.5 mL) THF (2 ml) was added dropwise and the mixture was stirred at 0° C. for 1 h then warmed to rt and stirred 16 h. The reaction was quenched with water and the product was extracted with EtOAc. The organic phase was washed with brine, dried (Na$_2$SO$_4$), filtered and concentrated. The residue was purified by flash chromatography (Biotage; 0%-30% EtOAc/ hexane) to afford (S,E)-isopropyl 2-(tert-butoxy)-2-(4-(4,4-dimethylpiperidin-1-yl)-5-(4-(4-fluorophenethoxy)phenyl)-6-(2-methoxyvinyl)-2-methylpyridin-3-yl)acetate (40 mg, 0.062 mmol, 54.7% yield). $^1$H NMR (500 MHz, CDCl$_3$) δ 7.58 (d, J=12.3 Hz, 1H), 7.31 (br. s., 1H), 7.16 (d, J=7.7 Hz, 1H), 7.11-7.01 (m, 3H), 6.99-6.92 (m, 2H), 6.07 (br. s., 1H), 5.50 (d, J=12.1 Hz, 1H), 5.09 (dt, J=12.5, 6.3 Hz, 1H), 4.30-4.16 (m, 2H), 3.52 (s, 3H), 3.21 (d, J=12.0 Hz, 1H), 3.13 (t, J=6.9 Hz, 2H), 2.87 (t, J=11.7 Hz, 1H), 2.59 (s, 3H), 2.27 (d, J=11.7 Hz, 1H), 2.09-1.97 (m, 1H), 1.55 (br. s., 3H), 1.39-1.28 (m, 1H), 1.25-1.16 (m, 15H), 1.07 (d, J=9.1 Hz, 1H), 0.90 (s, 3H), 0.66 (s, 3H). LCMS (M+H)=647.5.

for 3 h. Mixture was then filtered and purified by prep HPLC to afford(S)-2-(tert-butoxy)-2-(4-(4,4-dimethylpiperidin-1-yl)-5-(4-(4-fluorophenethoxy)phenyl)-6-(2-methoxyethyl)-2-methylpyridin-3-yl)acetic acid (15.7 mg, 0.026 mmol, 55.8% yield). $^1$H NMR (500 MHz, DMSO-d$_6$) δ 7.41-7.35 (m, 2H), 7.21 (d, J=7.7 Hz, 1H), 7.14 (t, J=8.6 Hz, 2H), 7.07-6.98 (m, 3H), 5.84 (br. s., 1H), 4.24 (d, J=8.8 Hz, 2H), 3.56-3.44 (m, 3H), 3.08 (s, 3H), 3.05 (t, J=6.6 Hz, 3H), 2.85-2.74 (m, 1H), 2.61-2.56 (m, 2H), 2.45 (s, 3H), 2.16 (br. s., 1H), 1.48 (br. s., 1H), 1.29 (br. s., 1H), 1.18 (br. s., 1H), 1.12 (s, 9H), 1.01 (d, J=9.5 Hz, 1H), 0.84 (s, 3H), 0.59 (s, 3H). LCMS (M+H)=607.2.

EXAMPLE 57 and 58

EXAMPLE 59

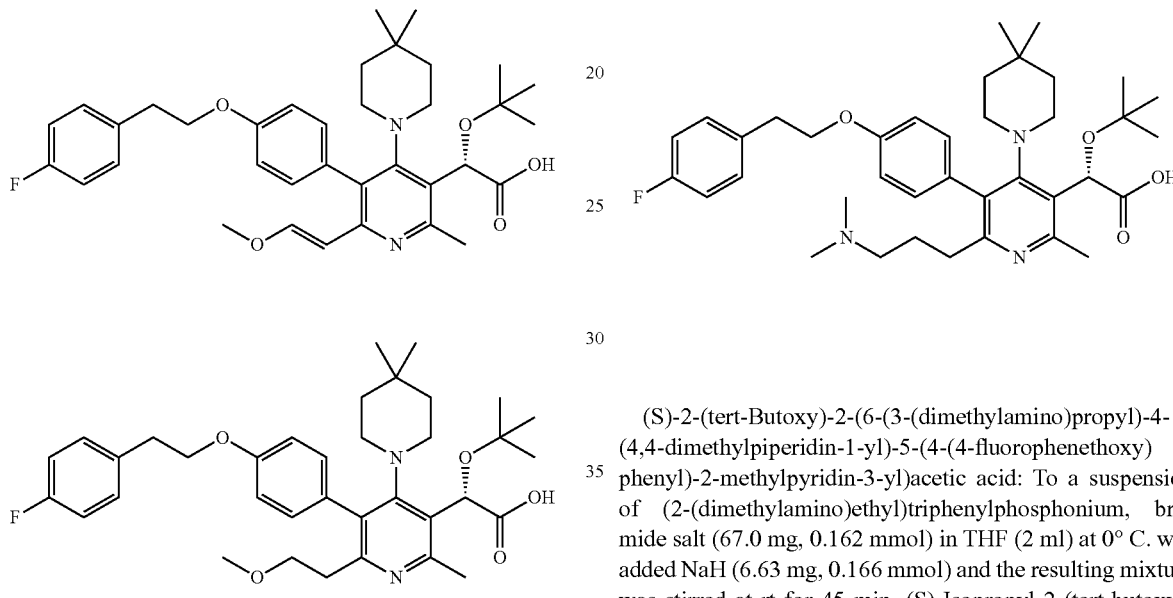

(S,E)-2-(tert-Butoxy)-2-(4-(4,4-dimethylpiperidin-1-yl)-5-(4-(4-fluorophenethoxy)phenyl)-6-(2-methoxyvinyl)-2-methylpyridin-3-yl)acetic acid & (S)-2-(tert-butoxy)-2-(4-(4,4-dimethylpiperidin-1-yl)-5-(4-(4-fluorophenethoxy)phenyl)-6-(2-methoxyethyl)-2-methylpyridin-3-yl)acetic acid: To a solution of (S,E)-isopropyl 2-(tert-butoxy)-2-(4-(4,4-dimethylpiperidin-1-yl)-5-(4-(4-fluorophenethoxy)phenyl)-6-(2-methoxyvinyl)-2-methylpyridin-3-yl)acetate (30 mg, 0.046 mmol) in ethanol (1 mL) was added 10N NaOH (0.046 mL, 0.464 mmol) and the resulting mixture was heated at 80° C. for 5 h. Mixture was then cooled and purified by prep HPLC to afford (S,E)-2-(tert-butoxy)-2-(4-(4,4-dimethylpiperidin-1-yl)-5-(4-(4-fluorophenethoxy)phenyl)-6-(2-methoxyvinyl)-2-methylpyridin-3-yl)acetic acid (20 mg, 0.033 mmol, 71.3% yield). $^1$H NMR (500 MHz, DMSO-d$_6$) δ 7.44 (d, J=12.1 Hz, 1H), 7.41-7.32 (m, 2H), 7.14 (t, J=8.8 Hz, 3H), 7.05-7.02 (m, 2H), 5.81 (s, 1H), 5.34 (d, J=12.1 Hz, 1H), 4.24 (d, J=10.3 Hz, 2H), 3.44 (s, 3H), 3.41 (br. s., 7H), 3.05 (t, J=6.6 Hz, 2H), 2.43 (s, 3H), 1.12 (s, 9H), 1.06-0.97 (m, 2H), 0.84 (s, 3H), 0.60 (s, 3H). LCMS (M+H)=605.2. The resulting acid was then diluted with ethanol (1 mL) and treated with 10% Pd-C (1.481 mg, 0.014 mmol) and stirred under balloon hydrogen atmosphere (S)-2-(tert-Butoxy)-2-(6-(3-(dimethylamino)propyl)-4-(4,4-dimethylpiperidin-1-yl)-5-(4-(4-fluorophenethoxy)phenyl)-2-methylpyridin-3-yl)acetic acid: To a suspension of (2-(dimethylamino)ethyl)triphenylphosphonium, bromide salt (67.0 mg, 0.162 mmol) in THF (2 ml) at 0° C. was added NaH (6.63 mg, 0.166 mmol) and the resulting mixture was stirred at rt for 45 min. (S)-Isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate (50 mg, 0.081 mmol) dissolved in THF (0.5 mL) was added dropwise and the mixture was stirred at 0° C. for 1 h then warmed to rt and stirred 2 h. The reaction was quenched with water and the product was extracted with EtOAc. The organic phase was washed with brine, dried (Na$_2$SO$_4$), filtered and concentrated. The residue was then treated with 10N NaOH (0.081 ml, 0.808 mmol) in ethanol (2 mL) at 80° C. for 4 h. Mixture was then cooled and neutralize with acetic acid. 10% Pd-C (17.20 mg, 0.016 mmol) was then added and the mixture was stirred under balloon hydrogen atmosphere for 3 h. Mixture was then filtered and purified by prep HPLC to afford (S)-2-(tert-butoxy)-2-(6-(3-(dimethylamino)propyl)-4-(4,4-dimethylpiperidin-1-yl)-5-(4-(4-fluorophenethoxy)phenyl)-2-methylpyridin-3-yl)acetic acid (11.4 mg, 0.018 mmol, 22.26% yield). $^1$H NMR (500 MHz, DMSO-d$_6$) δ 7.40-7.34 (m, 2H), 7.21 (d, J=8.1 Hz, 1H), 7.14 (t, J=9.0 Hz, 2H), 7.08-6.93 (m, 3H), 5.85 (s, 1H), 4.31-4.17 (m, 2H), 3.91 (s, 1H), 3.18 (s, 1H), 3.05 (t, J=6.6 Hz, 2H), 2.45 (s, 3H), 2.37 (s, 1H), 2.33-2.22 (m, 1H), 2.19 (br. s., 1H), 2.07 (d, J=5.5 Hz, 2H), 1.98 (s, 6H), 1.91 (s, 3H), 1.58 (s, 1H), 1.51 (br. s., 2H), 1.13 (s, 9H), 1.01 (d, J=11.7 Hz, 1H), 0.85 (s, 3H), 0.59 (s, 3H). LCMS (M+H)=634.3.

EXAMPLE 60

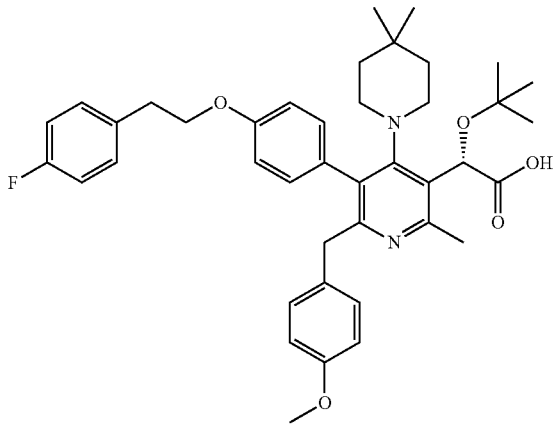 [SMILES: COc1ccc(Cc2nc(C)c([C@H](OC(C)(C)C)C(=O)O)c(N3CCC(C)(C)CC3)c2-c2ccc(OCCc3ccc(F)cc3)cc2)cc1]

(S)-2-(tert-Butoxy)-2-(4-(4,4-dimethylpiperidin-1-yl)-5-(4-(4-fluorophenethoxy)phenyl)-6-(4-methoxybenzyl)-2-methylpyridin-3-yl)acetic acid: A mixture of (4-methoxyphenyl)boronic acid (0.007 g, 0.046 mmol), (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.01 g, 0.015 mmol), sodium carbonate (0.06 ml, 0.120 mmol) in dioxane (1 mL) was degassed and refilled $N_2$ back. Pd(Ph$_3$P)$_4$ (0.004 g, 3.46 μmol) was added and degassed refilled $N_2$ back. The mixture was stirred in a sealed vial at 80° C. for 18 h. Removed the solvent under reduced pressure, the residue was dissolved in EtOH and filtered off the solid. The filtration was treated with sodium hydroxide (0.01 g, 0.250 mmol) at 80° C. for 4 h, then cooled and purified by prep-HPLC to afford (S)-2-(tert-butoxy)-2-(4-(4,4-dimethylpiperidin-1-yl)-5-(4-(4-fluorophenethoxy)phenyl)-6-(4-methoxybenzyl)-2-methylpyridin-3-yl)acetic acid (0.0012 g, 1.794 μmol, 12.27% yield). LCMS (M+H)=669.2. $^1$H NMR (500 MHz, DMSO-d$_6$) δ 7.42-7.34 (m, 2H), 7.18-7.08 (m, 3H), 7.00 (d, J=8.8 Hz, 2H), 6.91 (d, J=8.1 Hz, 1H), 6.82-6.78 (m, J=8.4 Hz, 2H), 6.74-6.69 (m, J=8.4 Hz, 2H), 5.77 (s, 1H), 4.29-4.20 (m, 2H), 3.74 (d, J=13.9 Hz, 1H), 3.66 (s, 3H), 3.56 (d, J=13.9 Hz, 1H), 3.06 (t, J=6.8 Hz, 2H), 2.75 (t, J=11.9 Hz, 1H), 2.45 (s, 3H), 2.18 (d, J=11.0 Hz, 1H), 1.95-1.82 (m, 1H), 1.52-1.45 (m, 1H), 1.32-1.21 (m, J=11.4 Hz, 1H), 1.19-1.04 (m, 11H), 1.00 (d, J=14.3 Hz, 1H), 0.84 (s, 3H), 0.59 (s, 3H).

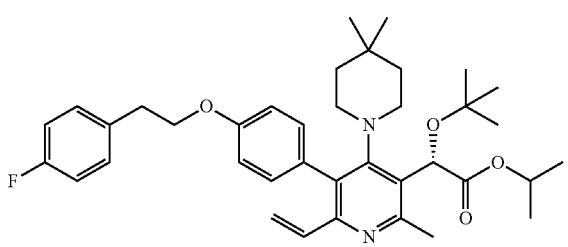 [SMILES: C=Cc1nc(C)c([C@H](OC(C)(C)C)C(=O)OC(C)C)c(N2CCC(C)(C)CC2)c1-c1ccc(OCCc2ccc(F)cc2)cc1]

(S)-Isopropyl 2-(tert-butoxy)-2-(4-(4,4-dimethylpiperidin-1-yl)-5-(4-(4-fluorophenethoxy)phenyl)-2-methyl-6-vinylpyridin-3-yl)acetate: To a suspension of methyltriphenylphosphonium bromide (90 mg, 0.323 mmol) in THF (1 ml) at 0° C. was added sodium hydride (13 mg, 0.325 mmol) and the resulting mixture was stirred at rt for 45 min. (S)-Isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate (100 mg, 0.162 mmol) dissolved in THF (0.5 mL) was added dropwise and the mixture was stirred at 0° C. for 1 h, then warmed to rt and stirred 2 h. The reaction was quenched with water and the product was extracted with EtOAc. The organic phase was washed with brine, dried (Na$_2$SO$_4$), filtered and concentrated. The residue was purified by silica gel flash chromatography (EtOAc/hexane: 0%-30%) to afford (S)-isopropyl 2-(tert-butoxy)-2-(4-(4,4-dimethylpiperidin-1-yl)-5-(4-(4-fluorophenethoxy)phenyl)-2-methyl-6-vinylpyridin-3-yl)acetate (0.05 g, 0.081 mmol, 50.2% yield). 1H NMR (500 MHz, CDCl$_3$) δ 7.33-7.27 (m, 2H), 7.16 (dd, J=8.6, 2.1 Hz, 1H), 7.11 (dd, J=8.5, 2.0 Hz, 1H), 7.08-7.02 (m, 2H), 7.00-6.94 (m, 2H), 6.51-6.42 (m, 1H), 6.36-6.29 (m, 1H), 6.11 (s, 1H), 5.23 (dd, J=10.6, 2.5 Hz, 1H), 5.14-5.03 (m, 1H), 4.24 (td, J=6.8, 3.5 Hz, 2H), 3.26-3.18 (m, 1H), 3.14 (t, J=6.9 Hz, 2H), 2.93-2.85 (m, 1H), 2.65 (s, 3H), 2.34-2.24 (m, 1H), 2.07 (s, 1H), 1.42 (s, 2H), 1.25-1.21 (m, 7H), 1.20 (s, 9H), 1.08 (d, J=12.0 Hz, 1H), 0.91 (s, 3H), 0.67 (s, 3H). LCMS (M+H)=617.4.

EXAMPLE 61

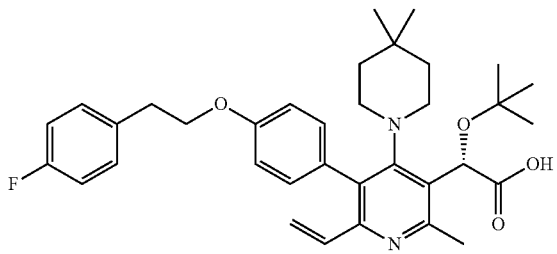 [SMILES: C=Cc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-5-(4-(4-fluorophenethoxy)phenyl)-2-methyl-6-vinylpyridin-3-yl)acetic acid: (S)-Isopropyl 2-(tert-butoxy)-2-(4-(4,4-dimethylpiperidin-1-yl)-5-(4-(4-fluorophenethoxy)phenyl)-2-methyl-6-vinylpyridin-3-yl)acetate (10 mg, 0.016 mmol) was dissolved in EtOH (1 ml) and added sodium hydroxide (0.01 g, 0.250 mmol). The mixture was heated at 80° C. for 18 h, then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-vinylpyridin-3-yl)acetic acid (0.0021 g, 3.65 μmol, 22.54% yield). LCMS (M+H)=575.2.

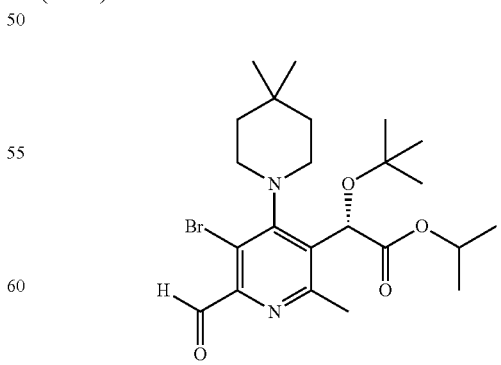

Isopropyl (S)-2-(5-bromo-4-(4,4-dimethylpiperidin-1-yl)-6-formyl-2-methylpyridin-3-yl)-2-(tert-butoxy)acetate: To a stirred solution of (S)-isopropyl 2-(5-bromo-4-(4,4- dimethylpiperidin-1-yl)-6-(hydroxymethyl)-2-methylpyridin-3-yl)-2-(tert-butoxy)acetate (1.0 g, 2.1 mmol) in CH₂Cl₂ (19 ml) was added Dess-Martin periodinane (1.3 g, 3.1 mmol) at once at rt. After 16 h, the reaction mixture was diluted with ether, washed with 1M NaOH followed by brine. The organic phase was dried over (Na₂SO₄), concentrated and purified on silica gel (Biotage, EtOAc/hexanes gradient, 0-100% over 10 CVs) to afford (S)-isopropyl 2-(5-bromo-4-(4,4-dimethylpiperidin-1-yl)-6-formyl-2-methylpyridin-3-yl)-2-(tert-butoxy)acetate (960 mg, 1.99 mmol, 96% yield). ¹H NMR (500 MHz, chloroform-d) δ 10.29 (s, 1H), 6.26 (br s, 1H), 5.12-4.97 (m, 1H), 4.15-4.05 (m, 1H), 3.54 (t, J=12.1 Hz, 1H), 2.94 (d, J=10.9 Hz, 1H), 2.71 (d, J=11.0 Hz, 1H), 2.662.62 (m, 3H), 1.59 (br s, 1H), 1.51 (br s, 1H), 1.41-1.35 (m, 1H), 1.30-1.25 (m, 1H), 1.22-1.18 (m, 12H), 1.16-1.13 (m, 3H), 1.11-1.03 (m, 6H). LCMS (M+H)=483.0, 485.0.

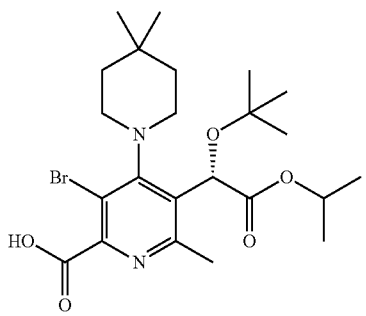 [SMILES: Cc1nc(C(=O)O)c(Br)c(N2CCC(C)(C)CC2)c1[C@H](OC(C)(C)C)C(=O)OC(C)C]

(S)-3-Bromo-5-(1-(tert-butoxy)-2-isopropoxy-2-oxoethyl)-4-(4,4-dimethylpiperidin-1-yl)-6-methylpicolinic acid: To a solution of (S)-isopropyl 2-(5-bromo-4-(4,4-dimethylpiperidin-1-yl)-6-formyl-2-methylpyridin-3-yl)-2-(tert-butoxy)acetate (2.0 g, 4.1 mmol) in DMSO (41 ml) was added potassium phosphate monobasic (1.69 g, 12.4 mmol) in water (10 mL) followed by sodium chlorite (1.12 g, 12.4 mmol) in water (10 mL) and the mixture was stirred overnight. A ppt formed immediately. As the reaction stirred, the precipitated material stuck to the sides of the flask. After stirring overnight, the solution was poured away and the solids were taken up in EtOAc and were then washed with brine, dried (Na₂SO₄), filtered and concentrated to afford the expected product. The DMSO solution also contained some product. It was diluted with EtOAc and washed with Brine. The organic phase was dried over Na₂SO₄, and concentrated and was combined with the material isolated from the ppt. The combined material afforded a quantitative amount of (S)-3-bromo-5-(1-(tert-butoxy)-2-isopropoxy-2-oxoethyl)-4-(4,4-dimethylpiperidin-1-yl)-6-methylpicolinic acid (quantitative). LCMS (M+H)=499.04.

(S)-Isopropyl 2-(5-bromo-4-(4,4-dimethylpiperidin-1-yl)-2-methylpyridin-3-yl)-2-(tert-butoxy)acetate: To a solution of (S)-3-bromo-5-(1-(tert-butoxy)-2-isopropoxy-2-oxoethyl)-4-(4,4-dimethylpiperidin-1-yl)-6-methylpicolinic acid (1.3 g, 2.60 mmol) in toluene (30 mL) was added water (0.234 mL, 13.01 mmol) followed by diphenylphophoryl azide (1.125 mL, 5.21 mmol) and the resulting mixture was heated at 90° C. for 2 h. Then, the mixture was cooled to room temp, diluted with EtOAc (100 mL) and washed with sat. NaHCO₃, water and brine. The organic layer was dried (Na₂SO₄), filtered and concentrated. The residue was then purified by Biotage (5-50% EtOAc/hexane) to afford (S)-isopropyl 2-(5-bromo-4-(4,4-dimethylpiperidin-1-yl)-2-methylpyridin-3-yl)-2-(tert-butoxy)acetate (800 mg, 1.757 mmol, 67.5% yield) as off-white solid. ¹H NMR (500 MHz, CDCl₃) δ 8.46 (s, 1H), 6.27 (br. s., 1H), 5.11-4.98 (m, 1H), 4.03 (t, J=10.6 Hz, 1H), 3.45 (t, J=11.3 Hz, 1H), 2.92 (d, J=11.3 Hz, 1H), 2.60-2.55 (m, 3H), 1.62-1.55 (m, 2H), 1.47 (d, J=12.6 Hz, 1H), 1.37 (d, J=13.1 Hz, 1H), 1.25-1.20 (m, 12H), 1.15 (d, J=6.1 Hz, 3H), 1.09 (s, 3H), 1.04 (s, 3H). LCMS (M+2H)=457.4.

EXAMPLE 62

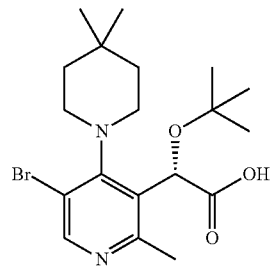 [SMILES: Cc1ncc(Br)c(N2CCC(C)(C)CC2)c1[C@H](OC(C)(C)C)C(=O)O]

(S)-2-(5-Bromo-4-(4,4-dimethylpiperidin-1-yl)-2-methylpyridin-3-yl)-2-(tert-butoxy)acetic acid: A mixture of (S)-isopropyl 2-(5-bromo-4-(4,4-dimethylpiperidin-1-yl)-2-methylpyridin-3-yl)-2-(tert-butoxy)acetate (20 mg, 0.044 mmol) and 10N NaOH (0.044 mL, 0.439 mmol) in ethanol (1 mL) was heated at 80° C. for 5 h. Mixture was then cooled and purified by prep HPLC to afford (S)-2-(5-bromo-4-(4,4-dimethylpiperidin-1-yl)-2-methylpyridin-3-yl)-2-(tert-butoxy)acetic acid (11.9 mg, 0.029 mmol, 65.6% yield). ¹H NMR (500 MHz, DMSO-d₆) δ 8.42 (s, 1H), 5.94 (br. s., 1H), 3.91 (t, J=11.6 Hz, 1H), 2.97 (br. s., 1H), 2.47-2.41 (m, 3H), 1.63-1.48 (m, 2H), 1.42 (d, J=12.1 Hz, 1H), 1.32 (d, J=12.5 Hz, 1H), 1.15 (s, 9H), 1.03 (s, 3H), 0.99 (s, 3H). 2 piperidine hysrogens are not resolved. LCMS (M+H)=413.0.

EXAMPLE 63

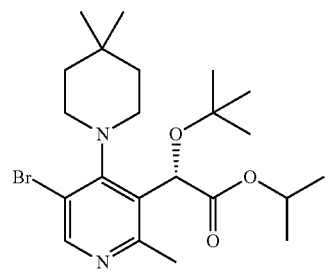

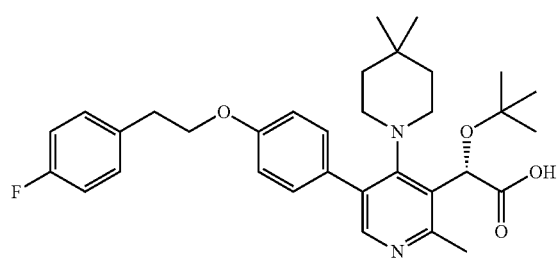 [SMILES: Cc1ncc(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methylpyridin-3-yl)acetic acid: A mixture of (S)-isopropyl 2-(5-bromo-4-(4,4-dimethylpiperidin-1-yl)-2-methylpyridin-3-yl)-2-(tert-butoxy)acetate (80 mg, 0.176 mmol), 2-(4-(4-fluorophenethoxy)phenyl)-6-methyl-1,3,6,2-dioxazaborocane-4,8-dione (98 mg, 0.263 mmol), 2-dicyclohexylphosphino-2',6'-dimethoxybiphenyl (14.42 mg, 0.035 mmol) and 2M $K_3PO_4$ (0.659 mL, 1.317 mmol) in 1,4-dioxane (3 mL) and water (0.600 mL) was degassed for 10 min. Then, $Pd(OAc)_2$ (3.94 mg, 0.018 mmol) was added, degassed for 5 min and the mixture was heated at 80° C. for 3 h. After cooling to room temp, water was added and the mixture was extracted with ethyl acetate, washed with brine, dried ($Na_2SO_4$), filtered and concentrated. The residue was then treated with 10N NaOH (0.176 mL, 1.757 mmol) in EtOH (3 mL) at 80° C. for 5 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-2-methylpyridin-3-yl)acetic acid (72 mg, 0.131 mmol, 74.7% yield) as white solid. $^1H$ NMR (500 MHz, DMSO-$d_6$) δ 7.99 (s, 1H), 7.37 (dd, J=8.4, 5.5 Hz, 2H), 7.25-7.18 (m, J=8.8 Hz, 2H), 7.13 (t, J=9.0 Hz, 2H), 7.04-6.97 (m, J=8.8 Hz, 2H), 5.82 (s, 1H), 4.29-4.13 (m, 2H), 3.05 (t, J=6.6 Hz, 2H), 2.47 (s, 3H), 1.54 (br. s., 1H), 1.30 (br. s., 2H), 1.11 (s, 9H), 0.86 (br. s., 3H), 0.73 (br. s., 3H). 6 piperidine hydrogens are not resolved. LCMS (M+H)=549.4.

EXAMPLE 64

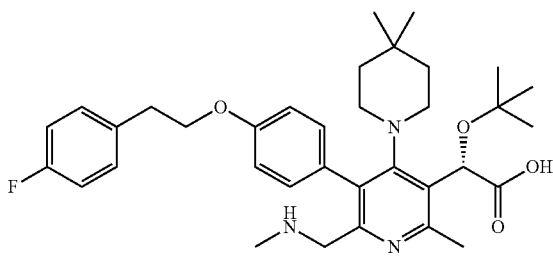 [SMILES: CNCc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-5-(4-(4-fluorophenethoxy)phenyl)-2-methyl-6-((methylamino)methyl)pyridin-3-yl)acetic acid: To a solution of methanamine (0.1 mL, 0.200 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.03 g, 0.750 mmol) was added and heated at 80° C. for 4 h. Then, cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((methylamino)methyl)pyridin-3-yl)acetic acid (0.0114 g, 0.019 mmol, 43.9% yield). LCMS (M+H)=592. $^1H$ NMR (500 MHz, DMSO-$d_6$) δ 7.41-7.34 (m, 2H), 7.23 (d, J=7.7 Hz, 1H), 7.14 (t, J=8.6 Hz, 2H), 7.06-6.97 (m, 3H), 5.59 (s, 1H), 4.28-4.18 (m, 2H), 3.37 (s, 1H), 3.06 (t, J=6.6 Hz, 2H), 2.90 (s, 1H), 2.74 (s, 1H), 2.55 (s, 1H), 2.48 (s, 3H), 2.36 (s, 3H), 2.15 (br. s., 1H), 1.49 (br. s., 1H), 1.28 (br. s., 1H), 1.13 (d, J=13.6 Hz, 1H), 1.08 (s, 9H), 1.00 (d, J=9.9 Hz, 1H), 0.83 (br. s., 3H), 0.61 (br. s., 3H).

EXAMPLE 65

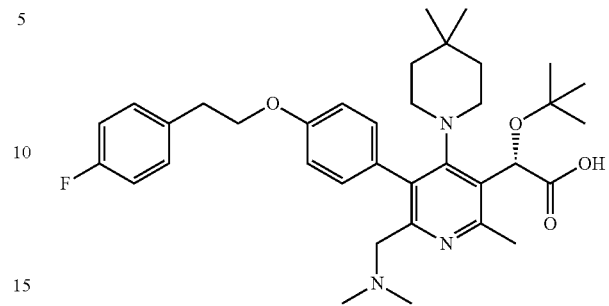

(S)-2-(tert-Butoxy)-2-(6-((dimethylamino)methyl)-4-(4,4-dimethylpiperidin-1-yl)-5-(4-(4-fluorophenethoxy)phenyl)-2-methylpyridin-3-yl)acetic acid: To a solution of dimethylamine/THF (0.2 mL, 0.400 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 3 h. Sodium hydroxide (0.03 g, 0.750 mmol) was added and heated at 80° C. for 3 h, then cooled and purified by prep HPLC to afford (S)-2-(tert-butoxy)-2-(6-((dimethylamino)methyl)-4-(4,4-dimethylpiperidin-1-yl)-5-(4-(4-fluorophenethoxy)phenyl)-2-methylpyridin-3-yl)acetic acid (0.0231 g, 87%). LCMS (M+H)=606.2. $^1H$ NMR (500 MHz, DMSO-$d_6$) δ 7.42-7.34 (m, 1H), 7.14 (t, J=8.6 Hz, 2H), 7.05-6.94 (m, 3H), 5.83 (br. s., 1H), 4.32-4.16 (m, 2H), 3.59-3.26 (m, 7H), 3.16 (d, J=13.6 Hz, 1H), 3.05 (d, J=7.7 Hz, 1H), 2.85-2.76 (m, 1H), 2.47 (s, 3H), 2.17 (br. s., 1H), 2.07 (s, 6H), 1.50 (br. s., 1H), 1.30 (br. s., 1H), 1.18 (d, J=12.8 Hz, 1H), 1.12 (s, 9H), 1.02 (d, J=12.1 Hz, 1H), 0.85 (br. s., 3H), 0.61 (br. s., 3H).

EXAMPLE 66

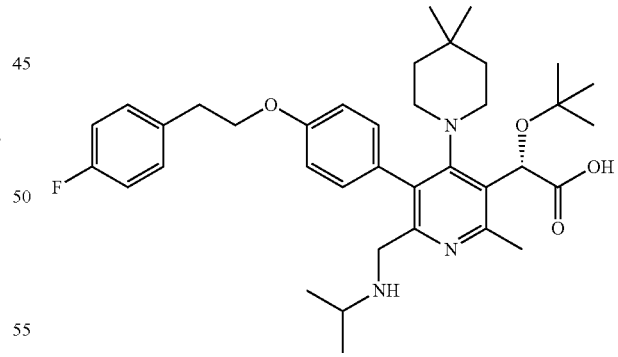

(S)-2-(tert-Butoxy)-2-(4-(4,4-dimethylpiperidin-1-yl)-5-(4-(4-fluorophenethoxy)phenyl)-6-((isopropylamino)methyl)-2-methylpyridin-3-yl)acetic acid: To a solution of isopropaneamine (0.05 mL, 0.770 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.03 g, 0.750 mmol) was added and heated at 80° C. for 3 h, then cooled and purified by prep HPLC to afford (S)-2-(tert-butoxy)-2-(4-(4,4-dimethylpiperidin-1-yl)-5-(4-(4-fluorophenethoxy)phenyl)-6-((isopropylamino)methyl)-2-methylpyridin-3-yl)acetic acid (0.0221 g, 0.036 mmol, 81% yield). LCMS (M+H): 620.3.

EXAMPLE 67

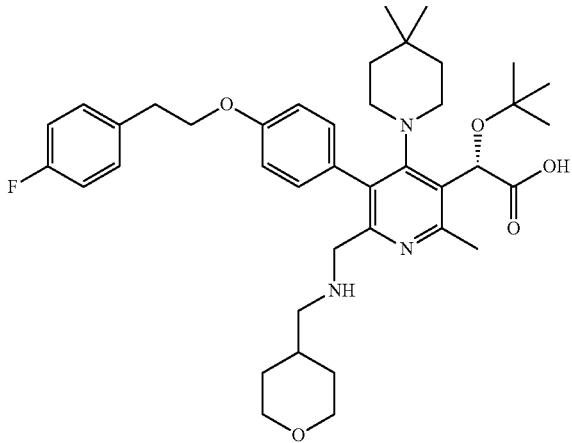 [SMILES: Cc1nc(CNCC2CCOCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-((((tetrahydro-2H-pyran-4-yl)methyl)amino)methyl)pyridin-3-yl)acetic acid: To a solution of (tetrahydro-2H-pyran-4-yl)methanamine (0.1 g, 0.868 mmol) in ethanol (0.5 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.06 g, 0.088 mmol) and the mixture was stirred at rt for 2 h. Sodium hydroxide (0.03 g, 0.750 mmol) was added and heated at 80° C. for 3 h, then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((((tetrahydro-2H-pyran-4-yl)methyl)amino)methyl)pyridin-3-yl)acetic acid (0.0342 g, 0.051 mmol, 57.7% yield). $^1$H NMR (500 MHz, DMSO-$d_6$) δ 7.44-7.35 (m, 2H), 7.24 (d, J=8.8 Hz, 1H), 7.14 (t, J=8.8 Hz, 2H), 7.05 (s, 2H), 7.01 (d, J=8.1 Hz, 1H), 5.74 (br. s., 1H), 4.31-4.17 (m, 2H), 3.82-3.72 (m, 2H), 3.47 (d, J=13.9 Hz, 2H), 3.31 (d, J=13.9 Hz, 1H), 3.24-3.12 (m, 3H), 3.05 (d, J=6.2 Hz, 1H), 2.79 (t, J=8.3 Hz, 1H), 2.48 (s, 3H), 2.36 (d, J=5.5 Hz, 2H), 2.22-2.13 (m, J=8.1 Hz, 1H), 1.97-1.92 (m, 1H), 1.57-1.44 (m, 4H), 1.35-1.23 (m, 1H), 1.16 (d, J=10.6 Hz, 1H), 1.11 (s, 9H), 1.08-0.98 (m, 3H), 0.85 (br. s., 3H), 0.61 (br. s., 3H). LCMS (M+H)=676.2.

EXAMPLE 68

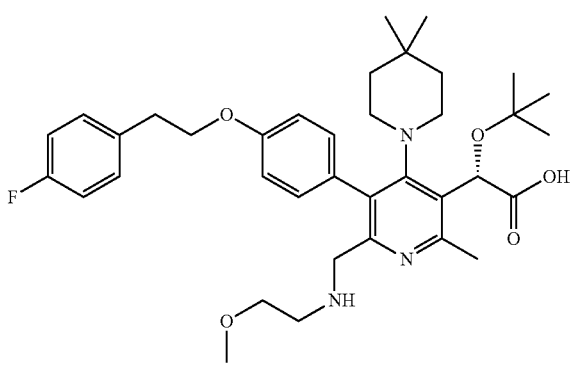 [SMILES: COCCNCc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-5-(4-(4-fluorophenethoxy)phenyl)-6-(((2-methoxyethyl)amino)methyl)-2-methylpyridin-3-yl)acetic acid: To a solution of 2-methoxyethanamine (0.1 g, 1.331 mmol) in ethanol (0.5 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.06 g, 0.088 mmol) and the mixture was stirred at rt for 2 h. Sodium hydroxide (0.03 g, 0.750 mmol) was added and heated at 80° C. for 3 h. Then, cooled and purified by prep HPLC to afford (S)-2-(tert-butoxy)-2-(4-(4,4-dimethylpiperidin-1-yl)-5-(4-(4-fluorophenethoxy)phenyl)-6-(((2-methoxyethyl)amino)methyl)-2-methylpyridin-3-yl)acetic acid (0.040 g, 0.063 mmol, 71.7% yield). $^1$H NMR (500 MHz, DMSO-$d_6$) δ 7.41-7.35 (m, 2H), 7.22 (d, J=8.1 Hz, 1H), 7.14 (t, J=8.8 Hz, 2H), 7.05 (s, 2H), 7.01 (d, J=8.4 Hz, 1H), 5.79 (s, 1H), 4.32-4.14 (m, 2H), 3.46 (d, J=13.9 Hz, 1H), 3.43-3.35 (m, J=9.2 Hz, 3H), 3.31 (d, J=4.8 Hz, 1H), 3.17 (s, 3H), 3.06 (t, J=6.2 Hz, 2H), 2.83-2.76 (m, J=13.0, 13.0 Hz, 1H), 2.62-2.57 (m, 2H), 2.48 (s, 3H), 2.21-2.14 (m, 1H), 1.99-1.92 (m, 1H), 1.55-1.43 (m, 1H), 1.35-1.24 (m, 1H), 1.17 (d, J=12.1 Hz, 1H), 1.12 (s, 9H), 1.05-0.98 (m, J=11.4 Hz, 1H), 0.85 (br. s., 3H), 0.61 (br. s., 3H). LCMS (M+H)=636.3.

EXAMPLE 69

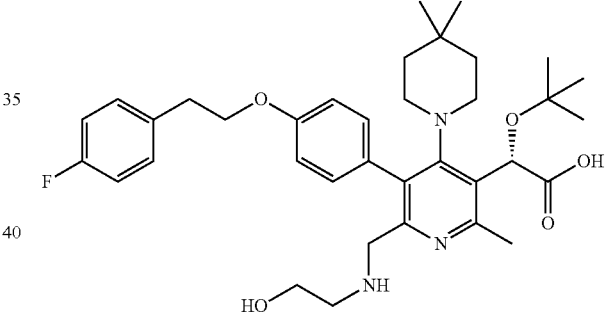

(S)-2-(tert-Butoxy)-2-(4-(4,4-dimethylpiperidin-1-yl)-5-(4-(4-fluorophenethoxy)phenyl)-6-(((2-hydroxyethyl)amino)methyl)-2-methylpyridin-3-yl)acetic acid: To a solution of 2-aminoethanol (0.02 g, 0.327 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.03 g, 0.750 mmol) was added and heated at 80° C. for 4 h. then, cooled and purified by prep HPLC to afford (S)-2-(tert-butoxy)-2-(4-(4,4-dimethylpiperidin-1-yl)-5-(4-(4-fluorophenethoxy)phenyl)-6-(((2-hydroxyethyl)amino)methyl)-2-methylpyridin-3-yl)acetic acid (0.0116 g, 0.019 mmol, 42.5% yield). $^1$H NMR (500 MHz, DMSO-$d_6$) δ 7.43-7.34 (m, 2H), 7.23 (d, J=8.1 Hz, 1H), 7.14 (t, J=8.8 Hz, 2H), 7.07-6.91 (m, 3H), 5.69 (br. s., 1H), 4.31-4.16 (m, 2H), 3.60 (d, J=14.7 Hz, 1H), 3.36 (d, J=13.9 Hz, 1H), 3.72-3.24 (m, 7H), 3.06 (t, J=6.4 Hz, 1H), 2.83-2.71 (m, 2H), 2.64 (br. s., 2H), 2.48 (s, 3H), 2.16 (br. s., 1H), 1.49 (br. s., 1H), 1.28 (br. s., 1H), 1.14 (br. s., 1H), 1.10 (s, 9H), 1.01 (d, J=10.6 Hz, 1H), 0.84 (br. s., 3H), 0.61 (br. s., 3H). LCMS (M+H)=622.2.

EXAMPLE 70

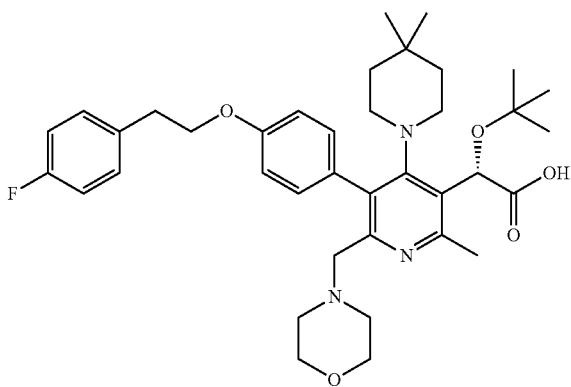

(S)-2-(tert-Butoxy)-2-(4-(4,4-dimethylpiperidin-1-yl)-5-(4-(4-fluorophenethoxy)phenyl)-2-methyl-6-(morpholinomethyl)pyridin-3-yl)acetic acid: To a solution of morpholine (0.04 g, 0.459 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.03 g, 0.750 mmol) was added and heated at 80° C. for 3 h. Then, cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(morpholinomethyl)pyridin-3-yl)acetic acid (0.0232 g, 0.036 mmol, 82% yield). $^1$H NMR (500 MHz, DMSO-$d_6$) δ 7.42-7.32 (m, 3H), 7.14 (t, J=8.6 Hz, 2H), 7.06-6.93 (m, 3H), 5.81 (br. s., 1H), 4.34-4.14 (m, 2H), 3.63-3.27 (m, 4H), 3.21-2.99 (m, 5H), 2.85-2.77 (m, 1H), 2.46 (s, 3H), 2.18 (br. s., 5H), 1.98-1.92 (m, 1H), 1.57-1.45 (m, 1H), 1.30 (br. s., 1H), 1.16 (br. s., 1H), 1.11 (s, 9H), 1.02 (d, J=13.9 Hz, 1H), 0.85 (br. s., 3H), 0.60 (br. s., 3H). LCMS ((M+H)=648.4.

EXAMPLE 71

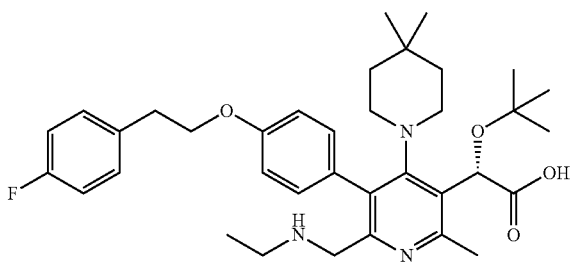

(S)-2-(tert-Butoxy)-2-(4-(4,4-dimethylpiperidin-1-yl)-6-((ethylamino)methyl)-5-(4-(4-fluorophenethoxy)phenyl)-2-methylpyridin-3-yl)acetic acid: To a solution of ethanamine (0.04 g, 0.621 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.03 g, 0.750 mmol) was added and heated at 80° C. for 4 h. Then, cooled down and purified by prep HPLC to afford (S)-2-(tert-butoxy)-2-(4-(4,4-dimethylpiperidin-1-yl)-6-((ethylamino)methyl)-5-(4-(4-fluorophenethoxy)phenyl)-2-methylpyridin-3-yl)acetic acid (0.0202 g, 0.033 mmol, 74.5% yield). $^1$H NMR (500 MHz, DMSO-$d_6$) δ 7.40-7.34 (m, 2H), 7.25 (d, J=8.1 Hz, 1H), 7.14 (t, J=8.8 Hz, 2H), 7.06-6.94 (m, 3H), 5.63 (s, 1H), 4.30-4.18 (m, 2H), 3.65 (d, J=14.7 Hz, 2H), 3.36 (d, J=14.7 Hz, 1H), 2.90 (s, 1H), 2.74 (s, 2H), 2.63 (d, J=7.0 Hz, 2H), 2.49 (s, 3H), 2.23-2.12 (m, 1H), 1.50 (br. s., 1H), 1.28 (br. s., 1H), 1.20-1.11 (m, 1H), 1.09 (s, 9H), 1.01 (t, J=7.2 Hz, 4H), 0.84 (br. s., 3H), 0.61 (br. s., 3H). LCMS (M+H)=606.2.

EXAMPLE 72

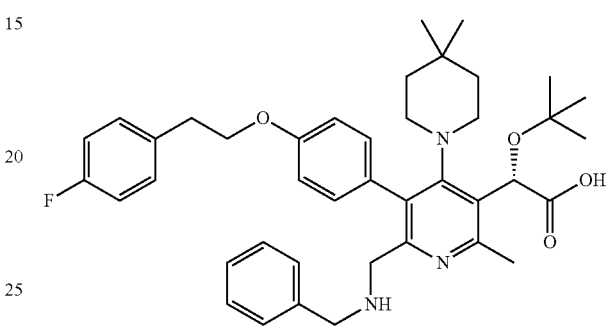

(S)-2-(6-((Benzylamino)methyl)-4-(4,4-dimethylpiperidin-1-yl)-5-(4-(4-fluorophenethoxy)phenyl)-2-methylpyridin-3-yl)-2-(tert-butoxy)acetic acid: To a solution of phenylmethanamine (0.04 g, 0.373 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.03 g, 0.750 mmol) was added and heated at 80° C. for 3 h. Then, cooled and purified by prep HPLC to afford (S)-2-(6-((benzylamino)methyl)-4-(4,4-dimethylpiperidin-1-yl)-5-(4-(4-fluorophenethoxy)phenyl)-2-methylpyridin-3-yl)-2-(tert-butoxy)acetic acid (0.0157 g, 0.023 mmol, 52.0% yield). $^1$H NMR (500 MHz, DMSO-d6) δ 7.42-7.35 (m, 2H), 7.28-7.11 (m, 8H), 7.04 (q, J=8.4 Hz, 2H), 6.95 (d, J=7.7 Hz, 1H), 5.82 (br. s., 1H), 4.22 (dd, J=11.7, 6.6 Hz, 2H), 3.69-3.58 (m, 3H), 3.46-3.25 (m, 5H), 3.05 (d, J=6.6 Hz, 1H), 2.80 (br. s., 1H), 2.49 (s, 3H), 2.23-2.11 (m, J=12.5 Hz, 1H), 1.98-1.92 (m, 1H), 1.56-1.42 (m, 1H), 1.34-1.23 (m, 1H), 1.18 (d, J=12.1 Hz, 1H), 1.13 (s, 9H), 1.02 (d, J=12.5 Hz, 1H), 0.85 (br. s., 3H), 0.61 (br. s., 3H). LCMS (M+H)=668.2.

EXAMPLE 73

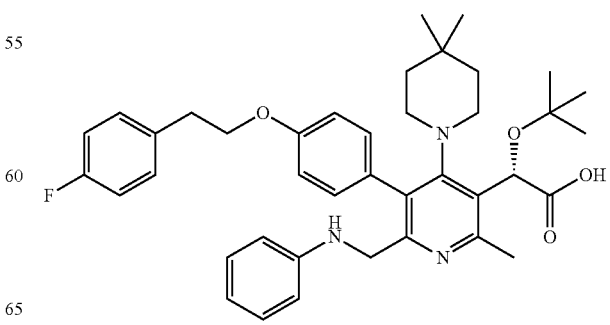

(S)-2-(tert-Butoxy)-2-(4-(4,4-dimethylpiperidin-1-yl)-5-(4-(4-fluorophenethoxy)phenyl)-2-methyl-6-((phenylamino)methyl)pyridin-3-yl)acetic acid: To a solution of aniline (0.025 g, 0.263 mmol) in THF (2 mL) was added t-BuOK (0.03 g, 0.267 mmol), the mixture was stirred at rt for 5 min then (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.06 g, 0.088 mmol) was added and stirred at rt for 4 days. Sodium hydroxide (0.04 g, 1.000 mmol) was added and heated at 80° C. for 4 h, then cooled and purified by prep HPLC to afford(S)-2-(tert-butoxy)-2-(4-(4,4-dimethylpiperidin-1-yl)-5-(4-(4-fluorophenethoxy)phenyl)-2-methyl-6-((phenylamino)methyl)pyridin-3-yl)acetic acid (0.0207 g, 0.032 mmol, 36.1% yield). $^1$H NMR (500 MHz, DMSO-d6) δ 7.45-7.35 (m, J=6.6, 6.6 Hz, 1H), 7.33 (d, J=8.1 Hz, 1H), 7.19-7.10 (m, 3H), 7.09-6.99 (m, 4H), 6.55-6.48 (m, J=7.3, 7.3 Hz, 1H), 6.45 (d, J=8.1 Hz, 2H), 5.88 (br. s., 1H), 4.30-4.18 (m, 2H), 3.91 (d, J=14.7 Hz, 1H), 3.72 (d, J=14.7 Hz, 1H), 3.06 (t, J=6.4 Hz, 2H), 2.88-2.79 (m, 1H), 2.54 (s, 3H), 2.25-2.19 (m, J=12.1 Hz, 1H), 2.03-1.90 (m, 1H), 1.51 (br. s., 1H), 1.34-1.17 (m, 2H), 1.15 (s, 9H), 1.04 (d, J=12.5 Hz, 1H), 0.86 (br. s., 3H), 0.62 (br. s., 3H) 4 protons were missed). LCMS (M+H)=654.2.

EXAMPLE 74

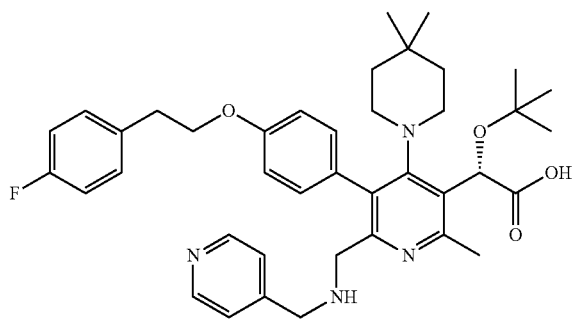 [SMILES: Cc1nc(CNCc2ccncc2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(((pyridin-4-ylmethyl)amino)methyl)pyridin-3-yl)acetic acid: To a solution of pyridin-4-ylmethanamine (20 mg, 0.185 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.025 g, 0.625 mmol) was added and heated at 80° C. for 4 h, then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((pyridin-4-ylmethyl)amino)methyl)pyridin-3-yl)acetic acid (0.0189 g, 0.027 mmol, 62.5% yield). $^1$H NMR (500 MHz, DMSO-d6) δ 8.39 (d, J=5.1 Hz, 2H), 7.40-7.32 (m, 2H), 7.20-7.11 (m, 5H), 7.08-6.98 (m, 2H), 6.93 (d, J=6.2 Hz, 1H), 5.81 (br. s., 1H), 4.30-4.13 (m, 2H), 3.37 (d, J=13.6 Hz, 1H), 3.27 (d, J=13.6 Hz, 1H), 3.05 (t, J=6.6 Hz, 2H), 2.80 (br. s., 1H), 2.50 (br. s., 3H), 2.22-2.14 (m, J=5.1 Hz, 1H), 2.02-2.00 (m, 1H), 1.50 (br. s., 1H), 1.29 (br. s., 1H), 1.19 (br. s., 1H), 1.13 (s, 9H), 1.02 (d, J=12.8 Hz, 1H), 0.85 (br. s., 3H), 0.60 (br. s., 3H). LCMS (M+H)=669.2.

EXAMPLE 75

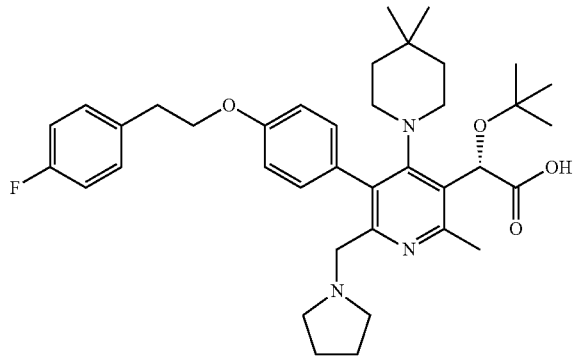 [SMILES: Cc1nc(CN2CCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(pyrrolidin-1-ylmethyl)pyridin-3-yl)acetic acid: To a solution of pyrrolidine (0.020 g, 0.281 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.025 g, 0.625 mmol) was added and heated at 80° C. for 3 h, then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(pyrrolidin-1-ylmethyl)pyridin-3-yl)acetic acid (0.0176 g, 0.028 mmol, 63.5% yield). $^1$H NMR (500 MHz, DMSO-d6) δ 7.37 (t, J=6.6 Hz, 2H), 7.31 (d, J=8.4 Hz, 1H), 7.14 (t, J=8.6 Hz, 2H), 7.02 (s, 2H), 6.99 (d, J=8.8 Hz, 1H), 5.80 (s, 1H), 4.31-4.13 (m, 2H), 3.46 (d, J=13.2 Hz, 1H), 3.23 (d, J=12.5 Hz, 1H), 3.05 (t, J=6.6 Hz, 2H), 2.80 (br. s., 1H), 2.47 (s, 3H), 2.43 (br. s., 4H), 2.18 (br. s., 1H), 1.61 (br. s., 4H), 1.50 (br. s., 1H), 1.33-1.23 (m, J=5.9 Hz, 1H), 1.17 (d, J=11.0 Hz, 1H), 1.14-1.09 (m, 9H), 1.02 (d, J=12.1 Hz, 1H), 0.85 (br. s., 3H), 0.61 (br. s., 3H). LCMS (M+H)=632.2.

EXAMPLE 76

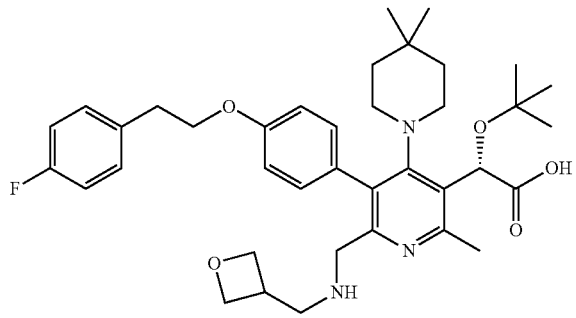 [SMILES: Cc1nc(CNCC2COC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(((oxetan-3-ylmethyl)amino)methyl)pyridin-3-yl)acetic acid: To a solution of oxetan-3-ylmethanamine (0.01 g, 0.115 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h.

Sodium hydroxide (0.025 g, 0.625 mmol) was added and heated at 80° C. for 3 h, then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((oxetan-3-ylmethyl)amino)methyl)pyridin-3-yl)acetic acid (0.0074 g, 0.011 mmol, 25.8% yield). $^1$H NMR (500 MHz, DMSO-d6) δ 7.42-7.34 (m, 2H), 7.24 (d, J=8.4 Hz, 1H), 7.14 (t, J=8.8 Hz, 2H), 7.05 (s, 2H), 7.02 (d, J=8.4 Hz, 1H), 5.77 (s, 1H), 4.58-4.47 (m, 2H), 4.29-4.21 (m, 2H), 4.18 (t, J=5.9 Hz, 2H), 3.46 (d, J=13.9 Hz, 1H), 3.65-3.33 (m, 5H), 3.28 (d, J=13.9 Hz, 1H), 3.06 (t, J=6.4 Hz, 2H), 2.97-2.90 (m, 1H), 2.83-2.76 (m, J=9.5 Hz, 1H), 2.48 (s, 3H), 2.21-2.14 (m, J=9.9 Hz, 1H), 1.97-1.92 (m, 1H), 1.49 (br. s., 1H), 1.34-1.23 (m, 1H), 1.17 (d, J=12.1 Hz, 1H), 1.14-1.08 (m, 9H), 1.02 (d, J=13.2 Hz, 1H), 0.85 (br. s., 3H), 0.61 (br. s., 3H). LCMS (M+H)=648.2.

EXAMPLE 77

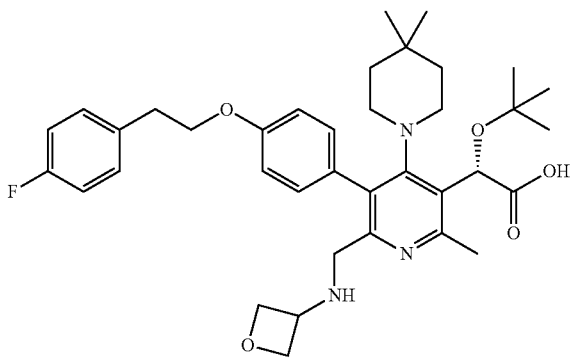 [SMILES: Cc1nc(CNC2COC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-((oxetan-3-ylamino)methyl)pyridin-3-yl)acetic acid: To a solution of oxetan-3-amine (0.03 g, 0.410 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.045 g, 0.066 mmol) and the mixture was stirred at rt for 2 h. Sodium hydroxide (0.050 g, 1.250 mmol) was added and heated at 80° C. for 3 h, then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((oxetan-3-ylamino)methyl)pyridin-3-yl)acetic acid (0.0049 g, 7.31 μmol, 11.11% yield). LCMS (M+H)=634.2.

EXAMPLE 78

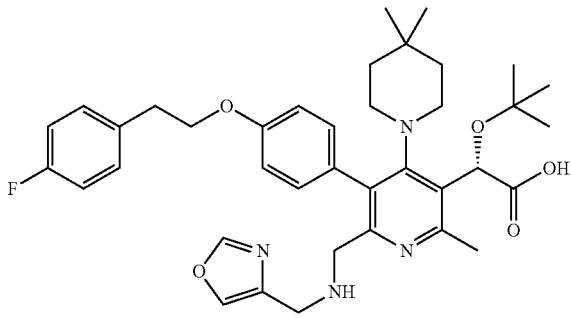 [SMILES: Cc1nc(CNCc2cocn2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(((oxazol-4-ylmethyl)amino)methyl)pyridin-3-yl)acetic acid: To a solution of oxazol-4-ylmethanamine, HCl (0.02 g, 0.149 mmol) and TEA (0.05 ml, 0.359 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 2 h. Sodium hydroxide (0.025 g, 0.625 mmol) was added and heated at 80° C. for 4 h. Then, cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((oxazol-4-ylmethyl)amino)methyl)pyridin-3-yl)acetic acid (0.0042 g, 6.38 μmol, 14.53% yield). $^1$H NMR (500 MHz, DMSO-d6) δ 8.23 (s, 1H), 7.76 (s, 1H), 7.43-7.35 (m, 2H), 7.21 (d, J=8.1 Hz, 1H), 7.15 (t, J=8.6 Hz, 2H), 7.08-7.02 (m, 2H), 6.98 (d, J=8.4 Hz, 1H), 5.81 (br. s., 1H), 4.31-4.15 (m, 2H), 3.44 (d, J=13.6 Hz, 2H), 3.38-3.30 (m, 3H), 3.30 (d, J=13.9 Hz, 1H), 3.06 (t, J=6.4 Hz, 2H), 2.80 (br. s., 1H), 2.48 (s, 3H), 2.17 (br. s., 1H), 1.50 (br. s., 1H), 1.29 (br. s., 1H), 1.18 (d, J=13.6 Hz, 1H), 1.12 (s, 9H), 1.02 (d, J=15.4 Hz, 1H), 0.85 (br. s., 3H), 0.60 (br. s., 3H). LCMS (M+H)=659.1

EXAMPLE 79

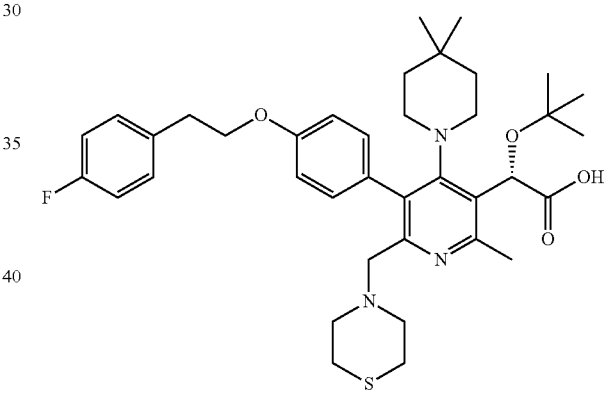

(S)-2-(tert-Butoxy)-2-(4-(4,4-dimethylpiperidin-1-yl)-5-(4-(4-fluorophenethoxy)phenyl)-2-methyl-6-(thiomorpholinomethyl)pyridin-3-yl)acetic acid: To a solution of thiomorpholine (0.03 g, 0.291 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 18 h. Sodium hydroxide (0.03 g, 0.750 mmol) was added and heated at 80° C. for 2 h. Then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(thiomorpholinomethyl)pyridin-3-yl)acetic acid (0.0226 g, 0.034 mmol, 78% yield). $^1$H NMR (500 MHz, DMSO-d$_6$) δ 7.41-7.35 (m, 2H), 7.33 (d, J=8.4 Hz, 1H), 7.14 (t, J=8.6 Hz, 2H), 7.03 (s, 2H), 6.98 (s, 1H), 5.82 (br. s., 1H), 4.31-4.15 (m, 2H), 3.20 (d, J=12.5 Hz, 1H), 3.06 (d, J=7.7 Hz, 3H), 2.80 (br. s., 1H), 2.48-2.34 (m, 12H), 2.19 (d, J=10.3 Hz, 1H), 2.01-1.92 (m, 1H), 1.56-1.43 (m, 1H), 1.35-1.25 (m, 1H), 1.17 (d, J=13.6 Hz, 1H), 1.12 (s, 9H), 1.02 (d, J=12.5 Hz, 1H), 0.85 (s., 3H), 0.60 (s., 3H). LCMS (M+H)=664.2.

EXAMPLE 80

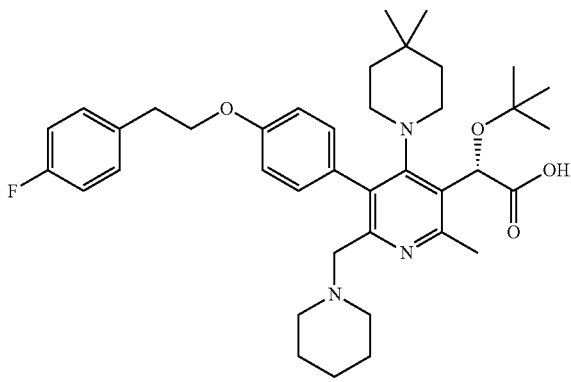 [SMILES: Cc1nc(CN2CCCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(piperidin-1-ylmethyl)pyridin-3-yl)acetic acid: To a solution of piperidine (0.03 g, 0.352 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 18 h. Sodium hydroxide (0.03 g, 0.750 mmol) was added and the mixture was heated at 80° C. for 3 h. Then cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(piperidin-1-ylmethyl)pyridin-3-yl)acetic acid (0.0238 g, 0.037 mmol, 84% yield). $^1$H NMR (500 MHz, DMSO-d6) δ 7.40-7.32 (m, 3H), 7.14 (t, J=8.8 Hz, 2H), 7.01 (s, 2H), 6.97 (d, J=9.2 Hz, 1H), 5.83 (br. s., 1H), 4.33-4.18 (m, 2H), 3.34 (br. s., 3H), 3.12-3.02 (m, 1H), 2.80 (br. s., 1H), 2.46 (s, 3H), 2.18 (br. s., 3H), 2.14 (br. s., 2H), 1.99-1.91 (m, 1H), 1.50 (br. s., 1H), 1.34 (br. s., 4H), 1.30 (br. s., 3H), 1.17 (d, J=12.5 Hz, 1H), 1.12 (s, 9H), 1.02 (d, J=12.1 Hz, 1H), 0.85 (br. s., 3H), 0.60 (br. s., 3H). LCMS (M+H)=646.2.

EXAMPLE 81

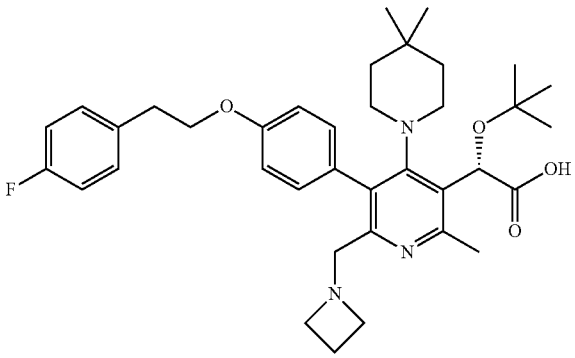 [SMILES: Cc1nc(CN2CCC2)c(-c2ccc(OCCc3ccc(F)cc3)cc2)c(N2CCC(C)(C)CC2)c1[C@H](OC(C)(C)C)C(=O)O]

(S)-2-(6-(Azetidin-1-ylmethyl)-4-(4,4-dimethylpiperidin-1-yl)-5-(4-(4-fluorophenethoxy)phenyl)-2-methylpyridin-3-yl)-2-(tert-butoxy)acetic acid: To a solution of azetidine (0.03 g, 0.525 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 18 h. Sodium hydroxide (0.03 g, 0.750 mmol) was added and heated at 80° C. for 2 h. Then, cooled and purified by prep HPLC to afford (S)-2-(6-(azetidin-1-ylmethyl)-4-(4,4-dimethylpiperidin-1-yl)-5-(4-(4-fluorophenethoxy)phenyl)-2-methylpyridin-3-yl)-2-(tert-butoxy)acetic acid (0.0179 g, 0.027 mmol, 62.1% yield). $^1$H NMR (500 MHz, DMSO-d6) δ 7.40-7.35 (m, 2H), 7.26 (d, J=9.2 Hz, 1H), 7.14 (t, J=8.6 Hz, 2H), 7.04-6.97 (m, 3H), 5.75 (br. s., 1H), 4.27-4.18 (m, 2H), 3.44 (d, J=13.6 Hz, 3H), 3.29 (br. s., 1H), 3.08-2.99 (m, 2H), 2.76 (d, J=17.6 Hz, 1H), 2.46 (s, 3H), 2.14 (br. s., 1H), 1.96 (t, J=7.2 Hz, 2H), 1.49 (br. s., 1H), 1.28 (br. s., 1H), 1.16 (d, J=9.9 Hz, 1H), 1.12-1.07 (m, 9H), 1.03 (d, J=9.5 Hz, 4H), 0.84 (br. s., 3H), 0.60 (br. s., 3H). LCMS (M+H)=618.2.

EXAMPLE 82

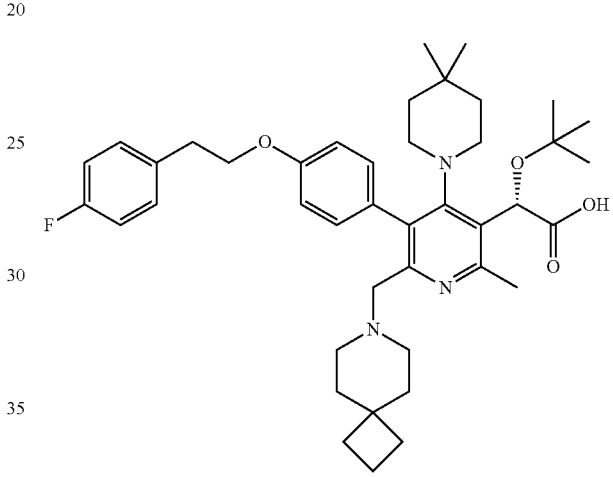

(S)-2-(6-(7-Azaspiro[3.5]nonan-7-ylmethyl)-4-(4,4-dimethylpiperidin-1-yl)-5-(4-(4-fluorophenethoxy)phenyl)-2-methylpyridin-3-yl)-2-(tert-butoxy)acetic acid: To a solution of 7-azaspiro[3.5]nonane (0.05 g, 0.399 mmol) in ethanol (1 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.05 g, 0.073 mmol) and the mixture was stirred at rt for 18 h. EtOH (1 ml) and sodium hydroxide (0.03 g, 0.750 mmol) were added and the mixture was heated at 80° C. for 3 h. Then, cooled and purified by prep HPLC to afford (S)-2-(6-(7-azaspiro[3.5]nonan-7-ylmethyl)-4-(4,4-dimethylpiperidin-1-yl)-5-(4-(4-fluorophenethoxy)phenyl)-2-methylpyridin-3-yl)-2-(tert-butoxy)acetic acid (0.0465 g, 0.068 mmol, 93% yield). $^1$H NMR (500 MHz, DMSO-d6) δ 7.42-7.30 (m, 3H), 7.14 (t, J=8.8 Hz, 2H), 7.01 (s, 2H), 6.97 (d, J=8.8 Hz, 1H), 5.86 (s, 1H), 4.30-4.14 (m, 2H), 3.30-3.20 (m, 1H), 3.09 (br. s., 2H), 3.04 (t, J=6.4 Hz, 2H), 2.84-2.76 (m, 1H), 2.46 (s, 3H), 2.23-2.04 (m, 5H), 1.98-1.92 (m, 1H), 1.82-1.72 (m, 2H), 1.67-1.59 (m, 4H), 1.53-1.46 (m, 1H), 1.40 (br. s., 4H), 1.34-1.23 (m, 1H), 1.21-1.14 (m, 1H), 1.12 (s, 9H), 1.04-0.93 (m, 1H), 0.85 (br. s., 3H), 0.60 (br. s., 3H). LCMS (M+H)=686.3.

EXAMPLE 83

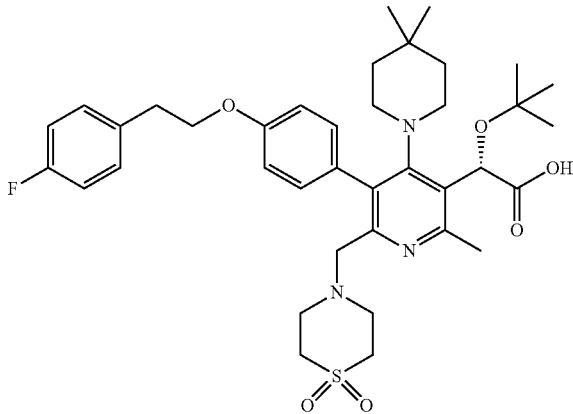 [SMILES: Cc1nc(CN2CCS(=O)(=O)CC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-6-((1,1-dioxidothiomorpholino)methyl)-5-(4-(4-fluorophenethoxy)phenyl)-2-methylpyridin-3-yl)acetic acid: To a solution of thiomorpholine 1,1-dioxide (0.03 g, 0.222 mmol) in ethanol (2 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.03 g, 0.044 mmol) and the mixture was stirred at rt for 18 h. Sodium hydroxide (0.03 g, 0.750 mmol) was added and heated at 80° C. for 3 h. Then, cooled and purified by prep HPLC to afford (S)-2-(tert-butoxy)-2-(4-(4,4-dimethylpiperidin-1-yl)-6-((1,1-dioxidothiomorpholino)methyl)-5-(4-(4-fluorophenethoxy)phenyl)-2-methylpyridin-3-yl)acetic acid (0.0117 g, 0.017 mmol, 38.3% yield). $^1$H NMR (500 MHz, DMSO-d6) δ 7.41-7.30 (m, 3H), 7.15 (t, J=8.8 Hz, 2H), 7.09-6.97 (m, 3H), 5.84 (br. s., 1H), 4.33-4.15 (m, 2H), 3.38 (br. s., 1H), 3.26-3.20 (m, 1H), 3.05 (t, J=6.6 Hz, 2H), 3.01-2.93 (m, 2H), 2.90 (s, 3H), 2.84-2.77 (m, J=12.5 Hz, 1H), 2.76-2.66 (m, 4H), 2.47 (s, 3H), 2.24-2.14 (m, 1H), 2.02-1.92 (m, 1H), 1.50 (br. s., 1H), 1.30 (br. s., 1H), 1.18 (d, J=12.1 Hz, 1H), 1.13 (s, 9H), 1.02 (br. s., 1H), 0.85 (br. s., 3H), 0.60 (br. s., 3H). LCMS (M+H)=696.1.

EXAMPLE 84

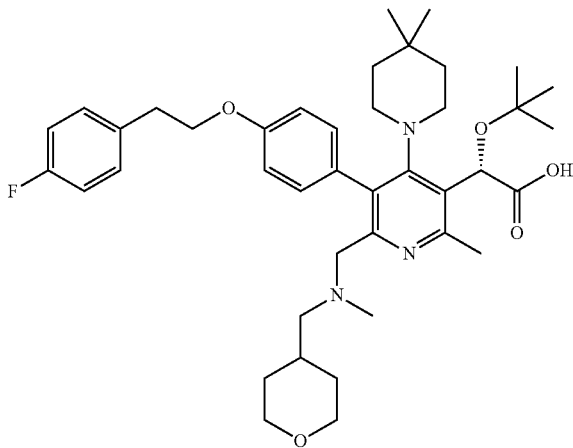

(S)-2-(tert-Butoxy)-2-(4-(4,4-dimethylpiperidin-1-yl)-5-(4-(4-fluorophenethoxy)phenyl)-2-methyl-6-((methyl((tetrahydro-2H-pyran-4-yl)methyl)amino)methyl)pyridin-3-yl)acetic acid: To a solution of N-methyl-1-(tetrahydro-2H-pyran-4-yl)methanamine (0.04 g, 0.310 mmol) in ethanol (0.5 mL) was added (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.05 g, 0.073 mmol). The mixture was stirred at rt for 1 h and sodium hydroxide (0.04 g, 1.000 mmol) was added. Then, the reaction mixture was heated at 80° C. for 2.5 h, cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((methyl((tetrahydro-2H-pyran-4-yl)methyl)amino)methyl)pyridin-3-yl)acetic acid (0.0477 g, 0.069 mmol, 95% yield). LCMS (M+H)=690.3.

EXAMPLE 85

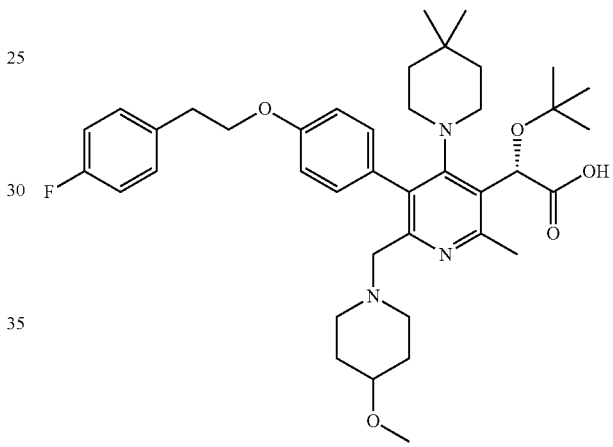

(S)-2-(tert-Butoxy)-2-(4-(4,4-dimethylpiperidin-1-yl)-5-(4-(4-fluorophenethoxy)phenyl)-6-((4-methoxypiperidin-1-yl)methyl)-2-methylpyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) and 4-methoxypiperidine (0.02 g, 0.174 mmol) in EtOH (1 mL) was stirred for 2 h. Sodium hydroxide (0.04 g, 1.000 mmol) was added and stirred at 80° C. for 2 h. The, cooled and purified by prep HPLC to afford (S)-2-(tert-butoxy)-2-(4-(4,4-dimethylpiperidin-1-yl)-5-(4-(4-fluorophenethoxy)phenyl)-6-((4-methoxypiperidin-1-yl)methyl)-2-methylpyridin-3-yl)acetic acid (0.0116 g, 0.017 mmol, 78% yield). $^1$H NMR (500 MHz, DMSO-d6) δ 7.37 (dd, J=8.4, 5.9 Hz, 2H), 7.32 (d, J=8.8 Hz, 1H), 7.13 (t, J=8.8 Hz, 2H), 7.01 (s, 2H), 6.97 (d, J=9.2 Hz, 1H), 5.83 (s, 1H), 4.28-4.14 (m, 2H), 3.35-3.27 (m, 1H), 3.16 (s, 3H), 3.13-3.00 (m, 4H), 2.85-2.76 (m, 1H), 2.45 (s, 4H), 2.43-2.32 (m, 2H), 2.21-2.12 (m, 1H), 2.02-1.92 (m, 3H), 1.68 (d, J=11.0 Hz, 2H), 1.54-1.44 (m, 1H), 1.33-1.15 (m, 4H), 1.12 (s, 9H), 1.05-0.96 (m, 1H), 0.84 (br. s., 3H), 0.60 (br. s., 3H); LCMS (M+H)=676.2.

EXAMPLE 86

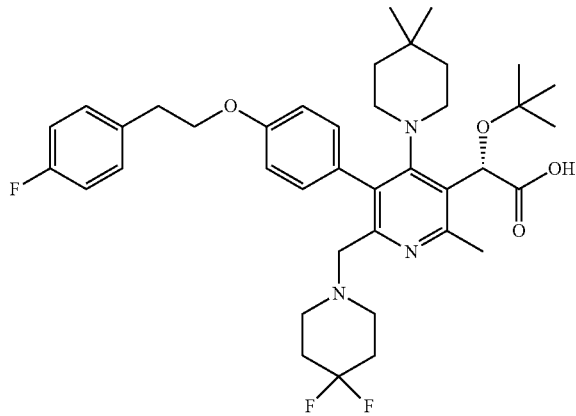 [SMILES: Cc1nc(CN2CCC(F)(F)CC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((4,4-difluoropiperidin-1-yl)methyl)-4-(4,4-dimethylpiperidin-1-yl)-5-(4-(4-fluorophenethoxy)phenyl)-2-methylpyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol), 4,4-difluoropiperidine, HCl (0.015 g, 0.095 mmol) and TEA (0.02 ml, 0.143 mmol) in EtOH (1 mL) was stirred for 2 h. Sodium hydroxide (0.04 g, 1.000 mmol) was added and the reaction mixture was stirred at 80° C. for 2 h. Then, cooled and purified by prep HPLC to afford (S)-2-(tert-butoxy)-2-(6-((4,4-difluoropiperidin-1-yl)methyl)-4-(4,4-dimethylpiperidin-1-yl)-5-(4-(4-fluorophenethoxy)phenyl)-2-methylpyridin-3-yl)acetic acid (0.0128 g, 0.019 mmol, 86% yield). H NMR (500 MHz, DMSO-d6) δ 7.40-7.30 (m, 3H), 7.14 (t, J=9.0 Hz, 2H), 7.06-6.97 (m, 3H), 5.80 (s, 1H), 4.28-4.17 (m, 2H), 3.37 (br. s., 1H), 3.22 (d, J=12.4 Hz, 1H), 3.13 (d, J=12.3 Hz, 1H), 3.05 (t, J=6.8 Hz, 2H), 2.80 (br. s., 1H), 2.46 (s, 3H), 2.38-2.26 (m, 4H), 2.22-2.11 (m, 1H), 1.99-1.93 (m, 1H), 1.87-1.70 (m, 4H), 1.58-1.44 (m, 1H), 1.37-1.25 (m, 1H), 1.20-1.14 (m, 1H), 1.12 (s, 9H), 1.03 (d, J=6.2 Hz, 1H), 0.84 (br. s., 3H), 0.60 (br. s., 3H). LCMS (M+H)=682.2.

EXAMPLE 87

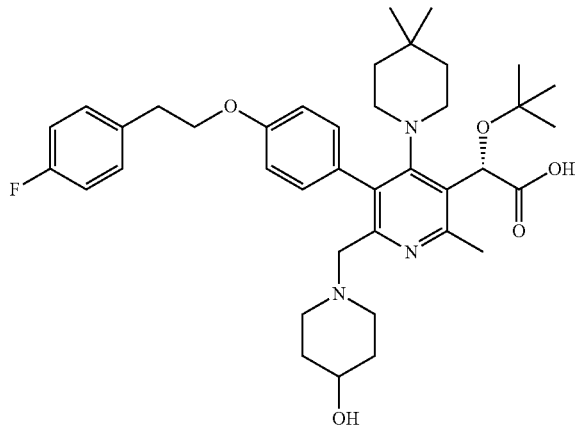 [SMILES: Cc1nc(CN2CCC(O)CC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-6-((4-hydroxypiperidin-1-yl)methyl)-2-methylpyridin-3-yl)acetic acid: A solution of piperidin-4-ol (0.02 g, 0.198 mmol) and (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) in EtOH (1 mL) was stirred for 2 h. Sodium hydroxide (0.04 g, 1.000 mmol) was added and the reaction mixture was stirred at 80° C. for 2 h. Then, cooled down and purified by prep HPLC to afford (S)-2-(tert-butoxy)-2-(4-(4,4-dimethylpiperidin-1-yl)-5-(4-(4-fluorophenethoxy)phenyl)-6-((4-hydroxypiperidin-1-yl)methyl)-2-methylpyridin-3-yl)acetic acid (0.0133 g, 0.020 mmol, 91% yield). $^1$H NMR (500 MHz, DMSO-d6) δ 7.39-7.29 (m, 3H), 7.13 (t, J=8.6 Hz, 2H), 7.01 (s, 2H), 6.97 (d, J=9.2 Hz, 1H), 5.82 (s, 1H), 4.31-4.13 (m, 2H), 3.47 (br. s., 5H), 3.34 (br. s., 2H), 3.09 (d, J=5.1 Hz, 2H), 3.05 (t, J=6.6 Hz, 2H), 2.83-2.76 (m, 1H), 2.46 (s, 3H), 2.41 (br. s., 1H), 2.22-2.11 (m, 1H), 1.94 (d, J=11.0 Hz, 2H), 1.57 (d, J=11.0 Hz, 2H), 1.54-1.42 (m, 1H), 1.28 (d, J=9.5 Hz, 2H), 1.21-1.16 (m, 1H), 1.12 (s, 9H), 1.03 (br. s., 1H), 0.84 (br. s., 3H), 0.60 (br. s., 3H). LCMS (M+H)=662.2.

EXAMPLE 88

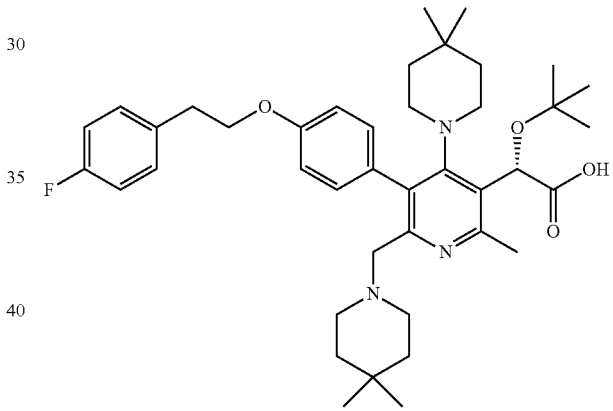

(S)-2-(tert-Butoxy)-2-(4-(4,4-dimethylpiperidin-1-yl)-6-((4,4-dimethylpiperidin-1-yl)methyl)-5-(4-(4-fluorophenethoxy)phenyl)-2-methylpyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) and 4,4-dimethylpiperidine (0.02 g, 0.177 mmol) in EtOH (1 mL) was stirred for 2 h. Sodium hydroxide (0.04 g, 1.000 mmol) was added and the reaction mixture was stirred at 80° C. for 2 h. Then, cooled and purified by prep HPLC to afford (S)-2-(tert-butoxy)-2-(4-(4,4-dimethylpiperidin-1-yl)-6-((4,4-dimethylpiperidin-1-yl)methyl)-5-(4-(4-fluorophenethoxy)phenyl)-2-methylpyridin-3-yl)acetic acid (0.0136 g, 0.019 mmol, 88% yield). $^1$HNMR (500 MHz, DMSO-d6) δ 7.36 (dt, J=8.3, 5.8 Hz, 3H), 7.13 (t, J=8.8 Hz, 2H), 7.01 (s, 2H), 6.97 (d, J=8.4 Hz, 1H), 5.80 (s, 1H), 4.31-4.16 (m, 2H), 3.37 (br. s., 2H), 3.14 (s, 2H), 3.04 (t, J=6.8 Hz, 2H), 2.86-2.75 (m, 1H), 2.45 (s, 3H), 2.30-2.13 (m, 5H), 1.96-1.91 (m, 1H), 1.55-1.40 (m, 1H), 1.34-1.25 (m, 1H), 1.25-1.14 (m, 5H), 1.11 (s, 9H), 1.05-0.96 (m, 1H), 0.84 (br. s., 3H), 0.84-0.80 (m, 6H), 0.60 (br. s., 3H). LCMS (M+H)=674.2.

EXAMPLE 89

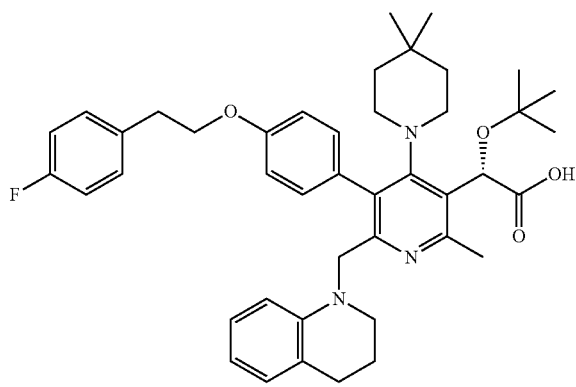 [SMILES: Cc1nc(CN2CCCc3ccccc32)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((3,4-dihydroquinolin-1(2H)-yl)methyl)-4-(4,4-dimethylpiperidin-1-yl)-5-(4-(4-fluorophenethoxy)phenyl)-2-methylpyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) and 1,2,3,4-tetrahydroquinoline (0.02 g, 0.150 mmol) in THF (0.5 mL) was added potassium tert-butoxide (0.008 g, 0.071 mmol) and stirred at rt for 18 h. Sodium hydroxide (0.04 g, 1.000 mmol) was added and the reaction mixture was stirred at 80° C. for 2 h. Then, cooled and purified by prep HPLC to afford (S)-2-(tert-butoxy)-2-(6-((3,4-dihydroquinolin-1(2H)-yl)methyl)-4-(4,4-dimethylpiperidin-1-yl)-5-(4-(4-fluorophenethoxy)phenyl)-2-methylpyridin-3-yl)acetic acid (0.0084 g, 0.012 mmol, 55.2% yield). $^1$H NMR (500 MHz, DMSO-$d_6$) δ 7.36 (dd, J=8.1, 5.9 Hz, 2H), 7.30 (d, J=8.4 Hz, 1H), 7.13 (t, J=8.8 Hz, 3H), 7.10-7.05 (m, 1H), 7.02 (dd, J=8.4, 2.2 Hz, 1H), 6.78 (d, J=7.3 Hz, 1H), 6.73 (t, J=7.7 Hz, 1H), 6.35 (t, J=7.3 Hz, 1H), 6.19 (d, J=8.4 Hz, 1H), 5.84 (s, 1H), 4.32-4.17 (m, 2H), 4.13 (d, J=16.1 Hz, 1H), 4.04 (d, J=16.1 Hz, 1H), 3.35-3.23 (m, 2H), 3.14-3.08 (m, J=5.5 Hz, 1H), 3.04 (t, J=6.6 Hz, 2H), 2.82 (t, J=12.5 Hz, 1H), 2.66-2.57 (m, J=4.8 Hz, 2H), 2.41 (s, 3H), 2.22 (d, J=12.1 Hz, 1H), 1.97 (t, J=12.1 Hz, 1H), 1.77 (dd, J=11.4, 5.5 Hz, 2H), 1.55-1.44 (m, 1H), 1.34-1.26 (m, 1H), 1.17 (d, J=12.8 Hz, 1H), 1.12 (s, 9H), 1.03 (d, J=11.7 Hz, 1H), 0.85 (s, 3H), 0.60 (s, 3H). LCMS (M+H)=694.2.

EXAMPLE 90

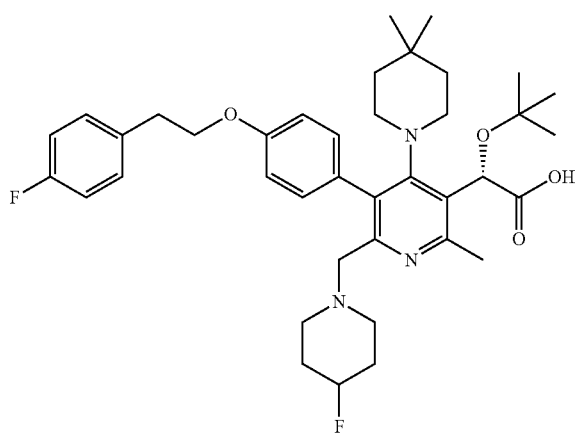 [SMILES: Cc1nc(CN2CCC(F)CC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-6-((4-fluoropiperidin-1-yl)methyl)-2-methylpyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol), 4-fluoropiperidine, HCl (0.015 g, 0.107 mmol) and TEA (0.02 ml, 0.143 mmol) in EtOH (1 mL) was stirred for 2 h. Sodium hydroxide (0.04 g, 1.000 mmol) was added and the reaction mixture was stirred at 80° C. for 2 h. Then, cooled and purified by prep HPLC to afford (S)-2-(tert-butoxy)-2-(4-(4,4-dimethylpiperidin-1-yl)-5-(4-(4-fluorophenethoxy)phenyl)-6-((4-fluoropiperidin-1-yl)methyl)-2-methylpyridin-3-yl)acetic acid (0.0115 g, 0.017 mmol, 77% yield). $^1$H NMR (500 MHz, DMSO-d6) δ 7.38 (d, J=5.5 Hz, 1H), 7.13 (t, J=8.8 Hz, 2H), 7.06-6.94 (m, 3H), 5.85 (s, 1H), 4.66-4.44 (m, 1H), 4.29-4.15 (m, 2H), 3.31-3.24 (m, 1H), 3.18-3.12 (m, 1H), 3.09-3.01 (m, 3H), 2.85-2.75 (m, 1H), 2.46 (s, 3H), 2.41-2.25 (m, 2H), 2.22-2.04 (m, 3H), 1.99-1.92 (m, 1H), 1.80-1.63 (m, 2H), 1.60-1.44 (m, 3H), 1.35-1.23 (m, 1H), 1.20-1.15 (m, 1H), 1.12 (s, 9H), 1.03 (br. s., 1H), 0.84 (br. s., 3H), 0.60 (br. s., 3H). LCMS (M+H)=664.2.

EXAMPLE 91

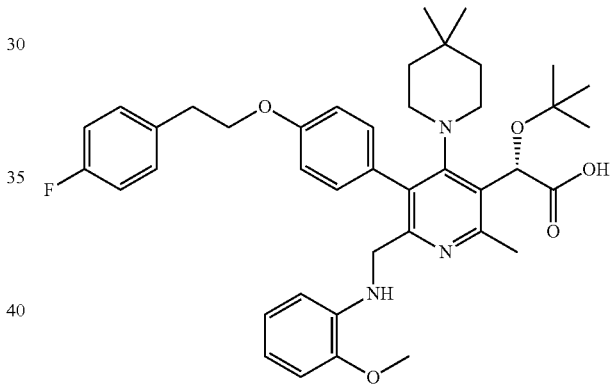

(S)-2-(tert-Butoxy)-2-(4-(4,4-dimethylpiperidin-1-yl)-5-(4-(4-fluorophenethoxy)phenyl)-6-(((2-methoxyphenyl)amino)methyl)-2-methylpyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) and 2-methoxyaniline (0.02 g, 0.162 mmol) in THF (0.5 mL) was added t-BuOK (0.008 g, 0.071 mmol) and stirred at rt for 4 h. Then, NaOH (0.04 g, 1.000 mmol) was added and the reaction mixture was stirred at 80° C. for 2 h. Then, cooled and purified by prep HPLC to afford (S)-2-(tert-butoxy)-2-(4-(4,4-dimethylpiperidin-1-yl)-5-(4-(4-fluorophenethoxy)phenyl)-6-(((2-methoxyphenyl)amino)methyl)-2-methylpyridin-3-yl)acetic acid (0.0088 g, 0.013 mmol, 58.7% yield). $^1$H NMR (500 MHz, DMSO-$d_6$) δ 7.44-7.36 (m, 2H), 7.32 (d, J=8.4 Hz, 1H), 7.15 (t, J=8.8 Hz, 2H), 7.11-7.04 (m, 3H), 6.80 (d, J=7.7 Hz, 1H), 6.70 (t, J=7.7 Hz, 1H), 6.53 (t, J=7.7 Hz, 1H), 6.17 (d, J=7.7 Hz, 1H), 5.87 (br. s., 1H), 4.30-4.21 (m, 2H), 3.98 (d, J=15.4 Hz, 1H), 3.80 (s, 3H), 3.68 (d, J=15.4 Hz, 1H), 3.35 (br. s., 1H), 3.07 (t, J=6.6 Hz, 2H), 2.81-2.81 (m, 1H), 2.88-2.79 (m, 1H), 2.28-2.19 (m, J=1.5 Hz, 1H), 2.02-1.92 (m, 1H), 1.56-1.47 (m, 1H), 1.35-1.27 (m, 1H), 1.20 (d, J=12.1 Hz, 1H), 1.15 (s, 9H), 1.05 (d, J=11.7 Hz, 1H), 0.86 (s, 3H), 0.62 (s, 3H). Me protons were not resolved. LCMS (M+H)=684.2.

EXAMPLE 92

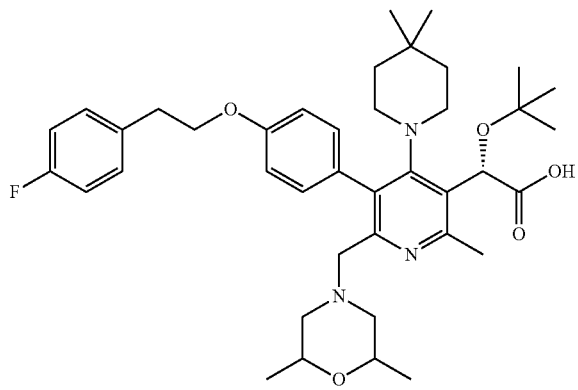 [SMILES: Cc1nc(CN2CC(C)OC(C)C2)c(-c2ccc(OCCc3ccc(F)cc3)cc2)c(N2CCC(C)(C)CC2)c1[C@H](OC(C)(C)C)C(=O)O]

(2S)-2-(tert-Butoxy)-2-(6-((2,6-dimethylmorpholino) methyl)-4-(4,4-dimethylpiperidin-1-yl)-5-(4-(4-fluorophenethoxy)phenyl)-2-methylpyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) and 2,6-dimethylmorpholine (0.02 g, 0.174 mmol) in EtOH (1 mL) was stirred for 18 h. Sodium hydroxide (0.015 g, 0.375 mmol) was added and the reaction mixture was stirred at 80° C. for 2 h. Then, cooled and purified by prep HPLC to afford (2S)-2-(tert-butoxy)-2-(6-((2,6-dimethylmorpholino)methyl)-4-(4,4-dimethylpiperidin-1-yl)-5-(4-(4-fluorophenethoxy)phenyl)-2-methylpyridin-3-yl)acetic acid (0.0102 g, 0.015 mmol, 68.8% yield). $^1$HNMR (500 MHz, DMSO-d6) δ 7.37 (dd, J=8.3, 5.7 Hz, 2H), 7.32 (d, J=8.8 Hz, 1H), 7.14 (t, J=8.8 Hz, 2H), 7.02 (br. s., 2H), 6.98 (d, J=8.4 Hz, 1H), 5.82 (br. s., 1H), 4.29-4.18 (m, 2H), 3.50-3.26 (m, 4H), 3.09-3.01 (m, 2H), 2.80 (br. s., 1H), 2.46 (s, 3H), 2.39 (d, J=10.6 Hz, 1H), 2.33 (d, J=11.4 Hz, 2H), 2.20 (d, J=12.8 Hz, 2H), 1.91 (s, 1H), 1.59 (t, J=10.6 Hz, 1H), 1.55-1.45 (m, 1H), 1.30 (br. s., 1H), 1.17 (d, J=13.2 Hz, 1H), 1.12 (s, 9H), 0.95 (d, J=6.2 Hz, 3H), 0.91 (d, J=6.2 Hz, 3H), 0.85 (br. s., 3H), 0.60 (br. s., 3H). LCMS (M+H)=676.2.

EXAMPLE 93

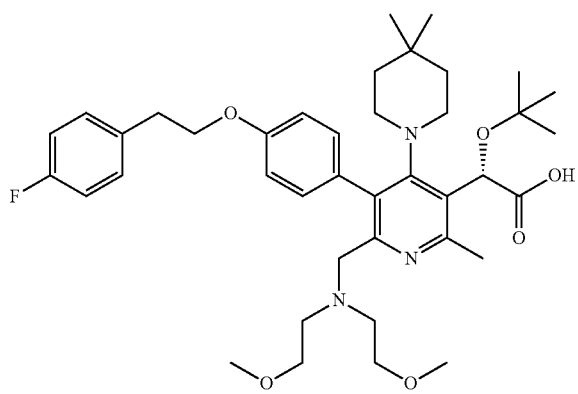 [SMILES: COCCN(CCOC)Cc1nc(C)c([C@H](OC(C)(C)C)C(=O)O)c(N2CCC(C)(C)CC2)c1-c1ccc(OCCc2ccc(F)cc2)cc1]

(S)-2-(6-((Bis(2-methoxyethyl)amino)methyl)-4-(4,4-dimethylpiperidin-1-yl)-5-(4-(4-fluorophenethoxy)phenyl)-2-methylpyridin-3-yl)-2-(tert-butoxy)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) and bis(2-methoxyethyl)amine (0.02 g, 0.150 mmol) in EtOH (1 mL) was stirred for 2 h. Sodium hydroxide (0.04 g, 1.000 mmol) was added and the reaction mixture was stirred at 80° C. for 2 h. Then, cooled and purified by prep HPLC to afford (S)-2-(6-((bis(2-methoxyethyl)amino)methyl)-4-(4,4-dimethylpiperidin-1-yl)-5-(4-(4-fluorophenethoxy)phenyl)-2-methylpyridin-3-yl)-2-(tert-butoxy)acetic acid (0.0127 g, 0.018 mmol, 83% yield). LCMS (M+H)=694.2.

EXAMPLE 94

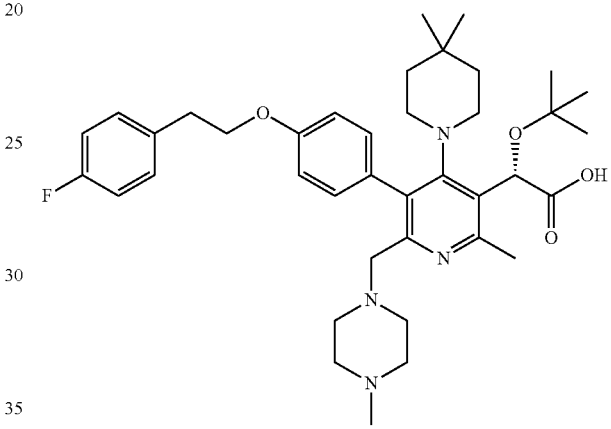

(S)-2-(tert-Butoxy)-2-(4-(4,4-dimethylpiperidin-1-yl)-5-(4-(4-fluorophenethoxy)phenyl)-2-methyl-6-((4-methylpiperazin-1-yl)methyl)pyridin-3-yl)acetic acid: A solution of 1-methylpiperazine (0.02 g, 0.200 mmol) and (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) in EtOH (1 mL) was stirred for 2 h. Sodium hydroxide (0.04 g, 1.000 mmol) was added and the reaction mixture was stirred at 80° C. for 2 h. Then, cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-((4-methylpiperazin-1-yl)methyl)pyridin-3-yl)acetic acid (0.0146 g, 0.021 mmol, 98% yield). $^1$H NMR (500 MHz, DMSO-d6) δ 7.41-7.30 (m, 3H), 7.14 (t, J=9.0 Hz, 2H), 7.01 (s, 2H), 6.97 (d, J=9.2 Hz, 1H), 5.83 (s, 1H), 4.31-4.15 (m, 2H), 3.57-3.25 (m, 4H), 3.12-3.00 (m, 4H), 2.85-2.75 (m, 1H), 2.55 (s, 2H), 2.45 (s, 3H), 2.20 (br. s., 4H), 2.09 (s, 3H), 1.98-1.93 (m, 1H), 1.55-1.42 (m, 1H), 1.31-1.23 (m, 1H), 1.20-1.15 (m, 1H), 1.12 (s, 9H), 1.05-0.97 (m, 1H), 0.85 (br. s., 3H), 0.60 (s, 3H). LCMS (M+H)=661.2.

EXAMPLE 95

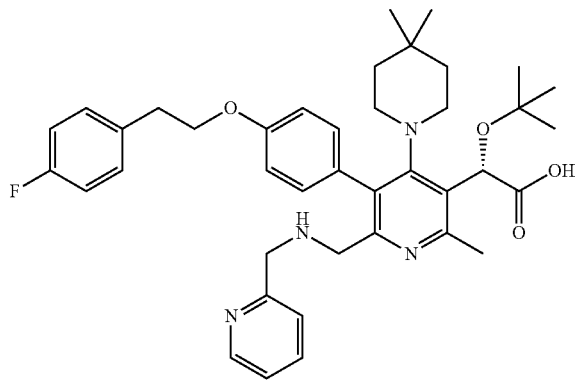 [SMILES: Cc1nc(CNCc2ccccn2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(((pyridin-2-ylmethyl)amino)methyl)pyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.015 g, 0.022 mmol) and pyridin-2-ylmethanamine (0.02 g, 0.185 mmol) in EtOH (1 mL) was stirred at rt for 2 h. Then, sodium hydroxide (0.04 g, 1.000 mmol) was added and the reaction mixture was stirred at 80° C. for 5 h, cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((pyridin-2-ylmethyl)amino)methyl)pyridin-3-yl)acetic acid (0.0048 g, 32%). LCMS (M+H)=669.2.

EXAMPLE 96

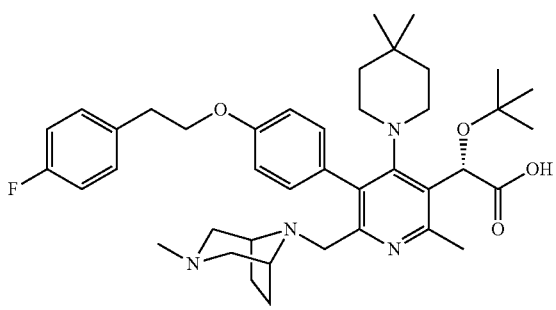 [SMILES: Cc1nc(CN2C3CCC2CN(C)C3)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-2-methyl-6-(((R,5S)-3-methyl-3,8-diazabicyclo[3.2.1]octan-8-yl)methyl)pyridin-3-yl)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.04 g, 0.059 mmol), (1R,5S)-3-methyl-3,8-diazabicyclo[3.2.1]octane, HCl (0.04 g, 0.246 mmol) and triethylamine (0.04 ml, 0.287 mmol) in EtOH (1 mL) was stirred for 2 h. Sodium hydroxide (0.04 g, 1.000 mmol) was added and the reaction mixture was stirred at 80° C. for 2 h. Then, cooled and purified by prep HPLC to afford (S)-2-(tert-butoxy)-2-(4-(4,4-dimethylpiperidin-1-yl)-5-(4-(4-fluorophenethoxy)phenyl)-2-methyl-6-(((1R,5S)-3-methyl-3,8-diazabicyclo[3.2.1]octan-8-yl)methyl)pyridin-3-yl) acetic acid (0.0394 g, 0.057 mmol, 98% yield). LCMS (M+H)=687.3.

EXAMPLE 97

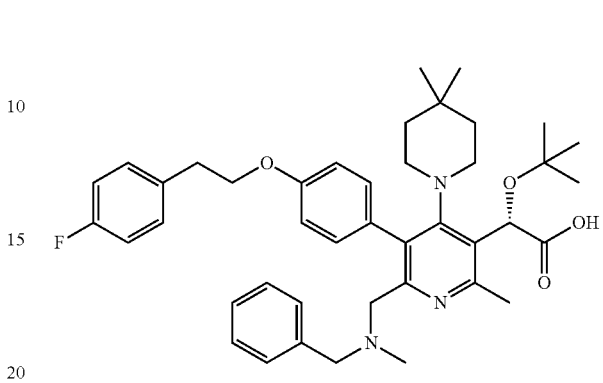

(S)-2-(6-((Benzyl(methyl)amino)methyl)-4-(4,4-dimethylpiperidin-1-yl)-5-(4-(4-fluorophenethoxy)phenyl)-2-methylpyridin-3-yl)-2-(tert-butoxy)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.012 g, 0.018 mmol) and N-methyl-1-phenylmethanamine (0.02 g, 0.165 mmol) in EtOH (1 mL) was stirred at rt for 2 h. Then, NaOH (0.01 g, 0.250 mmol) was added and the reaction mixture was stirred at 80° C. for 2 h, cooled and purified by prep HPLC to afford (S)-2-(6-((benzyl(methyl)amino)methyl)-4-(4,4-dimethylpiperidin-1-yl)-5-(4-(4-fluorophenethoxy)phenyl)-2-methylpyridin-3-yl)-2-(tert-butoxy)acetic acid (0.0082 g, 0.012 mmol, 68.5% yield). $^1$H NMR (500 MHz, DMSO-d6) δ 7.40-7.33 (m, 3H), 7.25-7.19 (m, 2H), 7.16 (s, 1H), 7.15-7.08 (m, 4H), 7.05-7.00 (m, 2H), 6.99-6.94 (m, J=8.4 Hz, 1H), 5.85 (s, 1H), 4.28-4.16 (m, 2H), 3.35-3.29 (m, 1H), 3.28-3.16 (m, 3H), 3.04 (t, J=6.6 Hz, 2H), 2.86-2.78 (m, 1H), 2.48 (s, 3H), 2.27-2.15 (m, 1H), 1.96-1.91 (m, 1H), 1.90 (s, 3H), 1.56-1.43 (m, 1H), 1.34-1.26 (m, 1H), 1.20-1.15 (m, 1H), 1.11 (s, 9H), 1.05-0.99 (m, 1H), 0.85 (br. s., 3H), 0.61 (br. s., 3H). LCMS (M+H)=682.3.

EXAMPLE 98

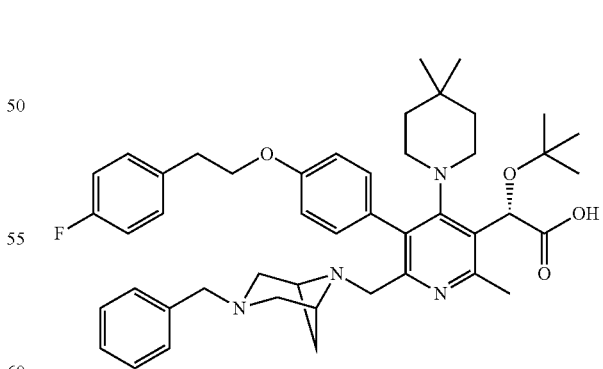

(2S)-2-(6-((3-Benzyl-3,6-diazabicyclo[3.1.1]heptan-6-yl)methyl)-4-(4,4-dimethylpiperidin-1-yl)-5-(4-(4-fluorophenethoxy)phenyl)-2-methylpyridin-3-yl)-2-(tert-butoxy) acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.012 g, 0.018 mmol), (1R,5S)-3-benzyl-3,6-diazabicyclo[3.1.1]heptane (0.03 g, 0.159 mmol) in EtOH (1 mL) was stirred for 2 h. Sodium hydroxide (0.01 g, 0.250 mmol) was added and the reaction mixture was stirred at 80° C. for 2 h, cooled and purified by prep HPLC to afford (2S)-2-(6-((3-benzyl-3,6-diazabicyclo[3.1.1]heptan-6-yl)methyl)-4-(4,4-dimethylpiperidin-1-yl)-5-(4-(4-fluorophenethoxy)phenyl)-2-methylpyridin-3-yl)-2-(tert-butoxy)acetic acid (0.0059 g, 7.80 µmol, 44.4% yield). LCMS (M+H)=749.3.

EXAMPLE 99

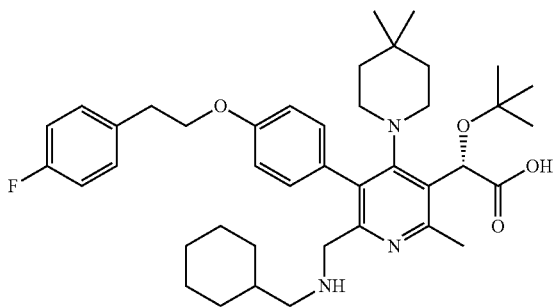 [SMILES: Cc1nc(CNCC2CCCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-(((cyclohexylmethyl)amino)methyl)-4-(4,4-dimethylpiperidin-1-yl)-5-(4-(4-fluorophenethoxy)phenyl)-2-methylpyridin-3-yl)acetic acid: To a stirring solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (0.04 g, 0.059 mmol) in EtOH (1 mL) was added cyclohexylmethanamine (0.05 g, 0.442 mmol). The mixture was stirred at rt for 2 h. Then, sodium hydroxide (0.03 g, 0.750 mmol) was added and stirred at 80° C. for 3 h, cooled and purified by prep HPLC to afford (S)-2-(tert-butoxy)-2-(6-(((cyclohexylmethyl)amino)methyl)-4-(4,4-dimethylpiperidin-1-yl)-5-(4-(4-fluorophenethoxy)phenyl)-2-methylpyridin-3-yl)acetic acid (0.0121 g, 0.018 mmol, 30.1% yield). $^1$H NMR (500 MHz, DMSO-d6) δ 7.37 (dd, J=8.3, 5.7 Hz, 2H), 7.23 (d, J=7.7 Hz, 1H), 7.14 (t, J=8.8 Hz, 2H), 7.04 (s, 2H), 7.01 (d, J=7.7 Hz, 1H), 5.71 (br. s., 1H), 4.28-4.17 (m, 2H), 3.53 (d, J=13.9 Hz, 1H), 3.33 (d, J=13.9 Hz, 1H), 3.05 (t, J=6.8 Hz, 2H), 2.83-2.75 (m, 1H), 2.48 (s, 3H), 2.36 (d, J=6.2 Hz, 2H), 2.20-2.13 (m, 1H), 1.99-1.91 (m, 1H), 1.67-1.54 (m, 5H), 1.54-1.42 (m, 1H), 1.31 (br. s., 2H), 1.24-0.96 (m, 15H), 0.84 (br. s., 3H), 0.80 (d, J=11.0 Hz, 2H), 0.61 (br. s., 3H). LCMS (M+H)=674.3.

EXAMPLE 100

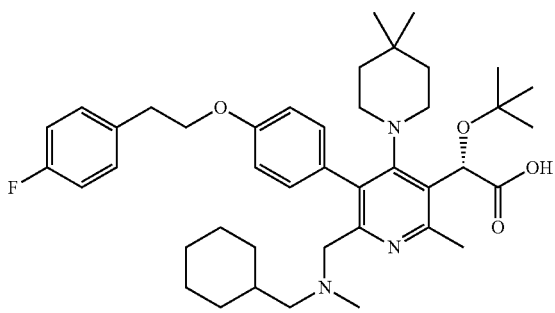 [SMILES: Cc1nc(CN(C)CC2CCCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-(((cyclohexylmethyl)(methyl)amino)methyl)-4-(4,4-dimethylpiperidin-1-yl)-5-(4-(4-fluorophenethoxy)phenyl)-2-methylpyridin-3-yl)acetic acid: To a solution of (S)-2-(tert-butoxy)-2-(6-(((cyclohexylmethyl)amino)methyl)-4-(4,4-dimethylpiperidin-1-yl)-5-(4-(4-fluorophenethoxy)phenyl)-2-methylpyridin-3-yl)acetic acid (0.0096 g, 0.014 mmol) in MeOH (0.2 mL) was added aq. formaldehyde (5 µl, 0.067 mmol). The mixture was stirred at rt for 2 h and then added sodium triacetoxyborohydride (0.015 g, 0.071 mmol). After 3 h, the crude mixture was purified by prep HPLC to afford (S)-2-(tert-butoxy)-2-(6-(((cyclohexylmethyl)(methyl)amino)methyl)-4-(4,4-dimethylpiperidin-1-yl)-5-(4-(4-fluorophenethoxy)phenyl)-2-methylpyridin-3-yl)acetic acid (0.0090 g, 0.013 mmol, 92% yield). $^1$H NMR (500 MHz, DMSO-d6) δ 7.44-7.34 (m, 3H), 7.13 (t, J=8.8 Hz, 2H), 7.03-6.93 (m, 3H), 5.76 (s, 1H), 4.27-4.16 (m, 2H), 3.15-3.09 (m, 1H), 3.07-3.00 (m, 3H), 2.84-2.75 (m, 1H), 2.45 (s, 3H), 2.13 (br. s., 2H), 1.98 (s, 3H), 1.50 (br. s., 6H), 1.31-1.23 (m, 1H), 1.17 (br. s., 2H), 1.09 (s, 9H), 1.03 (br. s., 4H), 0.84 (br. s., 3H), 0.61 (br. s., 5H). LCMS (M+H)=688.3.

EXAMPLE 101

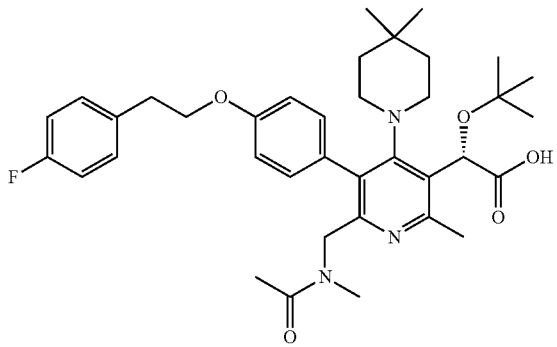 [SMILES: CC(=O)N(C)Cc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-5-(4-(4-fluorophenethoxy)phenyl)-2-methyl-6-((N-methylacetamido)methyl)pyridin-3-yl)acetic acid: Acetyl chloride (0.005 mL, 0.070 mmol) was added to a solution of (S)-2-(tert-butoxy)-2-(4-(4,4-dimethylpiperidin-1-yl)-5-(4-(4-fluorophenethoxy)phenyl)-2-methyl-6-((methylamino)methyl)pyridin-3-yl)acetic acid (0.015 g, 0.025 mmol) and TEA (0.02 ml, 0.143 mmol) in DCM (0.5 mL). The mixture was stirred at rt for 0.5 h, quenched by water, concentrated and purified by prep HPLC to afford (S)-2-(tert-butoxy)-2-(4-(4,4-dimethylpiperidin-1-yl)-5-(4-(4-fluorophenethoxy)phenyl)-2-methyl-6-((N-methylacetamido)methyl)pyridin-3-yl)acetic acid (0.0098 g, 0.015 mmol, 61.0% yield). LCMS (M+H)=534.2.

EXAMPLE 102

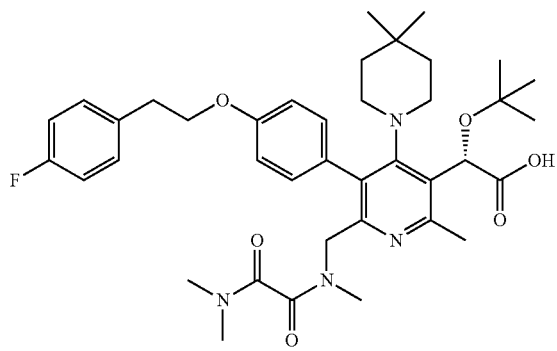 [SMILES: Cc1nc(CN(C)C(=O)C(=O)N(C)C)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((2-(dimethylamino)-N-methyl-2-oxoacetamido)methyl)-4-(4,4-dimethylpiperidin-1-yl)-5-(4-(4-fluorophenethoxy)phenyl)-2-methylpyridin-3-yl)acetic acid: To a solution of 2-(dimethylamino)-2-oxoacetic acid (30 mg, 0.256 mmol) in DCM (0.5 mL) was added oxalyl chloride (0.05 ml, 0.100 mmol). The mixture was stirred at rt for 1 h, concentrated to dryness under vacuum. The residue was dissolved in THF (0.5 ml) and added to a solution of (S)-2-(tert-butoxy)-2-(4-(4,4-dimethylpiperidin-1-yl)-5-(4-(4-fluorophenethoxy)phenyl)-2-methyl-6-((methylamino)methyl)pyridin-3-yl)acetic acid (0.015 g, 0.025 mmol) and TEA (0.06 ml, 0.430 mmol) in THF (0.5 ml). The mixture was stirred at rt for 2 h, removed the solvent and purified by prep HPLC to afford (S)-2-(tert-butoxy)-2-(6-((2-(dimethylamino)-N-methyl-2-oxoacetamido)methyl)-4-(4,4-dimethylpiperidin-1-yl)-5-(4-(4-fluorophenethoxy)phenyl)-2-methylpyridin-3-yl)acetic acid (0.0063 g, 9.12 µmol, 36.0% yield). LCMS (M+H)=691.2.

EXAMPLE 103

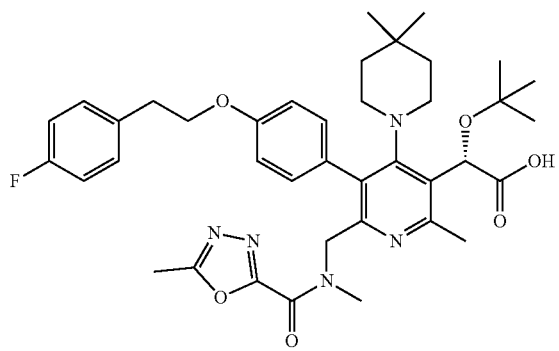 [SMILES: Cc1nnc(C(=O)N(C)Cc2nc(C)c([C@H](OC(C)(C)C)C(=O)O)c(N3CCC(C)(C)CC3)c2-c2ccc(OCCc3ccc(F)cc3)cc2)o1]

(S)-2-(tert-Butoxy)-2-(6-((N, 5-dimethyl-1,3,4-oxadiazole-2-carboxamido)methyl)-4-(4,4-dimethylpiperidin-1-yl)-5-(4-(4-fluorophenethoxy)phenyl)-2-methylpyridin-3-yl)acetic acid: To a solution of potassium 5-methyl-1,3,4-oxadiazole-2-carboxylate (0.101 g, 0.608 mmol) in DCM (0.5 mL) was added oxalyl chloride (0.190 ml, 0.380 mmol). The mixture was stirred at rt for 1 h, concentrated to dryness under vacuum. The residue was dissolved in DCM (0.5 mL) and added to a solution of (S)-2-(tert-butoxy)-2-(4-(4,4-dimethylpiperidin-1-yl)-5-(4-(4-fluorophenethoxy)phenyl)-2-methyl-6-((methylamino)methyl)pyridin-3-yl)acetic acid (0.09 g, 0.152 mmol) in DCM (0.5 mL). The mixture was stirred at rt for 2 h, then removed the solvent and purified by prep HPLC to afford (S)-2-(tert-butoxy)-2-(6-((N,5-dimethyl-1,3,4-oxadiazole-2-carboxamido)methyl)-4-(4,4-dimethylpiperidin-1-yl)-5-(4-(4-fluorophenethoxy)phenyl)-2-methylpyridin-3-yl)acetic acid (0.0151 g, 0.021 mmol, 13.86% yield). LCMS (M+H)=702.2.

EXAMPLE 104

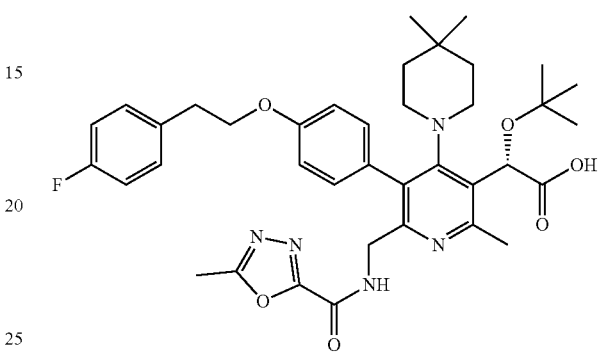

(S)-2-(tert-Butoxy)-2-(4-(4,4-dimethylpiperidin-1-yl)-5-(4-(4-fluorophenethoxy)phenyl)-2-methyl-6-((5-methyl-1,3,4-oxadiazole-2-carboxamido)methyl)pyridin-3-yl)acetic acid: To a solution of potassium 5-methyl-1,3,4-oxadiazole-2-carboxylate (30 mg, 0.181 mmol) in DCM (0.5 mL) was added oxalyl chloride (0.05 ml, 0.100 mmol). The mixture was stirred at rt for 1 h, concentrated to dryness under vacuum. The residue was dissolved in THF (0.5 mL) and added to a solution of (S)-2-(6-(aminomethyl)-4-(4,4-dimethylpiperidin-1-yl)-5-(4-(4-fluorophenethoxy)phenyl)-2-methylpyridin-3-yl)-2-(tert-butoxy)acetic acid (0.018 g, 0.031 mmol) and DIPEA (0.05 ml, 0.286 mmol) in THF (0.5 mL). The mixture was stirred at rt for 1 h and 0.1 ml of water was added and stirred at rt for 0.5 h. then, removed solvent in vacuum and purified by prep-HPLC to afford (S)-2-(tert-butoxy)-2-(4-(4,4-dimethylpiperidin-1-yl)-5-(4-(4-fluorophenethoxy)phenyl)-2-methyl-6-((5-methyl-1,3,4-oxadiazole-2-carboxamido)methyl)pyridin-3-yl)acetic acid (0.0077 g, 0.011 mmol, 35.9% yield). LCMS (M+H)=688.2.

EXAMPLE 105

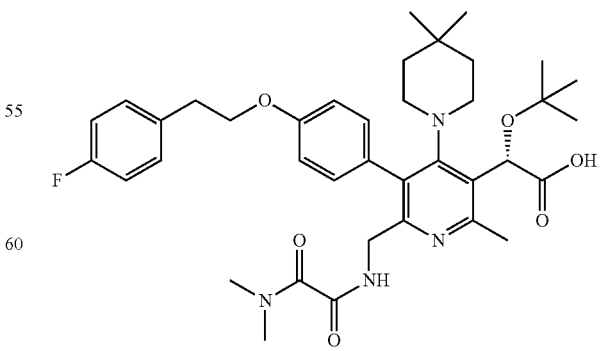

(S)-2-(tert-Butoxy)-2-(6-((2-(dimethylamino)-2-oxoacetamido)methyl)-4-(4,4-dimethylpiperidin-1-yl)-5-(4-(4-fluorophenethoxy)phenyl)-2-methylpyridin-3-yl)acetic acid: To a solution of 2-(dimethylamino)-2-oxoacetic acid (30 mg, 0.256 mmol) in DCM (0.5 mL) was added oxalyl chloride (0.05 ml, 0.100 mmol). The mixture was stirred at rt for 1 h, concentrated to dryness under vacuum. The residue was dissolved in THF (0.5 ml) and added to a solution of (S)-2-(6-(aminomethyl)-4-(4,4-dimethylpiperidin-1-yl)-5-(4-(4-fluorophenethoxy)phenyl)-2-methylpyridin-3-yl)-2-(tert-butoxy)acetic acid (0.015 g, 0.026 mmol) and in THF (0.5 ml). The mixture was stirred at rt, then removed the solvent and purified by prep HPLC to afford (S)-2-(tert-butoxy)-2-(6-((2-(dimethylamino)-2-oxoacetamido)methyl)-4-(4,4-dimethylpiperidin-1-yl)-5-(4-(4-fluorophenethoxy)phenyl)-2-methylpyridin-3-yl)acetic acid (0.0119 g, 0.018 mmol, 67.7% yield). LCMS (M+H)=677.3.

EXAMPLE 106

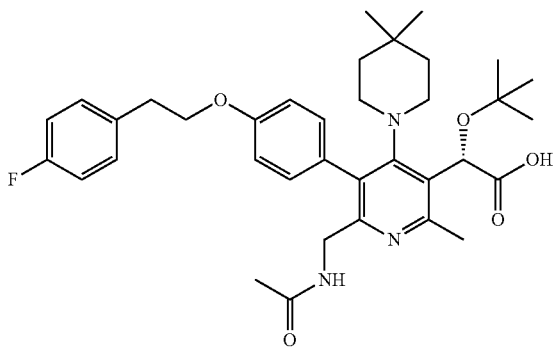 [SMILES: CC(=O)NCc1nc(C)c([C@H](OC(C)(C)C)C(=O)O)c(N2CCC(C)(C)CC2)c1-c1ccc(OCCc2ccc(F)cc2)cc1]

(S)-2-(6-(Acetamidomethyl)-4-(4,4-dimethylpiperidin-1-yl)-5-(4-(4-fluorophenethoxy)phenyl)-2-methylpyridin-3-yl)-2-(tert-butoxy)acetic acid: Acetyl chloride (0.005 mL, 0.070 mmol) was added to a solution of (S)-2-(6-(aminomethyl)-4-(4,4-dimethylpiperidin-1-yl)-5-(4-(4-fluorophenethoxy)phenyl)-2-methylpyridin-3-yl)-2-(tert-butoxy)acetic acid (0.015 g, 0.026 mmol) and DIPEA (0.01 ml, 0.057 mmol) in DCM (0.5 mL). The mixture was stirred at rt for 1 h and quenched by addition of water, removed the solvent and purified by prep HPLC to afford (S)-2-(6-(acetamidomethyl)-4-(4,4-dimethylpiperidin-1-yl)-5-(4-(4-fluorophenethoxy)phenyl)-2-methylpyridin-3-yl)-2-(tert-butoxy)acetic acid (0.0122 g, 0.020 mmol, 76% yield). LCMS (M+H)=620.3.

EXAMPLE 107

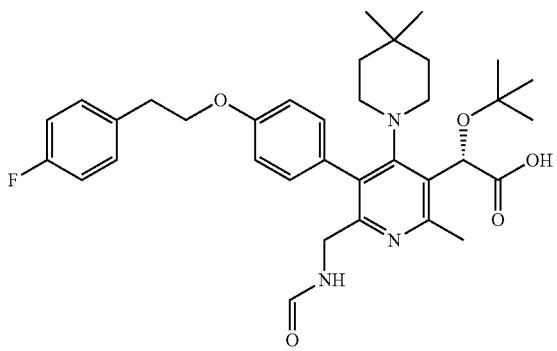 [SMILES: Cc1nc(CNC=O)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-5-(4-(4-fluorophenethoxy)phenyl)-6-(formamidomethyl)-2-methylpyridin-3-yl)acetic acid: (S)-2-(6-(Aminomethyl)-4-(4,4-dimethylpiperidin-1-yl)-5-(4-(4-fluorophenethoxy)phenyl)-2-methylpyridin-3-yl)-2-(tert-butoxy)acetic acid (0.015 g, 0.026 mmol) was added to a solution of formic acid (0.15 ml, 3.98 mmol) and acetic anhydride (0.3 mL, 3.18 mmol). The reaction mixtion was stirred at 50° C. for 48 h. The reaction mixture was quenched with water and purified by prep HPLC to afford (S)-2-(tert-butoxy)-2-(4-(4,4-dimethylpiperidin-1-yl)-5-(4-(4-fluorophenethoxy)phenyl)-6-(formamidomethyl)-2-methylpyridin-3-yl)acetic acid (0.0077 g, 0.013 mmol, 49.0% yield). $^1$H NMR (500 MHz, DMSO-$d_6$) δ 8.21-8.16 (m, 1H), 7.38 (dd, J=8.6, 5.7 Hz, 2H), 7.26 (d, J=8.4 Hz, 1H), 7.14 (t, J=8.8 Hz, 2H), 7.10-7.02 (m, 3H), 5.89 (s, 1H), 4.25 (d, J=8.4 Hz, 2H), 4.07-4.01 (m, 1H), 3.90-3.82 (m, 1H), 3.06 (t, J=6.6 Hz, 2H), 2.87-2.77 (m, 1H), 2.25-2.16 (m, 1H), 2.01-1.93 (m, 1H), 1.54-1.46 (m, 1H), 1.33-1.25 (m, 1H), 1.23-1.17 (m, 1H), 1.14 (s, 10H), 1.07-0.98 (m, 1H), 0.86 (s, 3H), 0.61 (s, 3H). LCMS (M+H)=606.2.

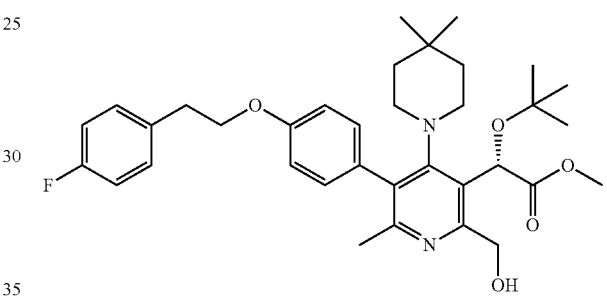

(S)-Methyl 2-(tert-butoxy)-2-(4-(4,4-dimethylpiperidin-1-yl)-5-(4-(4-fluorophenethoxy)phenyl)-2-(hydroxymethyl)-6-methylpyridin-3-yl)acetate: To a solution of (S)-2-(tert-butoxy)-2-(4-(4,4-dimethylpiperidin-1-yl)-5-(4-(4-fluorophenethoxy)phenyl)-2-(hydroxymethyl)-6-methylpyridin-3-yl)acetic acid (259 mg, 0.448 mmol) in $CH_2Cl_2$ (5 mL) and Methanol (0.5 mL) was added 2M TMS-diazomethane (0.246 mL, 0.492 mmol) and the resulting mixture was stirred at room temp for 2 h. Mixture was then concentrated and purified by Biotage (5-40% EtOAc/hexane) to afford (S)-methyl 2-(tert-butoxy)-2-(4-(4,4-dimethylpiperidin-1-yl)-5-(4-(4-fluorophenethoxy)phenyl)-2-(hydroxymethyl)-6-methylpyridin-3-yl)acetate (250 mg, 0.422 mmol, 94% yield) as viscous oil. $^1$H NMR (500 MHz, CDCl$_3$) δ 7.31 (br. s., 1H), 7.17 (d, J=7.1 Hz, 1H), 7.12-7.02 (m, 3H), 6.99 (d, J=8.5 Hz, 2H), 6.05 (s, 1H), 4.99 (d, J=14.7 Hz, 1H), 4.90 (br. s., 1H), 4.63 (dd, J=15.1, 4.7 Hz, 1H), 4.30-4.16 (m, 2H), 3.75 (s, 2H), 3.14 (t, J=6.9 Hz, 2H), 3.08 (d, J=12.0 Hz, 1H), 2.85 (t, J=12.1 Hz, 1H), 2.30 (d, J=11.0 Hz, 1H), 2.24 (s, 2H), 2.12 (t, J=11.6 Hz, 1H), 1.82 (br. s., 1H), 1.72 (d, J=5.5 Hz, 1H), 1.62-1.51 (m, 1H), 1.40-1.31 (m, 2H), 1.21 (s, 9H), 1.10 (d, J=12.9 Hz, 1H), 0.91 (br. s., 3H), 0.66 (br. s., 3H). LCMS (M+H)=593.4.

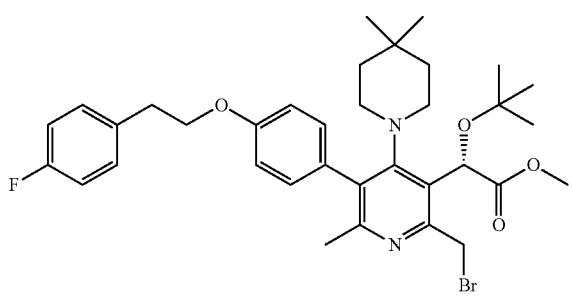 [SMILES: COC(=O)[C@@H](OC(C)(C)C)c1c(CBr)nc(C)c(-c2ccc(OCCc3ccc(F)cc3)cc2)c1N1CCC(C)(C)CC1]

(S)-Methyl 2-(2-(bromomethyl)-4-(4,4-dimethylpiperidin-1-yl)-5-(4-(4-fluorophenethoxy)phenyl)-6-methylpyridin-3-yl)-2-(tert-butoxy)acetate: To a solution of (S)-methyl 2-(tert-butoxy)-2-(4-(4,4-dimethylpiperidin-1-yl)-5-(4-(4-fluorophenethoxy)phenyl)-2-(hydroxymethyl)-6-methylpyridin-3-yl)acetate (250 mg, 0.422 mmol) in CH$_2$Cl$_2$ (5 mL) was added CBr$_4$ (154 mg, 0.464 mmol) followed by Ph$_3$P (122 mg, 0.464 mmol) and the resulting mixture was stirred at room temp for 3 h. Water (2 mL) was then added and the mixture was extracted with dichloromethane (10 mL), dried (Na$_2$SO$_4$), filtered and concentrated. The residue was then purified by Biotage (5-30% EtOAc/hexane) to afford (S)-methyl 2-(2-(bromomethyl)-4-(4,4-dimethylpiperidin-1-yl)-5-(4-(4-fluorophenethoxy)phenyl)-6-methylpyridin-3-yl)-2-(tert-butoxy)acetate (140 mg, 0.214 mmol, 50.6% yield) as viscous oil. $^1$H NMR (500 MHz, CDCl$_3$) δ 7.31 (br. s., 1H), 7.16 (d, J=7.1 Hz, 1H), 7.12-7.01 (m, 3H), 6.99 (t, J=5.9 Hz, 2H), 6.13 (s, 1H), 5.02 (d, J=9.8 Hz, 1H), 4.74 (d, J=9.9 Hz, 1H), 4.29-4.19 (m, 2H), 3.79 (s, 3H), 3.21 (d, J=11.2 Hz, 1H), 3.14 (t, J=6.9 Hz, 2H), 2.86 (t, J=11.7 Hz, 1H), 2.27 (br. s., 1H), 2.24 (s, 3H), 2.12-2.02 (m, 2H), 1.37 (d, J=4.6 Hz, 1H), 1.31-1.25 (m, 2H), 1.23 (s, 9H), 1.09 (d, J=12.5 Hz, 1H), 0.91 (br. s., 3H), 0.66 (br. s., 3H). LCMS (M+2H)=657.3.

EXAMPLE 108

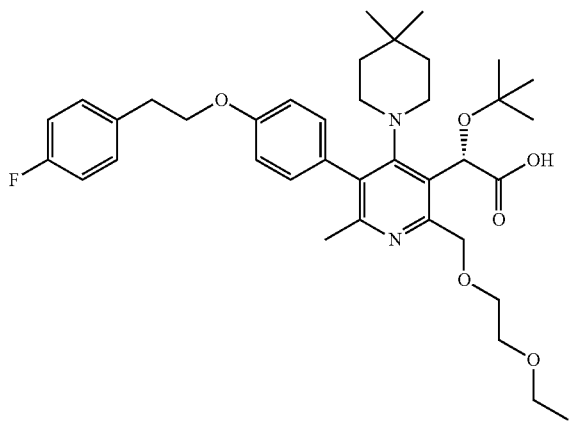 [SMILES: CCOCCOCc1nc(C)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-2-((2-ethoxyethoxy)methyl)-5-(4-(4-fluorophenethoxy)phenyl)-6-methylpyridin-3-yl)acetic acid: To a solution of anhydrous 2-ethoxyethanol (5.50 mg, 0.061 mmol) in THF (1) at 0° C. was added NaH (2.440 mg, 0.061 mmol) and the resulting mixture was stirred for 10 min. (S)-Methyl 2-(2-(bromomethyl)-4-(4,4-dimethylpiperidin-1-yl)-5-(4-(4-fluorophenethoxy)phenyl)-6-methylpyridin-3-yl)-2-(tert-butoxy)acetate (20 mg, 0.031 mmol) in THF (0.5 mL) was then added and the mixture was stirred for 4 h. At this point LCMS indicated completion of reaction. Mixture was then concentrated and treated with 10N NaOH (0.031 mL, 0.305 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-2-((2-ethoxyethoxy)methyl)-5-(4-(4-fluorophenethoxy)phenyl)-6-methylpyridin-3-yl)acetic acid (11.5 mg, 0.018 mmol, 57.9% yield). $^1$HNMR (500 MHz, DMSO-d$_6$) δ 7.42-7.33 (m, 2H), 7.23 (d, J=8.4 Hz, 1H), 7.14 (t, J=8.6 Hz, 2H), 7.08-6.98 (m, 3H), 5.82 (br. s., 1H), 4.68 (d, J=11.4 Hz, 1H), 4.54 (d, J=11.0 Hz, 1H), 4.29-4.17 (m, 2H), 3.61-3.51 (m, 2H), 3.51-3.47 (m, 2H), 3.43 (q, J=6.8 Hz, 2H), 3.06 (t, J=6.6 Hz, 2H), 2.78 (br. s., 1H), 2.17 (br. s., 1H), 2.10 (s, 3H), 1.50 (br. s., 1H), 1.30 (br. s., 1H), 1.12 (s, 9H), 1.11-1.07 (m, 3H), 1.01 (d, J=12.1 Hz, 1H), 0.84 (br. s., 3H), 0.60 (br. s., 3H). LCMS (M+H)=651.2.

EXAMPLE 109

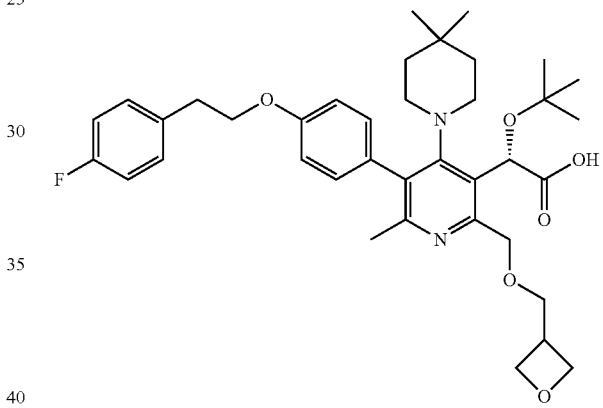

(S)-2-(tert-Butoxy)-2-(4-(4,4-dimethylpiperidin-1-yl)-5-(4-(4-fluorophenethoxy)phenyl)-6-methyl-2-((oxetan-3-ylmethoxy)methyl)pyridin-3-yl)acetic acid: To a solution of anhydrous oxetan-3-ylmethanol (5.38 mg, 0.061 mmol) in THF (1) at 0° C. was added NaH (2.440 mg, 0.061 mmol) and the resulting mixture was stirred for 10 min. (S)-Methyl 2-(2-(bromomethyl)-4-(4,4-dimethylpiperidin-1-yl)-5-(4-(4-fluorophenethoxy)phenyl)-6-methylpyridin-3-yl)-2-(tert-butoxy)acetate (20 mg, 0.031 mmol) in THF (0.5 mL) was then added and the mixture was stirred for 4 h. At this point LCMS indicated completion of reaction. Mixture was then concentrated and treated with 10N NaOH (0.031 mL, 0.305 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-5-(4-(4-fluorophenethoxy)phenyl)-6-methyl-2-((oxetan-3-ylmethoxy)methyl)pyridin-3-yl)acetic acid (11.5 mg, 0.018 mmol, 58.1% yield). $^1$H NMR (500 MHz, DMSO-d$_6$) δ 7.44-7.34 (m, 2H), 7.24 (d, J=8.1 Hz, 1H), 7.14 (t, J=8.8 Hz, 2H), 7.08-6.98 (m, 3H), 5.84 (br. s., 1H), 4.72 (d, J=11.0 Hz, 1H), 4.61 (t, J=6.8 Hz, 2H), 4.53 (d, J=11.4 Hz, 1H), 4.32 (dt, J=15.2, 6.0 Hz, 2H), 4.28-4.13 (m, 2H), 3.72-3.55 (m, 3H), 3.16 (dd, J=13.0, 6.8 Hz, 1H), 3.06 (t, J=6.4 Hz, 2H), 2.78 (d, J=12.5 Hz, 1H), 2.17 (br. s., 1H), 2.10 (s, 3H), 2.01-1.91 (m, 2H), 1.50 (br. s., 1H), 1.36-1.23 (m, 1H), 1.17 (br. s., 1H), 1.12 (s, 9H), 1.02 (d, J=12.1 Hz, 1H), 0.85 (br. s., 3H), 0.60 (br. s., 3H). LCMS (M+H)=649.1.

EXAMPLE 110

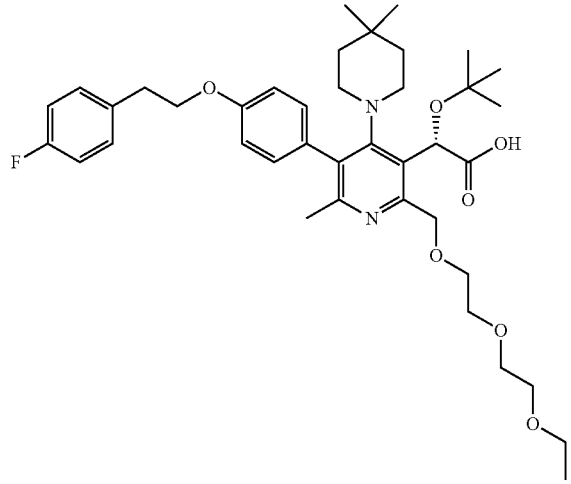 [SMILES: CCOCCOCCOCc1nc(C)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-2-((2-(2-ethoxyethoxy)ethoxy)methyl)-5-(4-(4-fluorophenethoxy)phenyl)-6-methylpyridin-3-yl)acetic acid: To a solution of anhydrous 2-(2-ethoxyethoxy)ethanol (8.19 mg, 0.061 mmol) in THF (1) at 0° C. was added NaH (2.440 mg, 0.061 mmol) and the resulting mixture was stirred for 10 min. (S)-Methyl 2-(2-(bromomethyl)-4-(4,4-dimethylpiperidin-1-yl)-5-(4-(4-fluorophenethoxy)phenyl)-6-methylpyridin-3-yl)-2-(tert-butoxy)acetate (20 mg, 0.031 mmol) in THF (0.5 mL) was then added and the mixture was stirred for 4 h. At this point LCMS indicated completion of reaction. Mixture was then concentrated and treated with 10N NaOH (0.031 mL, 0.305 mmol) in ethanol (1 mL) at 80° C. for 4 h. Mixture was then cooled and purified by prep HPLC to afford (S)-2-(tert-butoxy)-2-(4-(4,4-dimethylpiperidin-1-yl)-2-((2-(2-ethoxyethoxy)ethoxy)methyl)-5-(4-(4-fluorophenethoxy)phenyl)-6-methylpyridin-3-yl)acetic acid (14.6 mg, 0.021 mmol, 68.9% yield). $^1$H NMR (500 MHz, DMSO-$d_6$) δ 7.42-7.33 (m, 2H), 7.23 (d, J=8.4 Hz, 1H), 7.14 (t, J=8.6 Hz, 2H), 7.08-6.95 (m, 3H), 5.87 (br. s., 1H), 4.71 (d, J=11.0 Hz, 1H), 4.52 (d, J=10.6 Hz, 1H), 4.32-4.14 (m, 2H), 3.60-3.50 (m, 6H), 3.49-3.33 (m, 5H), 3.28 (br. s., 1H), 3.06 (t, J=6.8 Hz, 2H), 2.79 (br. s., 1H), 2.17 (br. s., 1H), 2.10 (s, 3H), 1.95 (br. s., 1H), 1.50 (br. s., 1H), 1.30 (br. s., 1H), 1.13 (s, 9H), 1.11-1.06 (m, 3H), 1.01 (br. s., 1H), 0.84 (br. s., 3H), 0.60 (br. s., 3H). LCMS (M+H)=695.2.

EXAMPLE 111

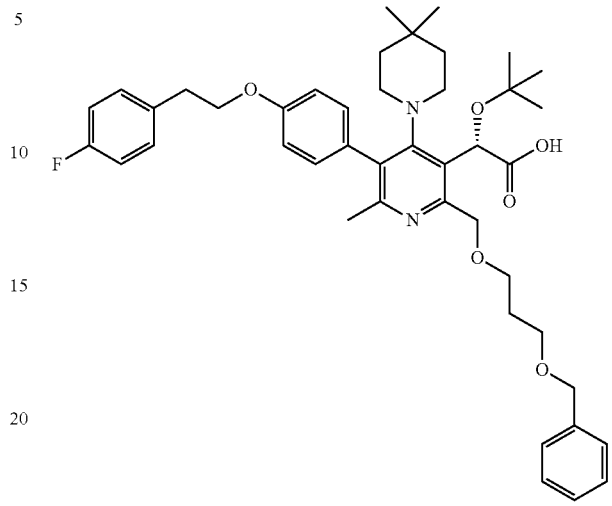

(S)-2-(2-((3-(Benzyloxy)propoxy)methyl)-4-(4,4-dimethylpiperidin-1-yl)-5-(4-(4-fluorophenethoxy)phenyl)-6-methylpyridin-3-yl)-2-(tert-butoxy)acetic acid: To a solution of anhydrous 3-(benzyloxy)propan-1-ol (10.14 mg, 0.061 mmol) in THF (1) at 0° C. was added NaH (2.440 mg, 0.061 mmol) and the resulting mixture was stirred for 10 min. (S)-Methyl 2-(2-(bromomethyl)-4-(4,4-dimethylpiperidin-1-yl)-5-(4-(4-fluorophenethoxy)phenyl)-6-methylpyridin-3-yl)-2-(tert-butoxy)acetate (20 mg, 0.031 mmol) in THF (0.5 mL) was then added and the mixture was stirred for 4 h. At this point LCMS indicated completion of reaction. Mixture was then concentrated and treated with 10N NaOH (0.031 mL, 0.305 mmol) in ethanol (1 mL) at 80° C. for 4 h. Mixture was then cooled and purified by prep HPLC to afford (S)-2-(2-((3-(benzyloxy)propoxy)methyl)-4-(4,4-dimethylpiperidin-1-yl)-5-(4-(4-fluorophenethoxy)phenyl)-6-methylpyridin-3-yl)-2-(tert-butoxy)acetic acid (8.2 mg, 0.011 mmol, 37.0% yield). $^1$H NMR (500 MHz, DMSO-$d_6$) δ 7.40-7.35 (m, 2H), 7.34-7.24 (m, 5H), 7.20 (d, J=8.1 Hz, 1H), 7.14 (t, J=8.8 Hz, 2H), 7.07-6.96 (m, 3H), 5.76 (br. s., 1H), 4.64-4.52 (m, 2H), 4.44 (s, 2H), 4.30-4.14 (m, 2H), 3.57-3.47 (m, 5H), 3.05 (t, J=6.4 Hz, 2H), 2.16 (br. s., 1H), 2.08 (s, 3H), 1.84-1.66 (m, 2H), 1.50 (br. s., 1H), 1.28 (d, J=8.8 Hz, 1H), 1.11 (s, 9H), 1.02 (br. s., 1H), 0.84 (br. s., 3H), 0.59 (br. s., 3H). LCMS (M+H)=727.2.

EXAMPLE 112

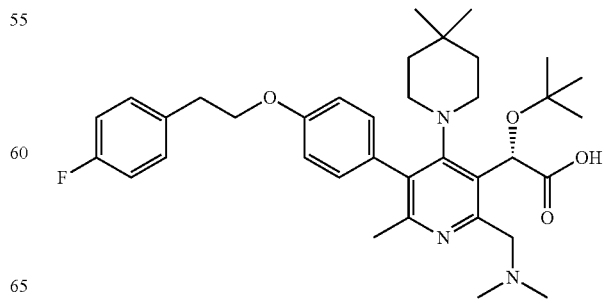

(S)-2-(tert-Butoxy)-2-(2-((dimethylamino)methyl)-4-(4,4-dimethylpiperidin-1-yl)-5-(4-(4-fluorophenethoxy)phenyl)-6-methylpyridin-3-yl)acetic acid: To a solution of dimethylamine (0.153 mL, 0.305 mmol) in ethanol (1.405 mg, 0.031 mmol) was added (S)-methyl 2-(2-(bromomethyl)-4-(4,4-dimethylpiperidin-1-yl)-5-(4-(4-fluorophenethoxy)phenyl)-6-methylpyridin-3-yl)-2-(tert-butoxy)acetate (20 mg, 0.031 mmol) and the resulting mixture was stirred at room temp for 16 h. Mixture was then treated with 10N NaOH (0.031 mL, 0.305 mmol) in ethanol (2 mL) at 80° C. for 4 h. Mixture was then cooled and purified by prep HPLC to afford (S)-2-(tert-butoxy)-2-(2-((dimethylamino)methyl)-4-(4,4-dimethylpiperidin-1-yl)-5-(4-(4-fluorophenethoxy)phenyl)-6-methylpyridin-3-yl)acetic acid (16.3 mg, 0.027 mmol, 88% yield). $^1$H NMR (500 MHz, DMSO-d$_6$) δ 7.41-7.31 (m, 2H), 7.21 (d, J=8.1 Hz, 1H), 7.14 (t, J=8.8 Hz, 2H), 7.10-6.94 (m, 3H), 5.76 (s, 1H), 5.07 (br. s., 1H), 4.29-4.18 (m, 2H), 3.71 (d, J=11.7 Hz, 1H), 3.09 (br. s., 1H), 3.05 (t, J=6.4 Hz, 2H), 2.66 (d, J=11.4 Hz, 1H), 2.59 (s, 6H), 2.21 (br. s., 1H), 2.11 (s, 3H), 2.00 (d, J=13.2 Hz, 1H), 1.84 (br. s., 1H), 1.29 (br. s., 1H), 1.16 (s, 9H), 1.05 (br. s., 2H), 0.86 (br. s., 3H), 0.59 (br. s., 3H). LCMS (M+H)=606.2.

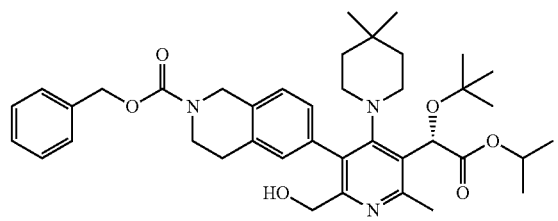 [SMILES: Cc1nc(CO)c(-c2ccc3c(c2)CCN(C(=O)OCc2ccccc2)C3)c(N2CCC(C)(C)CC2)c1[C@H](OC(C)(C)C)C(=O)OC(C)C]

(S)-Benzyl 6-(5-(1-(tert-butoxy)-2-isopropoxy-2-oxoethyl)-4-(4,4-dimethylpiperidin-1-yl)-2-(hydroxymethyl)-6-methylpyridin-3-yl)-3,4-dihydroisoquinoline-2(1H)-carboxylate: A mixture of (S)-isopropyl 2-(5-bromo-4-(4,4-dimethylpiperidin-1-yl)-6-(hydroxymethyl)-2-methylpyridin-3-yl)-2-(tert-butoxy)acetate (4 g, 8.24 mmol), benzyl 6-(6-methyl-4,8-dioxo-1,3,6,2-dioxazaborocan-2-yl)-3,4-dihydroisoquinoline-2(1H)-carboxylate (3.83 g, 9.06 mmol), 2-dicyclohexylphosphino-2',6'-dimethoxybiphenyl (0.677 g, 1.648 mmol) and 2M K$_3$PO$_4$ (30.9 mL, 61.8 mmol) in 1,4-dioxane (70 mL) and water (14.00 mL) was degassed for 10 min. Then, Pd(OAc)$_2$ (0.185 g, 0.824 mmol) was added, degassed for 5 min and mixture was heated at 80° C. for 3 h. After cooling to room temp, water was added and the mixture was extracted with ethyl acetate, washed with brine, dried (Na$_2$SO$_4$), filtered and concentrated. The residue was then purified by Biotage (5-40%EtOAc/hexane) to afford (S)-benzyl 6-(5-(1-(tert-butoxy)-2-isopropoxy-2-oxoethyl)-4-(4,4-dimethylpiperidin-1-yl)-2-(hydroxymethyl)-6-methylpyridin-3-yl)-3,4-dihydroisoquinoline-2(1H)-carboxylate (3.5 g, 5.21 mmol, 63.2% yield) as white foam. $^1$H NMR (500 MHz, CDCl$_3$) δ 7.46-7.33 (m, 5H), 7.19 (br. s., 1H), 7.11-6.88 (m, 2H), 6.02 (br. s., 1H), 5.24 (s, 2H), 5.16-5.07 (m, 1H), 4.98 (br. s., 1H), 4.78 (d, J=19.1 Hz, 1H), 4.74-4.64 (m, 1H), 4.44 (t, J=15.2 Hz, 1H), 4.12-3.99 (m, 1H), 3.89 (br. s., 1H), 3.77 (br. s., 2H), 3.36-3.16 (m, 1H), 2.65 (s, 3H), 2.40-2.24 (m, 1H), 2.16-2.05 (m, 1H), 2.01 (t, J=11.8 Hz, 1H), 1.70-1.50 (m, 2H), 1.44-1.32 (m, 1H), 1.28-1.22 (m, 6H), 1.21-1.18 (m, 9H), 1.14-1.02 (m, 1H), 0.92 (br. s., 3H), 0.72-0.57 (m, 3H). LCMS (M+H)=672.5.

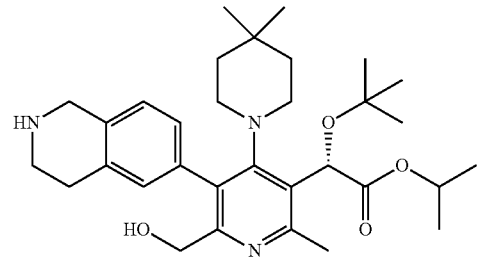 [SMILES: Cc1nc(CO)c(-c2ccc3c(c2)CCNC3)c(N2CCC(C)(C)CC2)c1[C@H](OC(C)(C)C)C(=O)OC(C)C]

(S)-Isopropyl 2-(tert-butoxy)-2-(4-(4,4-dimethylpiperidin-1-yl)-6-(hydroxymethyl)-2-methyl-5-(1,2,3,4-tetrahydroisoquinolin-6-yl)pyridin-3-yl)acetate, 2 HCl: To a solution of (S)-benzyl 6-(5-(1-(tert-butoxy)-2-isopropoxy-2-oxoethyl)-4-(4,4-dimethylpiperidin-1-yl)-2-(hydroxymethyl)-6-methylpyridin-3-yl)-3,4-dihydroisoquinoline-2(1H)-carboxylate (1.3 g, 1.935 mmol) in EtOH (25 mL) was added 1N HCl (3.87 mL, 3.87 mmol) solution followed by 10% Pd-C (0.412 g, 0.387 mmol) and the resulting mixture was stirred under balloon hydrogen atmosphere for 5 h. Mixture was then filtered through a small pad of celite, concentrated and dried under high vac overnight to afford (S)-isopropyl 2-(tert-butoxy)-2-(4-(4,4-dimethylpiperidin-1-yl)-6-(hydroxymethyl)-2-methyl-5-(1,2,3,4-tetrahydroisoquinolin-6-yl)pyridin-3-yl)acetate, 2 HCl (1.1 g, 1.801 mmol, 93% yield) as white solid. $^1$HNMR (500 MHz, CDCl$_3$) δ 10.41 (br. s., 1H), 7.33 (d, J=6.0 Hz, 1H), 7.25-7.10 (m, 1H), 7.05-6.88 (m, 1H), 5.58 (br. s., 1H), 5.15 (dt, J=12.2, 6.0 Hz, 1H), 4.66 (d, J=13.2 Hz, 1H), 4.50 (d, J=13.9 Hz, 3H), 3.79-3.69 (m, 1H), 3.59 (br. s., 1H), 3.52 (br. s., 1H), 3.29 (br. s., 2H), 2.97 (s, 3H), 2.72 (br. s., 3H), 1.44 (br. s., 1H), 1.40 (br. s., 1H), 1.31 (t, J=6.5 Hz, 6H), 1.26 (t, J=6.9 Hz, 1H), 1.20 (s, 9H), 0.95-0.80 (m, 6H). LCMS (M+H)=538.4.

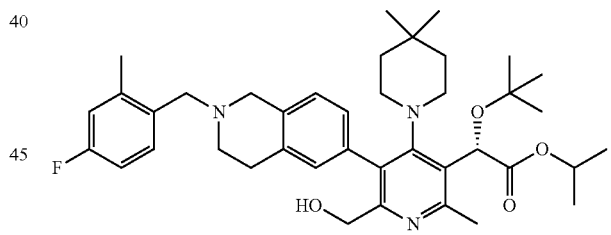

(S)-Isopropyl 2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(hydroxymethyl)-2-methylpyridin-3-yl)acetate: To a solution of (S)-isopropyl 2-(tert-butoxy)-2-(4-(4,4-dimethylpiperidin-1-yl)-6-(hydroxymethyl)-2-methyl-5-(1,2,3,4-tetrahydroisoquinolin-6-yl)pyridin-3-yl)acetate, 2 HCl (520 mg, 0.852 mmol) in MeOH (10 mL) was added TEA (0.237 mL, 1.703 mmol) and the resulting mixture was stirred for 10 min. Then, 4-fluoro-2-methylbenzaldehyde (235 mg, 1.703 mmol) in MeOH (1 mL) was added and the mixture was stirred for additional 2 h. NaCNBH$_3$ (161 mg, 2.55 mmol) was then added and the mixture was stirred at room temp for 16 h. Diluted with ater (10 mL) was and the mixture was extracted with ethyl acetate (50 mL), washed with brine, dried (Na$_2$SO$_4$), filtered and concentrated. The residue was then purified by Biotage (0-10% CH$_2$Cl$_2$/MeOH) to afford (S)-isopropyl 2-(tert-butoxy)-2-(4-(4,4-dimethylpiperidin-1-yl)-5-(2-(4-fluoro-2- methylbenzyl)-1,2,3,4-tetrahydroisoquinolin-6-yl)-6-(hydroxymethyl)-2-methylpyridin-3-yl)acetate (480 mg, 0.727 mmol, 85% yield) as white solid. $^1$H NMR (500 MHz, CDCl$_3$) δ 7.37-7.30 (m, 1H), 7.11-7.02 (m, 1H), 7.02-6.95 (m, 1H), 6.94-6.84 (m, 3H), 6.03 (br. s., 1H), 5.15-5.03 (m, 2H), 4.51-4.40 (m, 1H), 4.17-3.99 (m, 1H), 3.77-3.67 (m, 2H), 3.66 (s, 2H), 3.25 (br. s., 1H), 2.90 (d, J=5.2 Hz, 3H), 2.86-2.74 (m, 2H), 2.64 (s, 3H), 2.48-2.35 (m, 3H), 2.28-2.11 (m, 1H), 1.56 (br. s., 2H), 1.34 (d, J=15.3 Hz, 1H), 1.28-1.22 (m, 7H), 1.20 (s, 9H), 0.92 (br. s., 3H), 0.67 (br. s., 3H). LCMS (M+H)=660.5.

EXAMPLE 113

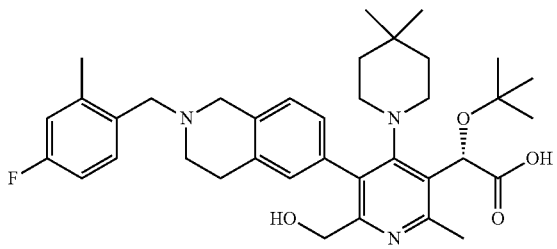 [SMILES: Cc1cc(F)ccc1CN1CCc2cc(-c3c(CO)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(hydroxymethyl)-2-methylpyridin-3-yl)acetic acid: A mixture of (S)-isopropyl 2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(hydroxymethyl)-2-methylpyridin-3-yl)acetate (40 mg, 0.061 mmol) and 10M NaOH (0.061 mL, 0.606 mmol) in EtOH (1 mL) was heated at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(hydroxymethyl)-2-methylpyridin-3-yl)acetic acid (23.9 mg, 0.039 mmol, 63.8% yield). $^1$H NMR (500 MHz, DMSO-d$_6$) δ 7.37-7.27 (m, 1H), 7.09 (s, 2H), 7.04 (d, J=9.5 Hz, 1H), 6.98 (t, J=7.7 Hz, 1H), 6.88 (br. s., 1H), 5.74 (d, J=8.4 Hz, 1H), 4.27-4.16 (m, 1H), 4.03 (d, J=13.6 Hz, 1H), 3.47 (br. s., 5H), 2.83 (br. s., 3H), 2.72 (br. s., 2H), 2.36 (br. s., 3H), 2.09 (br. s., 1H), 1.91 (br.s, 5H), 1.49 (br. s., 1H), 1.32-1.16 (m, 2H), 1.11 (s, 9H), 0.99 (br. s., 1H), 0.85 (br. s., 3H), 0.62 (br. s., 3H). LCMS (M+H)=618.2.

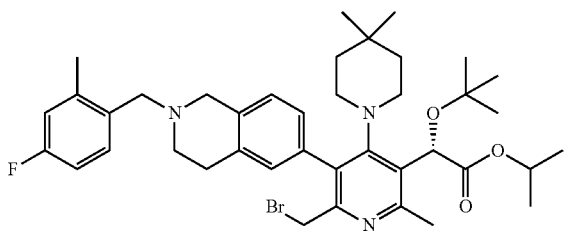 [SMILES: Cc1cc(F)ccc1CN1CCc2cc(-c3c(CBr)nc(C)c([C@H](OC(C)(C)C)C(=O)OC(C)C)c3N3CCC(C)(C)CC3)ccc2C1]

(S)-Isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate: To a solution of (S)-isopropyl 2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(hydroxymethyl)-2-methylpyridin-3-yl)acetate (480 mg, 0.727 mmol) in CH$_2$Cl$_2$ (10 mL) was added CBr$_4$ (265 mg, 0.800 mmol) followed by Ph$_3$P (210 mg, 0.800 mmol) and the resulting mixture was stirred at room temperature for 2 h. Mixture was then concentrated and purified by Biotage (5-40% EtOAc/hexane) to afford (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (370 mg, 0.512 mmol, 70.4% yield) as white solid. $^1$H NMR (500 MHz, CDCl$_3$) δ 7.39-7.30 (m, 1H), 7.24 (br. s., 1H), 7.08 (d, J=7.7 Hz, 1H), 6.97 (br. s., 1H), 6.95-6.80 (m, 2H), 6.06 (br. s., 1H), 5.18-5.02 (m, 1H), 4.36 (dd, J=13.0, 9.5 Hz, 1H), 4.23 (d, J=9.3 Hz, 1H), 3.78-3.69 (m, 2H), 3.66 (s, 2H), 3.26-3.14 (m, 1H), 2.94 (dd, J=12.5, 5.7 Hz, 2H), 2.90-2.79 (m, 2H), 2.78-2.71 (m, 1H), 2.63 (s, 3H), 2.43 (d, J=7.3 Hz, 3H), 2.24 (d, J=11.7 Hz, 1H), 1.93 (t, J=10.5 Hz, 1H), 1.54 (br. s., 2H), 1.41-1.30 (m, 1H), 1.25 (dt, J=10.6, 5.1 Hz, 6H), 1.20 (s, 9H), 1.07 (d, J=9.5 Hz, 1H), 0.92 (br. s., 3H), 0.66 (br. s., 3H). LCMS (M+2H)=724.4.

EXAMPLE 114

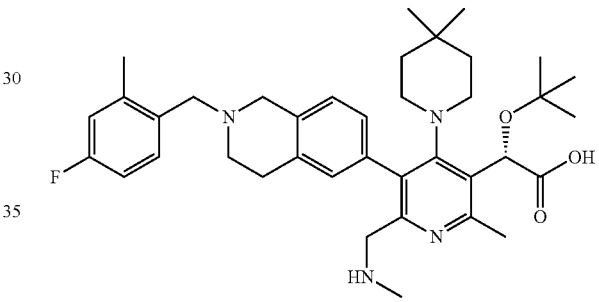

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((methylamino)methyl)pyridin-3-yl)acetic acid: A solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (0.1 g, 0.138 mmol) was added to methanamine/THF solution (2 mL, 4.00 mmol) dropwise at rt. The mixture was stirred at rt for 2 h and the solvent was removed under reduced pressure. The residue was treated with NaOH (0.1 g, 2.500 mmol) at 80° C. for 3 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((methylamino)methyl)pyridin-3-yl)acetic acid (40 mg, 0.063 mmol, 45.8% yield) as thick paste. $^1$H NMR (500 MHz, CDCl$_3$) δ 7.38-7.30 (m, 2H), 7.04 (d, J=7.7 Hz, 1H), 6.97-6.85 (m, 3H), 5.84 (br. s., 1H), 3.82-3.62 (m, 2H), 3.58-3.43 (m, 2H), 2.96-2.85 (m, 4H), 2.85-2.74 (m, 4H), 2.58 (s, 2H), 2.57-2.54 (m, 5H), 2.43 (d, J=8.4 Hz, 3H), 2.06 (s, 3H), 1.56 (br. s., 1H), 1.32 (br. s., 1H), 1.20 (s, 9H), 1.09 (d, J=11.3 Hz, 2H), 0.89 (br. s., 3H), 0.66 (br. s., 3H). LCMS (ESI) m/z (M+H)$^+$=631.2.

EXAMPLE 115

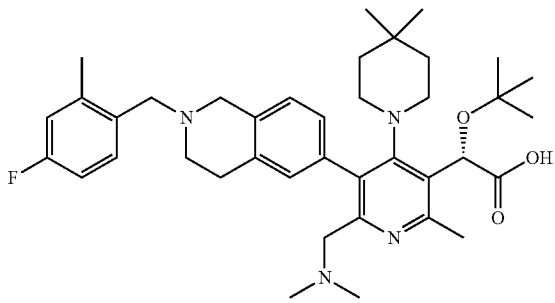 [SMILES: Cc1cc(F)ccc1CN1CCc2cc(-c3c(CN(C)C)nc(C)c([C@H](OC(C)(C)C)C(=O)O)c3N3CCC(C)(C)CC3)ccc2C1]

(S)-2-(tert-Butoxy)-2-(6-((dimethylamino)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl) acetic acid: To a solution of dimethylamine (0.138 mL, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(6-((dimethylamino)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid (3.1 mg, 4.81 µmol, 17.37% yield). $^1$H NMR (500 MHz, DMSO-$d_6$) δ 7.38-7.29 (m, 1H), 7.29-7.16 (m, 1H), 7.13-6.93 (m, 3H), 6.84 (s, 1H), 5.78 (d, J=7.7 Hz, 1H), 3.67-3.59 (m, 4H), 3.57 (br. s., 1H), 3.43 (br. s., 4H), 3.27 (d, J=12.1 Hz, 1H), 3.19-3.13 (m, 1H), 3.09-2.97 (m, 1H), 2.81 (br. s., 2H), 2.72-2.60 (m, 2H), 2.47 (s, 3H), 2.36 (br. s., 3H), 2.11 (s, 4H), 1.48 (br. s., 1H), 1.24 (br. s., 1H), 1.19 (d, J=8.8 Hz, 1H), 1.10 (s, 9H), 0.98 (br. s., 1H), 0.85 (br. s., 3H), 0.60 (br. s., 3H). LCMS (M+H)=645.2.

EXAMPLE 116

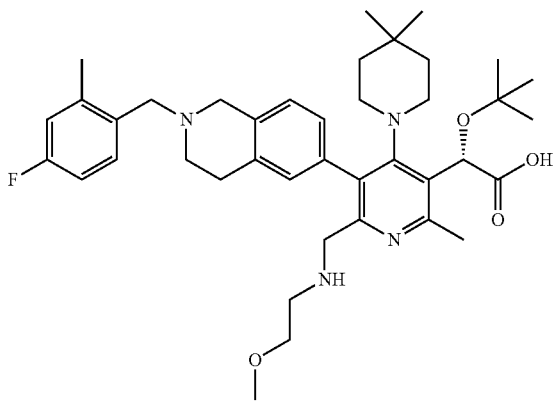 [SMILES: COCCNCc1nc(C)c([C@H](OC(C)(C)C)C(=O)O)c(N2CCC(C)(C)CC2)c1-c1ccc2c(c1)CCN(Cc1ccc(F)cc1C)C2]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(((2-methoxyethyl)amino)methyl)-2-methylpyridin-3-yl)acetic acid: To a solution of 2-methoxyethanamine (20.78 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(((2-methoxyethyl)amino)methyl)-2-methylpyridin-3-yl)acetic acid (17.7 mg, 0.026 mmol, 95% yield). $^1$H NMR (500 MHz, DMSO-$d_6$) δ 7.41-7.23 (m, 1H), 7.16-6.93 (m, 4H), 6.87 (br. s., 1H), 5.74 (d, J=11.4 Hz, 1H), 3.55-3.24 (m, 12H), 2.83 (br. s., 3H), 2.75-2.66 (m, 3H), 2.65-2.58 (m, 2H), 2.48 (s, 3H), 2.36 (br. s., 3H), 2.08 (br. s., 1H), 1.78 (d, J=12.5 Hz, 1H), 1.49 (br. s., 1H), 1.25 (br. s., 1H), 1.18 (d, J=13.9 Hz, 1H), 1.11 (s, 9H), 0.99 (br. s., 1H), 0.85 (br. s., 3H), 0.61 (br. s., 3H). LCMS (M+H)=675.2.

EXAMPLE 117

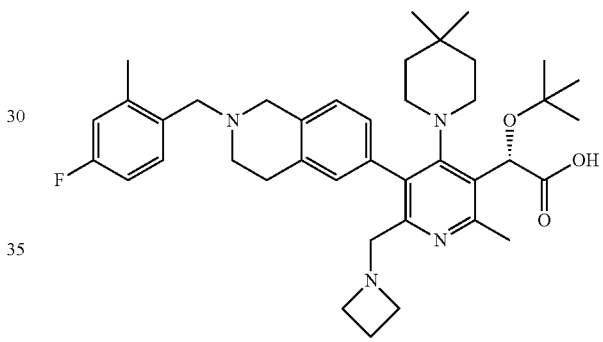

(S)-2-(6-(Azetidin-1-ylmethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid: To a solution of azetidine (15.80 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(6-(azetidin-1-ylmethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (13.9 mg, 0.021 mmol, 76% yield). $^1$H NMR (500 MHz, DMSO-$d_6$) δ 7.39-7.24 (m, 1H), 7.17-7.02 (m, 3H), 6.98 (t, J=7.9 Hz, 1H), 6.89-6.76 (m, 1H), 5.70 (d, J=11.7 Hz, 1H), 3.62 (br. s., 3H), 3.49 (br. s., 2H), 3.33-3.20 (m, 5H), 2.82 (br. s., 1H), 2.78 (br. s., 1H), 2.74 (s, 2H), 2.69 (br. s., 1H), 2.45 (s, 2H), 2.38-2.29 (m, 3H), 2.05 (br. s., 1H), 2.00-1.93 (m, 2H), 1.75 (d, J=13.9 Hz, 1H), 1.48 (br. s., 1H), 1.24 (br. s., 1H), 1.15 (br. s., 1H), 1.10 (s, 9H), 1.07-1.00 (m, 2H), 0.97 (br. s., 1H), 0.84 (br. s., 3H), 0.60 (br. s., 3H). LCMS (M+H)=657.2.

EXAMPLE 118

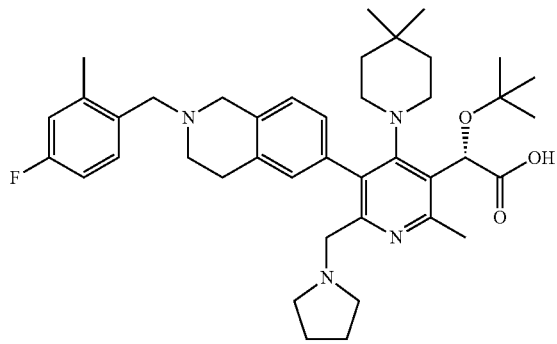 [SMILES: Cc1cc(F)ccc1CN1CCc2cc(-c3c(CN4CCCC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(pyrrolidin-1-ylmethyl)pyridin-3-yl)acetic acid: To a solution of pyrrolidine (19.68 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(pyrrolidin-1-ylmethyl)pyridin-3-yl)acetic acid (15.6 mg, 0.023 mmol, 84% yield). $^1$H NMR (500 MHz, DMSO-$d_6$) δ 7.38-7.27 (m, 1H), 7.19 (d, J=8.1 Hz, 1H), 7.11-6.92 (m, 3H), 6.85 (s, 1H), 5.75 (d, J=8.4 Hz, 1H), 3.52 (d, J=13.2 Hz, 2H), 3.43 (br. s., 2H), 3.24-3.09 (m, 2H), 2.82 (br. s., 2H), 2.64 (s, 2H), 2.47-2.39 (m, 7H), 2.38-2.33 (m, 3H), 2.20 (br. s., 1H), 2.08 (br. s., 1H), 1.76 (br. s., 1H), 1.62 (br. s., 4H), 1.49 (br. s., 1H), 1.26 (br. s., 1H), 1.17 (br. s., 1H), 1.11 (s, 9H), 0.98 (br. s., 1H), 0.85 (br. s., 3H), 0.61 (br. s., 3H). LCMS (M+H)=671.2.

EXAMPLE 119

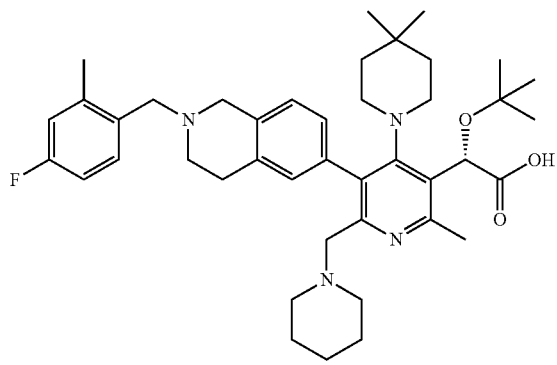 [SMILES: Cc1cc(F)ccc1CN1CCc2cc(-c3c(CN4CCCCC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(piperidin-1-ylmethyl)pyridin-3-yl)acetic acid: To a solution of piperidine (23.56 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(piperidin-1-ylmethyl)pyridin-3-yl)acetic acid (16.7 mg, 0.024 mmol, 88% yield). $^1$H NMR (500 MHz, DMSO-$d_6$) δ 7.39-7.25 (m, 1H), 7.21 (d, J=7.7 Hz, 1H), 7.12-7.02 (m, 2H), 7.01-6.93 (m, 1H), 6.84 (s, 1H), 5.79 (br. s., 1H), 3.37 (br. s., 6H), 3.02 (br. s., 1H), 2.82 (br. s., 2H), 2.73-2.67 (m, 2H), 2.45 (s, 3H), 2.36 (br. s., 3H), 2.27 (br. s., 1H), 2.20 (d, J=17.6 Hz, 2H), 2.12 (br. s., 2H), 1.49 (br. s., 1H), 1.37 (br. s., 3H), 1.30 (br. s., 3H), 1.24 (br. s., 1H), 1.17 (br. s., 1H), 1.11 (s, 9H), 1.03 (br. s., 1H), 0.99 (br. s., 1H), 0.85 (br. s., 3H), 0.66-0.52 (m, 3H). LCMS (M+H)=685.2.

EXAMPLE 120

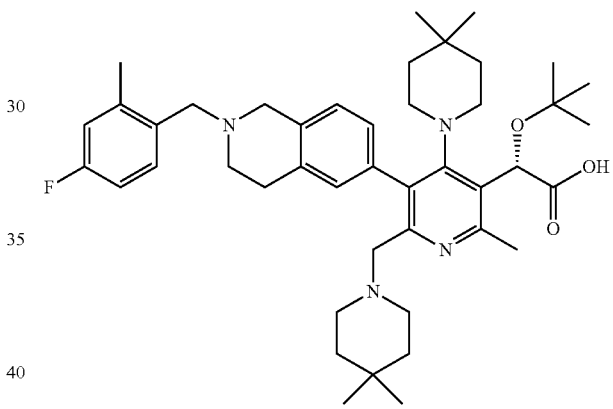

(S)-2-(tert-Butoxy)-2-(4-(4,4-dimethylpiperidin-1-yl)-6-((4,4-dimethylpiperidin-1-yl)methyl)-5-(2-(4-fluoro-2-methylbenzyl)-1,2,3,4-tetrahydroisoquinolin-6-yl)-2-methylpyridin-3-yl)acetic acid: To a solution of 4,4-dimethylpiperidine (31.3 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-6-((4,4-dimethylpiperidin-1-yl)methyl)-5-(2-(4-fluoro-2-methylbenzyl)-1,2,3,4-tetrahydroisoquinolin-6-yl)-2-methylpyridin-3-yl)acetic acid (19.5 mg, 0.027 mmol, 99% yield). $^1$H NMR (500 MHz, DMSO-$d_6$) δ 7.39-7.25 (m, 2H), 7.11-7.01 (m, 2H), 6.98 (t, J=7.5 Hz, 1H), 6.87-6.75 (m, 1H), 5.80 (br. s., 1H), 3.42 (br. s., 7H), 3.22 (br. s., 1H), 3.20-3.06 (m, 2H), 2.82 (br. s., 3H), 2.72 (br. s., 1H), 2.46 (s, 3H), 2.36 (br. s., 3H), 2.25 (br. s., 3H), 2.10 (br. s., 1H), 1.48 (br. s., 1H), 1.20 (br. s., 6H), 1.11 (s, 9H), 0.97 (d, J=16.1 Hz, 1H), 0.84 (d, J=4.0 Hz, 9H), 0.60 (br. s., 3H). LCMS (M+H)=713.2.

EXAMPLE 121

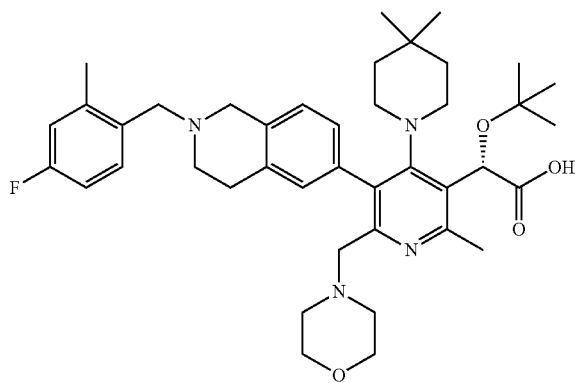 [SMILES: Cc1cc(F)ccc1CN1CCc2cc(-c3c(CN4CCOCC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(morpholinomethyl)pyridin-3-yl)acetic acid: To a solution of morpholine (24.11 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(morpholinomethyl)pyridin-3-yl)acetic acid (12.1 mg, 0.018 mmol, 63.7% yield). $^1$H NMR (500 MHz, DMSO-$d_6$) δ 7.38-7.25 (m, 1H), 7.22 (d, J=7.7 Hz, 1H), 7.11-7.02 (m, 2H), 6.99 (t, J=7.9 Hz, 1H), 6.90-6.80 (m, 1H), 5.83 (br. s., 1H), 3.62 (br. s., 4H), 3.44 (d, J=13.9 Hz, 3H), 3.37 (br. s., 3H), 3.18-3.09 (m, 1H), 2.82 (br. s., 2H), 2.46 (s, 3H), 2.36 (br. s., 3H), 2.21 (br. s., 3H), 2.11 (br. s., 1H), 1.48 (br. s., 1H), 1.25 (d, J=12.5 Hz, 1H), 1.18 (br. s., 1H), 1.12 (s, 9H), 0.99 (d, J=12.1 Hz, 1H), 0.85 (br. s., 3H), 0.66-0.52 (m, 3H). 4 piperidine hydrogens are not resolved. LCMS (M+H)=687.2.

EXAMPLE 122

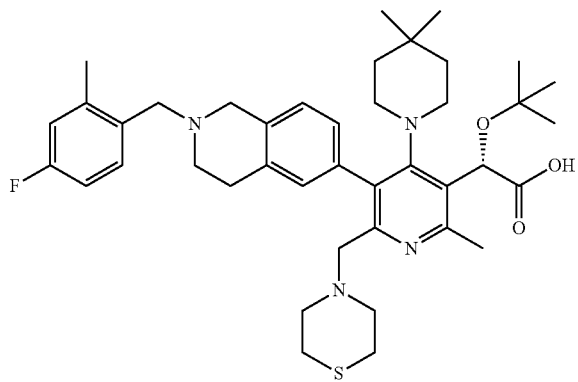

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(thiomorpholinomethyl)pyridin-3-yl)acetic acid: To a solution of thiomorpholine (28.6 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(thiomorpholinomethyl)pyridin-3-yl)acetic acid (14.9 mg, 0.021 mmol, 77% yield). $^1$H NMR (500 MHz, DMSO-$d_6$) δ 7.39-7.26 (m, 1H), 7.26-7.14 (m, 1H), 7.12-7.02 (m, 2H), 6.99 (t, J=8.8 Hz, 1H), 6.85 (br. s., 1H), 5.83 (br. s., 1H), 3.61 (d, J=4.4 Hz, 4H), 3.25-3.01 (m, 2H), 2.82 (br. s., 3H), 2.72 (br. s., 2H), 2.46 (br.s, 7H), 2.41 (br. s., 2H), 2.36 (br. s., 3H), 2.21 (br. s., 1H), 2.17-2.04 (m, 1H), 1.84 (br. s., 1H), 1.49 (br. s., 1H), 1.25 (d, J=10.6 Hz, 1H), 1.18 (br. s., 1H), 1.12 (s, 9H), 1.04 (d, J=10.3 Hz, 1H), 0.98 (d, J=10.3 Hz, 1H), 0.85 (br. s., 3H), 0.60 (br. s., 3H). LCMS (M+H)=703.2.

EXAMPLE 123

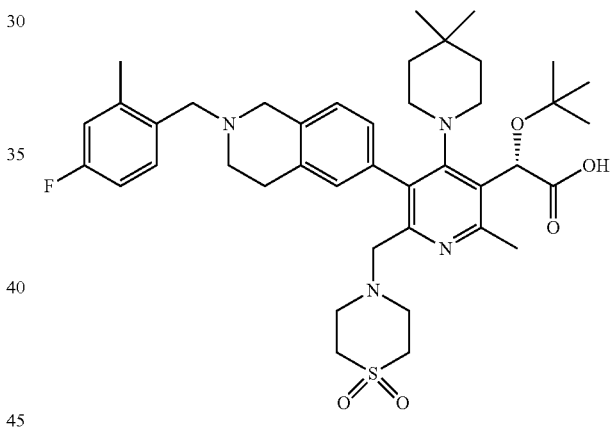

(S)-2-(tert-Butoxy)-2-(4-(4,4-dimethylpiperidin-1-yl)-6-((1,1-dioxidothiomorpholino)methyl)-5-(2-(4-fluoro-2-methylbenzyl)-1,2,3,4-tetrahydroisoquinolin-6-yl)-2-methylpyridin-3-yl)acetic acid: To a solution of thiomorpholine 1,1-dioxide (37.4 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-6-((1,1-dioxidothiomorpholino)methyl)-5-(2-(4-fluoro-2-methylbenzyl)-1,2,3,4-tetrahydroisoquinolin-6-yl)-2-methylpyridin-3-yl)acetic acid (15.8 mg, 0.021 mmol, 78% yield). $^1$H NMR (500 MHz, DMSO-$d_6$) δ 7.40-7.27 (m, 1H), 7.25-7.15 (m, 1H), 7.14-6.96 (m, 3H), 6.90 (br. s., 1H), 5.79 (br. s., 1H), 3.61 (br. s., 4H), 3.47-3.34 (m, 3H), 3.34-3.18 (m, 2H), 2.94 (br. s., 2H), 2.84 (d, J=9.9 Hz, 3H), 2.77-2.68 (m, 6H), 2.47 (s, 3H), 2.36 (br. s., 3H), 2.12 (br. s., 1H), 1.89-1.79 (m, 1H), 1.49 (br. s., 1H), 1.35-1.14 (m, 2H), 1.12 (s, 9H), 1.06-0.91 (m, 1H), 0.85 (br. s., 3H), 0.61 (br. s., 3H). LCMS (M+H)=735.1.

EXAMPLE 124

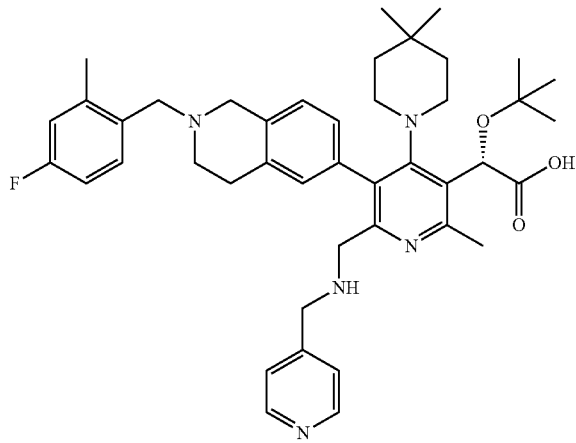 [SMILES: Cc1cc(F)ccc1CN1CCc2cc(-c3c(CNCc4ccncc4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((pyridin-4-ylmethyl)amino)methyl)pyridin-3-yl)acetic acid: To a solution of pyridin-4-ylmethanamine (29.9 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((pyridin-4-ylmethyl)amino)methyl)pyridin-3-yl)acetic acid (8.6 mg, 0.012 mmol, 43.9% yield). $^1$H NMR (500 MHz, DMSO-$d_6$) δ 8.40 (d, J=4.8 Hz, 2H), 7.33 (br. s., 1H), 7.18-7.11 (m, 2H), 7.08-6.94 (m, 4H), 6.88 (br. s., 1H), 5.76 (br. s., 1H), 3.66 (br. s., 2H), 3.61 (d, J=13.9 Hz, 4H), 3.38-3.35 (m, 5H), 3.32-3.27 (m, 2H), 2.82 (br. s., 2H), 2.70 (d, J=12.5 Hz, 2H), 2.39-2.32 (m, 3H), 2.08 (br. s., 1H), 1.77 (d, J=12.1 Hz, 1H), 1.49 (br. s., 1H), 1.24 (br. s., 1H), 1.17 (br. s., 1H), 1.12 (s, 9H), 1.04 (br. s., 1H), 0.99 (br. s., 1H), 0.85 (br. s., 3H), 0.60 (br. s., 3H). LCMS (M+H)=708.2.

EXAMPLE 125

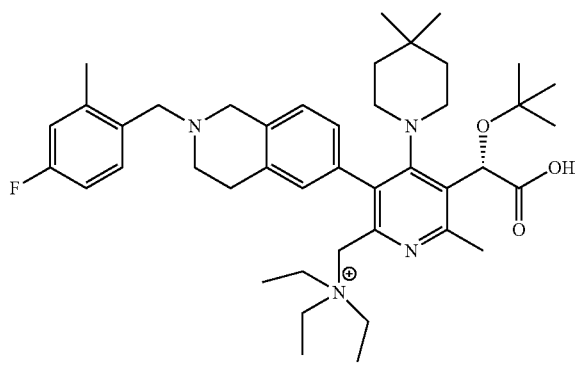 [SMILES: CC[N+](CC)(CC)Cc1nc(C)c([C@H](OC(C)(C)C)C(=O)O)c(N2CCC(C)(C)CC2)c1-c1ccc2c(c1)CCN(Cc1ccc(F)cc1C)C2]

(S)—N-((5-(tert-Butoxy(carboxy)methyl)-4-(4,4-dimethylpiperidin-1-yl)-3-(2-(4-fluoro-2-methylbenzyl)-1,2,3,4-tetrahydroisoquinolin-6-yl)-6-methylpyridin-2-yl)methyl)-N,N-diethylethanaminium: To a solution of pyrazin-2-ylmethanamine (15.10 mg, 0.138 mmol) in ethanol (1 mL) was added TEA (0.039 mL, 0.277 mmol) followed by pyrazin-2-ylmethanamine (15.10 mg, 0.138 mmol) and the resulting mixture was stirred at room temp for 16 h. At this point LCMS indicated TEA adduct instead of desired product. Mixture was then treated with 10N NaOH (0.028 mL, 0.277 mmol) at 80° C. for 4 h. Mixture was then cooled and purified by prep HPLC to afford (S)—N-((5-(tert-butoxy (carboxy)methyl)-4-(4,4-dimethylpiperidin-1-yl)-3-(2-(4-fluoro-2-methylbenzyl)-1,2,3,4-tetrahydroisoquinolin-6-yl)-6-methylpyridin-2-yl)methyl)-N,N-diethylethanaminium (13.1 mg, 0.017 mmol, 62.2% yield). $^1$H NMR (500 MHz, DMSO-$d_6$) δ 7.38-7.29 (m, 1H), 7.25-7.11 (m, 2H), 7.06 (d, J=9.9 Hz, 1H), 7.00 (t, J=8.4 Hz, 1H), 6.91 (s, 1H), 5.40 (s, 1H), 4.30 (d, J=15.0 Hz, 1H), 4.23 (d, J=14.7 Hz, 1H), 4.03 (d, J=14.7 Hz, 2H), 3.43 (dd, J=13.9, 7.0 Hz, 3H), 3.27 (td, J=13.2, 6.2 Hz, 3H), 2.86 (br. s., 2H), 2.71 (br. s., 3H), 2.53 (s, 2H), 2.38-2.34 (m, 3H), 2.04 (br. s., 1H), 1.63 (br. s., 1H), 1.51 (br. s., 1H), 1.24 (br. s., 1H), 1.14 (br. s., 1H), 1.07 (s, 9H), 1.05-0.98 (m, 9H), 0.93 (d, J=13.9 Hz, 1H), 0.85 (br. s., 3H), 0.73 (br. s., 1H), 0.62 (br. s., 3H). 4 piperidine hydrogens are not resolved. LCMS (M+H)=702.3.

EXAMPLE 126

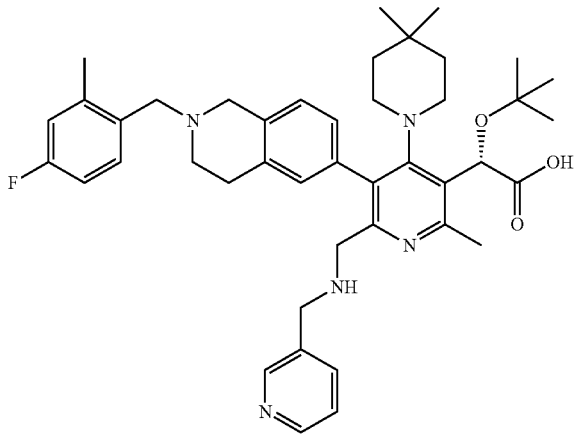 [SMILES: Cc1cc(F)ccc1CN1CCc2cc(-c3c(CNCc4cccnc4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((pyridin-3-ylmethyl)amino)methyl)pyridin-3-yl)acetic acid: To a solution of pyridin-3-ylmethanamine (29.9 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((pyridin-3-ylmethyl)amino)methyl)pyridin-3-yl)acetic acid (8.8 mg, 0.012 mmol, 44.9% yield). $^1$H NMR (500 MHz, DMSO-$d_6$) δ 8.59 (br. s., 2H), 7.85 (d, J=7.7 Hz, 1H), 7.59 (br. s., 1H), 7.48-7.42 (m, 1H), 7.41-7.31 (m, 1H), 7.22 (s, 1H), 7.26 (s, 1H), 7.16 (s, 1H), 7.05 (d, J=6.6 Hz, 1H), 5.83 (br. s., 1H), 4.39 (br. s., 3H), 4.20 (br. s., 3H), 3.54 (br. s., 1H), 3.43 (br. s., 2H), 3.30 (br. s., 1H), 3.13 (br. s., 1H), 2.57 (s, 2H), 2.55 (s, 3H), 2.45 (br. s., 3H), 2.22 (br. s., 1H), 1.53 (br. s., 1H), 1.26 (br. s., 2H), 1.14 (s, 9H), 1.01 (br. s., 1H), 0.88 (br. s., 3H), 0.65 (br. s., 3H). 4 piperidine hydrogens are not resolved. LCMS (M+H)=708.3.

EXAMPLE 127

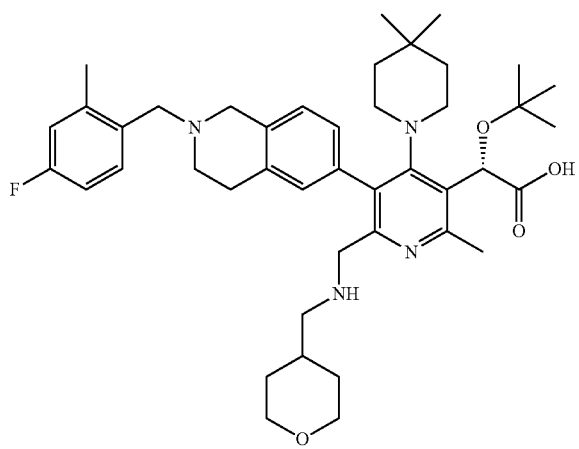 [SMILES: Cc1cc(F)ccc1CN1CCc2cc(-c3c(CNCC4CCOCC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((((tetrahydro-2H-pyran-4-yl)methyl)amino)methyl)pyridin-3-yl)acetic acid: To a solution of (tetrahydro-2H-pyran-4-yl)methanamine (31.9 mg, 0.277 mmol) in Ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((((tetrahydro-2H-pyran-4-yl)methyl)amino)methyl)pyridin-3-yl)acetic acid (5.0 mg, 6.99 µmol, 25.3% yield). $^1$H NMR (500 MHz, DMSO-$d_6$) δ 7.40-7.26 (m, 1H), 7.15-7.02 (m, 3H), 6.98 (t, J=7.9 Hz, 1H), 6.87 (br. s., 1H), 5.71 (d, J=8.8 Hz, 1H), 3.78 (d, J=9.9 Hz, 2H), 3.51 (d, J=14.3 Hz, 2H), 3.39 (d, J=13.2 Hz, 3H), 3.24-3.13 (m, 3H), 2.82 (br. s., 2H), 2.71 (br. s., 2H), 2.47 (s, 3H), 2.38-2.30 (m, 5H), 2.08 (br. s., 1H), 1.79 (d, J=11.0 Hz, 1H), 1.50 (br. s., 2H), 1.48-1.41 (m, 1H), 1.26 (br. s., 1H), 1.17 (d, J=13.2 Hz, 1H), 1.10 (s, 9H), 1.04 (d, J=7.0 Hz, 2H), 0.97 (d, J=11.4 Hz, 1H), 0.85 (br. s., 3H), 0.61 (br. s., 3H). 4 piperidine hydrogens are not resolved. LCMS (M+H)=715.2.

EXAMPLE 128

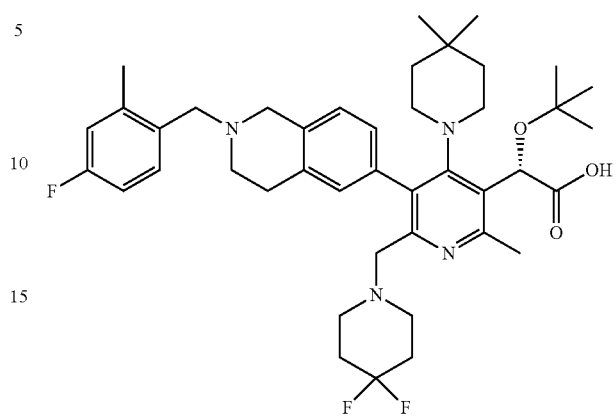

(S)-2-(tert-Butoxy)-2-(6-((4,4-difluoropiperidin-1-yl)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and 4,4-difluoropiperidine, HCl (21.80 mg, 0.138 mmol) in ethanol (1 mL) was added TEA (0.023 mL, 0.166 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(6-((4,4-difluoropiperidin-1-yl)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl) acetic acid (17.4 mg, 0.024 mmol, 87% yield). $^1$H NMR (500 MHz, DMSO-$d_6$) δ 7.37-7.27 (m, 1H), 7.25-7.16 (m, 1H), 7.13-7.02 (m, 2H), 6.99 (t, J=8.4 Hz, 1H), 6.91-6.79 (m, 1H), 5.80 (br. s., 1H), 3.61 (d, J=4.0 Hz, 4H), 3.23-3.10 (m, 2H), 2.87-2.79 (m, 3H), 2.68 (br. s., 1H), 2.46 (s, 3H), 2.42-2.26 (m, 8H), 2.11 (br. s., 1H), 1.87-1.67 (m, 5H), 1.49 (br. s., 1H), 1.25 (d, J=11.0 Hz, 1H), 1.19 (d, J=12.1 Hz, 1H), 1.11 (s, 9H), 1.04 (d, J=6.6 Hz, 1H), 0.98 (d, J=9.5 Hz, 1H), 0.85 (br. s., 3H), 0.64-0.55 (m, 3H). LCMS (M+H)=721.4.

EXAMPLE 129

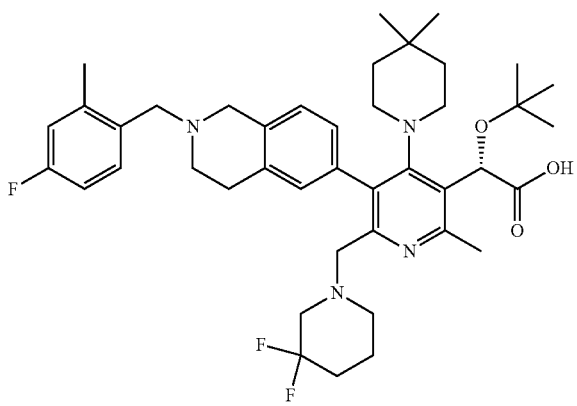 [SMILES: Cc1cc(F)ccc1CN1CCc2cc(-c3c(CN4CCCC(F)(F)C4)nc(C)c([C@H](OC(C)(C)C)C(=O)O)c3N3CCC(C)(C)CC3)ccc2C1]

(S)-2-(tert-Butoxy)-2-(6-((3,3-difluoropiperidin-1-yl)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and 3,3-difluoropiperidine, HCl (21.80 mg, 0.138 mmol) in ethanol (1 mL) was added TEA (0.023 mL, 0.166 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(6-((3,3-difluoropiperidin-1-yl)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid (12.9 mg, 0.018 mmol, 64.7% yield). $^1$H NMR (500 MHz, DMSO-$d_6$) δ 7.38-7.29 (m, 1H), 7.28-7.19 (m, 1H), 7.12-7.03 (m, 2H), 7.02-6.93 (m, 1H), 6.87-6.79 (m, 1H), 5.72 (br. s., 1H), 3.40 (br. s., 4H), 3.23 (s, 1H), 3.18-3.05 (m, 1H), 2.81 (br. s., 3H), 2.68 (br. s., 2H), 2.46 (s, 3H), 2.36 (d, J=3.7 Hz, 4H), 2.26 (br. s., 1H), 2.20 (br. s., 1H), 2.09 (br. s., 1H), 1.80 (d, J=7.3 Hz, 3H), 1.50 (br. s., 3H), 1.24 (br. s., 2H), 1.17 (br. s., 1H), 1.10 (s, 9H), 0.98 (d, J=12.1 Hz, 1H), 0.85 (br. s., 3H), 0.67-0.50 (m, 3H). LCMS (M+H)=721.2.

EXAMPLE 130

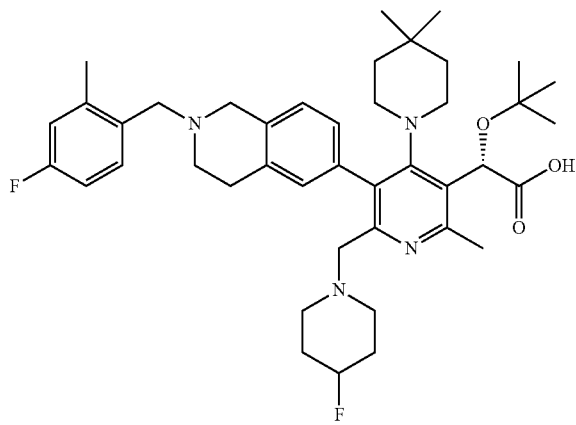 [SMILES: Cc1cc(F)ccc1CN1CCc2cc(-c3c(CN4CCC(F)CC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-((4-fluoropiperidin-1-yl)methyl)-2-methylpyridin-3-yl)acetic acid: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and 4-fluoropiperidine, HCl (19.31 mg, 0.138 mmol) in ethanol (1 mL) was added TEA (0.023 mL, 0.166 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-((4-fluoropiperidin-1-yl)methyl)-2-methylpyridin-3-yl)acetic acid (11.2 mg, 0.016 mmol, 57.6% yield). $^1$H NMR (500 MHz, DMSO-$d_6$) δ 7.38-7.29 (m, 1H), 7.20 (d, J=7.7 Hz, 1H), 7.12-7.03 (m, 2H), 6.99 (t, J=8.4 Hz, 1H), 6.88-6.80 (m, 1H), 5.76 (br. s., 1H), 4.62 (br. s., 1H), 4.52 (br. s., 1H), 3.40 (br. s., 4H), 3.20-3.05 (m, 3H), 2.87-2.78 (m, 3H), 2.73-2.65 (m, 2H), 2.45 (s, 3H), 2.36 (d, J=3.3 Hz, 4H), 2.21 (br. s., 1H), 2.18-2.05 (m, 3H), 1.82 (t, J=12.8 Hz, 1H), 1.71 (br. s., 2H), 1.56 (br. s., 2H), 1.49 (br. s., 2H), 1.25 (d, J=16.1 Hz, 1H), 1.18 (d, J=10.3 Hz, 1H), 1.11 (s, 9H), 1.04 (d, J=12.5 Hz, 1H), 0.85 (br. s., 3H), 0.65-0.57 (m, 3H). LCMS (M+H)=703.3.

EXAMPLE 131

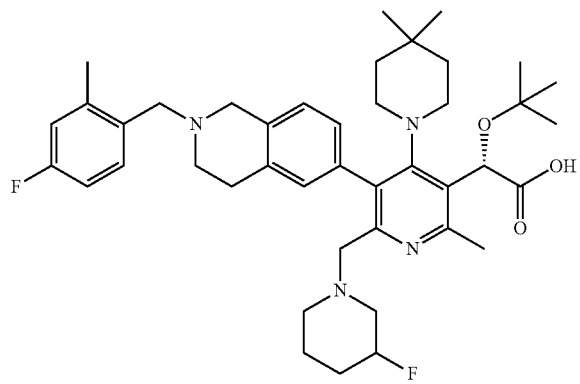 [SMILES: Cc1cc(F)ccc1CN1CCc2cc(-c3c(CN4CCCC(F)C4)nc(C)c([C@H](OC(C)(C)C)C(=O)O)c3N3CCC(C)(C)CC3)ccc2C1]

(2S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-((3-fluoropiperidin-1-yl)methyl)-2-methylpyridin-3-yl)acetic acid: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and 3-fluoropiperidine, HCl (19.31 mg, 0.138 mmol) in ethanol (1 mL) was added TEA (0.023 mL, 0.166 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (2S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-((3-fluoropiperidin-1-yl)methyl)-2-methylpyridin-3-yl)acetic acid (15.5 mg, 0.022 mmol, 80% yield). $^1$H NMR (500 MHz, DMSO-$d_6$) δ 7.37-7.29 (m, 1H), 7.22 (d, J=8.1 Hz, 1H), 7.11-7.01 (m, 2H), 6.99 (t, J=8.6 Hz, 1H), 6.87-6.79 (m, 1H), 5.74 (br. s., 1H), 4.45 (br. s., 1H), 3.61 (br. s., 2H), 3.46 (br. s., 2H), 3.19-3.11 (m, 2H), 3.11-3.00 (m, 2H), 2.82 (br. s., 3H), 2.69 (d, J=6.6 Hz, 2H), 2.46 (s, 3H), 2.39-2.33 (m, 3H), 2.25 (d, J=19.4 Hz, 1H), 2.18 (br. s., 1H), 2.13 (br. s., 1H), 2.09-1.96 (m, 1H), 1.77 (d, J=6.6 Hz, 2H), 1.58 (br. s., 1H), 1.49 (br. s., 1H), 1.42 (br. s., 1H), 1.26 (br. s., 2H), 1.17 (br. s., 1H), 1.10 (s, 9H), 1.06-0.94 (m, 1H), 0.85 (br. s., 3H), 0.65-0.49 (m, 3H). LCMS (M+H)=703.2.

EXAMPLE 132

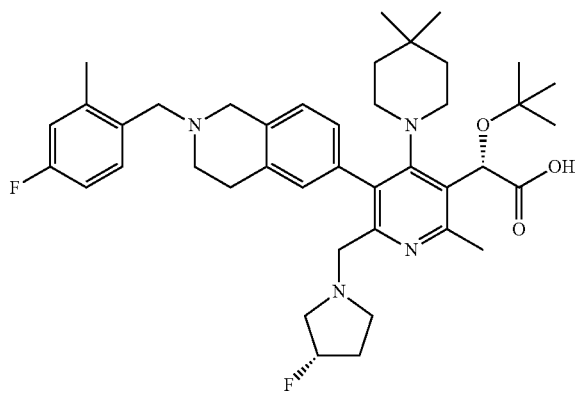 [SMILES: Cc1cc(F)ccc1CN1CCc2cc(-c3c(CN4CC[C@H](F)C4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(((S)-3-fluoropyrrolidin-1-yl)methyl)-2-methylpyridin-3-yl)acetic acid: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and (S)-3-fluoropyrrolidine, HCl (17.37 mg, 0.138 mmol) in ethanol (1 mL) was added TEA (0.023 mL, 0.166 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(((S)-3-fluoropyrrolidin-1-yl)methyl)-2-methylpyridin-3-yl)
acetic acid (11 mg, 0.016 mmol, 57.7% yield). $^1$H NMR (500 MHz, DMSO-$d_6$) δ 7.38-7.30 (m, 1H), 7.20 (d, J=7.7 Hz, 1H), 7.13-7.02 (m, 2H), 7.01-6.94 (m, 1H), 6.89-6.71 (m, 1H), 5.75 (d, J=5.1 Hz, 1H), 5.04 (br. s., 1H), 3.67-3.56 (m, 3H), 3.37 (d, J=11.4 Hz, 3H), 3.20-3.13 (m, 1H), 3.13-3.04 (m, 1H), 2.87-2.77 (m, 3H), 2.72 (br. s., 2H), 2.70-2.58 (m, 3H), 2.46 (s, 3H), 2.36 (d, J=3.7 Hz, 3H), 2.31-2.21 (m, 1H), 2.08 (br. s., 1H), 2.06-1.93 (m, 1H), 1.78 (dt, J=15.3, 7.9 Hz, 1H), 1.50 (br. s., 1H), 1.25 (d, J=9.5 Hz, 1H), 1.18 (d, J=8.8 Hz, 1H), 1.11 (s, 9H), 1.04 (d, J=12.5 Hz, 1H) 0.85 (br. s., 3H), 0.66-0.54 (m, 3H). LCMS (M+H)=689.4.

EXAMPLE 133

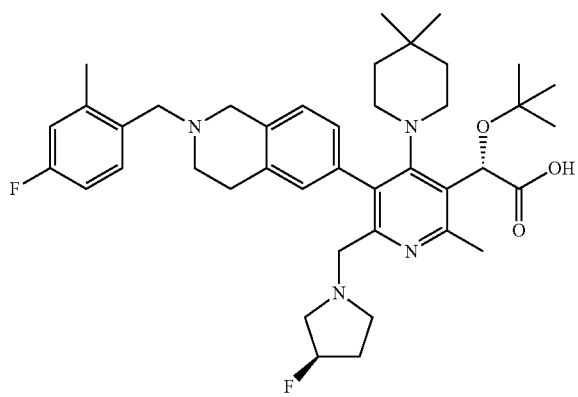 [SMILES: Cc1cc(F)ccc1CN1CCc2cc(-c3c(CN4CC[C@@H](F)C4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(((R)-3-fluoropyrrolidin-1-yl)methyl)-2-methylpyridin-3-yl)acetic acid: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and (R)-3-fluoropyrrolidine, HCl (17.37 mg, 0.138 mmol) in ethanol (1 mL) was added TEA (0.023 mL, 0.166 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(((R)-3-fluoropyrrolidin-1-yl)methyl)-2-methylpyridin-3-yl)
acetic acid (11.8 mg, 0.017 mmol, 61.9% yield). $^1$H NMR (500 MHz, DMSO-$d_6$) δ 7.38-7.28 (m, 1H), 7.24-7.15 (m, 1H), 7.12-7.02 (m, 2H), 6.99 (t, J=8.4 Hz, 1H), 6.89-6.74 (m, 1H), 5.76 (d, J=5.9 Hz, 1H), 5.17 (br. s., 1H), 5.05 (br. s., 1H), 3.43 (d, J=12.5 Hz, 2H), 3.35 (d, J=12.5 Hz, 2H), 3.19-3.08 (m, 1H), 2.86-2.77 (m, 3H), 2.72-2.58 (m, 4H), 2.46 (s, 3H), 2.39-2.32 (m, 3H), 2.28-2.15 (m, 2H), 2.14-1.94 (m, 2H), 1.85-1.68 (m, 2H), 1.49 (br. s., 1H), 1.25 (d, J=11.0 Hz, 1H), 1.18 (d, J=11.7 Hz, 1H), 1.11 (s, 9H), 1.04 (d, J=8.4 Hz, 1H), 0.85 (br. s., 3H), 0.64-0.57 (m, 3H). LCMS (M+H)=689.2.

EXAMPLE 134

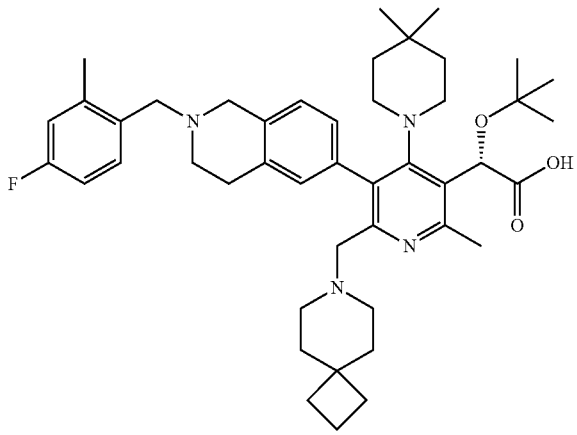 [SMILES: Cc1cc(F)ccc1CN1CCc2cc(-c3c(CN4CCC5(CCC5)CC4)nc(C)c([C@H](OC(C)(C)C)C(=O)O)c3N3CCC(C)(C)CC3)ccc2C1]

(S)-2-(6-(7-Azaspiro[3.5]nonan-7-ylmethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid: A solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and 7-azaspiro[3.5]nonane (17.32 mg, 0.138 mmol) in ethanol (1 mL) was stirred at room temp for 16 h. Mixture was then treated with 10N NaOH (0.028 mL, 0.277 mmol) at 80° C. for 4 h. Mixture was then cooled and purified by prep HPLC to afford (S)-2-(6-(7-azaspiro[3.5]nonan-7-ylmethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (14 mg, 0.019 mmol, 69.8% yield). $^1$H NMR (500 MHz, DMSO-$d_6$) δ 7.32 (br. s., 1H), 7.21 (d, J=8.1 Hz, 1H), 7.04 (d, J=8.4 Hz, 2H), 6.98 (br. s., 1H), 6.82 (br. s., 1H), 5.78 (br. s., 1H), 3.39 (br. s., 5H), 3.09 (br. s., 1H), 3.05-2.94 (m, 1H), 2.90 (s, 2H), 2.80 (br. s., 3H), 2.74 (br. s., 3H), 2.45 (br. s., 3H), 2.36 (br. s., 3H), 2.19 (br. s., 2H), 2.11 (br. s., 4H), 1.78 (br. s., 2H), 1.63 (br. s., 3H), 1.48 (br. s., 1H), 1.40 (br. s., 3H), 1.23 (br. s., 1H), 1.11 (br. s., 9H), 0.99 (br. s., 1H), 0.85 (br. s., 3H), 0.60 (br. s., 3H). LCMS (M+H)=725.3.

EXAMPLE 135

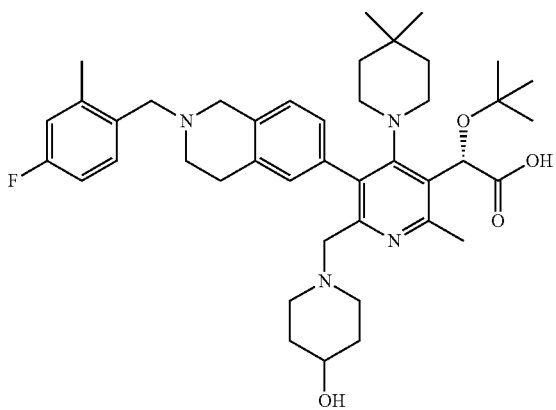 [SMILES: Cc1cc(F)ccc1CN1CCc2cc(-c3c(CN4CCC(O)CC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-((4-hydroxypiperidin-1-yl)methyl)-2-methylpyridin-3-yl)acetic acid: A solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and piperidin-4-ol (13.99 mg, 0.138 mmol) in ethanol (1 mL) was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-((4-hydroxypiperidin-1-yl)methyl)-2-methylpyridin-3-yl)acetic acid (11.7 mg, 0.017 mmol, 60.3% yield). $^1$H NMR (500 MHz, DMSO-d$_6$) δ 7.38-7.29 (m, 1H), 7.20 (d, J=7.7 Hz, 1H), 7.12-7.01 (m, 2H), 6.99 (t, J=7.5 Hz, 1H), 6.87-6.76 (m, 1H), 5.80 (br. s., 1H), 3.35 (br. s., 6H), 3.12 (s, 1H), 3.08-2.97 (m, 1H), 2.82 (br. s., 3H), 2.69 (d, J=6.2 Hz, 2H), 2.45 (s, 3H), 2.36 (d, J=2.9 Hz, 4H), 2.20 (br. s., 1H), 2.11 (d, J=10.6 Hz, 1H), 1.99 (d, J=10.6 Hz, 1H), 1.59 (br. s., 2H), 1.49 (br. s., 1H), 1.35-1.23 (m, 2H), 1.19 (d, J=9.2 Hz, 2H), 1.12 (s, 9H), 1.05 (br. s., 1H), 0.85 (br. s., 3H), 0.67-0.55 (m, 3H). LCMS (M+H)=701.3.

EXAMPLE 136

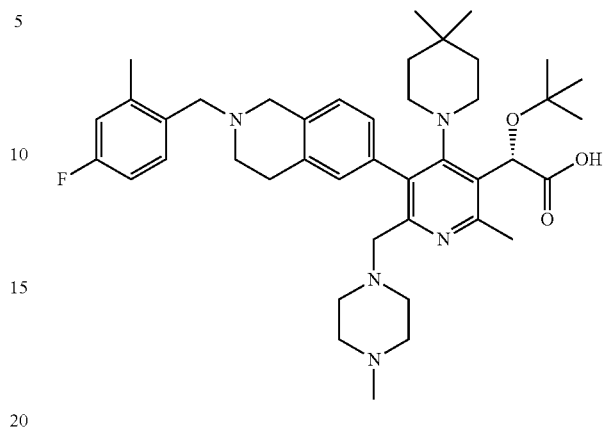

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((4-methylpiperazin-1-yl)methyl)pyridin-3-yl)acetic acid: A solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and 1-methylpiperazine (13.86 mg, 0.138 mmol) in ethanol (1 mL) was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((4-methylpiperazin-1-yl)methyl)pyridin-3-yl)acetic acid (17.4 mg, 0.025 mmol, 90% yield). $^1$H NMR (500 MHz, DMSO-d$_6$) δ 7.37-7.29 (m, 1H), 7.20 (d, J=7.7 Hz, 1H), 7.11-7.01 (m, 2H), 6.98 (t, J=8.6 Hz, 1H), 6.88-6.79 (m, 1H), 5.79 (br. s., 1H), 3.45 (br. s., 6H), 3.17-3.10 (m, 1H), 3.08-2.99 (m, 1H), 2.86-2.77 (m, 3H), 2.73-2.66 (m, 2H), 2.45 (s, 3H), 2.36 (s, 3H), 2.22 (br. s., 7H), 2.09 (d, J=4.0 Hz, 4H), 1.88-1.75 (m, 1H), 1.49 (br. s., 1H), 1.25 (d, J=13.2 Hz, 1H), 1.17 (br. s., 1H), 1.11 (s, 9H), 0.98 (d, J=6.2 Hz, 1H), 0.85 (br. s., 3H), 0.65-0.51 (m, 3H). LCMS (M+H)=700.3.

EXAMPLE 137

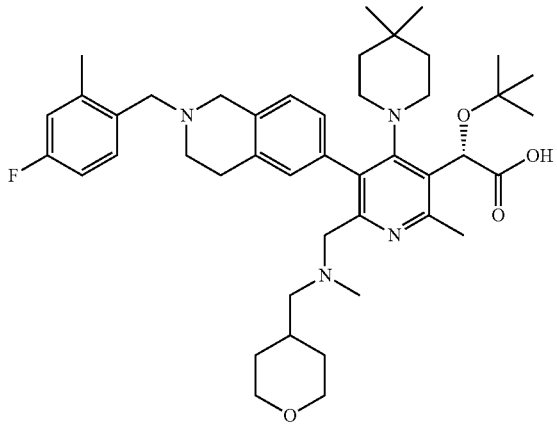 [SMILES: Cc1cc(F)ccc1CN1CCc2cc(-c3c(CN(C)CC4CCOCC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((methyl((tetrahydro-2H-pyran-4-yl)methyl)amino)methyl)pyridin-3-yl)acetic acid: To a solution of N-methyl-1-(tetrahydro-2H-pyran-4-yl)methanamine (35.8 mg, 0.277 mmol) in ethanol (1 mL) was added (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol) and the resulting mixture was stirred at room temp for 16 h. Mixture was then treated with 10N NaOH (0.028 mL, 0.277 mmol) at 80° C. for 4 h. Mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((methyl((tetrahydro-2H-pyran-4-yl)methyl)amino)methyl)pyridin-3-yl)acetic acid (15 mg, 0.021 mmol, 74.4% yield). $^1$H NMR (500 MHz, DMSO-$d_6$) δ 7.38-7.26 (m, 1H), 7.24-7.14 (m, 1H), 7.11-7.01 (m, 2H), 7.01-6.90 (m, 1H), 6.87-6.76 (m, 1H), 5.78 (d, J=9.5 Hz, 1H), 3.74-3.64 (m, 2H), 3.61 (br. s., 3H), 3.57 (br. s., 1H), 3.31 (d, J=11.7 Hz, 1H), 3.24-3.05 (m, 4H), 2.80 (br. s., 3H), 2.69 (dd, J=16.1, 5.9 Hz, 2H), 2.45 (s, 3H), 2.38-2.32 (m, 3H), 2.23-2.15 (m, 1H), 2.15-2.07 (m, 1H), 2.05-1.94 (m, 5H), 1.48 (br. s., 1H), 1.35 (d, J=7.7 Hz, 3H), 1.30-1.14 (m, 2H), 1.09 (s, 9H), 0.98 (br. s., 1H), 0.89 (br. s., 1H), 0.84 (br. s., 3H), 0.81-0.71 (m, 1H), 0.60 (br. s., 3H). LCMS (M+H)=729.3.

EXAMPLE 138

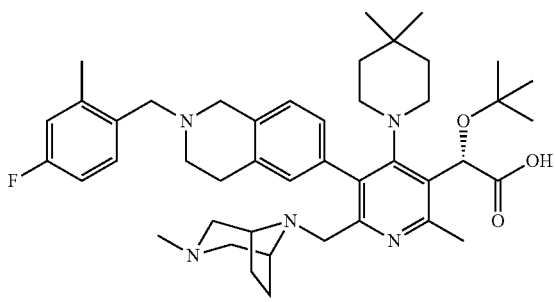 [SMILES: Cc1cc(F)ccc1CN1CCc2cc(-c3c(CN4C5CCC4CN(C)C5)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((1R,5S)-3-methyl-3,8-diazabicyclo[3.2.1]octan-8-yl)methyl)pyridin-3-yl)acetic acid: A solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (20 mg, 0.028 mmol), (1R,5S)-3-methyl-3,8-diazabicyclo[3.2.1]octane, HCl (22.51 mg, 0.138 mmol) and triethylamine (0.027 mL, 0.194 mmol) in EtOH (1 mL) was stirred for 2 h. Then, 10N NaOH (0.100 mL, 1.000 mmol) was added and the reaction mixture was stirred at 80° C. for 2 h. the reaction mixture was then cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((R,5S)-3-methyl-3,8-diazabicyclo[3.2.1]octan-8-yl)methyl)pyridin-3-yl)acetic acid (17.8 mg, 0.025 mmol, 89% yield). $^1$H NMR (500 MHz, DMSO-$d_6$) δ 7.38-7.26 (m, 2H), 7.13-7.02 (m, 2H), 7.01-6.95 (m, 1H), 6.90-6.83 (m, 1H), 5.83 (br. s., 1H), 3.36 (br. s., 1H), 3.24 (d, J=12.1 Hz, 1H), 3.07 (d, J=12.1 Hz, 1H), 2.98 (d, J=12.5 Hz, 1H), 2.91 (br. s., 1H), 2.89-2.79 (m, 4H), 2.73-2.66 (m, 2H), 2.47-2.43 (m, 3H), 2.42-2.30 (m, 5H), 2.21-2.09 (m, 1H), 2.08-2.04 (m, 3H), 1.87 (d, J=9.9 Hz, 1H), 1.76 (br. s., 1H), 1.68 (br. s., 1H), 1.65-1.56 (m, 2H), 1.50 (br. s., 1H), 1.34-1.15 (m, 2H), 1.12 (s, 9H), 0.99 (d, J=8.4 Hz, 1H), 0.86 (br. s., 3H), 0.67-0.57 (m, 3H). 6 piperidine hydrogens are not resolved. LCMS (M+H)=726.3.

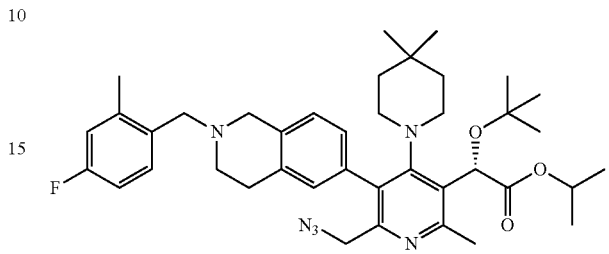

(S)-Isopropyl 2-(6-(azidomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (200 mg, 0.277 mmol) in DMF (4 mL) was added NaN$_3$ (27.0 mg, 0.415 mmol) and the resulting mixture was stirred at room temp for 3 h. Water (10 mL) was then added and the mixture was extracted with ethyl acetate (25 mL), washed with brine (20 mL), dried (Na$_2$SO$_4$), filtered and concentrated to afford (S)-isopropyl 2-(6-(azidomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (180 mg, 0.263 mmol, 95% yield). $^1$H NMR (500 MHz, CDCl$_3$) δ 7.38-7.31 (m, 1H), 7.12-6.99 (m, 2H), 6.97-6.84 (m, 3H), 6.06 (br. s., 1H), 5.11 (dq, J=9.6, 6.3 Hz, 1H), 4.23-4.02 (m, 2H), 3.75-3.68 (m, 2H), 3.66 (s, 2H), 3.25 (d, J=12.3 Hz, 1H), 2.93 (br.s., 2H), 83-2.72 (m, 2H), 2.65 (s, 3H), 2.43 (d, J=6.1 Hz, 3H), 2.24 (d, J=12.1 Hz, 1H), 1.96 (t, J=11.8 Hz, 1H), 1.55 (br. s., 1H), 1.42-1.30 (m, 1H), 1.24 (dt, J=10.9, 5.6 Hz, 7H), 1.20 (d, J=2.8 Hz, 9H), 1.08 (d, J=9.6 Hz, 1H), 0.92 (br. s., 3H), 0.66 (br. s., 3H). LCMS (M+H)=685.5. Used as is in the next step without further purification.

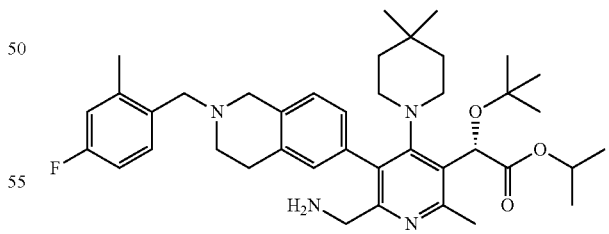

(S)-Isopropyl 2-(6-(aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy) acetate: A mixture of (S)-isopropyl 2-(6-(azidomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (180 mg, 0.263 mmol) and Ph$_3$P (103 mg, 0.394 mmol) in 9:1 THF/H$_2$O (10 mL) was refluxed for 2 h. Then, cooled, diluted with ethyl acetate (50 mL) and washed with water, dried (Na₂SO₄), filtered and concentrated. The residue was then purified by Biotage (10-100% CH₂Cl₂/MeOH) to afford (S)-isopropyl 2-(6-(aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (120 mg, 0.182 mmol, 69.3% yield) as thick paste. ¹H NMR (500 MHz, CDCl₃) δ 7.38-7.29 (m, 1H), 7.09-6.97 (m, 2H), 6.95-6.83 (m, 3H), 6.07 (br. s., 1H), 5.16-5.04 (m, 1H), 3.74-3.67 (m, 2H), 3.65 (s, 2H), 3.63-3.43 (m, 1H), 3.23 (d, J=11.3 Hz, 1H), 2.96-2.84 (m, 3H), 2.84-2.72 (m, 2H), 2.66-2.59 (m, 3H), 2.46-2.39 (m, 3H), 2.29 (br. s., 1H), 2.22 (d, J=6.6 Hz, 1H), 2.16-2.06 (m, 1H), 1.99-1.75 (m, 2H), 1.54 (br. s., 1H), 1.43-1.30 (m, 1H), 1.24 (ddd, J=9.9, 6.2, 3.9 Hz, 7H), 1.20 (s, 9H), 1.10-1.00 (m, 1H), 0.91 (br. s., 3H), 0.66 (br. s., 3H). LCMS (M+H)=659.7.

EXAMPLE 139

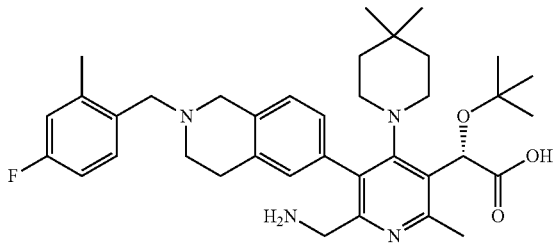 [SMILES: Cc1cc(F)ccc1CN1CCc2cc(-c3c(CN)nc(C)c([C@H](OC(C)(C)C)C(=O)O)c3N3CCC(C)(C)CC3)ccc2C1]

(S)-2-(6-(Aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid: A mixture of (S)-isopropyl 2-(6-(aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (15 mg, 0.023 mmol) in ethanol (1 mL) and 10N NaOH (0.028 mL, 0.277 mmol) was heated at 80° C. for 4 h. Mixture was then cooled and purified by prep HPLC to afford (S)-2-(6-(aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (7.7 mg, 0.012 mmol, 54.8% yield). ¹H NMR (500 MHz, DMSO-d₆) δ 7.40-7.27 (m, 1H), 7.18-7.07 (m, 2H), 7.07-6.94 (m, 2H), 6.90-6.83 (m, 1H), 5.59-5.54 (m, 1H), 3.85-3.68 (m, 1H), 3.62 (s, 2H), 2.84 (br. s., 1H), 2.77 (br. s., 1H), 2.72 (br. s., 2H), 2.44 (br. s., 1H), 2.38-2.32 (m, 3H), 1.90 (s, 3H), 1.50 (br. s., 1H), 1.24 (br. s., 1H), 1.15 (br. s., 1H), 1.12-1.04 (m, 9H), 0.97 (d, J=7.0 Hz, 1H), 0.85 (br. s., 3H), 0.62 (br. s., 3H). 8 piperidine hydrogens are not resolved. LCMS (M+H)=617.3.

EXAMPLE 140

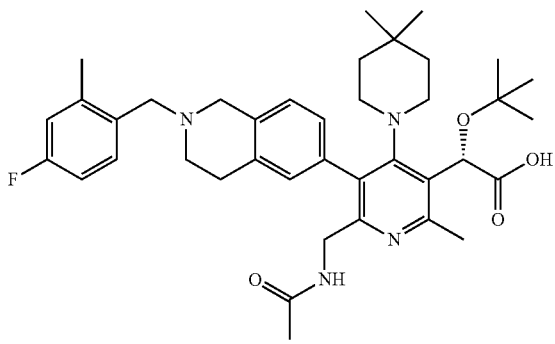 [SMILES: CC(=O)NCc1nc(C)c([C@H](OC(C)(C)C)C(=O)O)c(N2CCC(C)(C)CC2)c1-c1ccc2c(c1)CCN(Cc1ccc(F)cc1C)C2]

(S)-2-(6-(Acetamidomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid: To a solution of (S)-2-(6-(aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (15 mg, 0.024 mmol) in DCM (0.5 mL) was added TEA (0.06 ml, 0.430 mmol) followed by acetyl chloride (1.902 µl, 0.027 mmol) and the resulting mixture was stirred at room temp for 2 h. Mixture was then concentrated and purified by prep HPLC to afford (S)-2-(6-(acetamidomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (10.4 mg, 0.016 mmol, 64.9% yield). ¹H NMR (500 MHz, DMSO-d₆) δ 7.86 (br. s., 1H), 7.38-7.29 (m, 1H), 7.17-7.02 (m, 3H), 6.98 (td, J=8.5, 2.8 Hz, 1H), 6.93-6.87 (m, 1H), 5.84 (d, J=11.0 Hz, 1H), 4.10-3.95 (m, 1H), 3.92-3.75 (m, 1H), 2.83 (br. s., 3H), 2.76-2.66 (m, 2H), 2.39-2.34 (m, 3H), 2.12 (d, J=10.3 Hz, 1H), 1.83-1.78 (m, 3H), 1.49 (br. s., 1H), 1.32-1.18 (m, 2H), 1.14 (d, J=1.8 Hz, 9H), 1.07-0.95 (m, 1H), 0.86 (s, 3H), 0.61 (s, 3H). 8 piperidine hydrogen as are not resolved. LCMS (M+H)=659.3.

EXAMPLE 141

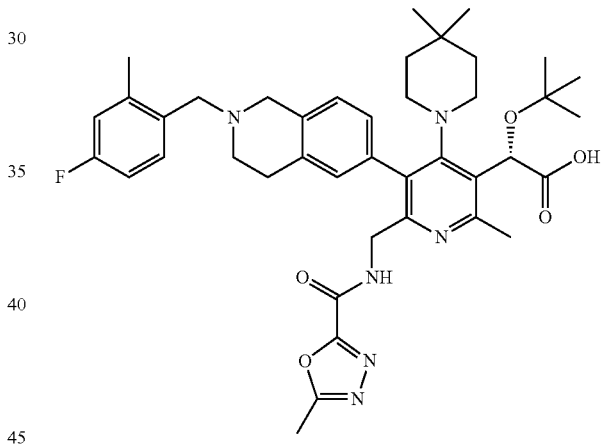

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((5-methyl-1,3,4-oxadiazole-2-carboxamido)methyl)pyridin-3-yl)acetic acid: To a solution of potassium 5-methyl-1,3,4-oxadiazole-2-carboxylate (4.45 mg, 0.027 mmol) in DCM (0.5 mL) was added oxalyl chloride (0.013 mL, 0.027 mmol). After 1 h, the mixture was added to a pre-stirred solution of (S)-2-(6-(aminomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (15 mg, 0.024 mmol) and TEA (10.17 µl, 0.073 mmol) in DCM (0.5 mL). The resulting mixture was stirred at roomtemp for 2 h and then concentrated and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((5-methyl-1,3,4-oxadiazole-2-carboxamido)methyl)pyridin-3-yl)acetic acid (1.5 mg, 2.064 µmol, 8.49% yield). ¹H NMR (500 MHz, DMSO-d₆) δ 7.40-7.31 (m, 2H), 7.18-7.07 (m, 2H), 7.04 (d, J=9.9 Hz, 1H), 7.02-6.96 (m, 1H), 6.91-6.73 (m, 1H), 5.46-5.39 (m, 1H), 4.34 (d, J=13.2

Hz, 1H), 4.09-3.94 (m, 2H), 3.63 (br. s., 3H), 3.05 (br. s., 1H), 2.88-2.79 (m, 3H), 2.77-2.68 (m, 4H), 2.58 (s, 3H), 2.39-2.30 (m, 3H), 2.10 (br. s., 1H), 1.52 (br. s., 1H), 1.24 (br. s., 2H), 1.14 (br. s., 1H), 1.09 (s, 9H), 0.96 (br. s., 1H), 0.85 (br. s., 3H), 0.63 (br. s., 3H). LCMS (M+H)=727.2.

EXAMPLE 142

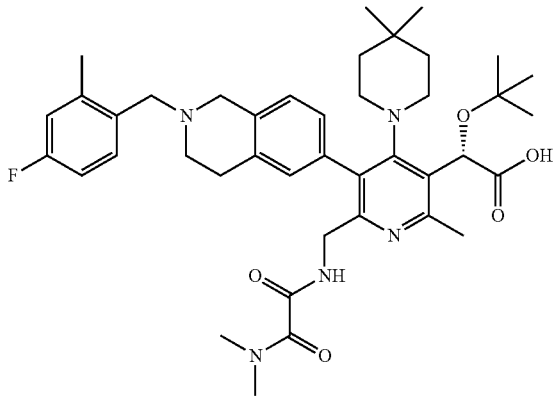 [SMILES: Cc1cc(F)ccc1CN1CCc2cc(-c3c(CNC(=O)C(=O)N(C)C)nc(C)c([C@H](OC(C)(C)C)C(=O)O)c3N3CCC(C)(C)CC3)ccc2C1]

(S)-2-(tert-Butoxy)-2-(6-((2-(dimethylamino)-2-oxoacetamido)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid: To a solution of 2-(dimethylamino)-2-oxoacetic acid (3.13 mg, 0.027 mmol) in DCM (0.5 mL) was added oxalyl chloride (0.013 ml, 0.027 mmol). After 1 h, the mixture was added to a pre-stirred solution of(S)-2-(6-(aminomethyl)-4-(4,4-dimethyl-piperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (15 mg, 0.024 mmol) and TEA (0.06 ml, 0.430 mmol) in DCM (0.5 mL). The resulting mixture was stirred at roomtemp for 2 h and then concentrated and purified by prep HPLC to afford (S)-2-(tert-butoxy)-2-(6-((2-(dimethylamino)-2-oxoacetamido)methyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)acetic acid (5.1 mg, 7.12 μmol, 29.3% yield). $^1$H NMR (500 MHz, DMSO-d$_6$) δ 8.70 (br. s., 1H), 7.43-7.32 (m, 1H), 7.19-7.10 (m, 2H), 7.04 (d, J=10.3 Hz, 1H), 6.98 (td, J=8.4, 2.6 Hz, 1H), 6.92 (s, 1H), 5.82 (d, J=11.0 Hz, 1H), 4.27-4.08 (m, 1H), 3.98-3.77 (m, 1H), 3.62-3.49 (m, 1H), 3.12-3.00 (m, 3H), 2.85 (s, 6H), 2.76-2.67 (m, 3H), 2.47 (s, 3H), 2.38-2.30 (m, 4H), 2.13 (d, J=11.0 Hz, 1H), 1.49 (br. s., 1H), 1.35-1.17 (m, 2H), 1.13 (d, J=2.2 Hz, 9H), 1.08-0.94 (m, 1H), 0.86 (s, 3H), 0.61 (s, 3H). 4 piperidine hydrogens are not resolved. LCMS (M+H)=716.3.

EXAMPLE 143

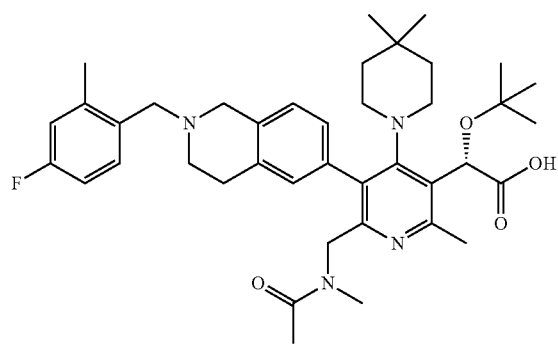 [SMILES: CC(=O)N(C)Cc1nc(C)c([C@H](OC(C)(C)C)C(=O)O)c(N2CCC(C)(C)CC2)c1-c1ccc2c(c1)CCN(Cc1ccc(F)cc1C)C2]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((N-methylacetamido)methyl)pyridin-3-yl)acetic acid: To a solution of (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((methylamino)methyl)pyridin-3-yl)acetic acid (12 mg, 0.019 mmol) in DCM (0.5 mL) was added TEA (7.95 μl, 0.057 mmol) followed by acetyl chloride (1.488 μl, 0.021 mmol) and the resulting mixture was stirred at room temp for 1 h. Mixture was then concentrated and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((N-methylacetamido)methyl)pyridin-3-yl)acetic acid (6.2 mg, 9.21 μmol, 48.4% yield). $^1$H NMR (500 MHz, DMSO-d$_6$) δ 7.41-7.27 (m, 1H), 7.19-7.02 (m, 3H), 6.98 (t, J=8.6 Hz, 1H), 6.92 (d, J=17.2 Hz, 1H), 5.86 (d, J=7.3 Hz, 1H), 4.44-4.27 (m, 1H), 4.13-3.99 (m, 1H), 3.67-3.54 (m, 3H), 2.84 (br. s., 3H), 2.73 (d, J=11.4 Hz, 2H), 2.66-2.60 (m, 2H), 2.46 (d, J=3.7 Hz, 3H), 2.37 (d, J=3.7 Hz, 3H), 1.99-1.87 (m, 2H), 1.83 (s, 1H), 1.81-1.73 (m, 1H), 1.49 (br. s., 1H), 1.35-1.16 (m, 2H), 1.14 (s, 9H), 1.08-0.95 (m, 1H), 0.86 (s, 3H), 0.60 (br. s., 3H). 4 piperidine hydrogens are not resolved. LCMS (M+H)=673.3.

EXAMPLE 144, 145 and 146

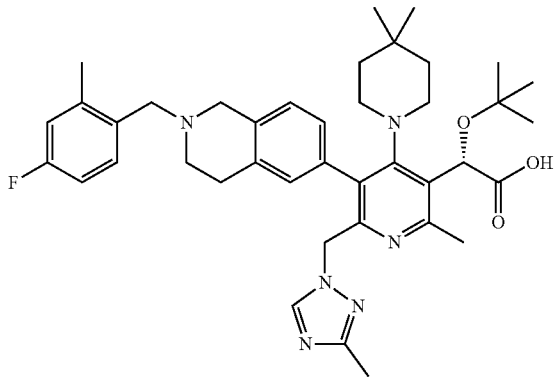

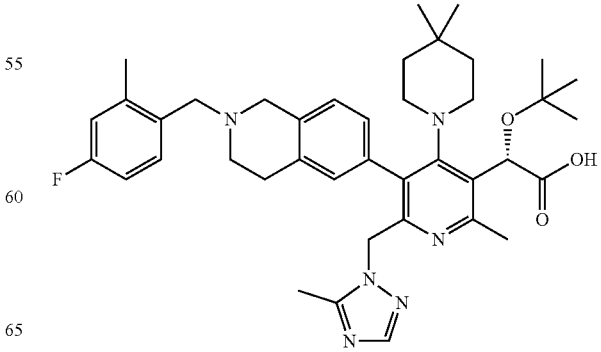

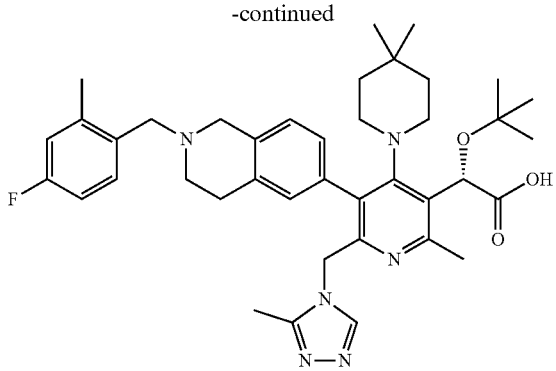

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((3-methyl-1H-1,2,4-triazol-1-yl)methyl)pyridin-3-yl)acetic acid, (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((5-methyl-1H-1,2,4-triazol-1-yl)methyl)pyridin-3-yl)acetic acid and (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((3-methyl-4H-1,2,4-triazol-4-yl)methyl)pyridin-3-yl)acetic acid: A solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (0.030 g, 0.042 mmol) and 3-methyl-1H-1,2,4-triazole (0.02 g, 0.241 mmol) in THF (0.5 mL) was added t-BuOK (0.008 g, 0.071 mmol) and stirred at rt for 4 h. Sodium hydroxide (0.04 g, 1.000 mmol) was added and the reaction mixture was stirred at 80° C. for 2 h. Then, cooled and purified by prep HPLC to afford three product.

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((3-methyl-1H-1,2,4-triazol-1-yl)methyl)pyridin-3-yl)acetic acid (0.0037 g, 5.31 μmol, 12.79% yield). LCMS (M+H)=683.2.

(S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((5-methyl-1H-1,2,4-triazol-1-yl)methyl)pyridin-3-yl)acetic acid (0.0086 g, 0.012 mmol, 29.1% yield). (M+H)=683.2.

(S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((5-methyl-1H-1,2,4-triazol-1-yl)methyl)pyridin-3-yl)acetic acid (0.0112 g, 0.016 mmol, 38.3% yield). (M+H)=683.2.

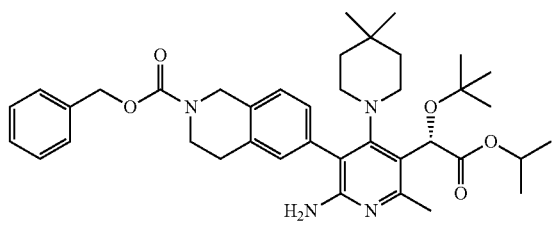 [SMILES: Cc1nc(N)c(-c2ccc3c(c2)CCN(C(=O)OCc2ccccc2)C3)c(N2CCC(C)(C)CC2)c1[C@H](OC(C)(C)C)C(=O)OC(C)C]

(S)-Benzyl 6-(2-amino-5-(1-(tert-butoxy)-2-isopropoxy-2-oxoethyl)-4-(4,4-dimethylpiperidin-1-yl)-6-methylpyridin-3-yl)-3,4-dihydroisoquinoline-2(1H)-carboxylate: A mixture of (S)-isopropyl 2-(6-amino-5-bromo-4-(4,4-dimethylpiperidin-1-yl)-2-methylpyridin-3-yl)-2-(tert-butoxy)acetate (90 mg, 0.191 mmol), benzyl 6-(6-methyl-4,8-dioxo-1,3,6,2-dioxazaborocan-2-yl)-3,4-dihydroisoquinoline-2(1H)-carboxylate (97 mg, 0.230 mmol), 2-dicyclohexylphosphino-2',6'-dimethoxyphenyl (15.71 mg, 0.038 mmol) and 2M K$_3$PO$_4$ (0.717 mL, 1.435 mmol) in 1,4-dioxane (2 mL) and Water (0.400 mL) was degassed for 10 min. Then, Pd(OAc)$_2$ (4.30 mg, 0.019 mmol) was added, degassed for 5 min and mixture was heated at 80° C. for 3 h. After cooling to room temp, water was added and the mixture was extracted with ethyl acetate, washed with brine, dried (Na$_2$SO$_4$), filtered and concentrated. The residue was then purified by Biotage (5-40% EtOAc/hexane) to afford (S)-benzyl 6-(2-amino-5-(1-(tert-butoxy)-2-isopropoxy-2-oxoethyl)-4-(4,4-dimethylpiperidin-1-yl)-6-methylpyridin-3-yl)-3,4-dihydroisoquinoline-2(1H)-carboxylate (90 mg, 0.137 mmol, 71.6% yield) as white foam. $^1$H NMR (500 MHz, CDCl$_3$) δ 7.49-7.34 (m, 5H), 7.26-7.13 (m, 2H), 7.10-6.96 (m, 1H), 5.89 (br. s., 1H), 5.24 (s, 2H), 5.14-5.02 (m, 1H), 4.76 (br. s., 1H), 4.72-4.63 (m, 1H), 4.25-4.15 (m, 1H), 3.87 (d, J=12.1 Hz, 1H), 3.77 (br. s., 1H), 3.32 (d, J=12.6 Hz, 1H), 2.91 (br. s., 1H), 2.84 (t, J=12.5 Hz, 1H), 2.48 (s, 3H), 2.32-2.21 (m, 1H), 2.01-1.90 (m, 1H), 1.57-1.50 (m, 1H), 1.28-1.22 (m, 7H), 1.20 (s, 9H), 1.18 (br. s., 1H), 1.14 (s, 1H), 1.12-1.01 (m, 2H), 0.90 (s, 3H), 0.68-0.58 (m, 3H). LCMS (M+H)=657.6.

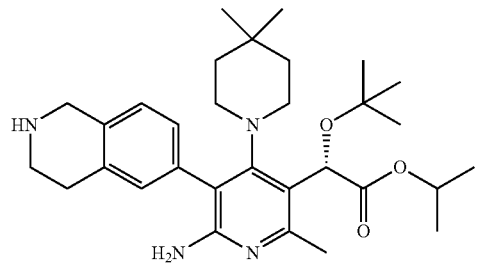 [SMILES: Cc1nc(N)c(-c2ccc3c(c2)CCNC3)c(N2CCC(C)(C)CC2)c1[C@H](OC(C)(C)C)C(=O)OC(C)C]

(S)-Isopropyl 2-(6-amino-4-(4,4-dimethylpiperidin-1-yl)-2-methyl-5-(1,2,3,4-tetrahydroisoquinolin-6-yl)pyridin-3-yl)-2-(tert-butoxy)acetate, 2 HCl: To a solution of (S)-benzyl 6-(2-amino-5-(1-(tert-butoxy)-2-isopropoxy-2-oxoethyl)-4-(4,4-dimethylpiperidin-1-yl)-6-methylpyridin-3-yl)-3,4-dihydroisoquinoline-2(1H)-carboxylate (90 mg, 0.137 mmol) in EtOH (2) was added 1N HCl (0.274 mL, 0.274 mmol) solution followed by 10% Pd-C (29.2 mg, 0.027 mmol) and the resulting mixture was stirred under balloon hydrogen atmosphere for 5 h. Mixture was then filtered through a small pad of celite, concentrated and dried under high vac overnight to afford (S)-isopropyl 2-(6-amino-4-(4,4-dimethylpiperidin-1-yl)-2-methyl-5-(1,2,3,4-tetrahydroisoquinolin-6-yl)pyridin-3-yl)-2-(tert-butoxy)acetate, 2 HCl (80 mg, 0.134 mmol, 98% yield) as white solid. $^1$H NMR (500 MHz, CDCl$_3$) δ 7.37 (br. s., 1H), 7.27-7.18 (m, 1H), 7.00 (br. s., 1H), 6.68 (br. s., 1H), 6.55 (br. s., 1H), 5.49 (d, J=6.3 Hz, 1H), 5.11 (dt, J=12.4, 6.1 Hz, 1H), 4.48 (br. s., 2H), 3.64 (br. s., 1H), 3.50 (br. s., 1H), 3.33 (br. s., 1H), 3.21 (d, J=18.0 Hz, 2H), 2.66 (d, J=8.5 Hz, 3H), 1.91 (br. s., 1H), 1.80 (br. s., 2H), 1.35-1.26 (m, 9H), 1.19 (s, 9H), 0.84 (br. s., 6H). LCMS (M+H)=523.5.

EXAMPLE 147

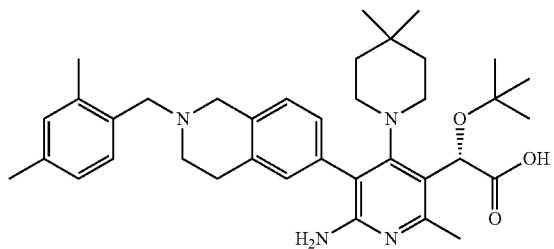 [SMILES: Cc1ccc(CN2CCc3cc(-c4c(N)nc(C)c([C@H](OC(C)(C)C)C(=O)O)c4N4CCC(C)(C)CC4)ccc3C2)c(C)c1]

(S)-2-(6-Amino-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid: To a solution of (S)-isopropyl 2-(6-amino-4-(4,4-dimethylpiperidin-1-yl)-2-methyl-5-(1,2,3,4-tetrahydroisoquinolin-6-yl)pyridin-3-yl)-2-(tert-butoxy)acetate, 2 HCl (20 mg, 0.034 mmol) in MeOH (1) was added TEA (0.00936 mL, 0.067 mmol) and the resulting mixture was stirred for 10 min. Then, 4-fluoro-2-methylbenzaldehyde (9.28 mg, 0.067 mmol) in MeOH (1 mL) was added and the mixture was stirred for additional 2 h. NaCNBH$_3$ (6.33 mg, 0.101 mmol) was then added and the mixture was stirred at room temp for 16 h. Diluted with water (10 mL) and the mixture was extracted with ethyl acetate (50 mL), washed with brine, dried (Na$_2$SO$_4$), filtered and concentrated. The residue was then treated with 10N NaOH (0.034 mL, 0.336 mmol) in ethanol (1 mL) at 80° C. for 4 h. Mixture was then cooled and purified by prep HPLC to afford(S)-2-(6-amino-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetic acid (8.4 mg, 0.014 mmol, 41.5% yield). $^1$H NMR (500 MHz, DMSO-d$_6$) δ 7.40-7.29 (m, 1H), 7.18-7.09 (m, 1H), 7.07-7.02 (m, 2H), 7.01-6.94 (m, 1H), 6.92-6.83 (m, 1H), 5.69 (d, J=6.6 Hz, 1H), 4.93 (br. s., 1H), 3.62 (br. s., 3H), 2.91-2.77 (m, 3H), 2.72 (br. s., 2H), 2.36 (d, J=4.0 Hz, 3H), 2.29 (s, 3H), 2.20 (br. s., 1H), 2.08 (br. s., 1H), 1.46 (br. s., 1H), 1.24 (br. s., 2H), 1.18 (d, J=11.7 Hz, 1H), 1.13 (s, 9H), 0.98 (d, J=16.9 Hz, 3H), 0.84 (br. s., 3H), 0.60 (br. s., 3H). LCMS (M+H)=603.3.

EXAMPLE 148

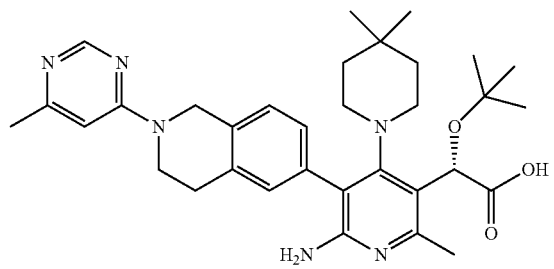 [SMILES: Cc1cc(N2CCc3cc(-c4c(N)nc(C)c([C@H](OC(C)(C)C)C(=O)O)c4N4CCC(C)(C)CC4)ccc3C2)ncn1]

(S)-2-(6-Amino-4-(4,4-dimethylpiperidin-1-yl)-2-methyl-5-(2-(6-methylpyrimidin-4-yl)-1,2,3,4-tetrahydroisoquinolin-6-yl)pyridin-3-yl)-2-(tert-butoxy)acetic acid: A mixture of (S)-isopropyl 2-(6-amino-4-(4,4-dimethylpiperidin-1-yl)-2-methyl-5-(1,2,3,4-tetrahydroisoquinolin-6-yl)pyridin-3-yl)-2-(tert-butoxy)acetate, 2 HCl (20 mg, 0.034 mmol), 4-chloro-6-methylpyrimidine (21.58 mg, 0.168 mmol), K$_2$CO$_3$ (27.8 mg, 0.201 mmol) and NaI (10.07 mg, 0.067 mmol) in dioxane (2 mL) was heated at 85° C. for 48 hrs. The mixture was diluted with EtOAc, washed with water, dried (Na$_2$SO$_4$), filtered and concentrated. The residue was then treated with 10N NaOH (0.034 mL, 0.336 mmol) in ethanol (1 mL) at 80° C. for 4 h. Mixture was then cooled and purified by prep HPLC to afford (S)-2-(6-amino-4-(4,4-dimethylpiperidin-1-yl)-2-methyl-5-(2-(6-methylpyrimidin-4-yl)-1,2,3,4-tetrahydroisoquinolin-6-yl)pyridin-3-yl)-2-(tert-butoxy)acetic acid (9.1 mg, 0.016 mmol, 47.3% yield). $^1$H NMR (500 MHz, DMSO-d$_6$) δ 8.42 (s, 1H), 7.37 (dd, J=11.4, 7.7 Hz, 1H), 7.16 (br. s., 1H), 7.05-6.95 (m, 1H), 6.77 (s, 1H), 5.69 (d, J=6.2 Hz, 1H), 4.94 (br. s., 1H), 4.90-4.83 (m, 1H), 4.80 (br. s., 1H), 4.77-4.66 (m, 1H), 3.92-3.83 (m, 1H), 3.80 (br. s., 1H), 2.99-2.86 (m, 2H), 2.80 (br. s., 1H), 2.31-2.25 (m, 6H), 1.46 (br. s., 1H), 1.24 (br. s., 1H), 1.18 (br. s., 1H), 1.13 (s, 9H), 0.96 (br. s., 1H), 0.81 (br. s., 3H), 0.59 (br. s., 1.3H), 0.49 (br. s., 1.7H). 4 piperidine hydrogens are not resolved. LCMS (M+H)=573.2.

EXAMPLE 149

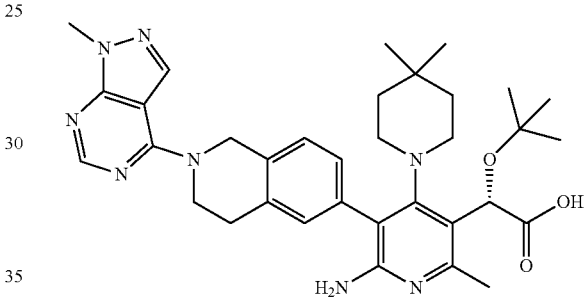

(S)-2-(6-Amino-4-(4,4-dimethylpiperidin-1-yl)-2-methyl-5-(2-(1-methyl-1H-pyrazolo[3,4-d]pyrimidin-4-yl)-1,2,3,4-tetrahydroisoquinolin-6-yl)pyridin-3-yl)-2-(tert-butoxy)acetic acid: A mixture of (S)-isopropyl 2-(6-amino-4-(4,4-dimethylpiperidin-1-yl)-2-methyl-5-(1,2,3,4-tetrahydroisoquinolin-6-yl)pyridin-3-yl)-2-(tert-butoxy)acetate, 2 HCl (20 mg, 0.034 mmol), 4-chloro-1-methyl-1H-pyrazolo[3,4-d]pyrimidine (28.3 mg, 0.168 mmol), K$_2$CO$_3$ (32.5 mg, 0.235 mmol) and NaI (10.07 mg, 0.067 mmol) in dioxane (2 mL) was heated at 85° C. for 48 hrs. The mixture was diluted with EtOAc, washed with water, dried (Na$_2$SO$_4$), filtered and concentrated. The residue was then treated with 10N NaOH (0.034 mL, 0.336 mmol) in ethanol (1 mL) at 80° C. for 4 h. Mixture was then cooled and purified by prep HPLC to afford (S)-2-(6-amino-4-(4,4-dimethylpiperidin-1-yl)-2-methyl-5-(2-(1-methyl-1H-pyrazolo[3,4-d]pyrimidin-4-yl)-1,2,3,4-tetrahydroisoquinolin-6-yl)pyridin-3-yl)-2-(tert-butoxy)acetic acid (9.3 mg, 0.015 mmol, 45.2% yield). $^1$H NMR (500 MHz, DMSO-d$_6$) δ 8.43 (br. s., 1H), 8.34 (s, 1H), 7.54 (br. s., 1H), 7.33-7.16 (m, 1H), 7.09 (s, 1H), 5.65 (br. s., 1H), 5.24-5.11 (m, 1H), 5.11-4.97 (m, 1H), 4.17 (br. s., 1H), 4.09 (d, J=19.8 Hz, 1H), 3.94 (s, 3H), 3.06 (br. s., 1H), 2.33 (s, 3H), 1.45 (br. s., 1H), 1.24 (br. s., 3H), 1.14 (d, J=2.6 Hz, 9H), 0.80 (br. s., 6H). 6 piperidine hydrogens are not resolved. LCMS (M+H)=613.2.

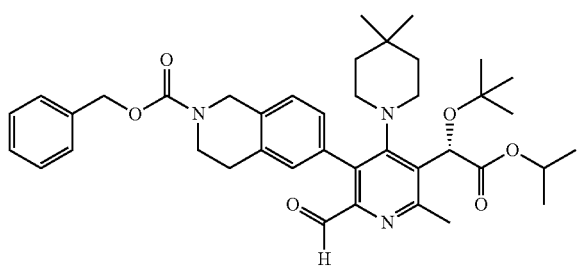 [SMILES: Cc1nc(C=O)c(-c2ccc3c(c2)CCN(C(=O)OCc2ccccc2)C3)c(N2CCC(C)(C)CC2)c1[C@H](OC(C)(C)C)C(=O)OC(C)C]

(S)-Benzyl 6-(5-(1-(tert-butoxy)-2-isopropoxy-2-oxoethyl)-4-(4,4-dimethylpiperidin-1-yl)-2-formyl-6-methylpyridin-3-yl)-3,4-dihydroisoquinoline-2(1H)-carboxylate:
To a stirred solution of (S)-benzyl 6-(5-(1-(tert-butoxy)-2-isopropoxy-2-oxoethyl)-4-(4,4-dimethylpiperidin-1-yl)-2-(hydroxymethyl)-6-methylpyridin-3-yl)-3,4-dihydroisoquinoline-2(1H)-carboxylate (1 g, 1.488 mmol) in CH$_2$Cl$_2$ (5 mL) was added Dess-MartinPeriodinane (0.758 g, 1.786 mmol) at once at rt. After 2 h, the reaction mixture was diluted with ethyl acetate (50 mL), washed with sat. NaHCO$_3$ (10 ml), brine (10 mL), dried (Na$_2$SO$_4$), filtered and concentrated to give yellow paste which was purified by Biotage (5-30% EtOAc/hexane) to afford(S)-benzyl 6-(5-(1-(tert-butoxy)-2-isopropoxy-2-oxoethyl)-4-(4,4-dimethylpiperidin-1-yl)-2-formyl-6-methylpyridin-3-yl)-3,4-dihydroisoquinoline-2(1H)-carboxylate (750 mg, 1.120 mmol, 75% yield) as white foam. $^1$H NMR (500 MHz, CDCl$_3$) δ 9.88 (s, 1H), 7.54-7.31 (m, 4H), 7.26-7.05 (m, 3H), 6.07 (br. s., 1H), 5.30-5.20 (m, 2H), 5.17-5.07 (m, 1H), 4.83 (br. s., 1H), 4.80-4.61 (m, 1H), 3.91 (br. s., 1H), 3.83 (br. s., 1H), 3.77 (br. s., 1H), 3.26 (br. s., 1H), 2.92 (br. s., 2H), 2.73 (s, 3H), 2.39-2.19 (m, 1H), 1.64 (br. s., 1H), 1.56 (br. s., 1H), 1.34 (d, J=18.0 Hz, 1H), 1.25 (ddd, J=11.0, 6.4, 4.1 Hz, 6H), 1.19 (d, J=2.4 Hz, 9H), 1.15-1.09 (m, 1H), 1.06 (d, J=8.2 Hz, 1H), 0.93 (br. s., 3H), 0.88 (br. s., 1H), 0.70 (br. s., 1H), 0.66 (br. s., 2H). LCMS (M+H2O)=688.7.

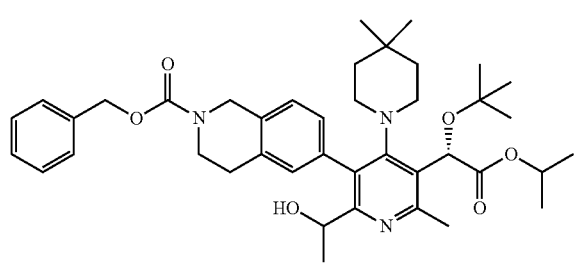 [SMILES: Cc1nc(C(C)O)c(-c2ccc3c(c2)CCN(C(=O)OCc2ccccc2)C3)c(N2CCC(C)(C)CC2)c1[C@H](OC(C)(C)C)C(=O)OC(C)C]

Benzyl 6-(5-((S)-1-(tert-butoxy)-2-isopropoxy-2-oxoethyl)-4-(4,4-dimethylpiperidin-1-yl)-2-(1-hydroxyethyl)-6-methylpyridin-3-yl)-3,4-dihydroisoquinoline-2(1H)-carboxylate: To a solution of (S)-benzyl 6-(5-(1-(tert-butoxy)-2-isopropoxy-2-oxoethyl)-4-(4,4-dimethylpiperidin-1-yl)-2-formyl-6-methylpyridin-3-yl)-3,4-dihydroisoquinoline-2(1H)-carboxylate (650 mg, 0.970 mmol) in THF (10 mL) at −78° C. was added 3M methylmagnesium bromide (0.356 mL, 1.067 mmol) and the resulting mixture was stirred for 1 h. Then, sat. NH$_4$Cl was added and the mixture was extracted with ethyl acetate, dried (Na$_2$SO$_4$), filtered and concentrated. The residue was then purified by Biotage (5-100% EtOAc/hexane) to afford benzyl 6-(5-((S)-1-(tert-butoxy)-2-isopropoxy-2-oxoethyl)-4-(4,4-dimethylpiperidin-1-yl)-2-(1-hydroxyethyl)-6-methylpyridin-3-yl)-3,4-dihydroisoquinoline-2(1H)-carboxylate (600 mg, 0.875 mmol, 90% yield) as a mixture of diastereomers. LCMS (M+H)=686.6.

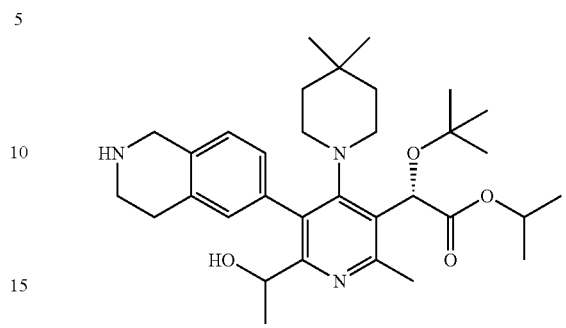

(2S)-Isopropyl 2-(tert-butoxy)-2-(4-(4,4-dimethylpiperidin-1-yl)-6-(1-hydroxyethyl)-2-methyl-5-(1,2,3,4-tetrahydroisoquinolin-6-yl)pyridin-3-yl)acetate, 2 HCl: To a solution of benzyl 6-(5-((S)-1-(tert-butoxy)-2-isopropoxy-2-oxoethyl)-4-(4,4-dimethylpiperidin-1-yl)-2-(1-hydroxyethyl)-6-methylpyridin-3-yl)-3,4-dihydroisoquinoline-2(1H)-carboxylate (650 mg, 0.948 mmol) in EtOH (10 mL) was added 1N HCl (1.895 mL, 1.895 mmol) solution followed by 10% Pd-C (202 mg, 0.190 mmol) and the resulting mixture was stirred under balloon hydrogen atmosphere for 5 h. Mixture was then filtered through a small pad of celite, concentrated and dried under high vac overnight to afford (2S)-isopropyl 2-(tert-butoxy)-2-(4-(4,4-dimethylpiperidin-1-yl)-6-(1-hydroxyethyl)-2-methyl-5-(1,2,3,4-tetrahydroisoquinolin-6-yl)pyridin-3-yl)acetate, 2 HCl (590 mg, 0.944 mmol, 100% yield) as mixture of diastereomers. LCMS (M+H)=552.5.

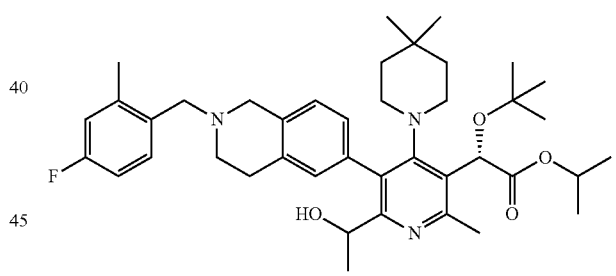

(2S)-Isopropyl 2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(1-hydroxyethyl)-2-methylpyridin-3-yl)acetate: To a solution of (2S)-isopropyl 2-(tert-butoxy)-2-(4-(4,4-dimethylpiperidin-1-yl)-6-(1-hydroxyethyl)-2-methyl-5-(1,2,3,4-tetrahydroisoquinolin-6-yl)pyridin-3-yl)acetate, 2 HCl (300 mg, 0.480 mmol) in MeOH (5 mL) was added TEA (0.134 mL, 0.960 mmol) and the resulting mixture was stirred for 10 min. 4-fluoro-2-methylbenzaldehyde (133 mg, 0.960 mmol) in MeOH (0.5 mL) was then added and the mixture was stirred for additional 2 h. Sodium cyanoborohydride (91 mg, 1.441 mmol) was added and the mixture was stirred at room temp for 16 h. Water (10 mL) was then added and the mixture was extracted with ethyl acetate (50 mL), washed with brine, dried (Na$_2$SO$_4$), filtered and concentrated. The residue was then purified by Biotage (0-10% CH$_2$Cl$_2$/MeOH) to afford (2S)-isopropyl 2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(1-hydroxyethyl)-2-methylpyridin-3-yl)acetate (200 mg, 0.297 mmol, 61.8% yield) as inseparable mixture of diastereomers. LCMS (M+H)=674.7.

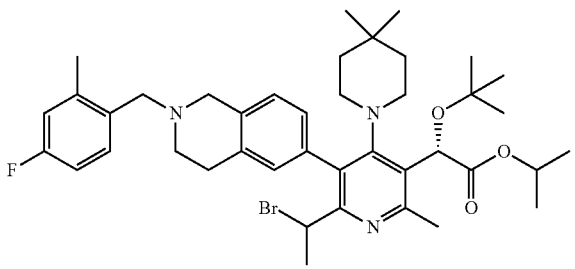 [SMILES: Cc1cc(F)ccc1CN1CCc2cc(-c3c(C(C)Br)nc(C)c([C@H](OC(C)(C)C)C(=O)OC(C)C)c3N3CCC(C)(C)CC3)ccc2C1]

(2S)-Isopropyl 2-(6-(1-bromoethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate: To a solution of (2S)-isopropyl 2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(1-hydroxyethyl)-2-methylpyridin-3-yl)acetate (200 mg, 0.297 mmol) in CH$_2$Cl$_2$ (5 mL) was added CBr$_4$ (128 mg, 0.386 mmol) followed by Ph$_3$P (101 mg, 0.386 mmol) and the resulting mixture was stirred at room temperature for 2 h. Water (2 mL) was added and the mixture was extracted with dichloromethane (10 mL), dried (Na$_2$SO$_4$), filtered and concentrated. The residue was then purified by Biotage (5-30% EtOAc/hexane) to afford (2S)-isopropyl 2-(6-(1-bromoethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (160 mg, 0.217 mmol, 73.2% yield) as a mixture of diastereomers. LCMS (M+2H)=738.6.

EXAMPLE 150 and 151

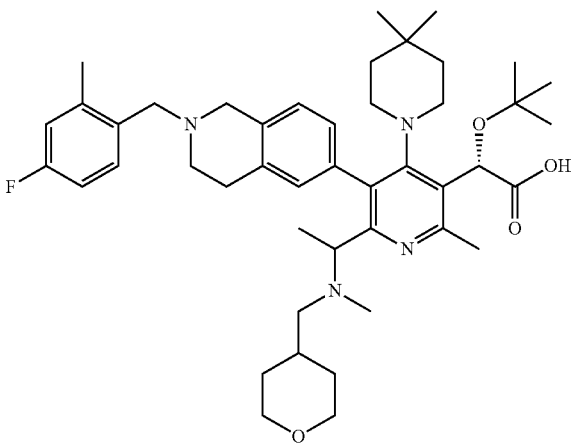 [SMILES: Cc1cc(F)ccc1CN1CCc2cc(-c3c(C(C)N(C)CC4CCOCC4)nc(C)c([C@H](OC(C)(C)C)C(=O)O)c3N3CCC(C)(C)CC3)ccc2C1]

(2S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(1-(methyl((tetrahydro-2H-pyran-4-yl)methyl)amino)ethyl)pyridin-3-yl)acetic acid: To a solution of N-methyl-1-(tetrahydro-2H-pyran-4-yl)methanamine (35.1 mg, 0.271 mmol) in ethanol (1 mL) was added (2S)-isopropyl 2-(6-(1-bromoethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy) acetate (40 mg, 0.054 mmol) and the resulting mixture was stirred at room temp for 16 h. Then, 10N NaOH (0.054 mL, 0.543 mmol) was added and the mixture was heated at 80° C. for 4 h. Mixture was cooled and purified by prep HPLC to afford two diastereomers. Diastereomer 1: $^1$H NMR (500 MHz, DMSO-d$_6$) δ 7.39-7.24 (m, 2H), 7.09 (d, J=7.7 Hz, 1H), 7.04 (d, J=10.3 Hz, 1H), 7.01-6.93 (m, 1H), 6.84-6.76 (m, 1H), 5.76 (d, J=12.5 Hz, 1H), 3.72 (d, J=9.2 Hz, 1H), 3.68-3.52 (m, 2H), 3.23-3.04 (m, 2H), 2.89-2.71 (m, 5H), 2.71-2.59 (m, 2H), 2.47 (s, 3H), 2.36 (d, J=2.6 Hz, 3H), 2.14 (d, J=3.3 Hz, 3H), 2.09-2.02 (m, 1H), 1.98-1.93 (m, 1H), 1.47 (d, J=10.6 Hz, 3H), 1.34 (d, J=12.1 Hz, 1H), 1.26 (d, J=13.9 Hz, 1H), 1.17 (d, J=12.5 Hz, 1H), 1.12-1.03 (m, 12H), 0.97 (d, J=10.6 Hz, 2H), 0.85 (s, 3H), 0.60 (br. s., 3H). six piperidine hydrogens are not resolved. LCMS (M+H)=743.3 and diastereomer 2: $^1$H NMR (500 MHz, DMSO-d$_6$) δ 7.34-7.27 (m, 1H), 7.15-7.06 (m, 1H), 7.03 (d, J=8.1 Hz, 1H), 6.99-6.94 (m, 2H), 6.92-6.85 (m, 1H), 5.86 (br. s., 1H), 3.85 (d, J=6.6 Hz, 1H), 3.71-3.56 (m, 3H), 3.51 (br. s., 1H), 3.05 (q, J=11.0 Hz, 2H), 2.83 (br. s., 3H), 2.74-2.67 (m, 2H), 2.48 (s, 3H), 2.38-2.30 (m, 3H), 2.06 (s, 2H), 2.08 (s, 3H), 1.91 (s, 2H), 1.48 (br. s., 1H), 1.34 (d, J=9.9 Hz, 1H), 1.27-1.18 (m, 6H), 1.15-1.10 (m, 9H), 0.84 (br. s., 3H), 0.80-0.67 (m, 2H), 0.58 (br. s., 3H). six piperidine hydrogens are not resolved. LCMS (M+H)=743.3.

EXAMPLE 152 and 153

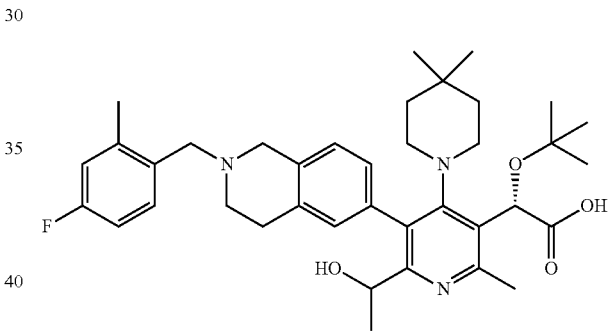

(2S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(1-hydroxyethyl)-2-methylpyridin-3-yl)acetic acid: A mixture of (2S)-isopropyl 2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(1-hydroxyethyl)-2-methylpyridin-3-yl)acetate (40 mg, 0.059 mmol) and 10N NaOH (0.059 mL, 0.594 mmol) in ethanol (1 mL) was heated at 80° C. for 4 h. Mixture was then cooled and purified by prep HPLC to afford two diastereomers.

Diastereomer 1: First eluting, $^1$H NMR (500 MHz, DMSO-d$_6$) δ 7.38-7.27 (m, 1H), 7.17-7.09 (m, 2H), 7.05 (d, J=10.3 Hz, 1H), 6.98 (td, J=8.4, 2.6 Hz, 1H), 6.88 (s, 1H), 5.76 (d, J=9.9 Hz, 1H), 3.70-3.64 (m, 4H), 2.88-2.78 (m, 3H), 2.77-2.66 (m, 2H), 2.38-2.34 (m, 3H), 2.09 (d, J=12.1 Hz, 1H), 1.48 (d, J=9.9 Hz, 1H), 1.33-1.22 (m, 1H), 1.18 (d, J=13.2 Hz, 1H), 1.12 (s, 9H), 1.04-0.98 (m, 3H), 0.85 (s, 3H), 0.61 (s, 3H). 8 piperidine hydrogens are not resolved. LCMS (M+H)=632.3. Diastereomer 2: Second eluting, $^1$H NMR (500 MHz, DMSO-d$_6$) δ 7.38-7.27 (m, 1H), 7.16-7.02 (m, 2H), 7.02-6.95 (m, 2H), 6.94-6.89 (m, 1H), 5.80-5.72 (m, 1H), 2.84 (br. s., 2H), 2.79 (br. s., 1H), 2.77-2.65 (m, 3H), 2.39-2.33 (m, 3H), 2.14 (d, J=9.9 Hz, 1H), 1.47 (br. s., 1H), 1.26 (dd, J=14.1, 6.1 Hz, 4H), 1.18 (br. s., 1H), 1.14-1.10 (m, 9H), 1.05-0.90 (m, 2H), 0.85 (s, 3H), 0.59 (s, 3H). 8 piperidine hydrogens are not resolved. LCMS (M+H)=632.3.

EXAMPLE 154

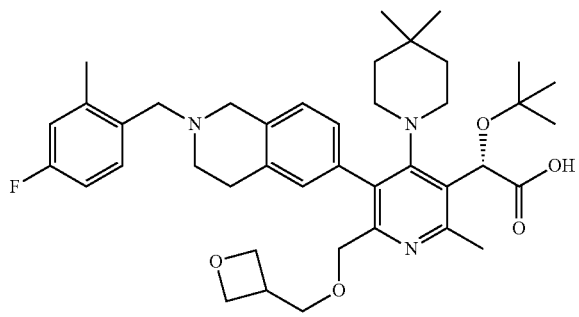 [SMILES: Cc1cc(F)ccc1CN1CCc2cc(-c3c(COCC4COC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((oxetan-3-ylmethoxy)methyl)pyridin-3-yl)acetic acid: To a solution of oxetan-3-ylmethanol (0.03 g, 0.341 mmol) in THF (0.6 mL) and (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (0.018 g, 0.025 mmol) in THF (0.6 mL) was added t-BuOK (0.015 g, 0.134 mmol) and the mixture was stirred at rt for 1 h. Then, EtOH (0.5 ml) and sodium hydroxide (0.03 g, 0.750 mmol) were added and heated at 80° C. for 3 h. Then, cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-((oxetan-3-ylmethoxy)methyl)pyridin-3-yl)acetic acid (0.0146 g, 0.021 mmol, 83% yield). LCMS (M+H)=688.4.

EXAMPLE 155

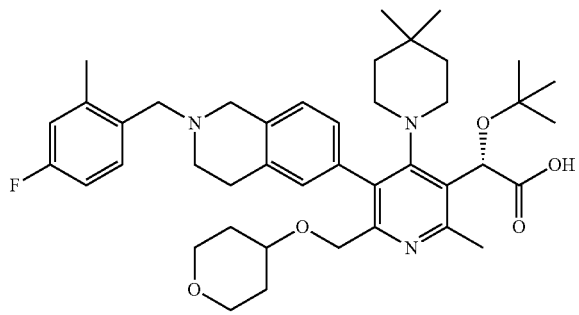 [SMILES: Cc1cc(F)ccc1CN1CCc2cc(-c3c(COC4CCOCC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((tetrahydro-2H-pyran-4-yl)oxy)methyl)pyridin-3-yl)acetic acid: To a solution of tetrahydro-2H-pyran-4-ol (0.02 g, 0.196 mmol) in dioxane (0.5 mL) was added t-BuOK (0.015 g, 0.134 mmol) then (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (0.018 g, 0.025 mmol). The mixture was stirred at rt for 1 h, then EtOH (0.5 ml) and sodium hydroxide (0.02 g, 0.500 mmol) were added and heated at 80° C. for 3 h. Then, cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((tetrahydro-2H-pyran-4-yl)oxy)methyl)pyridin-3-yl)acetic acid (0.0090 g, 0.013 mmol, 50.5% yield). LCMS (M+H)=702.3.

EXAMPLE 156

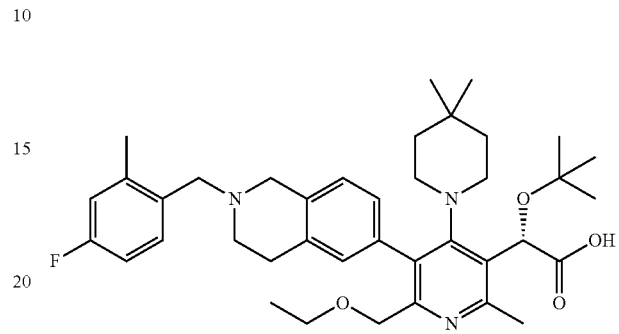

(S)-2-(tert-Butoxy)-2-(4-(4,4-dimethylpiperidin-1-yl)-6-(ethoxymethyl)-5-(2-(4-fluoro-2-methylbenzyl)-1,2,3,4-tetrahydroisoquinolin-6-yl)-2-methylpyridin-3-yl)acetic acid: To a solution of ethanol (0.05 ml, 0.856 mmol) and (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (0.018 g, 0.025 mmol) in dioxane (0.5 mL) was added t-BuOK (0.015 g, 0.134 mmol). The mixture was stirred at rt for 2 h. Then, EtOH (0.5 ml) and sodium hydroxide (0.03 g, 0.750 mmol) were added and heated at 80° C. for 2 h. Then, cooled and purified by prep HPLC to afford (S)-2-(tert-butoxy)-2-(4-(4,4-dimethylpiperidin-1-yl)-6-(ethoxymethyl)-5-(2-(4-fluoro-2-methylbenzyl)-1,2,3,4-tetrahydroisoquinolin-6-yl)-2-methylpyridin-3-yl)acetic acid (0.0132 g, 0.020 mmol, 80% yield). LCMS (M+H)=646.3.

EXAMPLE 157

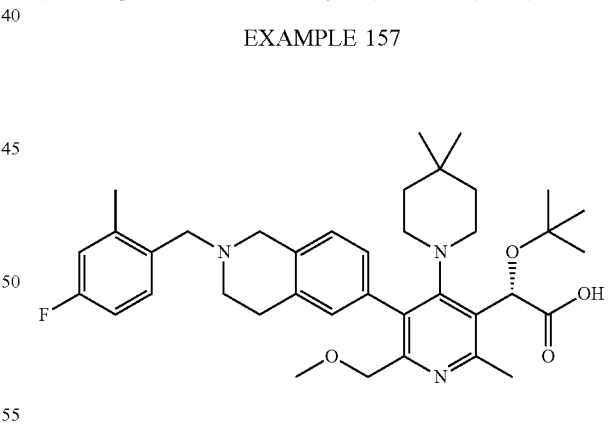

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(methoxymethyl)-2-methylpyridin-3-yl)acetic acid: To a solution of (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (0.018 g, 0.025 mmol) and methanol (0.05 ml, 1.236 mmol) in dioxane (0.5 mL) was added t-BuOK (0.015 g, 0.134 mmol) and the mixture was stirred at rt for 2 h. Then, EtOH (0.5 ml) and sodium hydroxide (0.03 g, 0.750 mmol) were added and the mixture was heated at 80° C. for 2 h, cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(methoxymethyl)-2-methylpyridin-3-yl)acetic acid (0.0146 g, 0.022 mmol, 87% yield). LCMS (M+H)=632.2.

EXAMPLE 158

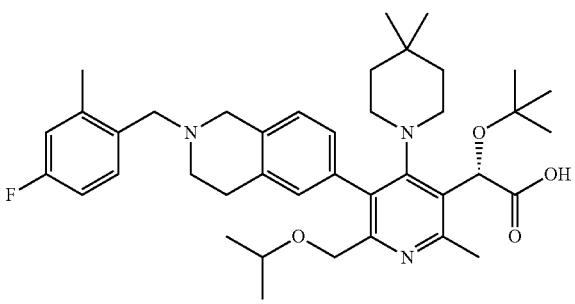 [SMILES: Cc1cc(F)ccc1CN1CCc2cc(-c3c(COC(C)C)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-6-(isopropoxymethyl)-2-methylpyridin-3-yl)acetic acid: To a solution of 2-propanol (0.05 ml, 0.649 mmol) and (S)-isopropyl 2-(6-(bromomethyl)-4-(4,4-dimethylpiperidin-1-yl)-5-(2-(4-fluoro-2-methylbenzyl)-1,2,3,4-tetrahydroisoquinolin-6-yl)-2-methylpyridin-3-yl)-2-(tert-butoxy)acetate (0.018 g, 0.025 mmol) in THF (0.6 mL) was added t-BuOK (0.015 g, 0.134 mmol). The mixture was stirred at rt for 2 h, then EtOH (0.5 ml) and sodium hydroxide (0.03 g, 0.750 mmol) were added and heated at 80° C. for 2 h, cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-6-(isopropoxymethyl)-2-methylpyridin-3-yl)acetic acid (0.0066 g, 9.50 μmol, 38.2% yield). LCMS (M+H)=660.2.

EXAMPLE 159

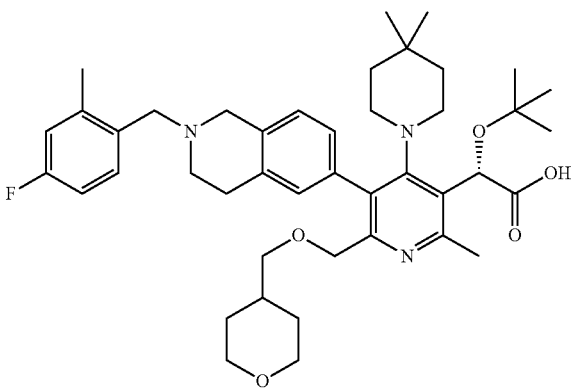 [SMILES: Cc1cc(F)ccc1CN1CCc2cc(-c3c(COCC4CCOCC4)nc(C)c([C@H](OC(C)(C)C)C(=O)O)c3N3CCC(C)(C)CC3)ccc2C1]

(S)-2-(tert-Butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((tetrahydro-2H-pyran-4-yl)methoxy)methyl)pyridin-3-yl)acetic acid: To a solution of (tetrahydro-2H-pyran-4-yl)methanol (0.02 g, 0.172 mmol) in dioxane (0.5 mL) was added t-BuOK (0.015 g, 0.134 mmol) and (S)-isopropyl 2-(6-(bromomethyl)-4-(4,4-dimethylpiperidin-1-yl)-5-(2-(4-fluoro-2-methylbenzyl)-1,2,3, 4-tetrahydroisoquinolin-6-yl)-2-methylpyridin-3-yl)-2-(tert-butoxy)acetate (0.02 g, 0.028 mmol). The mixture was stirred at rt for 2 h, then EtOH (0.5 ml) and sodium hydroxide (0.2 g, 5.00 mmol) were added. The mixture was heated at 80° C. for 3 h, cooled and purified by prep HPLC to afford (S)-2-(tert-butoxy)-2-(4-(4,4-dimethylpiperidin-1-yl)-5-(2-(4-fluoro-2-methylbenzyl)-1,2,3,4-tetrahydroisoquinolin-6-yl)-2-methyl-6-(((tetrahydro-2H-pyran-4-yl)methoxy)methyl)pyridin-3-yl)acetic acid (0.0131 g, 0.018 mmol, 66.1% yield). LCMS (M+H)=716.4.

EXAMPLE 160

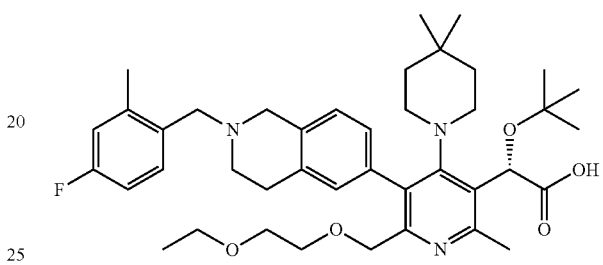

(S)-2-(tert-Butoxy)-2-(4-(4,4-dimethylpiperidin-1-yl)-6-((2-ethoxyethoxy)methyl)-5-(2-(4-fluoro-2-methylbenzyl)-1,2,3,4-tetrahydroisoquinolin-6-yl)-2-methylpyridin-3-yl)acetic acid: To a solution of 2-ethoxyethanol (0.1 g, 1.110 mmol) in dioxane (0.5 mL) was added t-BuOK (0.015 g, 0.134 mmol) and (S)-isopropyl 2-(6-(bromomethyl)-4-(4,4-dimethylpiperidin-1-yl)-5-(2-(4-fluoro-2-methylbenzyl)-1, 2,3,4-tetrahydroisoquinolin-6-yl)-2-methylpyridin-3-yl)-2-(tert-butoxy)acetate (0.02 g, 0.028 mmol). The mixture was stirred at rt for 2 h. Ethanol (0.5 ml) and sodium hydroxide (0.2 g, 5.00 mmol) were added and heated at 80° C. for 3 h, cooled and purified by prep HPLC to afford (S)-2-(tert-butoxy)-2-(4-(4,4-dimethylpiperidin-1-yl)-6-((2-ethoxyethoxy)methyl)-5-(2-(4-fluoro-2-methylbenzyl)-1,2,3,4-tetrahydroisoquinolin-6-yl)-2-methylpyridin-3-yl)acetic acid (0.0164 g, 0.024 mmol, 86% yield). LCMS (M+H)=690.3.

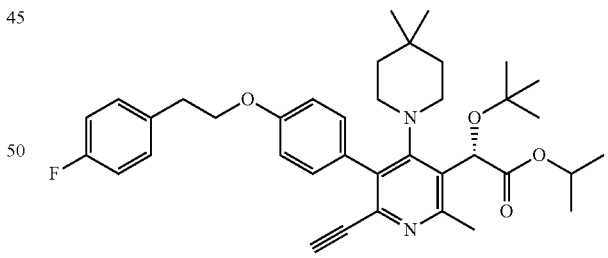

Isopropyl (S)-2-(tert-butoxy)-2-(4-(4,4-dimethylpiperidin-1-yl)-6-ethynyl-5-(4-(4-fluorophenethoxy)phenyl)-2-methylpyridin-3-yl)acetate: Dimethyl (1-diazo-2-oxopropyl)phosphonate (109 mg, 0.57 mmol) was added to a stirring solution of (S)-isopropyl 2-(tert-butoxy)-2-(4-(4,4-dimethylpiperidin-1-yl)-5-(4-(4-fluorophenethoxy)phenyl)-6-formyl-2-methylpyridin-3-yl)acetate (310 mg, 0.501 mmol) and $K_2CO_3$ (312 mg, 2.254 mmol) in MeOH (5 ml) at rt. The reaction was stirred for 1 hr. The reaction was concentrated, adsorbed onto celite and was purified on silica gel (Biotage, EtOAc/hexanes gradient 0-100% over 10CVs). (S)-isopropyl 2-(tert-butoxy)-2-(4-(4,4-dimethylpiperidin- 1-yl)-6-ethynyl-5-(4-(4-fluorophenethoxy)phenyl)-2-methylpyridin-3-yl)acetate (275 mg, 0.447 mmol, 89% yield). $^1$H NMR (500 MHz, CDCl$_3$) δ 7.33-7.28 (m, 3H), 7.12-7.07 (m, 1H), 7.07-6.99 (m, 2H), 6.96 (d, J=8.8 Hz, 2H), 6.00 (br. s., 1H), 5.10 (dt, J=12.6, 6.2 Hz, 1H), 4.22 (qd, J=6.9, 2.3 Hz, 2H), 3.24 (br. s., 1H), 3.12 (t, J=6.9 Hz, 2H), 2.94 (s, 2H), 2.63-2.58 (m, 3H), 2.27-2.15 (m, 1H), 2.09 (d, J=19.7 Hz, 1H), 1.41-1.31 (m, 1H), 1.29-1.25 (m, 2H), 1.24-1.20 (m, 6H), 1.19-1.16 (m, 9H), 1.09 (d, J=10.1 Hz, 1H), 0.90 (br. s., 3H), 0.69 (br. s., 3H). LCMS (M+H): 615.30.

EXAMPLE 161

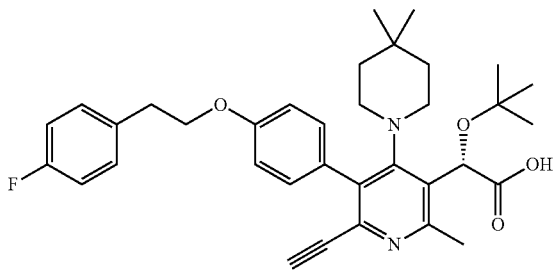 [SMILES: C#Cc1nc(C)c([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-6-ethynyl-5-(4-(4-fluorophenethoxy)phenyl)-2-methylpyridin-3-yl)acetic acid: NaOH (5M, aq) (27 µl, 0.14 mmol) was added to a stirring solution of (S)-isopropyl 2-(tert-butoxy)-2-(4-(4,4-dimethylpiperidin-1-yl)-6-ethynyl-5-(4-(4-fluorophenethoxy)phenyl)-2-methylpyridin-3-yl)acetate (12 mg, 0.020 mmol) in EtOH (0.2 ml) at 80° C. The reaction was stirred for 5 hrs and then the crude material was purified via preparative LC/MS to give desired product (7.0 mg). $^1$H NMR (500 MHz, DMSO-d6) δ 7.36 (dd, J=8.1, 5.9 Hz, 2H), 7.26 (d, J=7.0 Hz, 1H), 7.14-7.04 (m, 3H), 7.01 (d, J=6.2 Hz, 2H), 5.82 (s, 1H), 4.29-4.19 (m, 2H), 3.80 (s, 1H), 3.05 (t, J=6.6 Hz, 2H), 2.54 (s, 6H), 2.47 (s, 3H), 1.25 (br. s., 2H), 1.13 (s, 9H), 0.74 (br. s., 6H). LCMS (M+H)=573.16.

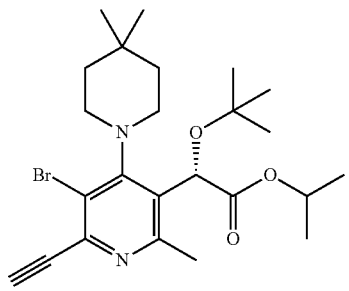 [SMILES: C#Cc1nc(C)c([C@H](OC(C)(C)C)C(=O)OC(C)C)c(N2CCC(C)(C)CC2)c1Br]

Isopropyl (S)-2-(5-bromo-4-(4,4-dimethylpiperidin-1-yl)-6-ethynyl-2-methylpyridin-3-yl)-2-(tert-butoxy)acetate: Dimethyl (1-diazo-2-oxopropyl)phosphonate (358 µl, 2.38 mmol) was added to a stirring solution of (S)-isopropyl 2-(5-bromo-4-(4,4-dimethylpiperidin-1-yl)-6-formyl-2-methylpyridin-3-yl)-2-(tert-butoxy)acetate (960 mg, 1.99 mmol) and K$_2$CO$_3$ (1.2 g, 8.9 mmol) in MeOH (10 ml) at rt. The reaction was stirred for 1 hr. The reaction was concentrated, adsorbed onto celite and was purified on silica gel (Biotage, EtOAc/hexanes gradient, 0-100% gradient over 10CVs) to give the expected product (S)-isopropyl 2-(5-bromo-4-(4,4-dimethylpiperidin-1-yl)-6-ethynyl-2-methylpyridin-3-yl)-2-(tert-butoxy)acetate (830 mg, 1.731 mmol, 87% yield). 1H NMR (500 MHz, CDCl$_3$) δ 6.24 (br. s., 1H), 5.11-4.99 (m, 1H), 4.03 (br. s., 1H), 3.56-3.42 (m, 1H), 3.41 (s, 1H), 2.99-2.84 (m, 1H), 2.64 (d, J=7.9 Hz, 2H), 2.57 (br. s., 3H), 1.23-1.22 (m, 3H), 1.21-1.18 (m, 12H), 1.14 (d, J=6.3 Hz, 3H), 1.09-1.02 (m, 6H). LCMS (M+H): 479.10, 481.05.

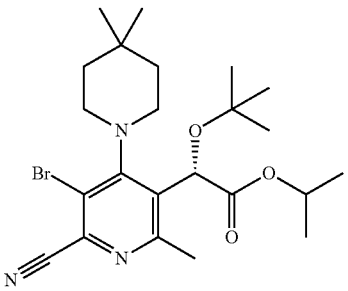 [SMILES: Cc1nc(C#N)c(Br)c(N2CCC(C)(C)CC2)c1[C@H](OC(C)(C)C)C(=O)OC(C)C]

Isopropyl (S)-2-(5-bromo-6-cyano-4-(4,4-dimethylpiperidin-1-yl)-2-methylpyridin-3-yl)-2-(tert-butoxy)acetate: Under N$_2$, tert-butyl nitrite (412 µl, 3.46 mmol) was added to a stirring solution of (S)-isopropyl 2-(5-bromo-4-(4,4-dimethylpiperidin-1-yl)-6-ethynyl-2-methylpyridin-3-yl)-2-(tert-butoxy)acetate (830 mg, 1.73 mmol) and 2-methylpyridine 1-oxide (378 mg, 3.46 mmol) in THF (12 ml) at rt under N$_2$. The reaction was warmed to 70° C. and stirred overnight. LCMS showed a mixture of starting material and product. The reaction was concentrated, adsorbed onto celite and was purified on silica gel (Biotage, EtOAc/hexanes gradient, 0-100% over 10CVs) to give the expected product (S)-isopropyl 2-(5-bromo-6-cyano-4-(4,4-dimethylpiperidin-1-yl)-2-methylpyridin-3-yl)-2-(tert-butoxy)acetate (306 mg, 0.637 mmol, 36.8% yield). 1H NMR (500 MHz, CDCl$_3$) δ 6.20 (br. s., 1H), 5.06 (quin, J=6.3 Hz, 1H), 4.07-3.91 (m, 1H), 3.50-3.33 (m, 1H), 3.00-2.83 (m, 1H), 2.71-2.62 (m, 1H), 2.58 (s, 3H), 1.59 (br. s., 1H), 1.52 (br. s., 2H), 1.39 (d, J=11.8 Hz, 1H), 1.21 (d, J=6.3 Hz, 3H), 1.20 (s, 9H), 1.16 (d, J=6.1 Hz, 3H), 1.06 (d, J=18.1 Hz, 6H). LCMS (M+H): 480.10, 482.05.

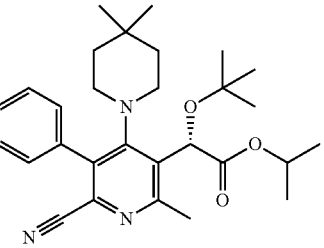

Isopropyl (S)-2-(tert-butoxy)-2-(6-cyano-4-(4,4-dimethylpiperidin-1-yl)-5-(4-(4-fluorophenethoxy)phenyl)-2-methylpyridin-3-yl)acetate: (S)-Isopropyl 2-(5-bromo-6-cyano-4-(4,4-dimethylpiperidin-1-yl)-2-methylpyridin-3-yl)-2-(tert-butoxy)acetate (18 mg, 0.037 mmol), 2-(4-(4-fluorophenethoxy)phenyl)-6-methyl-1,3,6,2-dioxazaborocane-4,8-dione (21 mg, 0.056 mmol), 2-dicyclohexylphosphino-2',6'-dimethoxybiphenyl (3.1 mg, 7.5 µmol), Pd(OAc)$_2$ (0.841 mg, 3.75 µmol), potassium phosphate tribasic (60 mg, 0.28 mmol) were combined under N$_2$. 1,4-Dioxane (0.6 ml), water (0.1 ml) was added and the reaction was stirred at 80° C. After 3 h, the reaction was concentrated, adsorbed onto celite and was purified on silica gel (Biotage, EtOAc/hexanes gradient, 0-100% over 10 CVs) to give the expected product (S)-isopropyl 2-(tert-butoxy)-2-(6-cyano-4-(4,4-dimethylpiperidin-1-yl)-5-(4-(4-fluorophenethoxy)phenyl)-2-methylpyridin-3-yl)acetate (10 mg, 0.016 mmol, 43% yield). LCMS (M+H): 616.25.

EXAMPLE 162

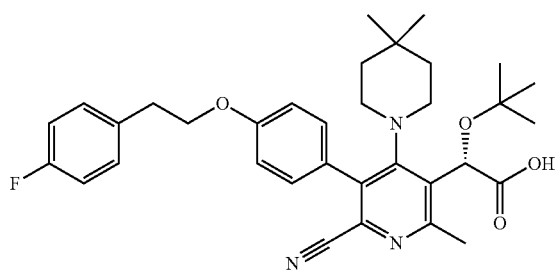 [SMILES: Cc1nc(C#N)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-cyano-4-(4,4-dimethylpiperidin-1-yl)-5-(4-(4-fluorophenethoxy)phenyl)-2-methylpyridin-3-yl)acetic acid: Trimethylstannanol (21 mg, 0.11 mmol) was added to a stirring solution of (S)-isopropyl 2-(tert-butoxy)-2-(6-cyano-4-(4,4-dimethylpiperidin-1-yl)-5-(4-(4-fluorophenethoxy)phenyl)-2-methylpyridin-3-yl)acetate (14 mg, 0.023 mmol) in DCE (909 µl) at 80° C. The reaction was stirred for 5 hrs. LCMS showed no rxn. The reaction was filtered and concentrated. The residue was taken up in 10:1 EtOH/H$_2$O and lithium hydroxide hydrate (1M) (23 µl, 0.023 mmol) was added at room temperature and the reaction was stirred overnight. LCMS showed no rxn. The reaction was warmed to 40° C. and stirred overnight. LCMS showed no rxn. The reaction was warmed to 50° C. and stirred for 6 hrs. LCMS showed no rxn. The reaction was warmed to 70° C. and stirred overnight. LCMS showed the expected product had formed. The crude material was purified via preparative LC/MS desired product (4.5 mg). $^1$H NMR (500 MHz, DMSO-d6) δ 7.38 (d, J=8.4 Hz, 3H), 7.21-7.04 (m, 5H), 5.64-5.48 (m, 1H), 4.28 (d, J=5.1 Hz, 2H), 3.12-3.00 (m, 1H), 2.57-2.46 (m, 8H), 1.91 (s, 1H), 1.25 (br. s., 2H), 1.10 (s, 9H), 0.77 (br. s., 6H), 0.33 (s, 1H). LCMS (M+H)=574.16.

EXAMPLE 163

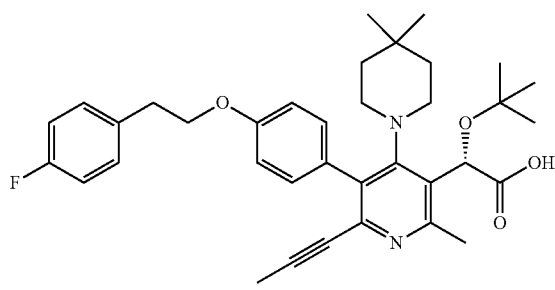 [SMILES: CC#Cc1nc(C)c([C@H](OC(C)(C)C)C(=O)O)c(N2CCC(C)(C)CC2)c1-c1ccc(OCCc2ccc(F)cc2)cc1]

(S)-2-(tert-butoxy)-2-(4-(4,4-dimethylpiperidin-1-yl)-5-(4-(4-fluorophenethoxy)phenyl)-2-methyl-6-(prop-1-yn-1-yl)pyridin-3-yl)acetic acid: Sodium bis(trimethylsilyl)amide, (1M/THF, 98 µl, 0.098 mmol) was added dropwise to a stirring solution of (S)-isopropyl 2-(tert-butoxy)-2-(4-(4,4-dimethylpiperidin-1-yl)-6-ethynyl-5-(4-(4-fluorophenethoxy)phenyl)-2-methylpyridin-3-yl)acetate (50 mg, 0.081 mmol) in THF (1 ml) at −20° C. The reaction was allowed to stir for 15 min. Methyl iodide (15 µl, 0.24 mmol) was added dropwise. The reaction was stirred for 15 min then warmed to room temperature and stirred for 1 hr. LCMS showed expected product mass. The reaction was concentrated, adsorbed onto celite and was purified on silica gel (Biotage, EtOAc/hexanes gradient, 0-100% over 10 CVs) to afford (S)-isopropyl 2-(tert-butoxy)-2-(4-(4,4-dimethylpiperidin-1-yl)-5-(4-(4-fluorophenethoxy)phenyl)-2-methyl-6-(prop-1-yn-1-yl)pyridin-3-yl)acetate (50 mg, 0.080 mmol) which was taken up in 1 mL of EtOH and treated with 0.1 ml of 5N aq. NaOH. The mixture was stirred at 80° C. overnight. The crude material was purified via preparative LC/MS to give the desired product (5.8 mg). $^1$H NMR (500 MHz, DMSO-d6) δ 7.36 (dd, J=8.4, 5.9 Hz, 2H), 7.25 (br. s., 1H), 7.11 (t, J=9.0 Hz, 2H), 7.06-6.96 (m, 3H), 5.80 (s, 1H), 4.29-4.19 (m, 2H), 3.05 (t, J=6.6 Hz, 2H), 2.54 (s, 6H), 2.45 (s, 3H), 1.76 (s, 3H), 1.25 (br. s., 2H), 1.12 (s, 9H), 0.71 (br. s., 6H). LCMS (M+H)=587.16.

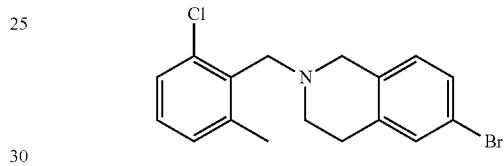

6-Bromo-2-(2-chloro-6-methylbenzyl)-1,2,3,4-tetrahydroisoquinoline: To a solution of 6-bromo-1,2,3,4-tetrahydroisoquinoline (1.25 g, 5.88 mmol) in DCM (25 mL) was added 2-chloro-6-methylbenzaldehyde (1.0 g, 6.5 mmol) and acetic acid (0.337 mL, 5.88 mmol) in DCM (25 mL). Then sodium triacetoxyborohydride (1.62 g, 7.64 mmol) was added. The mixture was stirred at r.t for 16 hrs. The mixture was quenched with water and extracted with EtOAc. The organic layer was washed with brine, dried over Na$_2$SO$_4$ and concentrated. The residue was purified by recrystallization with EtOAc to give 6-bromo-2-(2-chloro-6-methylbenzyl)-1,2,3,4-tetrahydroisoquinoline (1.44 g, 4.11 mmol, 69.8% yield). LCMS (M+H): 350.00, 352.00.

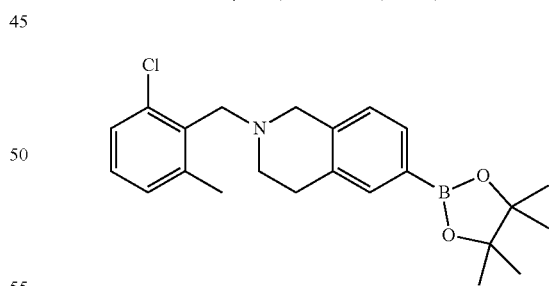

2-(2-Chloro-6-methylbenzyl)-6-(4,4,5,5-tetramethyl-1,3,2-dioxaborolan-2-yl)-1,2,3,4-tetrahydroisoquinoline: 6-Bromo-2-(2-chloro-6-methylbenzyl)-1,2,3,4-tetrahydroisoquinoline (1.00 g, 2.85 mmol), 4,4,4',4',5,5,5',5'-octamethyl-2,2'-bi(1,3,2-dioxaborolane) (1.09 g, 4.28 mmol), Pd(dppf)Cl$_2$ (0.209 g, 0.285 mmol) and potassium acetate (0.840 g, 8.55 mmol) were combined in dioxane (10 mL) in a sealed bottle. The mixture was degassed and heated at 85° C. for 8 hrs. The mixture was diluted with EtOAc, washed with water, brine, dried over Na$_2$SO$_4$ and concentrated. The residue was purified by silica gel column (EtOAc/hexanes gradient 0-100% over 10CVs) to give 2-(2-chloro-6-methylbenzyl)-6-(4,4,5,5-tetramethyl-1,3,2-dioxaborolan-2-yl)-1,2,3,4-tetrahydroisoquinoline (1.05 g, 2.64 mmol, 93% yield). 1H NMR (400 MHz, CDCl₃) δ 7.57-7.51 (m, 2H), 7.23 (d, J=7.6 Hz, 1H), 7.14-7.06 (m, 2H), 7.02 (d, J=7.6 Hz, 1H), 3.83 (s, 2H), 3.71 (s, 2H), 2.88-2.76 (m, 4H), 2.46 (s, 3H), 1.34 (s, 12H). LCMS (M+H): 398.05.

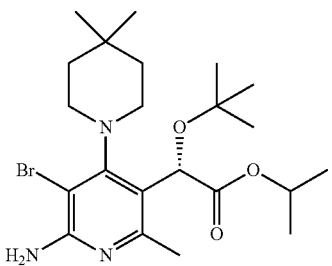 [SMILES: Cc1nc(N)c(Br)c(N2CCC(C)(C)CC2)c1[C@H](OC(C)(C)C)C(=O)OC(C)C]

Isopropyl (S)-2-(6-amino-5-bromo-4-(4,4-dimethylpiperidin-1-yl)-2-methylpyridin-3-yl)-2-(tert-butoxy)acetate: Water (18 μl, 1.0 mmol) followed by diphenylphosphoryl azide (87 μl, 0.40 mmol) was added to a stirring solution of (S)-3-bromo-5-(1-(tert-butoxy)-2-isopropoxy-2-oxoethyl)-4-(4,4-dimethylpiperidin-1-yl)-6-methylpicolinic acid (100 mg, 0.200 mmol) and TEA (56 μl, 0.40 mmol) in toluene (2 ml) at rt. The reaction was stirred at 90° C. for 2 hrs. The mixture was then cooled to room temperature, diluted with EtOAc and washed with sat. NaHCO₃ solution, water and brine. The organic layer was then dried (Na₂SO₄), filtered and concentrated. The residue was then purified by Biotage (EtOAc/hexane gradient, 0-100% over 10CVs) to afford (S)-isopropyl 2-(6-amino-5-bromo-4-(4,4-dimethylpiperidin-1-yl)-2-methylpyridin-3-yl)-2-(tert-butoxy)acetate (80 mg, 0.170 mmol, 85% yield) as white solid. ¹H NMR (500 MHz, CDCl₃) δ 6.11 (br. s., 1H), 5.02 (spt, J=6.3 Hz, 1H), 4.86 (s, 2H), 3.99 (t, J=12.0 Hz, 1H), 3.50-3.40 (m, 1H), 2.91 (d, J=11.5 Hz, 1H), 2.62 (d, J=11.8 Hz, 1H), 2.46-2.39 (m, 3H), 1.45-1.39 (m, 1H), 1.33 (dd, J=12.7, 2.3 Hz, 1H), 1.28-1.24 (m, 1H), 1.21-1.16 (m, 13H), 1.13 (d, J=6.1 Hz, 3H), 1.09-0.99 (m, 6H). LCMS (M+H): 472.05, 470.10.

EXAMPLE 164

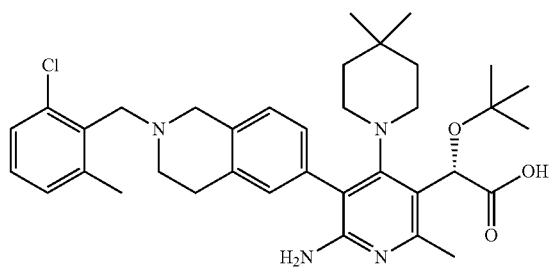 [SMILES: Cc1cccc(Cl)c1CN1CCc2cc(-c3c(N)nc(C)c([C@H](OC(C)(C)C)C(=O)O)c3N3CCC(C)(C)CC3)ccc2C1]

(S)-2-(6-Amino-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid: (S)-Isopropyl 2-(6-amino-5-bromo-4-(4,4-dimethylpiperidin-1-yl)-2-methylpyridin-3-yl)-2-(tert-butoxy)acetate (25 mg, 0.053 mmol), 2-(2-chloro-6-methylbenzyl)-6-(4,4,5,5-tetramethyl-1,3,2-dioxaborolan-2-yl)-1,2,3,4-tetrahydroisoquinoline (32 mg, 0.080 mmol), 2-dicyclohexylphosphino-2',6'-dimethoxybiphenyl (4.4 mg, 11 μmol), Pd(OAc)₂ (1.2 mg, 5.3 μmol) and potassium phosphate tribasic (85 mg, 0.40 mmol) in 1,4-dioxane (1 ml) and Water (0.2 ml) under N₂. The reaction was heated at 80° C. for 1 h. The reaction was concentrated and the residue was taken up in EtOH (1 mL) and then treated with NaOH (5 N aq) (106 μl, 0.531 mmol) and stirred at 80° C. overnight. The mixture was then cooled and the crude material was purified via preparative LC/MS to provide the product (3.0 mg). ¹H NMR (500 MHz, DMSO-d6) δ 7.28 (d, J=7.3 Hz, 1H), 7.24-7.16 (m, 2H), 7.16-7.08 (m, 1H), 7.05-6.99 (m, 1H), 6.87 (br. s., 1H), 5.71 (d, J=8.1 Hz, 1H), 4.82-4.73 (m, 0.6 H), 3.83 (br. s., 2H), 3.68 (br. s., 2H), 2.86-2.73 (m, 5H), 2.47-2.41 (m, 3H), 2.36-2.05 (m, 5H), 1.47 (br. s., 1H), 1.25 (br. s., 2H), 1.19-1.08 (m, 13H), 1.05-0.92 (m, 1H), 0.84 (br. s., 3H), 0.59 (br. s., 3H). LCMS (M+H)=619.16.

EXAMPLE 165

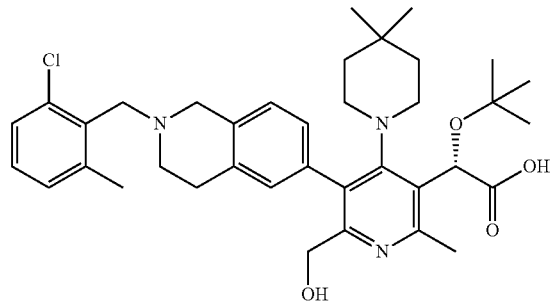 [SMILES: Cc1cccc(Cl)c1CN1CCc2cc(-c3c(CO)nc(C)c([C@H](OC(C)(C)C)C(=O)O)c3N3CCC(C)(C)CC3)ccc2C1]

(S)-2-(tert-butoxy)-2-(5-(2-(2-chloro-6-methylbenzyl)-1,2,3,4-tetrahydroisoquinolin-6-yl)-4-(4,4-dimethylpiperidin-1-yl)-6-(hydroxymethyl)-2-methylpyridin-3-yl)acetic acid: (S)-Isopropyl 2-(5-bromo-4-(4,4-dimethylpiperidin-1-yl)-6-(hydroxymethyl)-2-methylpyridin-3-yl)-2-(tert-butoxy)acetate (34 mg, 0.070 mmol), 2-(2-chloro-6-methylbenzyl)-6-(4,4,5,5-tetramethyl-1,3,2-dioxaborolan-2-yl)-1,2,3,4-tetrahydroisoquinoline (42 mg, 0.11 mmol), 2-dicyclohexylphosphino-2',6'-dimethoxybiphenyl (5.8 mg, 0.014 mmol), Pd(OAc)₂ (1.6 mg, 7.0 μmol) and potassium phosphate tribasic (111 mg, 0.525 mmol) were combined under N₂. 1,4-Dioxane (1.2 ml) and water (0.2 ml) were added under N₂. The reaction was heated at 80° C. for 2 h. The reaction was concentrated, adsorbed onto celite and was purified on silica gel (Biotage, EtOAc/hexanes gradient, 0-100% over 10 CVs) to afford (S)-isopropyl 2-(tert-butoxy)-2-(5-(2-(2-chloro-6-methylbenzyl)-1,2,3,4-tetrahydroisoquinolin-6-yl)-4-(4,4-dimethylpiperidin-1-yl)-6-(hydroxymethyl)-2-methylpyridin-3-yl)acetate (36 mg, 0.053 mmol) which was taken up in EtOH (1mL) and then treated with NaOH (5 N aq) (140 μl, 0.700 mmol) and stirred at 80° C. overnight. The mixture was then cooled to rt and the crude material was purified via preparative LC/MS to give the product (16.8 mg). ¹H NMR (500 MHz, DMSO-d6) δ 7.28 (d, J=7.7 Hz, 1H), 7.24-7.15 (m, 2H), 7.14-7.04 (m, 2H), 6.93-6.84 (m, 1H), 5.86 (d, J=9.2 Hz, 1H), 4.26-4.15 (m, 1H), 4.07-3.94 (m, 1H), 3.87-3.78 (m, 2H), 3.76-3.62 (m, 2H), 2.84-2.73 (m, 4H), 2.55-2.51 (m, 6H), 2.47-2.42 (m, 3H), 1.49 (br. s., 1H), 1.23 (d, J=10.6 Hz, 2H), 1.16-1.10 (m, 10H), 1.01 (br. s., 1H), 0.84 (br. s., 3H), 0.61 (br. s., 3H). LCMS (M+H)=634.16.

EXAMPLE 166

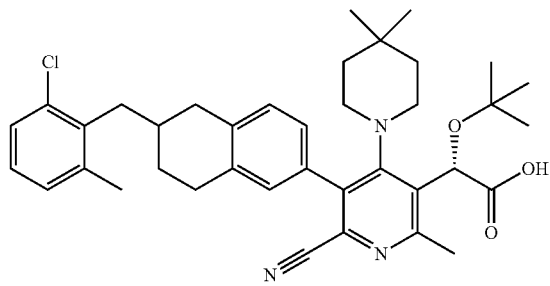 [SMILES: Cc1cccc(Cl)c1CC1CCc2cc(-c3c(C#N)nc(C)c([C@H](OC(C)(C)C)C(=O)O)c3N3CCC(C)(C)CC3)ccc2C1]

(S)-2-(tert-butoxy)-2-(5-(2-(2-chloro-6-methylbenzyl)-1,2,3,4-tetrahydroisoquinolin-6-yl)-6-cyano-4-(4,4-dimethylpiperidin-1-yl)-2-methylpyridin-3-yl)acetic acid: (S)-Isopropyl 2-(5-bromo-6-cyano-4-(4,4-dimethylpiperidin-1-yl)-2-methylpyridin-3-yl)-2-(tert-butoxy)acetate (34 mg, 0.071 mmol), 2-(2-chloro-6-methylbenzyl)-6-(4,4,5,5-tetramethyl-1,3,2-dioxaborolan-2-yl)-1,2,3,4-tetrahydroisoquinoline (42 mg, 0.11 mmol), 2-dicyclohexylphosphino-2',6'-dimethoxybiphenyl (5.8 mg, 0.014 mmol), Pd(OAc)$_2$ (1.6 mg, 7.1 µmol) and potassium phosphate tribasic (113 mg, 0.531 mmol) were combined under N$_2$. 1,4-Dioxane (1.2 ml) and water (0.2 ml) was added under N$_2$. The reaction was heated at 80° C. for 2 h. The reaction was concentrated, adsorbed onto celite and was purified on silica gel (Biotage, EtOAc/hexanes gradient, 0-100% over 10 CVs) to afford (S)-isopropyl 2-(tert-butoxy)-2-(5-(2-(2-chloro-6-methylbenzyl)-1,2,3,4-tetrahydroisoquinolin-6-yl)-6-cyano-4-(4,4-dimethylpiperidin-1-yl)-2-methylpyridin-3-yl)acetate (40 mg, 0.060 mmol, 84% yield). LCMS (M+H): 671.35 Lithium hydroxide hydrate (7.9 mg, 0.19 mmol) in 3 mL of water was added to a stirring solution of above (S)-isopropyl 2-(tert-butoxy)-2-(5-(2-(2-chloro-6-methylbenzyl)-1,2,3,4-tetrahydroisoquinolin-6-yl)-6-cyano-4-(4,4-dimethylpiperidin-1-yl)-2-methylpyridin-3-yl)acetate (115 mg, 0.171 mmol) in Ethanol (3 mL) at 70° C. The reaction was stirred overnight. Then an additional 4 mg of lithium hydroxide hydrate and 1 mL of water was added to the reaction and it was allowed to stir for 5 hrs. The reaction was purified by preparative reverse phase HPLC on a C18 column using a suitably buffered H$_2$O/CH$_3$CN gradient, and concentrated to give the expected product (S)-2-(tert-butoxy)-2-(5-(2-(2-chloro-6-methylbenzyl)-1,2,3,4-tetrahydroisoquinolin-6-yl)-6-cyano-4-(4,4-dimethylpiperidin-1-yl)-2-methylpyridin-3-yl)acetic acid (15 mg, 0.023 mmol, 14% yield). $^1$H NMR (400 MHz, methanol-d4) δ 7.36-7.17 (m, 5H), 7.13-7.05 (m, 1H), 5.90 (d, J=4.4 Hz, 1H), 4.96-4.86 (m, 5H), 4.18-3.90 (m, 3H), 3.17-2.94 (m, 4H), 2.60 (s, 3H), 2.51 (d, J=4.9 Hz, 3H), 1.43-1.27 (m, 4H), 1.18 (s, 9H), 0.94-0.69 (m, 6H). LCMS (M+H): 629.35.

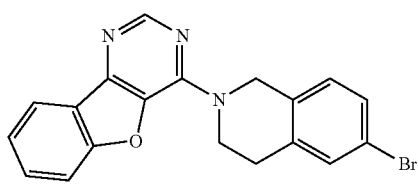 [SMILES: Brc1ccc2c(c1)CCN(c1ncnc3c1oc1ccccc13)C2]

4-(6-Bromo-3,4-dihydroisoquinolin-2 (1H)-yl)benzofuro[3,2-d]pyrimidine: A mixture of 4-chloro-benzo[4,5]furo[3,2-d]pyrimidine (1.06 g, 5.19 mmol), 6-bromo-1,2,3,4-tetrahydroisoquinoline (1.0 g, 4.7 mmol), potassium carbonate (1.95 g, 14.1 mmol) and sodium iodide (0.71 g, 4.7 mmol) in dioxane (50 mL) was heated at 90° C. for 6 hrs. The mixture was diluted with EtOAc and washed with water, brine, dried over Na$_2$SO$_4$ and concentrated. The residue was purified by recrystallization with EtOAc to give 4-(6-bromo-3,4-dihydroisoquinolin-2(1H)-yl)benzofuro[3,2-d]pyrimidine (1.2 g, 3.16 mmol, 66.9% yield). LCMS (M+H): 379.90, 381.90.

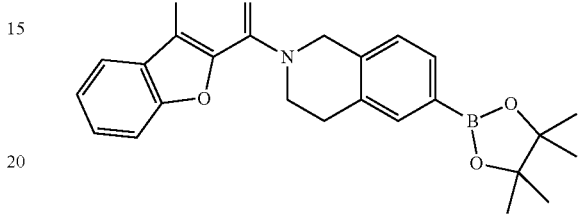

4-(6-(4,4,5,5-Betramethyl-1,3,2-dioxaborolan-2-yl)-3,4-dihydroisoquinolin-2(1H)-yl)benzofuro[3,2-d]pyrimidine: 4-(6-Bromo-3,4-dihydroisoquinolin-2(1H)-yl)benzofuro[3,2-d]pyrimidine (1.4 g, 3.7 mmol), 4,4,4',4',5,5,5',5'-octamethyl-2,2'-bi(1,3,2-dioxaborolane) (1.4 g, 5.5 mmol), Pd(dppf)Cl$_2$ (0.269 g, 0.368 mmol) and potassium acetate (1.08 g, 11.1 mmol) were combined in dioxane (15 mL) in a sealed microwave vial. The mixture was degassed and heated at 85° C. for 8 hrs. The mixture was diluted with EtOAc, washed with water, brine, dried over Na$_2$SO$_4$ and concentrated. The residue was purified by silica gel column (EtOAc/hexanes gradient 0-100% over 10CVs) to give 4-(6-(4,4,5,5-tetramethyl-1,3,2-dioxaborolan-2-yl)-3,4-dihydroisoquinolin-2(1H)-yl)benzofuro[3,2-d]pyrimidine (1.2 g, 2.8 mmol, 76% yield). $^1$H NMR (500 MHz, CDCl$_3$) δ 8.65 (s, 1H), 8.18 (d, J=7.7 Hz, 1H), 7.73-7.59 (m, 5H), 7.45 (ddd, J=7.8, 6.8, 1.3 Hz, 1H), 7.30 (d, J=7.6 Hz, 1H), 5.25 (s, 2H), 4.39 (t, J=5.9 Hz, 2H), 3.10 (t, J=5.8 Hz, 2H), 1.36 (s, 12H). LCMS (M+H): 428.10.

EXAMPLE 167

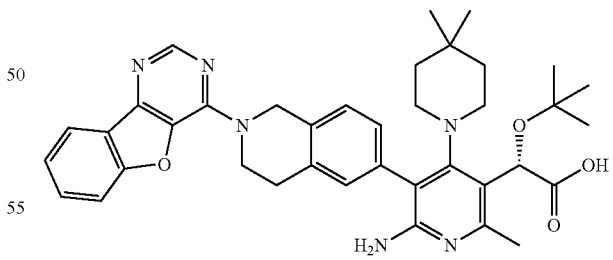

(S)-2-(6-amino-5-(2-(benzofuro[3,2-d]pyrimidin-4-yl)-1,2,3,4-tetrahydroisoquinolin-6-yl)-4-(4,4-dimethylpiperidin-1-yl)-2-methylpyridin-3-yl)-2-(tert-butoxy)acetic acid: (S)-Isopropyl 2-(6-amino-5-bromo-4-(4,4-dimethylpiperidin-1-yl)-2-methylpyridin-3-yl)-2-(tert-butoxy)acetate (20 mg, 0.043 mmol), 4-(6-(4,4,5,5-tetramethyl-1,3,2-dioxaborolan-2-yl)-3,4-dihydroisoquinolin-2(1H)-yl)benzofuro[3,2-d]pyrimidine (27 mg, 0.064 mmol), 2-dicyclohexylphosphino-2',6'-dimethoxybiphenyl (4.2 mg, 10 µmol), Pd(OAc)$_2$ (1.1 mg, 5.1 μmol) and potassium phosphate tribasic (68 mg, 0.32 mmol) were combined dry under N₂, and taken up in 1,4-dioxane (1 ml) and water (0.14 ml) under N₂. The reaction was heated at 80° C. for 1 h. The reaction was concentrated taken up in EtOH (1 mL) and treated with NaOH (0.1 ml, 0.4 mmol). The mixture was stirred for overnight at 80° C. The crude material was purified via preparative LC/MS to give the product (12.6 mg). ¹H NMR (500 MHz, DMSO-d6) δ 8.58 (d, J=2.2 Hz, 1H), 8.12 (d, J=7.7 Hz, 1H), 7.88 (d, J=7.7 Hz, 1H), 7.73 (t, J=7.5 Hz, 1H), 7.51 (t, J=7.5 Hz, 1H), 7.48-7.40 (m, 1H), 7.22-7.14 (m, 1H), 7.02 (s, 1H), 5.68 (d, J=5.5 Hz, 1H), 5.30-5.13 (m, 1H), 4.96 (br. s., 1H), 4.33 (br. s., 1H), 2.28 (s, 4H), 1.50 (br. s., 1H), 1.23 (s, 9H), 1.11 (s, 10H), 0.94-0.68 (m, 6H). LCMS (M+H)=649.15.

EXAMPLE 168

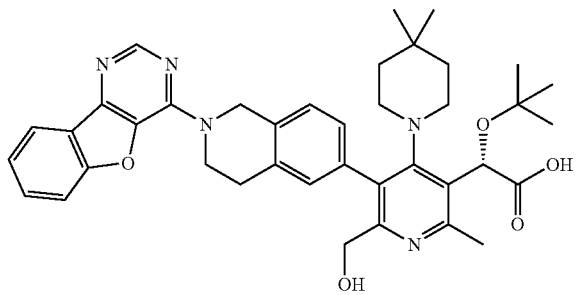 [SMILES: Cc1nc(CO)c(-c2ccc3c(c2)CCN(c2ncnc4c2oc2ccccc24)C3)c(N2CCC(C)(C)CC2)c1[C@H](OC(C)(C)C)C(=O)O]

(S)-2-(5-(2-(Benzofuro[3,2-d]pyrimidin-4-yl)-1,2,3,4-tetrahydroisoquinolin-6-yl)-4-(4,4-dimethylpiperidin-1-yl)-6-(hydroxymethyl)-2-methylpyridin-3-yl)-2-(tert-butoxy)acetic acid: In a pressure vial equipped with a magnetic stirring bar was added (S)-isopropyl 2-(5-bromo-4-(4,4-dimethylpiperidin-1-yl)-6-(hydroxymethyl)-2-methylpyridin-3-yl)-2-(tert-butoxy)acetate (30 mg, 0.062 mmol), 4-(6-(4,4,5,5-tetramethyl-1,3,2-dioxaborolan-2-yl)-3,4-dihydroisoquinolin-2(1H)-yl)benzofuro[3,2-d]pyrimidine (39.6 mg, 0.093 mmol), palladium (II) acetate (1.734 mg, 7.72 μmol), S-Phos (7.92 mg, 0.015 mmol) and potassium phosphate tribasic (98 mg, 0.463 mmol) in dioxane (1 mL) and water (0.200 mL). Argon was bubbled throught the mixture for 5 minutes while sonicating. The flask was capped and heated to 80° C. within a preheated aluminum block and was allowed to stir for 2 hours. LC/MS showed the desired product as a major peak. The reaction mixture was concentrated down under vacuum and was taken up in ethanol (1 mL), then NaOH (10N, 0.062 mL, 0.618 mmol) was added. The vial was sealed and the mixture was heated for 16 hours at 80° C. within a preheated aluminum block. LC/MS showed the reaction was complete, with the starting material consumed. The reaction was cooled to room temperature and filtered. The crude material was purified via preparative LC/MS to give the product (12.0 mg, 28%). ¹H NMR (500 MHz, DMSO-d₆) δ 8.63-8.50 (m, 1H), 8.12 (d, J=7.7 Hz, 1H), 7.86 (d, J=8.4 Hz, 1H), 7.72 (t, J=7.7 Hz, 1H), 7.51 (t, J=7.5 Hz, 1H), 7.47-7.38 (m, 1H), 7.28-7.19 (m, 1H), 7.06-7.00 (m, 1H), 5.82 (d, J=13.2 Hz, 1H), 5.39-5.23 (m, 1H), 5.14 (d, J=16.9 Hz, 1H), 4.35 (br. s., 1H), 4.30 (d, J=8.1 Hz, 1H), 4.26-4.16 (m, 1H), 4.10-3.96 (m, 1H), 3.31 (d, J=11.7 Hz, 1H), 3.08 (br. s., 2H), 2.82 (br. s., 1H), 2.55 (s, 5H), 2.10 (br. s., 1H), 1.77 (br. s., 1H), 1.44 (br. s., 1H), 1.21 (s, 4H), 1.17 (br. s., 1H), 1.12 (d, J=2.9 Hz, 11H), 0.99 (br. s., 1H), 0.94-0.84 (m, 1H), 0.84-0.71 (m, 3H), 0.53 (br. s., 1H), 0.39 (br. s., 2H). LCMS (M+H)=706.45.

EXAMPLE 169

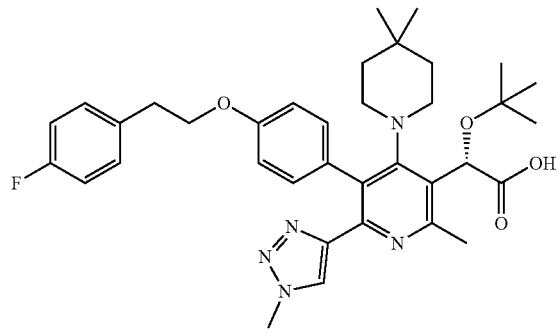 [SMILES: Cc1nc(-c2cn(C)nn2)c(-c2ccc(OCCc3ccc(F)cc3)cc2)c(N2CCC(C)(C)CC2)c1[C@H](OC(C)(C)C)C(=O)O]

(S)-2-(tert-butoxy)-2-(4-(4,4-dimethylpiperidin-1-yl)-5-(4-(4-fluorophenethoxy)phenyl)-2-methyl-6-(1-methyl-1H-1,2,3-triazol-4-yl)pyridin-3-yl)acetic acid: Sodium azide (7.9 mg, 0.12 mmol) was added to a stirring solution of methyl iodide (6.1 μl, 0.098 mmol) and copper(I) iodide (9.3 mg, 0.049 mmol) and (S)-isopropyl 2-(tert-butoxy)-2-(4-(4,4-dimethylpiperidin-1-yl)-6-ethynyl-5-(4-(4-fluorophenethoxy)phenyl)-2-methylpyridin-3-yl)acetate (30 mg, 0.049 mmol) in acetonitrile (1 ml) at rt. The reaction was warmed to 80° C. and allowed to stir for 1 hr. The reaction was concentrated and taken up in 1.5 mL of EtOH, and 0.1 mL of 5 N aq NaOH was added. The mixture was stirred at 80° C. overnight. The crude material was purified via preparative LC/MS to give the product (15.1 mg). ¹H NMR (500 MHz, DMSO-d6) δ 7.44 (s, 1H), 7.34 (dd, J=8.3, 5.7 Hz, 2H), 7.16-7.07 (m, 3H), 6.99 (ddd, J=18.1, 8.5, 2.4 Hz, 2H), 6.83 (dd, J=8.4, 2.6 Hz, 1H), 5.88 (br. s., 1H), 4.25-4.11 (m, 2H), 3.90-3.83 (m, 3H), 3.05-2.97 (m, 2H), 2.89-2.79 (m, 1H), 2.54 (s, 3H), 2.19 (d, J=11.4 Hz, 1H), 1.96-1.83 (m, 1H), 1.54-1.41 (m, 1H), 1.27 (d, J=16.1 Hz, 1H), 1.18 (d, J=12.1 Hz, 1H), 1.15-1.08 (m, 10H), 1.01 (d, J=12.8 Hz, 1H), 0.84 (s, 3H), 0.59 (s, 3H). LCMS (M+H)=630.16.

EXAMPLE 170

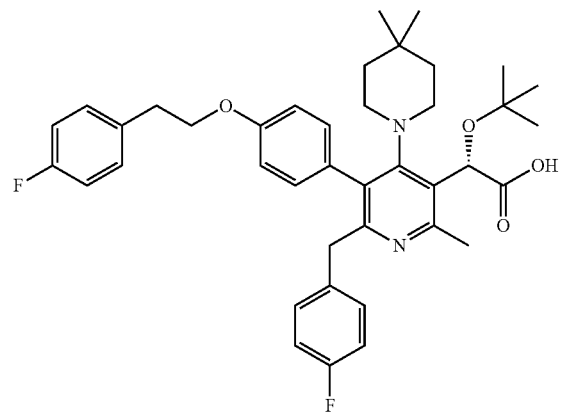 [SMILES: Cc1nc(Cc2ccc(F)cc2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(4-(4,4-dimethylpiperidin-1-yl)-6-(4-fluorobenzyl)-5-(4-(4-fluorophenethoxy)phenyl)-2-methylpyridin-3-yl)acetic acid: A mixture of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (23 mg, 0.034 mmol), DPPF (3.73 mg, 6.73 µmol), (4-fluorophenyl)boronic acid (14.1 mg, 0.101 mmol) and Cs₂CO₃ (22 mg, 0.067 mmol) in DMF (1 mL) was degassed and charged with N₂ (3×). The mixture was placed in a pre-heated oil bath 90° C. and allowed to stir at this temperature for 1 h. The reaction mixture was cooled to room temperature, adsorbed onto Celite and purified on a column of silica gel (EtOAc/Hex: 0 to 100% over 12 CVs) to afford 2-(tert-butoxy)-2-(4-(4,4-dimethylpiperidin-1-yl)-6-(4-fluorobenzyl)-5-(4-(4-fluorophenethoxy)phenyl)-2-methylpyridin-3-yl)acetate (S)-isopropyl 2-(tert-butoxy)-2-(4-(4,4-dimethylpiperidin-1-yl)-6-(4-fluorobenzyl)-5-(4-(4-fluorophenethoxy)phenyl)-2-methylpyridin-3-yl)acetate (10 mg, 0.014 mmol, 43% yield) (S)-isopropyl as a colorless oil. This oil was then taken up in EtOH (1 mL) and NaOH (5 M, 0.067 mL) was added. The resulting solution was heated to 80° C. with stirring for 2 h. LCMS shows conversion to desired product. The solution was cooled to room temperature and purified by preparative HPLC to afford (S)-2-(tert-butoxy)-2-(4-(4,4-dimethylpiperidin-1-yl)-6-(4-fluorobenzyl)-5-(4-(4-fluorophenethoxy)phenyl)-2-methylpyridin-3-yl)acetic acid (8.0 mg, 0.012 mmol, 36% yield). $^1$H NMR (500 MHz, DMSO-d6) δ 7.42-7.31 (m, 2H), 7.19-7.07 (m, 3H), 7.04-6.84 (m, 7H), 5.80 (s, 1H), 3.79 (d, J=13.9 Hz, 1H), 3.64 (d, J=14.3 Hz, 1H), 3.35 (br s, 1H), 3.05 (t, J=6.8 Hz, 2H), 2.76 (br s, 1H), 2.47 (s, 3H), 2.23 (br s, 1H), 1.50 (br s, 1H), 1.13 (s, 9H), 1.00 (br s, 1H), 0.85 (d, J=11.7 Hz, 3H), 0.59 (br s, 3H). LCMS (M+H)=657.3.

EXAMPLE 171

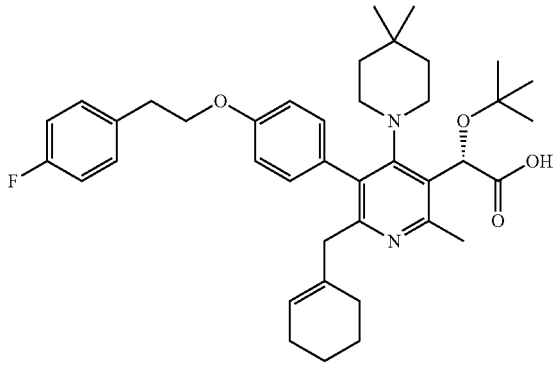 [SMILES: Cc1nc(CC2=CCCCC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-(cyclohex-1-en-1-ylmethyl)-4-(4,4-dimethylpiperidin-1-yl)-5-(4-(4-fluorophenethoxy)phenyl)-2-methylpyridin-3-yl)acetic acid: A mixture of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (25 mg, 0.037 mmol), cyclohex-1-en-1-ylboronic acid (18.4 mg, 0.146 mmol), DPPF (4.05 mg, 7.31 mol) and Cs₂CO₃ (24 mg, 0.073 mmol) in DMF (1 mL) was degassed and charged with N₂ (3×). The mixture was placed in a pre-heated oil bath 90° C. and allowed to stir at this temperature for 2 h. The reaction mixture was cooled to room temperature diluted with EtOAc washed with water, brine, dried (Na₂SO₄), filtered, concentrated, adsorbed onto Celite and purified on silica column (EtOAc/Hex: 0 to 50%) to afford the desired coupled product as a colorless oil. This oil was then taken up in EtOH (1 mL) NaOH (5 M, 0.067 mL) was added and the solution was heated to 80° C. with stirring for 2 h. LCMS shows conversion to desired product. The solution was cooled to room temperature and purified by preparative HPLC to afford (S)-2-(tert-butoxy)-2-(6-(cyclohex-1-en-1-ylmethyl)-4-(4,4-dimethylpiperidin-1-yl)-5-(4-(4-fluorophenethoxy)phenyl)-2-methylpyridin-3-yl) acetic acid (7.3 mg, 0.011 mmol, 31% yield). $^1$HNMR (500 MHz, DMSO-d6) δ 7.35 (dd, J=8.3, 5.7 Hz, 2H), 7.20-7.07 (m, 3H), 7.03-6.93 (m, 3H), 5.86 (s, 1H), 4.82 (br s, 1H), 4.30-4.18 (m, 2H), 3.12-3.01 (m, 2H), 2.92 (d, J=15.0 Hz, 1H), 2.79 (br s, 1H), 2.46 (s, 3H), 2.29-2.18 (m, 1H), 1.81 (br s, 2H), 1.66 (br s, 2H), 1.47-1.36 (m, 4H), 1.25 (s, 2H), 1.13 (s, 9H), 1.01 (br s, 1H), 0.85 (br s, 3H), 0.59 (br s, 3H). LCMS (M+H)=643.3.

EXAMPLE 172

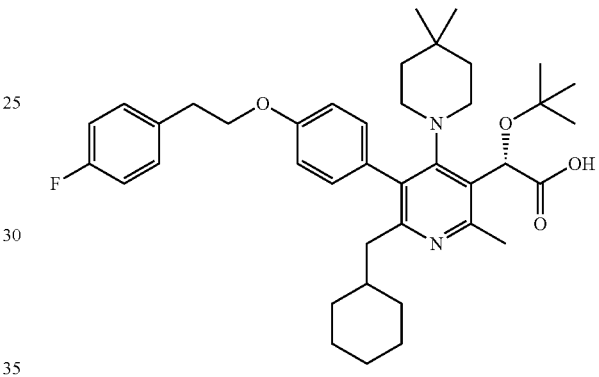

(S)-2-(tert-Butoxy)-2-(6-(cyclohexylmethyl)-4-(4,4-dimethylpiperidin-1-yl)-5-(4-(4-fluorophenethoxy)phenyl)-2-methylpyridin-3-yl)acetic acid: A mixture of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (22 mg, 0.031 mmol), cyclohex-1-en-1-ylboronic acid (15.8 mg, 0.126 mmol), DPPF (3.49 mg, 6.29 µmol) and Cs₂CO₃ (21 mg, 0.063 mmol) in DMF (1 mL) was degassed and charged with N₂ (3×). The mixture was placed in a pre-heated oil bath 90° C. and allowed to stir at this temperature for 2 h. The reaction mixture was cooled to room temperature, diluted with EtOAc washed with water, brine, dried (Na₂SO₄), filtered, concentrated, adsorbed onto Celite and purified on a silica column (EtOAc/Hex: 0 to 50%) to afford (S)-isopropyl 2-(tert-butoxy)-2-(6-(cyclohex-1-en-1-ylmethyl)-4-(4,4-dimethylpiperidin-1-yl)-5-(4-(4-fluorophenethoxy)phenyl)-2-methylpyridin-3-yl)acetate (7 mg, 10 µmol, 33% yield) as a colorless oil. (S)-Isopropyl 2-(tert-butoxy)-2-(6-(cyclohex-1-en-1-ylmethyl)-4-(4,4-dimethylpiperidin-1-yl)-5-(4-(4-fluorophenethoxy)phenyl)-2-methylpyridin-3-yl)acetate (7 mg, 10.22 µmol) was taken up in ethanol (1 mL) and Pd-C (1.09 mg, 10.2 µmol) was added. The mixture was evacuated and charged with H₂ (3×). The mixture was then stirred under an H₂ balloon for 2 h. LCMS shows conversion the reduced product. The mixture was filtered and to the solution containing (S)-isopropyl 2-(tert-butoxy)-2-(6-(cyclohexylmethyl)-4-(4,4-dimethylpiperidin-1-yl)-5-(4-(4-fluorophenethoxy)phenyl)-2-methylpyridin-3-yl)acetate was added NaOH (5 M) (0.020 mL, 102 µmol). The solution was then heated to 80° C. and stirred overnight. LCMS shows conversion to the desired product. The solution was cooled to room temperature and purified by preparative HPLC to afford (S)-2-(tert-butoxy)-2-(6-(cyclohexylmethyl)-4-(4,4-dimethylpiperidin-1-yl)-5-(4-(4-fluorophenethoxy)phenyl)-2-methylpyridin-3-yl)acetic acid (2.7 mg, 4.19 μmol, 41% yield (for final two steps)). ¹H NMR (500 MHz, DMSO-d6) δ 7.34 (dd, J=8.4, 5.9 Hz, 2H), 7.20-7.06 (m, 3H), 7.06-6.93 (m, 3H), 5.83 (s, 1H), 4.31-4.16 (m, 2H), 3.03 (t, J=6.8 Hz, 2H), 2.45 (s, 3H), 2.27 (dd, J=13.6, 7.3 Hz, 1H), 2.18 (dd, J=13.6, 6.6 Hz, 1H), 1.64 (br s, 1H), 1.56 (br s, 1H), 1.49 (br s, 4H), 1.36 (d, J=12.1 Hz, 1H), 1.11 (s, 9H), 1.07-0.98 (m, 3H), 0.88-0.72 (m, 4H), 0.67-0.52 (m, 4H). LCMS (M+H)=645.3.

EXAMPLE 173

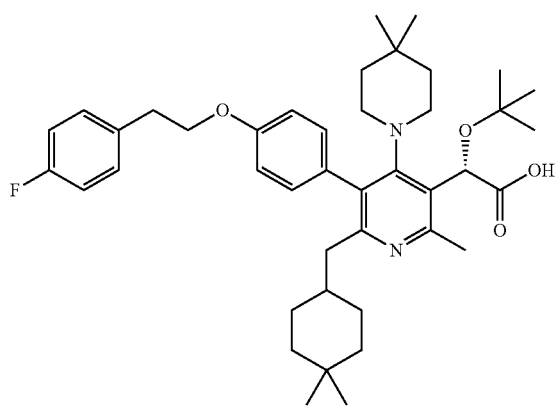 [SMILES: Cc1nc(CC2CCC(C)(C)CC2)c(-c2ccc(OCCc3ccc(F)cc3)cc2)c(N2CCC(C)(C)CC2)c1[C@H](OC(C)(C)C)C(=O)O]

(S)-2-(tert-Butoxy)-2-(6-((4,4-dimethylcyclohexyl)methyl)-4-(4,4-dimethylpiperidin-1-yl)-5-(4-(4-fluorophenethoxy)phenyl)-2-methylpyridin-3-yl)acetic acid: A mixture of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (37 mg, 0.055 mmol), 2-(4,4-dimethylcyclohex-1-en-1-yl)-4,4,5,5-tetramethyl-1,3,2-dioxaborolane (51.7 mg, 0.219 mmol), DPPF (6.07 mg, 10.9 μmol) and $Cs_2CO_3$ (35.6 mg, 0.109 mmol) in DMF (1 mL) was degassed and charged with $N_2$ (3×). The mixture was placed in a pre-heated oil bath 90° C. and allowed to stir at this temperature for 2 h. The reaction mixture was cooled to room temperature, diluted with EtOAc washed with water, brine, dried ($Na_2SO_4$), filtered, concentrated, adsorbed onto Celite and purified on a silica column (EtOAc/Hex: 0 to 50%) to afford (S)-isopropyl 2-(tert-butoxy)-2-(6-((4,4-dimethylcyclohex-1-en-1-yl)methyl)-4-(4,4-dimethylpiperidin-1-yl)-5-(4-(4-fluorophenethoxy)phenyl)-2-methylpyridin-3-yl)acetate (9 mg, 0.013 mmol, 23% yield) as a colorless oil. (S)-Isopropyl 2-(tert-butoxy)-2-(6-((4,4-dimethylcyclohex-1-en-1-yl)methyl)-4-(4,4-dimethylpiperidin-1-yl)-5-(4-(4-fluorophenethoxy)phenyl)-2-methylpyridin-3-yl)acetate was taken up in ethanol (1 mL) and Pd-C (1.34 mg, 12.6 mol) was added. The mixture was evacuated and charged with $H_2$ (3×). The mixture was then stirred under an $H_2$ balloon for 2 h. LCMS shows conversion to the reduced product (S)-isopropyl 2-(tert-butoxy)-2-(6-((4,4-dimethylcyclohexyl)methyl)-4-(4,4-dimethylpiperidin-1-yl)-5-(4-(4-fluorophenethoxy)phenyl)-2-methylpyridin-3-yl)acetate. The solution was filtered and to the filtrate was added NaOH (5 M) (0.02 mL, 100 μmol). The solution was then heated to 80° C. and stirred overnight. LCMS shows conversion to the desired acid. The solution was cooled to room temperature and purified by preparative HPLC to afford (S)-2-(tert-butoxy)-2-(6-((4,4-dimethylcyclohexyl)methyl)-4-(4,4-dimethylpiperidin-1-yl)-5-(4-(4-fluorophenethoxy)phenyl)-2-methylpyridin-3-yl)acetic acid (4.4 mg, 6.5 μmol, 52% yield). ¹H NMR (500 MHz, DMSO-d6) δ 7.34 (dd, J=8.3, 5.7 Hz, 2H), 7.18-7.07 (m, 3H), 7.05-6.94 (m, 3H), 5.80 (s, 1H), 4.24 (q, J=6.6 Hz, 2H), 3.04 (t, J=6.4 Hz, 2H), 2.45 (s, 3H), 2.30 (dd, J=13.6, 7.0 Hz, 1H), 2.21 (dd, J=13.4, 6.4 Hz, 2H), 1.90 (s, 2H), 1.56 (br s, 1H), 1.34 (d, J=11.7 Hz, 1H), 1.28-1.14 (m, 5H), 1.12 (s, 9H), 1.08-0.92 (m, 4H), 0.88-0.82 (m, 2H), 0.81 (s, 4H), 0.75 (s, 4H), 0.58 (br s, 2H). LCMS (M+H)=673.3.

EXAMPLE 174

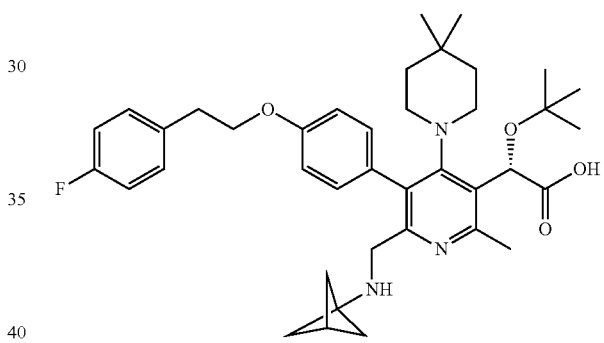

(S)-2-(6-((Bicyclo[1.1.1]pentan-1-ylamino)methyl)-4-(4,4-dimethylpiperidin-1-yl)-5-(4-(4-fluorophenethoxy)phenyl)-2-methylpyridin-3-yl)-2-(tert-butoxy)acetic acid: A solution of (S)-isopropyl 2-(6-(bromomethyl)-4-(4,4-dimethylpiperidin-1-yl)-5-(4-(4-fluorophenethoxy)phenyl)-2-methylpyridin-3-yl)-2-(tert-butoxy)acetate (11 mg, 0.016 mmol), bicyclo[1.1.1]pentan-1-amine (6.7 mg, 0.080 mmol) and N-ethyl-N-isopropylpropan-2-amine (16.6 mg, 0.129 mmol) in EtOH (1 mL) was stirred for 48 h. Next, NaOH (5 M) (0.032 mL, 0.161 mmol) was added. The reaction mixture was heated to 80° C. and then stirred at this temperature overnight. LCMS shows conversion to the desired acid. The solution was cooled to room temperature and purified by preparative HPLC to (S)-2-(6-((bicyclo[1.1.1]pentan-1-ylamino)methyl)-4-(4,4-dimethylpiperidin-1-yl)-5-(4-(4-fluorophenethoxy)phenyl)-2-methylpyridin-3-yl)-2-(tert-butoxy)acetic acid (2.7 mg, 4.2 μmol, 26% yield). ¹H NMR (500 MHz, DMSO-d6) δ 7.42-7.33 (m, 2H), 7.24 (d, J=7.7 Hz, 1H), 7.13 (t, J=8.8 Hz, 2H), 7.09-6.95 (m, 3H), 5.81 (br s, 1H), 4.23 (dt, J=13.5, 6.6 Hz, 2H), 3.11-2.99 (m, 2H), 2.47-2.42 (m, 3H), 1.90 (s, 2H), 1.56-1.45 (m, 4H), 1.23 (s, 5H), 1.18 (br s, 1H), 1.16-1.06 (m, 9H), 0.84 (br s, 3H), 0.60 (br s, 3H). LCMS (M+H)=644.3.

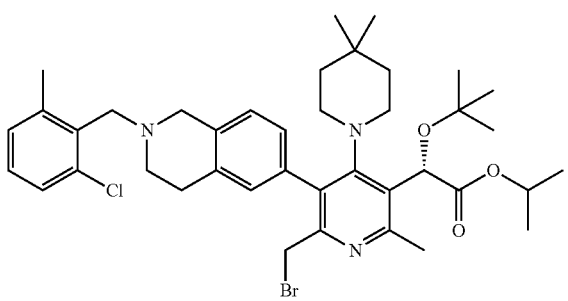 [SMILES: Cc1cccc(Cl)c1CN1CCc2cc(-c3c(CBr)nc(C)c([C@H](OC(C)(C)C)C(=O)OC(C)C)c3N3CCC(C)(C)CC3)ccc2C1]

Isopropyl (S)-2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate: (S)-Isopropyl 2-(5-bromo-4-(4,4-dimethylpiperidin-1-yl)-6-(hydroxymethyl)-2-methylpyridin-3-yl)-2-(tert-butoxy)acetate (0.50 g, 1.0 mmol), 2-(2-chloro-6-methylbenzyl)-6-(4,4,5,5-tetramethyl-1,3,2-dioxaborolan-2-yl)-1,2,3,4-tetrahydroisoquinoline (0.41 g, 1.0 mmol), 2-dicyclohexylphosphino-2',6'-dimethoxybiphenyl (0.085 g, 0.21 mmol), Pd(OAc)$_2$ (0.023 g, 0.10 mmol) and potassium phosphate tribasic (1.64 g, 7.72 mmol) were combined under N$_2$. 1,4-Dioxane (17.1 ml) and water (3.43 ml) were added under N$_2$. The reaction was heated at 80° C. with stirring for 2 h. The reaction mixture was concentrated, adsorbed onto Celite and was purified on silica gel (Biotage, EtOAc/hexanes gradient, 0-100% over 10 CVs) to afford (S)-isopropyl 2-(tert-butoxy)-2-(5-(2-(2-chloro-6-methylbenzyl)-1,2,3,4-tetrahydroisoquinolin-6-yl)-4-(4,4-dimethylpiperidin-1-yl)-6-(hydroxymethyl)-2-methylpyridin-3-yl)acetate (0.420 g, 0.621 mmol, 60% yield). To a solution of (S)-isopropyl 2-(tert-butoxy)-2-(5-(2-(2-chloro-6-methylbenzyl)-1,2,3,4-tetrahydroisoquinolin-6-yl)-4-(4,4-dimethylpiperidin-1-yl)-6-(hydroxymethyl)-2-methylpyridin-3-yl)acetate (400 mg, 0.591 mmol) in CH$_2$Cl$_2$ (5 mL) was added CBr$_4$ (255 mg, 0.769 mmol) followed by Ph$_3$P (202 mg, 0.769 mmol). The resulting mixture was stirred at room temperature for 2 h. Water (20 mL) was then added and the mixture was extracted with dichloromethane (2×20 mL), dried (Na$_2$SO$_4$), filtered and concentrated. The residue was then adsorbed onto Celite and then purified by Biotage (5-30% EtOAc/hexane) to afford (S)-isopropyl 2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate (135 mg, 0.183 mmol, 31% yield) as a mixture of diastereomers. $^1$H NMR (500 MHz, DMSO-d6) δ 7.26-7.04 (m, 5H), 6.96-6.87 (m, 1H), 6.04 (br s, 1H), 5.17-5.01 (m, 1H), 4.41-4.27 (m, 1H), 4.21 (d, J=9.3 Hz, 1H), 3.91-3.69 (m, 3H), 3.23-3.11 (m, 1H), 2.93-2.76 (m, 4H), 2.63-2.57 (m, 3H), 2.53-2.45 (m, 3H), 2.21 (d, J=11.0 Hz, 1H), 1.89 (t, J=11.8 Hz, 1H), 1.59 (br s, 3H), 1.52 (br s, 1H), 1.28-1.20 (m, 7H), 1.18 (d, J=2.7 Hz, 9H), 0.89 (br s, 3H), 0.69-0.58 (m, 3H). LCMS (M+H)=738.1, 740.1.

EXAMPLE 175

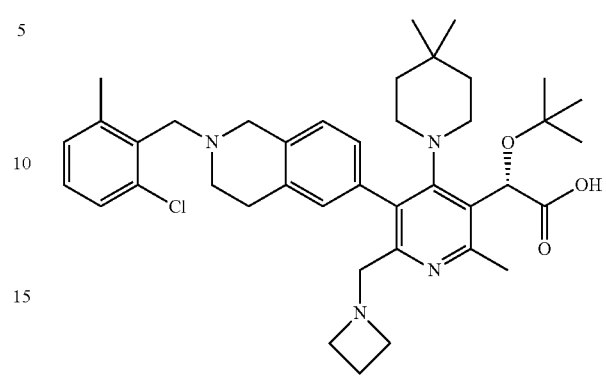

(S)-2-(6-(Azetidin-1-ylmethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid: A solution of (S)-isopropyl 2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate (20 mg, 0.027 mmol), azetidine (15.5 mg, 0.271 mmol) and N-ethyl-N-isopropylpropan-2-amine (28 mg, 0.22 mmol) in EtOH (1 mL) was stirred at room temperature overnight. NaOH (5 M) (0.054 mL, 0.27 mmol) was added. The reaction mixture was then heated to 80° C. and stirred at this temperature for 2 h. The mixture was then cooled to room temperature and purified by prep HPLC to afford (S)-2-(6-(azetidin-1-ylmethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid (12.5 mg, 0.0190 mmol, 69% yield) as a mixture of diastereomers. $^1$H NMR (500 MHz, DMSO-d6) δ 7.29 (d, J=7.3 Hz, 1H), 7.25-7.16 (m, 2H), 7.14-7.07 (m, 2H), 6.86-6.80 (m, 1H), 5.63 (d, J=12.1 Hz, 1H), 3.85-3.77 (m, 1H), 3.71-3.61 (m, 1H), 3.50 (br s, 1H), 2.79 (br s, 3H), 2.73 (d, J=7.0 Hz, 2H), 2.47-2.40 (m, 8H), 2.08-1.99 (m, 3H), 1.89 (s, 7H), 1.48 (br s, 2H), 1.22 (s, 8H), 1.07 (s, 11H), 0.86-0.79 (m, 3H), 0.58 (br s, 3H). LCMS (M+H)=673.3.

EXAMPLE 176

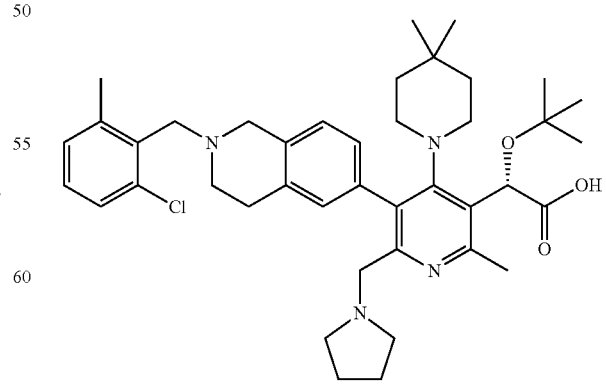

(S)-2-(tert-Butoxy)-2-(5-(2-(2-chloro-6-methylbenzyl)-1,2,3,4-tetrahydroisoquinolin-6-yl)-4-(4,4-dimethylpiperidin- 1-yl)-2-methyl-6-(pyrrolidin-1-ylmethyl)pyridin-3-yl)acetic acid: A solution of (S)-isopropyl 2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate (20 mg, 0.027 mmol), pyrrolidine (19.2 mg, 0.271 mmol) and N-ethyl-N-isopropylpropan-2-amine (28.0 mg, 0.216 mmol) in EtOH (1 mL) was stirred at room temperature overnight. Next, NaOH (5 M) (0.054 mL, 0.27 mmol) was added. The reaction mixture was heated to 80° C. and allowed to stir at this temperature for 2 h. The reaction mixture was then cooled to room temperature and purified by prep HPLC to afford (S)-2-(tert-butoxy)-2-(5-(2-(2-chloro-6-methylbenzyl)-1,2,3,4-tetrahydroisoquinolin-6-yl)-4-(4,4-dimethylpiperidin-1-yl)-2-methyl-6-(pyrrolidin-1-ylmethyl)pyridin-3-yl)acetic acid (12 mg, 0.017 mmol, 63% yield) as a mixture of diastereomers. $^1$H NMR (500 MHz, DMSO-d6) δ 7.29 (d, J=7.7 Hz, 1H), 7.26-7.14 (m, 4H), 7.13-7.04 (m, 1H), 6.88-6.75 (m, 1H), 5.71 (d, J=12.1 Hz, 1H), 3.85-3.75 (m, 2H), 3.73-3.62 (m, 1H), 2.84-2.70 (m, 5H), 2.59 (br. s., 2H), 2.48-2.45 (m, 3H), 2.45-2.40 (m, 4H), 2.06 (br. s., 1H), 1.90 (s, 2H), 1.65 (d, J=4.8 Hz, 5H), 1.47 (br. s., 1H), 1.22 (s, 3H), 1.16 (d, J=9.9 Hz, 1H), 1.08 (s, 10H), 0.96 (br s, 1H), 0.88-0.80 (m, 3H), 0.64-0.55 (m, 3H). LCMS (M+H)=687.3.

EXAMPLE 177

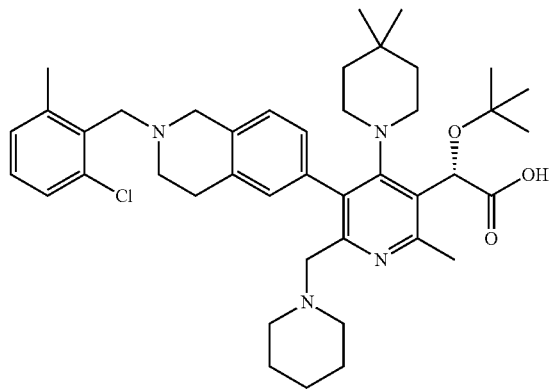 [SMILES: Cc1cccc(Cl)c1CN1CCc2cc(-c3c(CN4CCCCC4)nc(C)c([C@H](OC(C)(C)C)C(=O)O)c3N3CCC(C)(C)CC3)ccc2C1]

(S)-2-(tert-Butoxy)-2-(5-(2-(2-chloro-6-methylbenzyl)-1,2,3,4-tetrahydroisoquinolin-6-yl)-4-(4,4-dimethylpiperidin-1-yl)-2-methyl-6-(piperidin-1-ylmethyl)pyridin-3-yl)acetic acid: A solution of (S)-isopropyl 2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate (20 mg, 0.027 mmol), piperidine (23.0 mg, 0.271 mmol) and N-ethyl-N-isopropylpropan-2-amine (28.0 mg, 0.216 mmol) in EtOH (1 mL) was stirred at room temperature overnight. Next, NaOH (5 M) (0.054 mL, 0.27 mmol) was added. The reaction mixture was heated to 80° C. and allowed to stir at this temperature for 2 h. The reaction mixture was then cooled to room temperature and purified by prep HPLC to afford (S)-2-(tert-butoxy)-2-(5-(2-(2-chloro-6-methylbenzyl)-1,2,3,4-tetrahydroisoquinolin-6-yl)-4-(4,4-dimethylpiperidin-1-yl)-2-methyl-6-(piperidin-1-ylmethyl)pyridin-3-yl)acetic acid (12 mg, 0.018 mmol, 65% yield) as a mixture of diastereomers. $^1$H NMR (500 MHz, DMSO-d6) δ 7.29 (d, J=7.7 Hz, 1H), 7.25-7.13 (m, 3H), 7.13-7.01 (m, 1H), 6.85-6.77 (m, 1H), 5.78 (d, J=4.8 Hz, 1H), 3.83-3.71 (m, 1H), 3.70-3.58 (m, 1H), 3.32 (d, J=7.3 Hz, 1H), 3.22-3.14 (m, 1H), 3.14-2.99 (m, 1H), 2.84-2.70 (m, 4H), 2.46-2.36 (m, 7H), 2.34-2.22 (m, 3H), 2.18 (br s, 1H), 2.05 (br s, 1H), 1.90 (s, 1H), 1.47 (br s, 1H), 1.38 (br s, 4H), 1.29 (br s, 2H), 1.22 (s, 3H), 1.17 (br s, 1H), 1.09 (s, 10H), 0.96 (d, J=10.3 Hz, 1H), 0.82 (br s, 3H), 0.57 (br s, 3H). LCMS (M+H)=701.3.

EXAMPLE 178

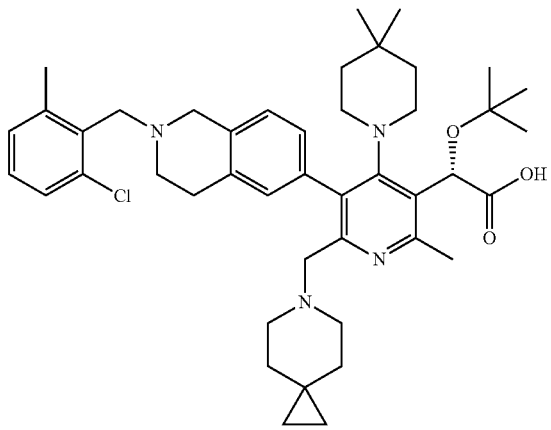 [SMILES: Cc1cccc(Cl)c1CN1CCc2cc(-c3c(CN4CCC5(CC4)CC5)nc(C)c([C@H](OC(C)(C)C)C(=O)O)c3N3CCC(C)(C)CC3)ccc2C1]

(S)-2-(6-(((6-Azaspiro[2.5]octan-6-yl)methyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid: A solution of (S)-isopropyl 2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate (20 mg, 0.027 mmol), 6-azaspiro[2.5]octane (30 mg, 0.27 mmol) and N-ethyl-N-isopropylpropan-2-amine (28 mg, 0.22 mmol) in EtOH (1 mL) was stirred at room temperature overnight. Next, NaOH (0.054 mL, 0.27 mmol) was added. The reaction mixture was heated to 80° C. and allowed to stir at this temperature for 2 h. The mixture was cooled to room temperature and then purified by prep HPLC to afford (S)-2-(6-(6-azaspiro[2.5]octan-6-ylmethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid (12 mg, 0.016 mmol, 61% yield) as a mixture of diastereomers. $^1$H NMR (500 MHz, DMSO-d6) δ 7.33-7.25 (m, 1H), 7.25-7.15 (m, 3H), 7.12-7.01 (m, 1H), 6.85-6.78 (m, 1H), 5.80 (br s, 1H), 3.83-3.76 (m, 1H), 3.71-3.62 (m, 1H), 3.37-3.25 (m, 1H), 3.21 (br s, 1H), 3.10 (d, J=7.7 Hz, 1H), 2.86-2.68 (m, 4H), 2.46-2.39 (m, 6H), 2.36 (br s, 1H), 2.34-2.24 (m, 2H), 2.20 (br s, 1H), 2.08 (br s, 1H), 1.90 (s, 3H), 1.47 (br s, 1H), 1.22 (s, 5H), 1.18 (br s, 3H), 1.09 (s, 9H), 0.96 (d, J=10.6 Hz, 1H), 0.83 (br. s., 3H), 0.64-0.55 (m, 3H), 0.17 (s, 4H). LCMS (M+H)=727.3.

EXAMPLE 179

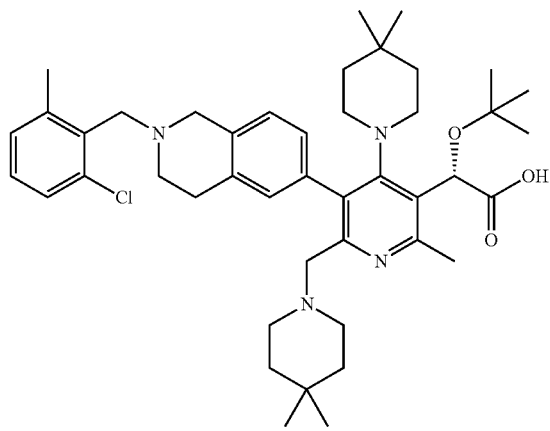 [SMILES: Cc1cccc(Cl)c1CN1CCc2cc(-c3c(CN4CCC(C)(C)CC4)nc(C)c([C@H](OC(C)(C)C)C(=O)O)c3N3CCC(C)(C)CC3)ccc2C1]

(S)-2-(tert-Butoxy)-2-(5-(2-(2-chloro-6-methylbenzyl)-1,2,3,4-tetrahydroisoquinolin-6-yl)-4-(4,4-dimethylpiperidin-1-yl)-6-((4,4-dimethylpiperidin-1-yl)methyl)-2-methylpyridin-3-yl)acetic acid: A solution of (S)-isopropyl 2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate (20 mg, 0.027 mmol), 4,4-dimethylpiperidine (30 mg, 0.27 mmol) and N-ethyl-N-isopropylpropan-2-amine (28 mg, 0.22 mmol) in EtOH (1 mL) was stirred at room temperature overnight. Next, NaOH (5 M) (0.054 mL, 0.27 mmol) was added. The reaction mixture was heated to 80° C. and allowed to stir at this temperature for 2 h. Finally, the mixture was cooled to room temperature and then purified by prep HPLC to afford (S)-2-(tert-butoxy)-2-(5-(2-(2-chloro-6-methylbenzyl)-1,2,3,4-tetrahydroisoquinolin-6-yl)-4-(4,4-dimethylpiperidin-1-yl)-6-((4,4-dimethylpiperidin-1-yl)methyl)-2-methylpyridin-3-yl)acetic acid (8.2 mg, 0.011 mmol, 42% yield) as a mixture of diastereomers. $^1$H NMR (500 MHz, DMSO-d6) δ 7.31-7.14 (m, 4H), 7.11-6.99 (m, 1H), 6.86-6.76 (m, 1H), 5.75 (d, J=4.8 Hz, 1H), 3.85-3.74 (m, 1H), 3.71-3.58 (m, 1H), 3.41-3.29 (m, 1H), 3.29-3.19 (m, 1H), 2.86-2.68 (m, 5H), 2.46-2.40 (m, 5H), 2.40-2.16 (m, 5H), 2.06 (br s, 1H), 1.46 (br s, 2H), 1.32-1.13 (m, 9H), 1.08 (s, 11H), 0.95 (d, J=11.0 Hz, 1H), 0.82 (s, 11H), 0.64-0.54 (m, 3H). LCMS (M+H)=729.3.

EXAMPLE 180

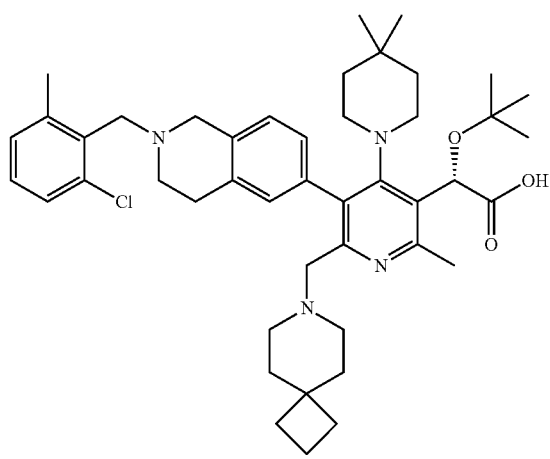 [SMILES: Cc1cccc(Cl)c1CN1CCc2cc(-c3c(CN4CCC5(CCC5)CC4)nc(C)c([C@H](OC(C)(C)C)C(=O)O)c3N3CCC(C)(C)CC3)ccc2C1]

(S)-2-(6-((7-Azaspiro[3.5]nonan-7-yl)methyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid: A solution of (S)-isopropyl 2-(6-(bromomethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetate (20 mg, 0.027 mmol), 7-azaspiro[3.5]nonane (33.9 mg, 0.271 mmol) and N-ethyl-N-isopropylpropan-2-amine (28 mg, 0.22 mmol) in EtOH (1 mL) was stirred at room temperature overnight. Next, NaOH (5 M) (0.054 mL, 0.27 mmol) was added. The reaction mixture was heated to 80° C. and allowed to stir at this temperature for 2 h. The reaction mixture was then cooled to room temperature and purified by prep HPLC to afford (S)-2-(6-(7-azaspiro[3.5]nonan-7-ylmethyl)-5-(2-(2-chloro-6-methylbenzyl)-1,2,3,4-tetrahydroisoquinolin-6-yl)-4-(4,4-dimethylpiperidin-1-yl)-2-methylpyridin-3-yl)-2-(tert-butoxy)acetic acid as a mixture of diastereomers. $^1$H NMR (500 MHz, DMSO-d6) δ 7.29 (d, J=7.3 Hz, 1H), 7.26-7.13 (m, 3H), 7.09-6.99 (m, 1H), 6.85-6.75 (m, 1H), 5.77 (br s, 1H), 3.83-3.75 (m, 1H), 3.70-3.61 (m, 1H), 3.40-3.27 (m, 1H), 3.21-3.09 (m, 1H), 2.83-2.70 (m, 5H), 2.45-2.39 (m, 7H), 2.26 (d, J=7.3 Hz, 1H), 2.16 (br s, 2H), 2.09 (br s, 1H), 1.79-1.72 (m, 3H), 1.64-1.56 (m, 4H), 1.41 (br s, 5H), 1.22 (s, 3H), 1.17 (br s, 1H), 1.09 (s, 10H), 0.95 (d, J=11.0 Hz, 1H), 0.85-0.80 (m, 3H), 0.63-0.54 (m, 3H). LCMS (M+H)=741.3.

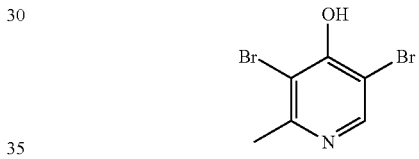

3,5-Bibromo-2-methylpyridin-4-ol: To a stirred solution of 2-methylpyridin-4-ol (5 g, 45.8 mmol) in DCM (56.4 ml) and MeOH (6.80 ml) was added tert-butylamine (9.81 ml, 93 mmol) and cooled to 0° C. Bromine (4.72 ml, 92 mmol) was added dropwise over 60 minutes. The reaction mixture was stirred at room temperature for 3 hours. The reaction mixture was filtered through a fine frit filter and the solid white material dried under vacuum for 18 hrs. $^1$H NMR (500 MHz, DMSO-d$_6$) δ 12.32 (br. s., 1H), 8.21 (s, 1H), 2.40 (s, 3H). LCMS (M+H)=267.7.

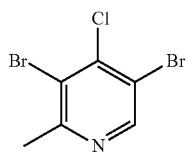

3,5-Dibromo-4-chloro-2-methylpyridine: To a solution of 3,5-dibromo-2-methylpyridin-4-ol (13.12 g, 49.2 mmol) in POCl$_3$ (13.74 ml, 147 mmol) was added triethylamine (6.85 ml, 49.2 mmol) at 0° C. slowly over 80 min. After addition ice bath was removed, and the reaction was heated to 80° C. and stirred for 3 h. The reaction mixture was then cooled and slowly quenched by adding it to crushed ice. The resulting suspension was extracted with DCM (250 ml). The organic layer was washed with saturated NaHCO$_3$ solution (250 mL) followed by water (250 mL) and brine (250 mL). The organic layer was dried (MgSO$_4$), filtered and concentrated to get 3,5-dibromo-4-chloro-2-methylpyridine (14.7 g, 51.5 mmol, 105% yield) as a off white solid. ¹H NMR (500 MHz, CDCl₃) δ 8.55 (s, 1H), 2.72 (s, 3H). LCMS (M+H)=285.7.

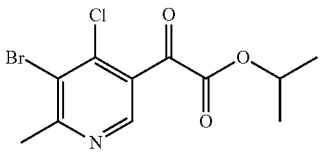 [SMILES: Cc1ncc(C(=O)C(=O)OC(C)C)c(Cl)c1Br]

Isopropyl 2-(5-bromo-4-chloro-6-methylpyridin-3-yl)-2-oxoacetate: To a −78° C. solution of 3,5-dibromo-4-chloro-2-methylpyridine (9.42 g, 33.0 mmol) and copper(I) bromide-dimethyl sulfide complex (0.339 g, 1.651 mmol) in THF (75 mL) was added dropwise isopropylmagnesium chloride (17.33 mL, 34.7 mmol) over 20 min. The reaction was allowed to warm to −10° C. for 60 min. The reaction mixture was then transferred via cannula to another flask containing a solution of isopropyl 2-chloro-2-oxoacetate (4.97 g, 33.0 mmol) in THF (75 ml) at −60° C. and allowed to warm to −10° C. for 2.5 hr. The reaction was then quenched with 10% solution of ammonium chloride and diethyl ether. The organic layer was washed with brine, collected, dried (MgSO₄), filtered and volatiles evaporated to give the crude material. The crude material was purified via silica gel (330 g column, 10-40% EtOAc:Hex) to give the product isopropyl 2-(5-bromo-4-chloro-6-methylpyridin-3-yl)-2-oxoacetate (3.45 g, 9.15 mmol, 27.7% yield) as a yellow oil that later solidified. ¹H NMR (500 MHz, METHANOL-d₄) δ 8.79 (s, 1H), 5.09 (dt, J=12.6, 6.2 Hz, 1H), 2.76 (s, 3H), 1.24-1.22 (m, 3H), 1.20 (d, J=6.3 Hz, 3H). LCMS (M+H)=321.8.

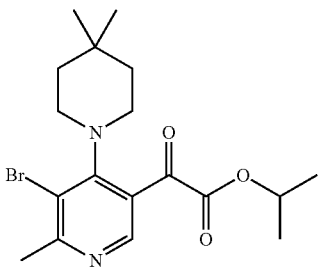 [SMILES: Cc1ncc(C(=O)C(=O)OC(C)C)c(N2CCC(C)(C)CC2)c1Br]

Isopropyl 2-(5-bromo-4-(4,4-dimethylpiperidin-1-yl)-6-methylpyridin-3-yl)-2-oxoacetate: To a 40 mL vial equipped with a stir bar was added isopropyl 2-(5-bromo-4-chloro-6-methylpyridin-3-yl)-2-oxoacetate (5 g, 15.60 mmol), DIPEA (3.00 ml, 17.16 mmol) and acetonitrile (10.40 ml), then 4,4-dimethylpiperidine (1.942 g, 17.16 mmol). The vial was capped and then placed in a heating block at 85° C. with stirring. LCMS analysis after 18 hrs found complete conversion. The reaction mixture was dissolved in Et₂O (100 mL) and water (100 mL) and transferred to a 500 mL separatory funnel. The mixture was agitated; the phases were separated. The aq. phase was back extracted with Et₂O (100 mL). The combined organics were washed with brine (50 mL). The solution was dried over MgSO₄; filtered; then concentrated in vacuo. The crude product was purified via silica gel purification (120 g column, 0-30% EtOAc:Hex) to give the product isopropyl 2-(5-bromo-4-(4,4-dimethylpiperidin-1-yl)-6-methylpyridin-3-yl)-2-oxoacetate (4.56 g, 11.48 mmol, 73.6% yield) as a yellow oil that partially solidified. ¹H NMR (500 MHz, CDCl₃) δ 8.45 (s, 1H), 5.26 (dt, J=12.5, 6.3 Hz, 1H), 3.20-3.14 (m, 4H), 2.76 (s, 3H), 1.52-1.48 (m, 4H), 1.42 (d, J=6.3 Hz, 6H), 1.04 (s, 6H). LCMS (M+H)=399.0.

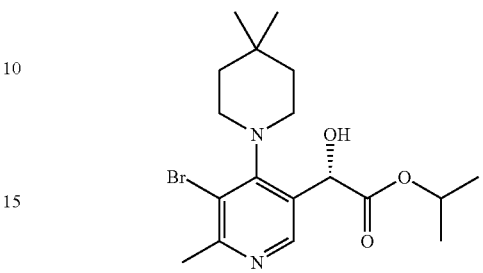

(S)-Isopropyl 2-(5-bromo-4-(4,4-dimethylpiperidin-1-yl)-6-methylpyridin-3-yl)-2-hydroxyacetate: To a 100 mL r.b. flask equipped with a stir bar was added isopropyl 2-(5-bromo-4-(4,4-dimethylpiperidin-1-yl)-6-methylpyridin-3-yl)-2-oxoacetate (2.5 g, 6.29 mmol). The flask was fitted with a rubber septum and then placed under N₂ atm (vac/fill ×3). To the flask was added toluene (17.98 ml). The flask was placed in a −35° C. bath (dichloroethane/dry ice). A thermometer was used to monitor the internal temperature. When the internal temp was −30° C., to the flask was added (R)-1-methyl-3,3-diphenylhexahydropyrrolo[1,2-c][1,3,2]oxazaborole (0.944 ml, 0.944 mmol). No exotherm was noted. To the stirred solution was added catecholborane (1.886 ml, 8.81 mmol) over 2 minutes. During the addition the temperature rose by 2° C. Within 5 minutes following the addition the temperature rose to −25° C. before falling to −30° C. The solution was stirred at −30° C. for 3 h. The flask was transferred to a −15 to −12° C. cold bath (chiller/circulator). The yellow solution was stirred for 1 day at −15 to −12° C. After 1 day, the solution was observed to be yellow in color; LCMS analysis indicated complete conversion, where a major peak corresponded to the desired product. The presence of two additional significant peaks which do not ionize well is consistent with the presence of the CBS catalyst and catechol. The reaction was quenched with 5 mL of 2M aq. sodium carbonate. The reaction was then diluted with 100 mL EtOAc and 100 mL 2M aq sodium carbonate and stirred vigorously for 2 hrs. The layers were separated and the organic layer collected and stirred vigorously for an additional 1 hr. The organic layer was washed with brine, dried over MgSO₄, filtered and evaporated to give the crude product. The crude product was purified on silica gel chromatography (80 g column, 10-40% EtOAc:Hex) to afford the product (S)-isopropyl 2-(5-bromo-4-(4,4-dimethylpiperidin-1-yl)-6-methylpyridin-3-yl)-2-hydroxyacetate (2 g, 5.01 mmol, 80% yield) as a yellow oil that solidified at RT. ¹H NMR (500 MHz, CDCl₃) δ 8.33 (s, 1H), 5.31 (d, J=6.9 Hz, 1H), 5.13-5.03 (m, 2H), 3.80 (br. s., 2H), 2.87-2.75 (m, 1H), 2.71 (s, 3H), 2.69-2.60 (m, 1H), 1.71-1.59 (m, 2H), 1.43 (d, J=14.8 Hz, 2H), 1.28 (d, J=6.1 Hz, 3H), 1.16 (d, J=6.3 Hz, 3H), 1.04 (s, 3H), 1.08 (s, 3H). LCMS (M+H)=399.0.

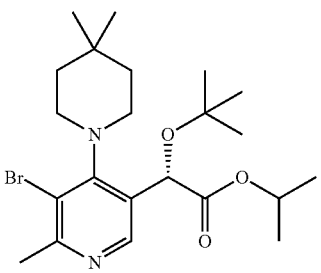 [SMILES: Cc1ncc([C@H](OC(C)(C)C)C(=O)OC(C)C)c(N2CCC(C)(C)CC2)c1Br]

(S)-Isopropyl 2-(5-bromo-4-(4,4-dimethylpiperidin-1-yl)-6-methylpyridin-3-yl)-2-(tert-butoxy)acetate: In a 250 ml round bottom flask fitted with a shlenk adaptor with rubber septum (with empty balloon attached), Isobutylene gas was vigorously bubbled for 30 minutes into a 0° C. solution of (S)-isopropyl 2-(5-bromo-4-(4,4-dimethylpiperidin-1-yl)-6-methylpyridin-3-yl)-2-hydroxyacetate (2 g, 5.01 mmol) and perchloric acid (0.861 mL, 10.02 mmol) in DCM (100 mL) until the volume doubled and the balloon filled to firmness. After 2 hrs, the isobutylene line was disconnected and needle pulled to just above the solution line then connected to a bubbler to monitor isobutylene gas exit. The ice bath was removed and warmed up to RT while monitoring for conversion. After 2 hrs the reaction appeared to go to full conversion according to LCMS. The reaction mixture was poured into a 1 L Erlenmeyer flask and made basic with 2M sodium carbonate while vigorously stirring. The organic layer was separated and washed with water, followed by brine, collected, dried (MgSO$_4$), filtered and volatiles evaporated to afford the crude product. The crude product was purified on silica gel (40 g column, 5-40% EtOAc:Hex) to afford the product (S)-isopropyl 2-(5-bromo-4-(4,4-dimethylpiperidin-1-yl)-6-methylpyridin-3-yl)-2-(tert-butoxy)acetate (1.95 g, 4.28 mmol, 85% yield) as a clear oil that later crystallized to a white solid. $^1$H NMR (500 MHz, CDCl$_3$) δ 8.61 (s, 1H), 5.61 (s, 1H), 5.01 (dt, J=12.5, 6.3 Hz, 1H), 3.81 (t, J=10.9 Hz, 1H), 3.60 (t, J=11.0 Hz, 1H), 2.76 (d, J=11.5 Hz, 1H), 2.69 (s, 3H), 2.64 (d, J=12.1 Hz, 1H), 1.63-1.51 (m, 2H), 1.46 (d, J=11.2 Hz, 1H), 1.38 (d, J=14.2 Hz, 1H), 1.26-1.22 (m, 12H), 1.20 (d, J=6.1 Hz, 3H), 1.09-1.03 (m, 6H). LCMS (M+H)=457.1.

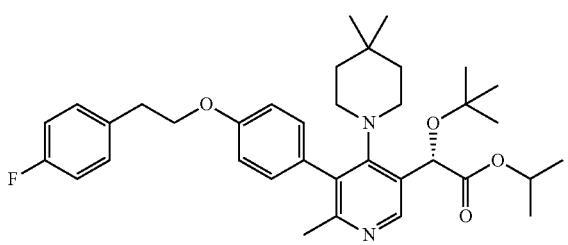 [SMILES: Cc1ncc([C@H](OC(C)(C)C)C(=O)OC(C)C)c(N2CCC(C)(C)CC2)c1-c1ccc(OCCc2ccc(F)cc2)cc1]

(S)-Isopropyl 2-(tert-butoxy)-2-(4-(4,4-dimethylpiperidin-1-yl)-5-(4-(4-fluorophenethoxy)phenyl)-6-methylpyridin-3-yl)acetate: To a solution of (S)-isopropyl 2-(5-bromo-4-(4,4-dimethylpiperidin-1-yl)-6-methylpyridin-3-yl)-2-(tert-butoxy)acetate (1 g, 2.196 mmol), (4-(4-fluorophenethoxy)phenyl)boronic acid (0.857 g, 3.29 mmol), 2-dicyclohexylphosphino-2',6'-dimethoxybiphenyl (0.180 g, 0.439 mmol), and potassium phosphate tribasic (3.50 g, 16.47 mmol) in 1,4-dioxane (36.6 ml) and water (7.32 ml) under N$_2$ was added Pd(OAc)$_2$ (0.049 g, 0.220 mmol). The reaction was heated at 80° C. for 2 h. The reaction was cooled, diluted with water and extracted with EtOAc. The organic layer was washed with brine, collected, dried over MgSO$_4$, filtered and volatiles evaporated to afford the crude product. The crude product was purified on silica gel (40 g column, 5-50% EtOAc:Hex) to give the product (S)-isopropyl 2-(tert-butoxy)-2-(4-(4,4-dimethylpiperidin-1-yl)-5-(4-(4-fluorophenethoxy)phenyl)-6-methylpyridin-3-yl)acetate (1.15 g, 1.947 mmol, 89% yield) as a brown oil. $^1$H NMR (400 MHz, CDCl$_3$) δ 8.68 (s, 1H), 7.30 (d, J=5.4 Hz, 1H), 7.27 (br. s., 1H), 7.18-7.11 (m, 1H), 7.09-7.01 (m, 3H), 6.98 (d, J=8.8 Hz, 2H), 5.52 (s, 1H), 5.04 (dt, J=12.6, 6.2 Hz, 1H), 4.24 (t, J=7.0 Hz, 2H), 3.13 (t, J=7.0 Hz, 2H), 2.93 (br. s., 1H), 2.65 (br. s., 1H), 2.51 (d, J=7.1 Hz, 1H), 2.39 (br. s., 1H), 2.23 (s, 3H), 1.41-1.31 (m, 1H), 1.27 (d, J=6.1 Hz, 4H), 1.25 (s, 9H), 1.23 (d, J=6.1 Hz, 4H), 1.16-1.02 (m, 1H), 0.86 (br. s., 3H), 0.72 (br. s., 3H). LCMS (M+H)=591.4.

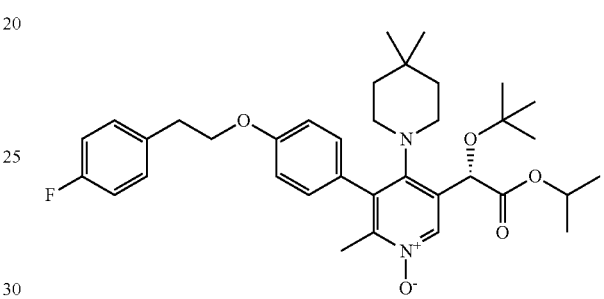

(S)-5-(1-(tert-Butoxy)-2-isopropoxy-2-oxoethyl)-4-(4,4-dimethylpiperidin-1-yl)-3-(4-(4-fluorophenethoxy)phenyl)-2-methylpyridine 1-oxide: To a stirred solution of (S)-isopropyl 2-(tert-butoxy)-2-(4-(4,4-dimethylpiperidin-1-yl)-5-(4-(4-fluorophenethoxy)phenyl)-6-methylpyridin-3-yl)acetate (1.15 g, 1.947 mmol) in DCM (10 ml) was added 77% mCPBA (0.654 g, 2.92 mmol) at rt over 5 min. After 4 h, the reaction mixture was washed with aq. sat. Na$_2$CO$_3$ (3×25 mL), dried (MgSO$_4$), filtered and concentrated to give (S)-5-(1-(tert-butoxy)-2-isopropoxy-2-oxoethyl)-4-(4,4-dimethylpiperidin-1-yl)-3-(4-(4-fluorophenethoxy)phenyl)-2-methylpyridine 1-oxide (1.1 g, 1.813 mmol, 93% yield) which was used in the next step without purification. $^1$H NMR (500 MHz, CDCl$_3$) δ 8.55 (s, 1H), 7.31-7.29 (m, 1H), 7.28-7.27 (m, 1H), 7.13-6.97 (m, 6H), 5.40 (s, 1H), 5.06-4.98 (m, 1H), 4.24 (t, J=6.9 Hz, 2H), 3.13 (t, J=6.9 Hz, 2H), 2.70 (br. s., 1H), 2.58-2.44 (m, 2H), 2.39-2.29 (m, 1H), 2.22 (s, 3H), 1.53-1.35 (m, 2H), 1.27 (s, 3H), 1.25 (s, 9H), 1.24 (s, 3H), 1.19-1.05 (m, 2H), 0.91 (br. s., 3H), 0.64 (br. s., 3H). LCMS (M+H)=607.4.

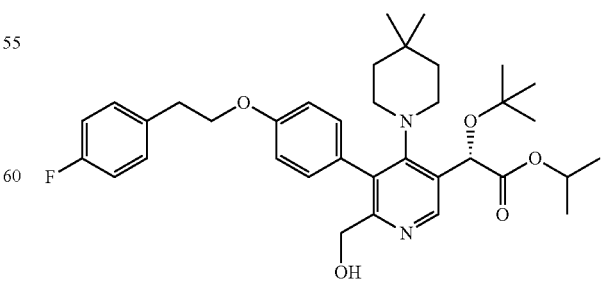

(S)-Isopropyl 2-(tert-butoxy)-2-(4-(4,4-dimethylpiperidin-1-yl)-5-(4-(4-fluorophenethoxy)phenyl)-6-(hydroxymethyl)pyridin-3-yl)acetate: To a stirred solution of (S)-5-(1-(tert-butoxy)-2-isopropoxy-2-oxoethyl)-4-(4,4-dimethylpiperidin-1-yl)-3-(4-(4-fluorophenethoxy)phenyl)-2-methylpyridine 1-oxide (75 mg, 0.124 mmol) anhydrous DMF (2 ml) was added trifluoroacetic anhydride (0.070 ml, 0.494 mmol) at room temperature. After 3 h, sat NaHCO$_3$ (5 mL) was added and the extracted with EtOAc. The organic layer was washed with water (2×), followed by brine, collected, dried over MgSO$_4$, filtered and volatiles evaporated to give the crude product which was purified on silica gel (12 g column, 5-60% EtOAc:Hex) to afford the product (S)-isopropyl 2-(tert-butoxy)-2-(4-(4,4-dimethylpiperidin-1-yl)-5-(4-(4-fluorophenethoxy)phenyl)-6-(hydroxymethyl)pyridin-3-yl)acetate (39 mg, 0.064 mmol, 52.0% yield) as a orange oil. LCMS (M+H)=607.4.

EXAMPLE 181

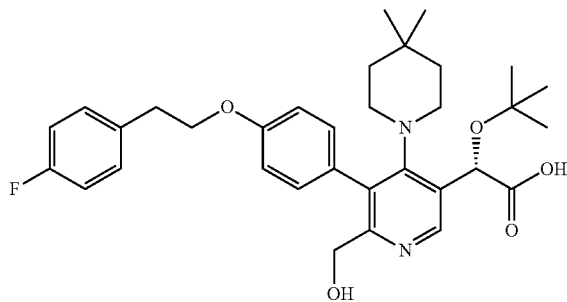 [SMILES: CC1(C)CCN(c2c([C@H](OC(C)(C)C)C(=O)O)cnc(CO)c2-c2ccc(OCCc3ccc(F)cc3)cc2)CC1]

(S)-2-(tert-butoxy)-2-(4-(4,4-dimethylpiperidin-1-yl)-5-(4-(4-fluorophenethoxy)phenyl)-6-(hydroxymethyl)pyridin-3-yl)acetic acid: To a solution of (S)-isopropyl 2-(tert-butoxy)-2-(4-(4,4-dimethylpiperidin-1-yl)-5-(4-(4-fluorophenethoxy)phenyl)-6-(hydroxymethyl)pyridin-3-yl) acetate (39 mg, 0.064 mmol) in EtOH (1mL) and water (0.111 mL) was added lithium hydroxide monohydrate (10.79 mg, 0.257 mmol) and heated at 75° C. for 60 minutes. The reaction was cooled to RT, filtered through a nylon 0.45μ frit filter purified via prep HPLC to afford (S)-2-(tert-butoxy)-2-(4-(4,4-dimethylpiperidin-1-yl)-5-(4-(4-fluorophenethoxy)phenyl)-6-(hydroxymethyl)pyridin-3-yl)acetic acid (18 mg, 0.032 mmol, 49.6% yield) as a lightly colored oil. $^1$H NMR (400 MHz, methanol-d$_4$) δ 8.60 (s, 1H), 7.36 (dd, J=8.6, 5.4 Hz, 2H), 7.31-7.25 (m, 1H), 7.17-7.01 (m, 5H), 5.33 (s, 1H), 4.50 (d, J=15.4 Hz, 1H), 4.30 (d, J=5.1 Hz, 1H), 4.29-4.24 (m, 2H), 3.12 (t, J=6.6 Hz, 2H), 3.05 (br. s., 2H), 2.85 (br. s., 2H), 1.44-1.27 (m, 4H), 1.26 (s, 9H), 0.85 (s, 6H). LCMS (M+H)=565.3.

EXAMPLE 182

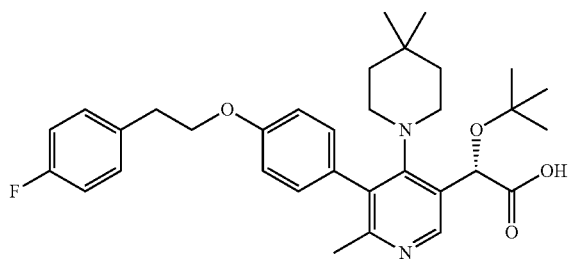 [SMILES: Cc1ncc([C@H](OC(C)(C)C)C(=O)O)c(N2CCC(C)(C)CC2)c1-c1ccc(OCCc2ccc(F)cc2)cc1]

(S)-2-(tert-Butoxy)-2-(4-(4,4-dimethylpiperidin-1-yl)-5-(4-(4-fluorophenethoxy)phenyl)-6-methylpyridin-3-yl)acetic acid: To a solution of (S)-isopropyl 2-(tert-butoxy)-2-(4-(4,4-dimethylpiperidin-1-yl)-5-(4-(4-fluorophenethoxy)phenyl)-6-methylpyridin-3-yl)acetate (26 mg, 0.044 mmol) in EtOH (1 mL) and water (0.1 ml) was added lithium hydroxide monohydrate (3.69 mg, 0.088 mmol) and heated at 75° C. for 30 min. After 30 minutes, the LCMS indicated the reaction was complete. The reaction was cooled to room temperature and purified via prep HPLC to afford the product (S)-2-(tert-butoxy)-2-(4-(4,4-dimethylpiperidin-1-yl)-5-(4-(4-fluorophenethoxy)phenyl)-6-methylpyridin-3-yl)acetic acid (15.7 mg, 0.029 mmol, 65% yield). $^1$H NMR (500 MHz, DMSO-d$_6$) δ 8.44 (s, 1H), 7.37 (dd, J=8.4, 5.9 Hz, 2H), 7.22-7.18 (m, 1H), 7.14-7.08 (m, 3H), 7.04 (d, J=9.5 Hz, 2H), 5.35 (s, 1H), 4.26 (t, J=6.1 Hz, 2H), 3.06 (t, J=7.0 Hz, 2H), 2.12 (s, 3H), 1.32 (br. s., 3H), 1.20 (s, 9H), 0.73 (br. s., 6H)$^1$H NMR (500 MHz, DMSO-d$_6$) δ 8.44 (s, 1H), 7.37 (dd, J=8.4, 5.9 Hz, 2H), 7.22-7.18 (m, 1H), 7.14-7.08 (m, 3H), 7.04 (d, J=9.5 Hz, 2H), 5.35 (s, 1H), 4.26 (t, J=6.1 Hz, 2H), 3.06 (t, J=7.0 Hz, 2H), 2.12 (s, 3H), 1.32 (br. s., 3H), 1.20 (s, 9H), 0.73 (br. s., 6H); 1 proton on the piperidine ring and the 4 protons of methylenes on the 4-fluorophenethoxy were not resolved via $^1$HNMR due to water suppression in the experiment. LCMS (M+H)=549.3.

EXAMPLE 183

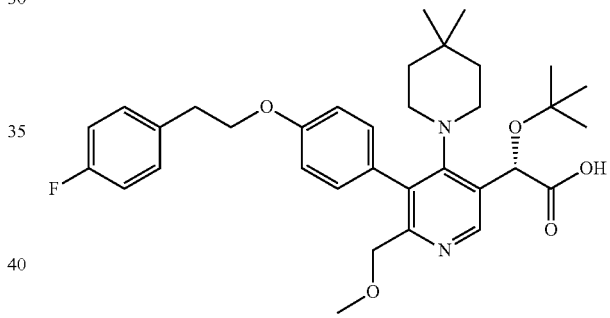

(S)-2-(tert-Butoxy)-2-(4-(4,4-dimethylpiperidin-1-yl)-5-(4-(4-fluorophenethoxy)phenyl)-6-(methoxymethyl)pyridin-3-yl)acetic acid: To a solution of (S)-isopropyl 2-(tert-butoxy)-2-(4-(4,4-dimethylpiperidin-1-yl)-5-(4-(4-fluorophenethoxy)phenyl)-6-(hydroxymethyl)pyridin-3-yl) acetate (29 mg, 0.048 mmol) and methyl iodide (0.026 mL, 0.053 mmol) in DMF (1 mL) was added sodium hydride (2.103 mg, 0.053 mmol) and stirred at RT for 2 hr. After 2 hr, the LCMS indicated complete conversion of starting material to product. The reaction was diluted with water and extracted with EtOAc. The organic layer was washed with brine, collected, dried over MgSO$_4$, filtered and volatiles evaporated to afford the crude product (S)-isopropyl 2-(tert-butoxy)-2-(4-(4,4-dimethylpiperidin-1-yl)-5-(4-(4-fluorophenethoxy)phenyl)-6-(methoxymethyl)pyridin-3-yl)acetate (30 mg, 0.048 mmol, 100% yield LCMS (M+H) =621.4. The above material was taken up EtOH (1 ml) and water (0.100 ml) and added lithium hydroxide monohydrate (3.46 mg, 0.082 mmol). The reaction was stirred and heated at 75° C. for 60 minutes. After 1 hr, the LCMS indicated the reaction was complete. The reaction was cooled to RT and then filtered through a 0.45 nylon filter, then purified on prep HPLC to give (S)-2-(tert-butoxy)-2-(4-(4,4-dimethylpiperidin-1-yl)-5-(4-(4-fluorophenethoxy)phenyl)-6-(methoxymethyl)pyridin-3-yl)acetic acid (7.4 mg, 0.013 mmol, 31% yield over 2 steps). $^1$H NMR (500 MHz, DMSO-d$_6$) δ 8.55 (s, 1H), 7.37 (dd, J=8.4, 5.5 Hz, 2H), 7.26-7.20 (m, 1H), 7.16-7.08 (m, 3H), 7.06-6.99 (m, 2H), 5.37 (s, 1H), 4.30-4.23 (m, 2H), 4.13-4.02 (m, 2H), 3.10 (s, 3H), 3.06 (t, J=6.8 Hz, 2H), 1.32 (br. s., 3H), 1.20 (s, 9H), 0.74 (br. s., 6H); 3 proton on the piperidine ring and the 4 protons of methylenes on the 4-fluorophenethoxy were not resolved via $^1$HNMR due to water suppression in the experiment. LCMS (M+H)=579.3.

EXAMPLE 184

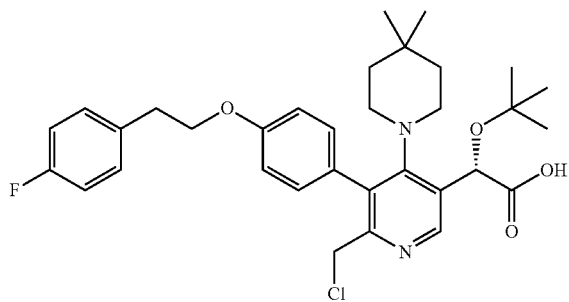

(S)-2-(tert-Butoxy)-2-(6-(chloromethyl)-4-(4,4-dimethyl-piperidin-1-yl)-5-(4-(4-fluorophenethoxy)phenyl)pyridin-3-yl)acetic acid: To a solution of (S)-isopropyl 2-(tert-butoxy)-2-(4-(4,4-dimethylpiperidin-1-yl)-5-(4-(4-fluorophenethoxy)phenyl)-6-(hydroxymethyl)pyridin-3-yl) acetate (25 mg, 0.041 mmol) in DCM (0.5 mL) in a 1 dram vial was added POCl$_3$ (0.012 mL, 0.124 mmol) and stirred for 24 hr at 50° C. The reaction material was transferred to a separatory funnel and washed with ice cold aqueous 2 M sodium carbonate solution. The organic layer was washed with brine, collected, dried over MgSO$_4$, filtered and volatiles evaporated to give the crude product (S)-isopropyl 2-(tert-butoxy)-2-(6-(chloromethyl)-4-(4,4-dimethylpiperidin-1-yl)-5-(4-(4-fluorophenethoxy)phenyl)pyridin-3-yl)acetate (25 mg, 0.040 mmol, 97% yield). LCMS (M+H) =625.3.

The above material was taken up in EtOH (1 ml) and water (0.1 ml) was added lithium hydroxide monohydrate (3.36 mg, 0.080 mmol) and heated at 75° C. for 60 minutes. After 1 hr, the LCMS indicated the reaction was not complete. Lithium hydroxide monohydrate (3.36 mg, 0.080 mmol) was added again to the reaction and heated for 1 more hr. After this time period the LCMS indicated the reaction complete. Some EtOH displacement of the Cl was observed. The reaction was cooled to RT and then filtered through a 0.45μ nylon filter and purified via prep HPLC to give (S)-2-(tert-butoxy)-2-(6-(chloromethyl)-4-(4,4-dimethylpiperidin-1-yl)-5-(4-(4-fluorophenethoxy)phenyl)pyridin-3-yl)acetic acid (0.8 mg, 0.0014 mmol, 3.4% yield over 2 steps). $^1$H NMR (500 MHz, DMSO-d$_6$) δ 8.63-8.55 (m, 1H), 7.40-7.35 (m, 2H), 7.31-7.27 (m, 1H), 7.20-7.16 (m, 1H), 7.12 (t, J=8.8 Hz, 2H), 7.07 (d, J=8.4 Hz, 2H), 5.38 (s, 1H), 4.41 (d, J=10.6 Hz, 1H), 4.34 (d, J=10.6 Hz, 1H), 4.30-4.24 (m, 2H), 3.09-3.02 (m, 2H), 1.33-1.23 (m, 3H), 1.22-1.19 (m, 9H), 0.74 (br. s., 6H); 3 proton on the piperidine ring and the 4 protons of methylenes on the 4-fluorophenethoxy were not resolved via $^1$HNMR due to water suppression in the experiment. LCMS (M+H)=583.3.

Biological Methods

Inhibition of HIV replication: A recombinant NL-RLuc proviral clone was constructed in which a section of the nef gene form NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit form Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results form at least 2 experiments were used to calculate the EC$_{50}$ values. Luciferase was quantitated using the Dual Luciferase kit form Promega (Madison, Wis.). Susceptibility of viruses to compounds was determined by incubation in the presence of serial dilutions of the compound. The 50% effective concentration (EC$_{50}$) was calculated by using the exponential form of the median effect equation where (Fa)=1/[1+(ED$_{50}$/drug conc.)$^m$](Johnson V A, Byington R T. Infectivity Assay. In *Techniques in HIV Research*. ed. Aldovini A, Walker B D. 71-76. New York: Stockton Press. 1990). Results are shown in Table 1. Activity equal to A refers to a compound having an EC$_{50}$≤100 nM, while B and C denote compounds having an EC$_{50}$ between 100 nM and 1 uM (B) or >1 uM (C).

TABLE 1

| Example | Activity | EC$_{50}$ μM |
|---|---|---|
| 1 | A | 0.003 |
| 2 | A | |
| 3 | A | |
| 4 | A | |
| 5 | A | |
| 6 | A | 0.020 |
| 7 | A | |
| 8 | A | |
| 9 | A | |
| 10 | A | |
| 11 | A | |
| 12 | A | |
| 13 | A | |
| 14 | A | |
| 15 | A | 0.051 |
| 16 | A | |
| 17 | A | |
| 18 | A | |
| 19 | A | |
| 20 | A | |
| 21 | A | |
| 22 | A | |
| 23 | A | |
| 24 | A | 0.001 |
| 25 | A | |
| 26 | A | |
| 27 | A | |
| 28 | A | |
| 29 | A | |
| 30 | A | |

TABLE 1-continued

| Example | Activity | EC$_{50}$ μM |
|---|---|---|
| 31 | A | 0.009 |
| 32 | A | |
| 33 | A | |
| 34 | A | |
| 35 | B | 0.316 |
| 36 | A | |
| 37 | A | |
| 38 | B | |
| 39 | A | |
| 40 | A | |
| 41 | A | |
| 42 | A | 0.004 |
| 43 | A | |
| 44 | A | |
| 45 | A | |
| 46 | A | |
| 47 | A | |
| 48 | A | |
| 49 | A | 0.001 |
| 50 | A | |
| 51 | A | |
| 52 | A | |
| 53 | A | |
| 54 | A | |
| 55 | A | |
| 56 | A | |
| 57 | A | 0.012 |
| 58 | A | |
| 59 | A | |
| 60 | A | |
| 61 | A | |
| 62 | A | |
| 63 | A | |
| 64 | A | |
| 65 | A | |
| 66 | A | |
| 67 | A | |
| 68 | A | |
| 69 | A | |
| 70 | A | |
| 71 | A | 0.002 |
| 72 | A | |
| 73 | A | |
| 74 | A | |
| 75 | A | |
| 76 | A | |
| 77 | A | 0.067 |
| 78 | A | |
| 79 | A | |
| 80 | A | |
| 81 | A | |
| 82 | A | |
| 83 | A | |
| 84 | A | |
| 85 | A | 0.001 |
| 86 | A | |
| 87 | A | |
| 88 | A | |
| 89 | A | |
| 90 | A | |
| 91 | A | 0.018 |
| 92 | A | |
| 93 | A | |
| 94 | A | |
| 95 | A | |
| 96 | A | |
| 97 | A | |
| 98 | A | |
| 99 | A | |
| 100 | A | 0.003 |
| 101 | A | |
| 102 | A | |
| 103 | A | |
| 104 | A | |
| 105 | A | |
| 106 | A | |
| 107 | A | |
| 108 | A | |

TABLE 1-continued

| Example | Activity | EC$_{50}$ μM |
|---|---|---|
| 109 | A | 0.005 |
| 110 | A | |
| 111 | A | |
| 112 | A | |
| 113 | A | |
| 114 | A | |
| 115 | A | |
| 116 | A | |
| 117 | A | |
| 118 | A | 0.002 |
| 119 | A | |
| 120 | A | |
| 121 | A | |
| 122 | A | |
| 123 | A | |
| 124 | A | |
| 125 | A | 0.016 |
| 126 | A | |
| 127 | A | |
| 128 | A | |
| 129 | A | |
| 130 | A | |
| 131 | A | |
| 132 | A | |
| 133 | A | |
| 134 | A | 0.001 |
| 135 | A | |
| 136 | A | |
| 137 | A | |
| 138 | A | |
| 139 | A | |
| 140 | A | |
| 141 | A | |
| 142 | A | |
| 143 | A | |
| 144 | A | 0.025 |
| 145 | A | |
| 146 | A | |
| 147 | A | |
| 148 | A | |
| 149 | A | |
| 150 | A | |
| 151 | A | |
| 152 | A | |
| 153 | A | |
| 154 | A | |
| 155 | A | 0.001 |
| 156 | A | |
| 157 | A | |
| 158 | A | |
| 159 | A | |
| 160 | A | |
| 161 | A | |
| 162 | A | 0.008 |
| 163 | A | |
| 164 | A | |
| 165 | A | |
| 166 | A | |
| 167 | A | |
| 168 | A | 0.001 |
| 169 | A | |
| 170 | A | |
| 171 | A | |
| 172 | A | |
| 173 | A | 0.035 |
| 174 | A | |
| 175 | A | |
| 176 | A | |
| 177 | A | |
| 178 | A | |
| 179 | A | 0.005 |
| 180 | A | |
| 181 | A | |
| 182 | A | |
| 183 | A | |
| 184 | A | 0.040 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

I wherein:
  $R^1$ is selected from hydrogen, halo, alkyl, haloalkyl, hydroxyalkyl, alkoxyalkyl, (alkoxy)alkoxyalkyl, ((cycloalkyl)alkoxy)alkyl, (cycloalkoxy)alkyl, haloalkoxyalkyl, (haloalkoxy)alkoxyalkyl, ((halocycloalkyl)alkoxy)alkyl, (halocycloalkoxy)alkyl, (halophenoxy)alkyl, $(Ar^1)$alkyl, $(Ar^2)$alkyl, $((R^{10})(R^{11})N)$alkyl, (trialkylammonium)alkyl, $(R^6)$alkyl, alkenyl, (alkoxy)alkenyl, hydroxy, alkoxy, $(Ar^1)$alkoxy, $(R^{10})(R^{11})N$, $CO_2R^{10}$, $CON(R^{10})(R^{11})$, $((Ar^1)$alkyl)imidazolyl, or halobenzimidazolyl;
  provided that when $R^1$ is hydrogen $R^5$ is not alkyl;
  $R^2$ is selected from halo, phenyl or tetrahydroisoquinolinyl and is substituted with 1 $R^7$ substituent and with 0-3 substituents selected from halo, alkyl, haloalkyl, alkoxy, and haloalkoxy;
  provided that when $R^2$ is halo, $R^1$ and $R^5$ are not simultaneously alkyl;
  $R^3$ is selected from azetidinyl, pyrrolidinyl, piperidinyl, piperazinyl, or homopiperidinyl substituted with 0-3 halo or alkyl substituents;
  $R^4$ is selected from alkyl or haloalkyl;
  $R^5$ is selected from hydrogen, alkyl, haloalkyl, hydroxy, hydroxyalkyl, alkoxy, alkoxyalkyl, (alkoxy)alkoxyalkyl, ((alkoxy)alkoxy)alkoxy)alkyl, ((benzyloxy)alkoxy)alkyl, $((R^{10})(R^{11})N)$alkyl, or $(R^6)$alkyl;
  provided that $R^1$ and $R^5$ are not simultaneously alkyl;
  $R^6$ is selected from (oxetanyl)alkyl, ((oxetanyl)alkoxy)alkyl, (tetrahydropyranyloxy)alkyl, (tetrahydropyranyl)alkoxy)alkyl, ((pyrrolidinonyl)alkoxy)alkyl, $(Ar^1O)$alkyl, $((Ar^1)$alkoxy)alkyl, $((Ar^2)$alkoxy)alkyl, (oxetanyl)oxy, $((R^8)(R^9)N)$alkoxy, alkylthio, alkylsulfonyl, or $(R^8)(R^9)N$;
  $R^7$ is selected from $(Ar^1)$alkyl, $(Ar^1)$alkoxy, N-alkoxycarbonyl, or $((Ar^1)$alkyl)HNCO;
  or $R^7$ is selected from pyrimidinyl, benzofuropyrimidinyl, or pyrazolopyrimidinyl substituted with 0-1 alkyl substituents;
  $R^8$ is selected from hydrogen, alkyl, (cycloalkyl)alkyl, alkoxyalkyl, (tetrahydropyanyl)alkyl, tetrahydropyanyl, or alkoxyphenyl;
  $R^9$ is selected from hydrogen or alkyl;
  or $(R^8)(R^9)N$ taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents;
  $R^{10}$ is selected from hydrogen, alkyl, or alkoxyalkyl;
  $R^{11}$ is selected from hydrogen, alkyl, (cycloalkyl)alkyl, hydroxyalkyl, alkoxyalkyl, (oxetanyl)alkyl, (tetrahydropyanyl)alkyl, $(Ar^1)$alkyl, $(Ar^2)$alkyl, $(((Ar^1)$alkyl)carbonyl)alkyl, oxetanyl, $Ar^1$, formyl, alkylcarbonyl, $(Ar^2)$carbonyl, (dialkylamino)oxoacetyl, or alkylsulfonyl;
  or $(R^{10})(R^{11})N$ taken together is selected from azetidinyl, bicyclo[1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 $(C_{3-7})$ spiroalkylenyl substituents;
  $Ar^1$ is phenyl substituted with 0-3 substituents selected from halo, alkyl, haloalkyl, alkoxy, and haloalkoxy; and
  $Ar^2$ is selected from pyrazolyl, oxazolyl, thiazolyl, triazolyl, oxadiazolyl, or pyridinyl and is substituted with 0-3 halo or alkyl substituents;
  or a pharmaceutically acceptable salt thereof.

2. A compound or salt of claim 1 wherein $R^1$ is hydrogen and $R^5$ is hydrogen, haloalkyl, hydroxyalkyl, alkoxyalkyl, (alkoxy)alkoxyalkyl, (((alkoxy)alkoxy)alkoxy)alkyl, ((benzyloxy)alkoxy)alkyl, $((R^{10})(R^{11})N)$alkyl, or $(R^6)$alkyl.

3. A compound or salt of claim 1 wherein $R^1$ is alkyl and $R^5$ is hydrogen, haloalkyl, hydroxyalkyl, alkoxyalkyl, (alkoxy)alkoxyalkyl, (((alkoxy)alkoxy)alkoxy)alkyl, ((benzyloxy)alkoxy)alkyl, $((R^{10})(R^{11})N)$alkyl, or $(R^6)$alkyl.

4. A compound or salt of claim 1 wherein $R^2$ is phenyl substituted with 1 $R^7$ substituent and with 0-3 substituents selected from halo, alkyl, haloalkyl, alkoxy, and haloalkoxy.

5. A compound or salt of claim 1 wherein $R^2$ is tetrahydroisoquinolinyl and is substituted with 1 $R^7$ substituent.

6. A compound or salt of claim 1 wherein $R^3$ is piperidinyl substituted with 0-3 halo or alkyl substituents.

7. A compound of or salt claim 1 wherein one of $R^1$ or $R^5$ are alkyl.

8. A compound or salt of claim 1 wherein $R^2$ is halo.

9. A compound or salt of claim 8 wherein one of $R^1$ or $R^5$ are alkyl.

10. A compound or salt of claim 1 wherein $R^7$ is selected from $(Ar^1)$alkyl, $(Ar^1)$alkoxy, N-alkoxycarbonyl, or $((Ar^1)$alkyl)HNCO.

11. A compound or salt of claim 1 wherein $R^7$ is selected from pyrimidinyl, benzofuropyrimidinyl, or pyrazolopyrimidinyl substituted with 0-1 alkyl substituents.

12. A compound or salt of claim 1 wherein $R^9$ is selected from hydrogen or alkyl.

13. A compound or salt of claim 1 wherein $(R^8)(R^9)N$ taken together is selected from azetidinyl, pyrrolidinyl, piperidinyl, (spirocyclobutyl)piperidinyl, piperazinyl, morpholinyl, thiomorpholinyl, or dioxidothiomorpholinyl, and is substituted with 0-3 alkyl or alkoxycarbonyl substituents.

14. A compound or salt of claim 1 wherein $R^{11}$ is selected from hydrogen, alkyl, (cycloalkyl)alkyl, hydroxyalkyl, alkoxyalkyl, (oxetanyl)alkyl, (tetrahydropyanyl)alkyl, $(Ar^1)$alkyl, $(Ar^2)$alkyl, $(((Ar^1)$alkyl)carbonyl)alkyl, oxetanyl, $Ar^1$, formyl, alkylcarbonyl, $(Ar^2)$carbonyl, (dialkylamino)oxoacetyl, or alkylsulfonyl.

15. A compound or salt of claim 1 wherein $(R^{10})(R^{11})N$ taken together is selected from azetidinyl, bicyclo[1.1.1]pentanyl, pyrrolidinyl, piperidinyl, piperazinyl, morpholinyl, thiomorpholinyl, dioxidothiomorpholinyl, [3.1.1]diazabicycloheptanyl, [3.2.1]diazabicyclooctanyl, or tetrhydroquinolinyl and is substituted with 0-3 halo, alkyl, haloalkyl, benzyl, hydroxy, alkoxy, or haloalkoxy substituents and with 0-1 ($C_{3-7}$)spiroalkylenyl substituents.

16. A pharmaceutical composition comprising a compound or salt of claim 1.

17. The pharmaceutical composition of claim 16 further comprising dolutegravir.

18. A method for treating HIV infection comprising administering a compound of claim 1, or a pharmaceutically acceptable salt thereof, to a patient in need thereof.

19. The method of claim 18 further comprising administration of dolutegravir.

* * * * *